US009085787B2

(12) United States Patent
Schaffer et al.

(10) Patent No.: US 9,085,787 B2
(45) **Date of Patent: *Jul. 21, 2015**

(54) CELLS, NUCLEIC ACIDS, ENZYMES AND USE THEREOF, AND METHODS FOR THE PRODUCTION OF SOPHOROLIPIDS

(71) Applicants: Steffen Schaffer, Herten (DE); Mirja Wessel, Bochum (DE); Anja Thiessenhusen, Muenster (DE)

(72) Inventors: Steffen Schaffer, Herten (DE); Mirja Wessel, Bochum (DE); Anja Thiessenhusen, Muenster (DE)

(73) Assignee: EVONIK DEGUSSA GmbH, Essen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/487,765

(22) Filed: Sep. 16, 2014

(65) Prior Publication Data

US 2015/0056660 A1 Feb. 26, 2015

Related U.S. Application Data

(62) Division of application No. 13/509,716, filed as application No. PCT/EP2010/065713 on Oct. 19, 2010, now Pat. No. 8,911,982.

(30) Foreign Application Priority Data

Nov. 18, 2009 (DE) ........................ 10 2009 046 799
Apr. 12, 2010 (DE) ........................ 10 2010 014 680

(51) Int. Cl.

| | |
|---|---|
| ***C12N 9/02*** | (2006.01) |
| ***C12N 9/10*** | (2006.01) |
| ***C12N 1/21*** | (2006.01) |
| ***C12P 19/44*** | (2006.01) |
| ***C12P 19/14*** | (2006.01) |
| *A61K 31/704* | (2006.01) |

(52) U.S. Cl.

CPC ............... *C12P 19/14* (2013.01); *A61K 31/704* (2013.01); *C12N 9/0071* (2013.01); *C12N 9/1029* (2013.01); *C12N 9/1051* (2013.01)

(58) Field of Classification Search

CPC .... C12P 19/44; A61K 31/704; C12N 9/0071; C12N 9/1029; C12N 9/1051

See application file for complete search history.

(56) References Cited

U.S. PATENT DOCUMENTS

| | | | |
|---|---|---|---|
| 8,604,227 | B2 | 12/2013 | Petrat et al. |
| 2010/0068773 | A1 | 3/2010 | Marx et al. |
| 2010/0190224 | A1 | 7/2010 | Poetter et al. |
| 2010/0291644 | A1 | 11/2010 | Marx et al. |
| 2010/0324257 | A1 | 12/2010 | Karau et al. |
| 2011/0039313 | A1 | 2/2011 | Verseck et al. |
| 2011/0118433 | A1 | 5/2011 | Poetter et al. |
| 2011/0171702 | A1 | 7/2011 | Reinecke et al. |
| 2011/0189742 | A1 | 8/2011 | Haas et al. |
| 2011/0257429 | A1 | 10/2011 | Schraven et al. |
| 2012/0264182 | A1 | 10/2012 | Reinecke et al. |
| 2013/0052700 | A1 | 2/2013 | Poetter et al. |
| 2013/0130319 | A1 | 5/2013 | Schaffer et al. |
| 2013/0165685 | A1 | 6/2013 | Hannen et al. |
| 2013/0183725 | A1 | 7/2013 | Poetter et al. |

OTHER PUBLICATIONS

Saerens et al., Biotechnology and Bioengineering 108(12):2923-2931, published online Jun. 23, 2011.*

Branden et al., Introduction to Protein Structure, Garland Publishing Inc., New York, p. 247, 1991.

Witkowski et al., Biochemistry 38:11643-11650, 1999.

Seffernick et al., J. Bacteriol. 183(8):2405-2410, 2001.

Saerens et al., FEMS Yeast Res 11:123-132, published online Nov. 12, 2010.

Van Bogaert, I.N.A., et al., "Importance of the cytochrome P450 monooxygenase CYP52 family for the sophorolipid-producing yeast *Candida bombicola*," FEMS Yeast Research, vol. 9, No. 1, pp. 87-94, (Feb. 2009).

Lottermoser, K., et al., "Cytochromes P450 of the Sophorose Lipid-producing Yeast *Candida apicola*: Heterogeneity and Polymerase Chain Reaction-mediated Cloning of Two Genes," Yeast, vol. 12, No. 6, pp. 565-575, (1996).

Van Bogaert, I.N.A., et al., "Knocking out the MFE-2 gene of *Candida bombicola* leads to improved medium-chain sophorolipid production," FEMS Yeast Research, vol. 9, No. 4, pp. 610-617, (Jun. 1, 2009).

Van Bogaert, I.N.A., et al., "Microbial production and application of sophorolipids," Applied Microbiology and Biotechnology, vol. 76, No. 1, pp. 23-34, (May 3, 2007).

Van Bogaert, I.N.A., et al., "Development of a transformation and selection system for the glycolipid-producing yeast *Candida bombicola*," Yeast, vol. 25, No. 4, pp. 273-278, (Apr. 1, 2008).

International Search Report Issued Jul. 20, 2011 in PCT/EP10/65713 Filed Oct. 19, 2010.

* cited by examiner

*Primary Examiner* — Delia Ramirez

(74) *Attorney, Agent, or Firm* — Oblon, McClelland, Maier & Neustadt, L.L.P.

(57) ABSTRACT

The invention relates to cells, nucleic acids, and enzymes, the use thereof for producing sophorolipids, and methods for producing sophorolipids.

25 Claims, 2 Drawing Sheets

Figure 1:
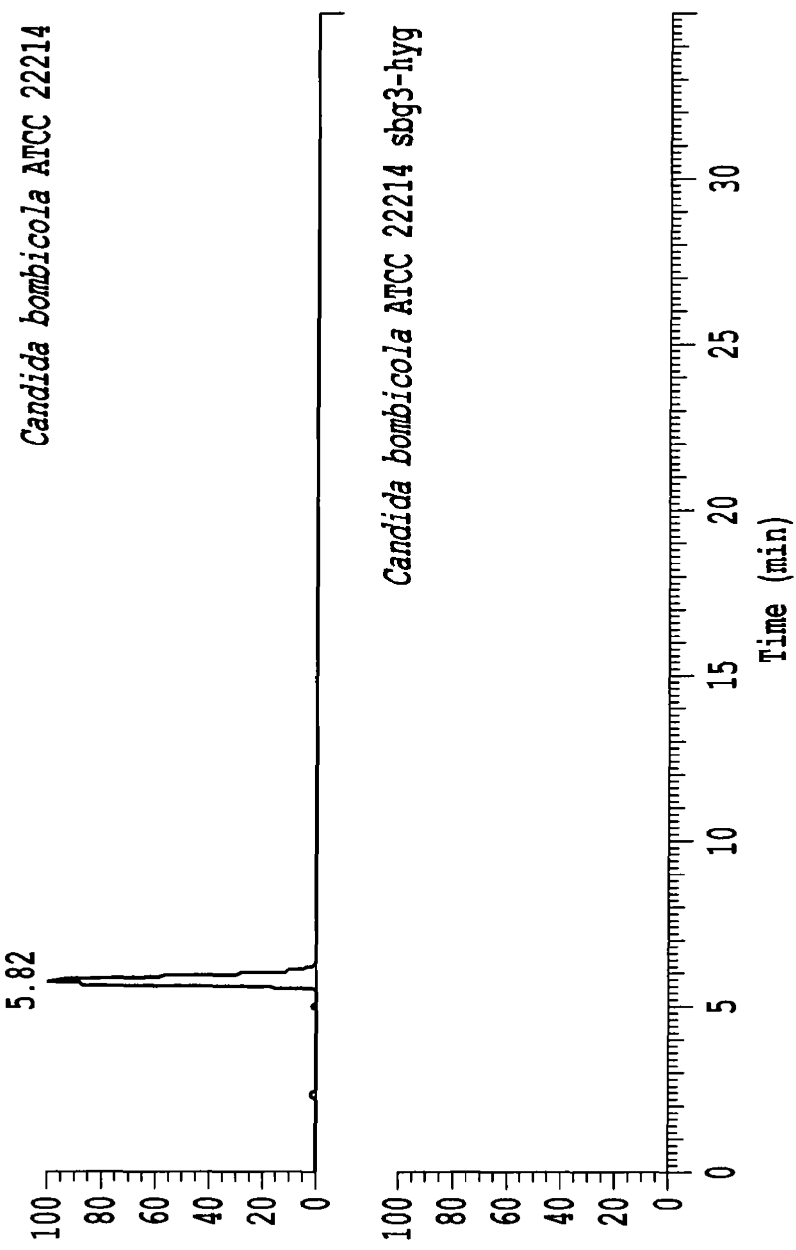

SEQUENCE LISTING

```
<160> NUMBER OF SEQ ID NOS: 90

<210> SEQ ID NO 1
<211> LENGTH: 18013
<212> TYPE: DNA
<213> ORGANISM: Candida bombicola

<400> SEQUENCE: 1

caaactcgac gctaaacaga ccttaaatga caccaatcaa tgtgaaaaaa tcaagttttt      60

ttgttcactc tatattgact gtttccgatg tgtgctatgc agccctcttt gaatcggtgg     120

aagcatgtag ttgaagaaag atggacgtag gagaaacatc aaactgaaca atagtaactt     180
```

```
aaacgtggtt tagaatgcaa gagcaggctc gctgctatgg cattcatagc caggaaagaa    240
acacggatga tctcacactt tgttggatcg acagtcggat ttttttgaaa atttatactt    300
ggcatacatc ttaatacagg ggtagaagga gaagtcgcga gagcgatttc tccgtcattt    360
attcgccgac aaatgtggat ccgtatttag cagattcgaa gtaaattgca ctcgacacca    420
cccacgtgat cgacactgtc gcgtcgatct ccatatatgt acgtgcctat ataaacaagc    480
aacacgcaga ttttgaaatc acatagggag ttgcccgtat gaatccggtt caaataataa    540
tactttgttt tcagatagga gaaacaaaac acccttggta ctcagaagac aaataacgat    600
ccattgtttt caactggaag aaataataca cattgatatt cagaagacaa ataactatcc    660
catttcttta gtatgtgcga aggtaaacag ttctatttca ccttaaaaac actactgaaa    720
gtgcgacata ctgtcgtacg taaaatataa aagcaatcac tatcatttcg ccattatcct    780
tgtcttgtaa taatccaaaa ctgagatcgg gaacggttcc cgttcttgac ataagcagga    840
gctgagaaca ggaacggttc ctggtcttga aatcagcagt aatagagaac gggattggtt    900
cccgttcttg acataagcag gaattggaaa caggaacggt tcccggtctt gacatcagca    960
gggatcgaaa acaggagcgg tttccggtct tgacatgata caaagaatga ttctttgtat   1020
cgggtctatg ggaggaaaaa cagctcattt tcacagaaaa tacagagaac aaaataattg   1080
aaagcgcgac ataatgtcgt acgtagaatt tagaagcaat tactcttatt tttccattat   1140
ccgcgctatt gtacacacac ccaaaccaga acgcgacttg agtgcaatgc ttactaacgc   1200
gcacattaat aagcaaatat agatacgcgg agagcacgcg aaatttgttt accagtacac   1260
tagtgcttag cacaatgaaa tagaccgtac tccggctgag gctcaaagtc cagaagttag   1320
agatttgcca gtttcgttac tagacggttc gttgtgccag gtatgtcgta cagcgcattt   1380
atcagggacg gaaatgggtc ttccatccct gttttggaat gcgctgtcga tccggacgca   1440
gcctcagccg cgtctatttc aaccccccat tagacaggcg gtacattagc tgtttggcct   1500
tcacgctaca gcataattct ccgtcatgtg tgtttccatg accaagaatt gttttggccc   1560
acgaaccaag atcatcgccg tcatataaac ccacattgga gtgttgactc tccatagctt   1620
gtcgttgaat gcaaacttga tgcccgcaaa agtgcttatt agcctacgca ctgattcgcc   1680
ccactctgcg agccacattt ccgctagctt aacatcaggc accgcaatcg gtgcctggac   1740
tgtctccggg ctcggccgag cccggttgag accatcttct tcaaattcat cttctgatag   1800
ctcatctaac atcctagagc tgttcctctt tttccttctt tttgttaatt ggtatttaaa   1860
ccaccaagtg tgtaaacttg tatttttgtc atccgagaga tatctaatag caagtttgcg   1920
attagttaca aatttgttgc gctcttgttc ggtactctta ttgaaacaag ggtgtcgact   1980
cgccaaattc catcggagaa aattgttcga tggatagctt tggagtctgt cccatcatga   2040
tacgaaaagc gtgaagctcc tctgacaatc aaaactttgt ttcaatgggg tgtaggatgg   2100
accccggatc caaacgaccg cgagtcaaaa aacctacggg tgcatttacc cgtagttgat   2160
ctggaaagtc gagatcaact ttttgtagtt tagttacatt catttcacgg tcgaaaaact   2220
cacacacaac gattgcagta tatttaccaa aatcgtctga agagaagcat ctgattgaga   2280
gttcaccatg acgaatccca taaacgacta ctccactgga cacaccgaca gacgccctgg   2340
ggatagtgaa actgaatttg tcggtataat ggcccgtctc acaggccggg cagaacactt   2400
tcatgtcctt tcgcaggtct cgacattgga caagtatgtt gtcgtgggtg acgacaaatt   2460
ggtcctcatc cttgaataag atgctccctt tgttctcagg aactggcacc attccattat   2520
gggcgaataa tttctgctca tcttcgggac tgatgccata ttcttctaac agaagacggc   2580
```

```
gctcacatgg gacctggtgc tctcgccggc ctctcaaatc gccggtgcat ctccacacgc   2640
aaattcacgg gtgtataccc ctgatcaaac gtatcttgcg cgttctgtta ttcattggag   2700
cgagggcccg atcctgtcct atcaaatgat ttcatgtggg aataatccat caattgttct   2760
ggattgaggt atacttcgag ctgtaaagat gtcgcttcta tgtcaagaat agtcggttaa   2820
acgcactcct tcaagattta catgatttac atgattcttc ataaagagca taaataaaga   2880
actgcagcca ttcttgagta aagtgctcag aataataaaa aggttgccac aggttgagtt   2940
aacatgggtt gattgaacca attaaggagg gaacgtttct tccatgggag gctaagaaac   3000
ttaagaaaac cgcacaacca caccgggagg agcgtgttga gctgtaagcg ttgttgagaa   3060
acgaggggac tctgggaagt cgggacccat ctcaatcttg gaatactcct gtaagagtct   3120
caccagagtt agcgaaagct ctgtcagggc gaattgttgg ccgagacaaa ttcggggacc   3180
gccattgaag ggcaagaatg cccacacatt atctagcttc aagttctccc atcgattggg   3240
attgaattcg tgggcgtcag gaccccaata cttgatgtcc ctgtggacca tgtaaattga   3300
atagtaaact gcggtgccct taggaacgaa gatcggatcc ttctgctcgg gaccaccacc   3360
tatgggtaga gttgtatctc tcacagcagt acggaagttc aatggcaata ccggcgcaag   3420
acgcaagact tcatttataa cttgcttcaa ataaggtgct tgcttcagaa gttcgaatga   3480
taaaggcctt tgctcctcct tggttccaaa atgatcgagg acctcctcac gtagtttgtt   3540
gaatacgtca ggatttctgg caaggaaatg aatagcgaag ctcaacgtag cagctgttgt   3600
atctctacca gcaatgagaa tgttgaaaat ttgatcacgt atcgtcactg ggtctcgggt   3660
aactttagcc atctcaagcg agaacacata gatgccacta gactctgcag cagcatcctt   3720
ctctgcaata gagttctcag cagcgaaaga tgtggcgtaa agagccttat caacgtagta   3780
gtcaatatag gactgagcac gtttcttgtg atctcggaat tccttagagt tgaacaacca   3840
gtagactttg cttgataggg tccgtttgaa agcgtaattc agtagaaagt tgtaggactc   3900
cacgaattgt tcggcagtaa tctccgaacc atcacgggct acaatacatg actgattctc   3960
agggttcaag ctctcgcagg actccccaaa taggaattca gtcgctgtat ccagcgtaag   4020
tttgtggaaa taatgttgaa catcaataaa ttggtccact ttcattgcac ggttcatctc   4080
ctttattaac tccgcagcat gactggaaat ctgatcaatt ctgcaaacct gatctttagt   4140
gaactgaggt ctcaacatcg atcgagactg tttccatcca tttccgctga gtgtaaatat   4200
cccttggcca aacacttttc ccactgtgtg gaaacgtgct ccaagaccaa aatcattgaa   4260
tttggttgcc aggattgtct taatgttttc tggctcgatt gtgaagattt ggtattgaag   4320
gggagcttgt cgaagatacg tccgtgcttt gaacttattg aagactctgt cgtattgaac   4380
ttccagtaag gtgtatgact tggccgtctt gatcatgtcc atggttcttt gtattcccag   4440
tgggaacgat ttctcaatga agcgaggcat actacacttg tgcctacgtg ctgcatagcg   4500
gtaccatagg agccagatag gctcgtgtag aactaagaaa gctacgaaga gcagtggcaa   4560
caagccagca acagcggata aactcattgg agttagaata atgtctttga ttaacatata   4620
tgtacttttc aatatgataa acggagaaat aacgcccggc tctatatgca agctgcatca   4680
accctaatat atattagcga gtttctcatg caggctgtag tttgagtcgc tgtaacctca   4740
gcctcaagac tcttacacca taggtagagt ttcgtcactg ggaaactcag ttactatcta   4800
aaccaaactg tgctaatgct caaacctatc actcagaatt tagattgaat caatctaagt   4860
ctgttgagaa acagatatgc atcaggggca cagactaaaa gctgctctca gcgagtaccc   4920
```

-continued

```
ttacctcttg agaaccctca aaatttaccc agcctgcagc atatcatgca ccatggttaa   4980
attcggaaat gaatttaccg gtggccttga accacgttcc tccaattatt taaggcaata   5040
acctgccact ctcttgattt gattaagaaa gactttcaat ttagcttctc cctacgaata   5100
ttcaatgagc ccttcatcac acaaacccct gattctcgct tgcggcttgc ctctttcagg   5160
ccatataatg cccgttttga gtctggtaca cggccttacg gacgacggat acgaagctac   5220
tgttgtgaca ggcagagcgt ttgaacaaaa agttcgagat gtgggtgcag actttgttcc   5280
tttagaaggg aacgcagatt ttgatgacca caccttagac gatctggtcc cgggccgtaa   5340
agacatggcc ccaagcttcg atcgtacagt tcaagatgtg gagcacatga tggtagctac   5400
tcttcctgag cagtttgccg ctattcagag ggctttcaaa aagctcagcg caagcggccg   5460
ccctgtcgtt cttgtcagtg aagtgctgtt tttcggtgca caccctatca gcctcggtgc   5520
tcctggtttc aaacccgctg gctggatttg tttaggggtt ttgcctcttt tgatccgcag   5580
tgatcatacc ttaggacttg acaacgacag gagccccgaa gcacatgcaa agaaactcgc   5640
tatgaaccac gctcttgagc accaaatttt cgttaaagcc actgctaagc acaaggaaat   5700
ctgccgagag ttaggttgca ctgaagatcc caaatttatc tgggagcaca gttacattgc   5760
tgcagacaag ttcctgcagc tgtgcccgcc ttctcttgag ttcagcagag accatctgcc   5820
tagcaacttc aaattcgccg gctcaacgcc caagcaccga actcaattca cccctccttc   5880
ctggtggggg gatgttctga gtgccaagcg agtcatcatg gtcactcaag gaacttttgc   5940
tgtcagttac aagcatctta ttgtgcctac tcttgaggcc ttgaaggacg agcctgacac   6000
tttaacagta gccatattgg gccgccgcgg tgccaagcta ccggatgatg ttgtggttcc   6060
tgagaatgct cgcgtgatcg actacttcaa ctacgatgct ctacttcctc acgttgatgc   6120
tcttgtctac aatggtggat atggcggact tcagcacagc ttaagccact ctgttccagt   6180
tgttattgct ggtgactctg aagacaagcc aatggtggca tcgagagctg aggccgctgg   6240
cgtggcaatt gatttgaaaa ctggcttgcc tacagtggag caaatcaaag aagctgttga   6300
ttcgataatt ggaaatccga aattccacga agcctcgaag aaggttcaaa tggagttgga   6360
aagccacaac tccttgaaaa ttcttgagga aagcatcgag gaaatcgcca gccatgactt   6420
tggtcttttg accaagagtg acgaggaaac tgaagatata cctgtcaaag ggccggcctt   6480
agcggtgagt tcttagaatc gtacgatcaa atcagatcag ggaagagagg tagggttttt   6540
tttatttatg tctttgtttt tattgattga aatttacaat acaacaacca tcaaattaat   6600
ttgaacaaac aacaacacac acacacactg caactttcaa aaaaataagt aaaaggaaga   6660
gaggagtttg ccaatatatt taccttcttc taattctgtt attttttta attgttttgt   6720
ggaaagaaag aagaaaaggc tgtcatgaat ttagtttacc tagaccttct ggttagcggt   6780
attgacgttc atttcaactg gaagaaggaa ttccagttcc tctccttcag cctcgtcggg   6840
atcctcctct ggaatatgct tgaggattcg cgcagggact cctcccacca cagtacgagg   6900
aggaacatct tctcgaacga cagcaccagc cgcaattgtt gagccatctc caatcgtaac   6960
acccggcagg acagtcacat tcgcaccaat ccatacatta ttccccacct tgataggaag   7020
agcatacaca attctcctcg cacgtttctc ggggctaata ggatgagtcg cagtcacgaa   7080
cgttgtattg ggccctacaa tcacctcatc accaaagatt attggagccg agtccaagaa   7140
gcaaacgttg aagttggcgt aaaagtgctc gcctacgctg atgttgaatc caaaatcaac   7200
tgagaatgga gcggtcagcc agacaatatc ctttgtttga ccaaaagtgt ctttgagaat   7260
ctcgaccttc ttgatataag cagcgtgatt tgactcaaaa gtacgacttt cacttgcaat   7320
```

```
ggtattgaac tccctaactt tctcactagt agccagggct ctaaacataa gatctggatc   7380
gtatggattg taaggaactc ctgagaccat cttctcatag ttttcattgc caggggtgtt   7440
tttgaggttt tttttggccc aagagaccat ttcctggtca atttcttttc taggagtcat   7500
tcctttgttt tgagggtcct tcgaggagtt tacaaccatt gaattctaga atgtgaggtg   7560
gaatgaggca aggaaggagg aacgtattga gttgtacctt aagatatctc aaagtgctta   7620
tctccgacta ccggaatatg ctccgggtaa tgcaagtcag tgtgcatatg ggtaaggtga   7680
tgcaagctaa ccctcagggc atatctaatt cgcgtgaggg ttattattgg tctacattac   7740
ctcagtcata gcccgtcaaa gcaaaagccc aaaatcagca cgaaatccca gagatagatt   7800
gttgctgtct cttcaagtac tacgacagtt ccctatatct acagattatc gtcacgagtg   7860
aattatgcag gataggtgac tcaggggtca taatcagagg aatccaatgt gctatttcaa   7920
ttaacgagtc cctttaatca gacaatgtat ggtgactcag ggccataac tagagaaatt   7980
cgatatgcta tttcaattaa tgagtgcctt taatcaaata atgtatgcaa gcagtggcca   8040
aaaataaatg aacgtcaaat ctctccgaga ccttgcaagt tcaccaattc agcgtaccat   8100
ccattgagtt caaggaggct ctgatggtcg ccctgctcca cgatgcgccc tcctgagaac   8160
acatatatga catctgcttt ctgaattgtt gataatctat gcgcaacggc gattgtagta   8220
cggcccttcg ctgctgcgtc gagtgctgct tgaactactt tctcagattc ggaatccaga   8280
gctgaggtgg cctcatcgag gaggagtacc tttggatttc tgatcagggc ccttgcaatt   8340
gcaattcgct gcttttgccc cccagatagc aacgatcccc tagatccgct gagcgtttcg   8400
tagccatcag gcaacgacat gatgaattcg tgaatgttcg ctttgcgagc ggcatcctca   8460
atcatctcct gcgttacttc agactcaggg ccagaccatc ccattagaat attctcacgt   8520
agcgtgcctg aataaagcat tggttcttgc tggactaaag caatgtgtga tctcaatgca   8580
ttcaggttat attcgcgtaa atctttccca tcgaaaagta cttgacctgc taatggatca   8640
taaaatcttt ccaccagtcc aatagtagta gacttaccgc atccactggc tccaactaga   8700
gcgatgtatt ggcccttttt gactgttaag ttgagatctt gtaaaactgg tacttgaggt   8760
cgagtaggat atcggaaatt cacatgacgg aactcaatat ctcctctcac cgactcctcg   8820
ggagcaacgt aaccttcctc actccataca tctatagaag gagtggcagt caagattctg   8880
taaatgttac gcgctgcatc tttggctgag ttcatgtttg gagcatagct gaaaatttgg   8940
ccagcggctt gagaacctgt aataatagcc atgaagacag tcatatatcc tgcgaccgaa   9000
gcttcacctc gtctcattac agtgcttccc caccaaaaaa cgagggctac cacccagggt   9060
gtcattcctt ccgagagtgc gtagtacaat gctgagcggg caatggcaat tctggagctg   9120
aaaatctgag agtctactgt ctttgtgtat tttacgacca cgtctaactc acgagttaag   9180
gactggactg tgcggacagc acttgtatac tcagatgcca tggagccact tcgttcgtaa   9240
acttctctcg cacgatccga taattgggta agaacccaga ctctgacgaa gccacacacc   9300
aacatgacag gaacaacaga cgtagccacg agtccaattc tccaattgaa aggtatacca   9360
gtaactatgc cgccaatcaa ggtcaccaga ctctgttgaa tttgaccgag ggtggcccca   9420
ctcaaaccct cgatcatttt agcttccttc gccaaaattg aggttagcgc acccggcgtg   9480
ttgtttttgt ggtcgaagaa tgcaatatcc attcgcatca attggcggaa caaagctaat   9540
ctgatatttt tgaccaactt atcagatgca agtgataaag cagctatagt gataaaagcc   9600
gtcatgaatg aaatgcagcc tacgaaaaaa taccaccatc ccatgatatt caccacatgc   9660
```

-continued

```
cgcatttttc cgtattcact gggaggtaga accatgcttc cagtggtttg gccagttatt   9720
attgccattg caggatagca atagcccaaa ataatggagg ctaaactacc aatgagaatg   9780
taaccccatt ctttcctatt cagcccccaa accagtttgg tattggtcat caacgtgcta   9840
tgtggggggt tgcgcacacc agggatgtca ttttcttgat attcaggagg ttgagtggtc   9900
tgagtacctg cactgtgaac actcaatgtg ctcacatcct tgggattgaa cttttcgttc   9960
agtgagtcca gaggcgaaat gtctagagct tcaatatcga ggacctcaac gttagtgctc  10020
tttgctttag ttactctttg agcatcaacc aaagctttat aaggcccttc tcgctgtatg  10080
agctcattgt gagtaccctg ctctatgacg ttacctttag acatgacaac tatcttgttg  10140
gcatccttga tcgtagagag tctgtgtgca acgactatag tggtacgacc ttcggccgct  10200
ttgtcgagcg catcttgaac gataccttca gatttggtat ccagagcaga agtcgcttca  10260
tcgagcagca gaattttagg gtctgagacg attgctcttg ctattgcaat gcgttgtttc  10320
tgaccaccgc tgagaagaaa tcctcgatct ccaacattgg tttggatgcc ttctgagaga  10380
gtctgaatga aatcccaggc attggcatct ttacaagctt gaatgatttt agcttcctta  10440
acatgctcgt cagcgaactc aatgtcagtg ccaatcaaac catagctgat attctcatat  10500
attgactctg aaaagagtac tggttcctgc tgaacataac caatttgttg acggagccat  10560
cttgtgttca ggtcgctaat ctcctggcca tccagagtaa cgcttccttc gagaggtaaa  10620
tagaacctct caagaatacc tacaattgta gacttccctg atcccgaggc acctaccagt  10680
gccacagtag atccagcagg aacttcaagg ctaaaatcgg agaggaccaa aacgtctggg  10740
cgactaggat atcggaactt gacatttttg agctcaattc tgccaacggc cttagtttgg  10800
gggacaattc ctttatctat ggactggcca tcgatgactg ggacacgatc aatggcctca  10860
ttgagaatgc tcgcggcagt gagacccttg acaagaaacc tcacgtttgg cgcgatattc  10920
ccaagctgga agcttccaag taacatagct gtgattacaa ctattatctt tccaacgtca  10980
gcactcccac taacgatttc tctggaaccc tgccacagag ctaaggcata cacccaaaaa  11040
gtactagccc atatgcacgc taacatgacc cccaatgagt aactgctccg cttcgattcc  11100
ttcacaacac gatcaagtac cttttcatac ttgacggcga gatgaggttg agcgccaaat  11160
gctactgtag tcctgacagc actgagagcc tcctccgcaa cggtagctcc agactgcgaa  11220
tatatcgcgt cagatctgag ctgatatttg gccatgaagg tggcgccagt tcccattgtg  11280
attaccatga accctacagc actcaggagg atgcaagcca gtttccattg cgaagcaaaa  11340
cttataacgg tggccgcaat gaaggaagct attccctgta cgacgtttcc aagcttgtcg  11400
ctgatcgctt cctgaattga gttggtatcg ttaatgattc tggtgctgac ctcgccacca  11460
cctagtttgt cgtaaaacgc gatattctgg cgaataacag cactcagata atgctttcgg  11520
taacgtcctg ccaacacttc gcctctgtcc acaagcagga agctctcgag aaacgcactg  11580
ccgagcatac caatgccaat atagacaaaa tagagagaca ggtgattcac cttatgctgg  11640
aactcattgc ccttgaggtc atatgaagtg aagtctctga atgtgttgaa gatggcgccc  11700
actactaacg tgaacattgg aagcgcggct ccatgcaccg ctgcaaaaaa aagcgcaagt  11760
atctccaaga aaacgtcaag gggagtgcaa aatctgaaca acctgaaaaa gcttgtggcg  11820
actctctttg tttcaagctg acttcgcaat acattggcct catgtggatc taacgcagag  11880
agcttctcct cgagaagctt gtccttagtc tcgatgagtt tctcacgctt ctctacctgt  11940
atatcatcca ccataagcca aaatcagaga gtgggacctg attcagaatc acacggaccc  12000
gtatatataa caatcacttt ccaacaatat agcgagtatt aatatatttc cgggtaaggg  12060
```

```
ttgttccgga cttatgcatt taatcacagg ttgcatcagc taaatatgtc agggccgacg  12120
gcgtaaattt agaaggttag gtcaagatcc atcggtcagg ccaatggagc tctactatga  12180
taggcagctg aagcgagaca agatatactt cagttgcgct ctctgaaaaa attattttgt  12240
gattctcact cagtggatgt ggcgacacac ggaaccaata atctcgccgg aaaggcggct  12300
gaacatcagt cttgcataag tgtgcaagtg gcctgagcac agcgtgcatt acccttacca  12360
tacattcggg gcaagttaaa tccagcatta tataaacttg attgacacaa atgggcataa  12420
aacaataaag tctcctatat ggccatcgag aaaccagtga tagttgcttg tgcctgccca  12480
ctagcggggc acgtgggccc agtgctcagc ctggtccgcg gtctactcaa tagaggatat  12540
gaggtgactt tcgtaacagg gaacgcattc aaggagaaag ttattgaggc aggatgcact  12600
ttcgtccctc tccaaggacg agctgactac catgaataca atctccctga aatcgctcca  12660
ggattgctca cgattcctcc aggccttgag cagaccggtt actcaatgaa tgagattttt  12720
gtgaaggcga ttcctgagca gtacgatgca cttcaaactg ctctaaaaca ggttgaggct  12780
gaaaataaat cagctgtggt gattggcgag accatgtttc taggggtgca tccgatatca  12840
ctgggtgccc caggtctcaa gccccaaggc gtaatcacgt taggaactat tccgtgcatg  12900
ctgaaagcag agaaggcgcc tggagttcct agtcttgagc caatgattga tactttagtg  12960
cggcaacaag tatttcaacc aggaactgac tctgagaagg agatcatgaa gacgctcggg  13020
gccacgaagg agcccgaatt tctcctggag aatatataca gcagccctga cagatttttg  13080
caactgtgcc ctccatctct tgaatttcac ttgacttcgc ctcctcctgg cttctcgttc  13140
gctggtagtg caccgcatgt aaagtctgct ggattagcaa ctccacctca cctgccgtct  13200
tggtggcctg atgtgctgag tgcgaagcgt ctgattgttg ttacacaagg aacagcagcc  13260
atcaactatg aagatctgct cattccagca ttgcaggcct ttgctgacga agaagacact  13320
ctcgtagttg gtatattggg cgtcaaaggg gcgtcacttc ctgatagcgt taaagttcct  13380
gcaaacgctc gaattgttga ttattttcct tacgatgagc tactaccgca tgcctctgtt  13440
ttcatataca acggtggata cggaggtctg cagcacagtt tgagccatgg cgttcccgtc  13500
atcatcggag gaggaatgtt ggtagacaag ccagctgttg cttcacgagc tgtatgggct  13560
ggtgttggtt atgatcttca aaccttgcag gcaacttctg agctagtctc cacggccgtt  13620
aaggaggtgt tggctactcc ctcgtatcac gagaaagcca tggcagtcaa gaaagagctt  13680
gaaaaataca agtctcttga tattctagag tcggcaatta gtgaattagc ttcttaacct  13740
ggctcttttt ctagatatgt ctgcgccctg ctcactgctt actggcctaa gctggtatta  13800
cggaccttaa tcaagtatca ccccaaggca atcgagagtc ttatcgagtc tctaggtaga  13860
tagatacacg ttttgatttt tcggcccact ttgtagaaaa atctcagtga tttcatggaa  13920
ttcagttaca aatactaatc tgataaacca agaactacac tcggtgttga gagcagaatt  13980
aaagggactt ggcgtctagc acaaaacgat acttgacgtc accactgtga acgcgcttcc  14040
aagcttcggc gatatagctg tactcaatca gctcaacatc acaggtgatg ttattttcac  14100
cacagaagtc cagcatctcc tgagtctctg gcaagccacc aatgtttgag taagtgatag  14160
atttatttcc agccaaatga gaggtcagaa ccttgagggg tccaatttga ccaacaacaa  14220
cgagacaccc accaatatca agggacttga ggtatggctc gaagtcgtgt tcaaagggaa  14280
tggtgtcgat gatcaggtca aatgtgccag cgaccgcctc gagctcattc ggatcagagg  14340
aagcaactac gcggctagca ccttgtgctt tcgctcctgc ggctttggcg tgactcctgc  14400
```

```
tgaacagtgt gacttcagag cccatggctg aggcaaattt gatagccatg gaaccaaggc  14460
ctccgagacc aactacaccg actctttttc caggtccggc gccgtgagcc ctcagaggag  14520
agtaggtagt gataccagca cagagaaggg gcgcagaagc tgccaagtcg aggttggagg  14580
ggattttgag cacaaactcc tcgcgagcaa gaatgtgttg cgaataccct cccttcgtga  14640
cttccccgtt ctttccgctg gaattgtaag tttgagtgcg tgaaacacac caattttctt  14700
tgcctaattt acagttcttg caagtacgac atgagtccac taagcagcca attccaacaa  14760
tgtcgccagc ttggaacttc ttgacggccg ggccgacagc agtggccctt ccaataatct  14820
catgcccacc aacaaaggga aattttgcat tgttccagtc gttgtgcgct gtatggagtt  14880
cactgtgaca aattccacaa taaaggatct cgatgcttac gtcgttgggt cggggatcgc  14940
gacgctcaat agtgccagga actgggtcgc tagttgtatc gtggactatg taggccttgc  15000
aagttgaagg catcgtgaat tttgactgat ccgagcgcag tactctacgt ttagcttgaa  15060
gtcgggagaa gggtccggat tagaagataa gcggcatcct gtgacaagca gtaaaaaaat  15120
gcacccaaaa taaaagttgt gctaaggacc aagagttaga ttaaattcac tacctgatta  15180
tgagctgttt agttttagaa ctttgttgct aaacaattat acgtggctat acaacctacc  15240
caaaatttac aacgccgctt agctaatgac tacgcaaccc tactggatta ggctagggct  15300
ccgagatagc gaaacgtggg gtagcgggcg acaggtcata tagagcccct accctactcg  15360
gtgcaggtta ccgacggacg acatttggag tagtgatttt gactttccaa agatggaatt  15420
tcctctgtag tgaaagatta ctgtatatat ttattggtcg catcgcttgc tcagtttgtg  15480
atccaaccca gggttaatag tggtttaagc tgaactgcgg tgggaagccc agccggtgaa  15540
aggagctttc tggagagcat acggcactaa tgagagcctc tgacaggctg cattcctttt  15600
cccgcacgta cctgatatcc catcatgcgg gaccaggtta gggagtgggt tcagggttta  15660
gatagtggag ctcattggta gctcaccagc gagctctgag tagatggctg tgtcacacat  15720
tgaggcagaa gtttttctgt ctgaagtact gaagatttct tgctttggca acagtaatgg  15780
ggccaggtcc gaaggctcgg caaacttaag ctcgaaatta gatgagcgta agattcactt  15840
aacaacaaat tcgcgaagtc ctaggaagcg cgactgacag aggagtgttt cgttcaacaa  15900
tttcgcgaag gattgcacta ctcaccaact catattaatt cagctaatgt ttctaatttt  15960
caaaactagt acggaagtct gcagttagac agctcttgcg tttgaagaac ttaggcgcga  16020
gatttctcag ctgtatctac acgtcttggg tcgacgcagc tgttggagcg aaccaacgca  16080
caactaacaa caaatcaagt agactaggga tacaagatta aaatcatacg taaagcatca  16140
tttatcatta ttgacaggca ctcaacaagc acaacggctc ggagatgaaa gcacactgct  16200
ctctgcattt taaaagggac atctagatga ggagggcagc agcagcaata gcaccgacag  16260
caacagggac ttggaggacc gaagcagcat taggggcagc tgacgcagtg cccttgctag  16320
agccagaagc cttaggagtg ccagaactct tagagttgcc agaagcagaa gatttgccgg  16380
atgcgctagc atcagcagca gaactcagag aagatgagga accggagtca gtggaggtcg  16440
attttatggg agtgaacttg tagagcatgt tcttagaact cttgtcagtg acaaagacgt  16500
ctccattggg ggcaacctcg atgtggttgg gagttgtgac gttgagctga gtgataatac  16560
tatagtcttc aggatcaata acaaccacgg agtggcccgc acggcaggca acgtaaacaa  16620
cgtcataaac gggatcgtaa cgagcgttga gaggacgtcc aggcatatcg atgctcttca  16680
caaccttgcc ggacttgggg ttgacaataa cagtattgtt ggagccttgg ttcgtaacga  16740
aaagttgctc acgtcgggag tcccaagcaa caccacttga aaacttgaca ttgtccccga  16800
```

```
gatcgaagga tttgacagag tagtcgttga ggtcgatggc tgcggcaagg ggctgtttca  16860
aagccaccgt gtagagtact ttgttgacct cgtcagcaac aagactcata ctgctggaga  16920
aattcttgcc gagagactca gatatattga tactcttggc ggatttgtca gtggtgctag  16980
catcgaatac ggctatgaca ctagacctcg cagaagagac gtaagcaagc ccagtgctct  17040
ggtcaacata gacatcacgc ggatgcggct gaatgtcatc ggggtactga acaccaaggc  17100
tgaggtcctt accattataa taggaaacag tgccctggcg ggtgttggta acccaaacac  17160
ggttgttatc gtagtcgcta tcaacgccat aaactgcgta gcgttgggta acatttccag  17220
tggtaccgat ggcaggctga acgtccctga caacagccag gctcttaggg tcaacctcga  17280
taaggtcgga ctggttcaca gggggacgac caacagagtt ggtaaggaaa agcctgtcat  17340
tggttctgtc ataagtgctt tggtagagac cgccgtactt actaaagtca gcgctttgag  17400
tctcgtaaga gagggtgcga gcatcaatcc cgacggcgag gagaagaaca gcaagagagt  17460
ggatagcaat cattagagct cagtaaaaac gctgttatgg tcaaaataac atttgtgaga  17520
tagtttccct atttatattt ctcgagaaag agccgtttgc gaaaatgggc gccaggcata  17580
attggccaag ggtaaatatg ggtcagggta tctttgggct cgggcggatt ctgcagatgg  17640
cccagagaga ttttcatcat cgaggcaagt tcaaagctcg aaactggcca cattgagcac  17700
cgtggtaaag attgaacgac tatatagtga tttcaattat gtcctgcatt agggcttggt  17760
tttttttctg actgcagcag tgcctattga ggaattcgca atgagagagc cctacggtct  17820
gtgctagatg taaaagatac gatcgagact tagatgcatc taccccagcc cttaccatct  17880
tatatgaggt tgagagattt atttttgttt ttagagatga ttcttcagca aaccagaagg  17940
gaatccggaa ggagttaggg ttaatgatcc agttagtgtt tgtagatatt atccagctcg  18000
tagatgagaa gcg                                                     18013
```

<210> SEQ ID NO 2
<211> LENGTH: 1617
<212> TYPE: DNA
<213> ORGANISM: Candida bombicola

<400> SEQUENCE: 2

```
atgttaatca aagacattat tctaactcca atgagtttat ccgctgttgc tggcttgttg     60
ccactgctct tcgtagcttt cttagttcta cacgagccta tctggctcct atggtaccgc    120
tatgcagcac gtaggcacaa gtgtagtatg cctcgcttca ttgagaaatc gttcccactg    180
ggaatacaaa gaaccatgga catgatcaag acggccaagt catacacctt actggaagtt    240
caatacgaca gagtcttcaa taagttcaaa gcacggacgt atcttcgaca agctcccctt    300
caataccaaa tcttcacaat cgagccagaa aacattaaga caatcctggc aaccaaattc    360
aatgattttg gtcttggagc acgtttccac acagtgggaa aagtgtttgg ccaagggata    420
tttacactca gcggaaatgg atggaaacag tctcgatcga tgttgagacc tcagttcact    480
aaagatcagg tttgcagaat tgatcagatt tccagtcatg ctgcggagtt aataaaggag    540
atgaaccgtg caatgaaagt ggaccaattt attgatgttc aacattattt ccacaaactt    600
acgctggata cagcgactga attcctattt ggggagtcct gcgagagctt gaaccctgag    660
aatcagtcat gtattgtagc ccgtgatggt tcggagatta ctgccgaaca attcgtggag    720
tcctacaact ttctactgaa ttacgctttc aaacggaccc tatcaagcaa agtctactgg    780
ttgttcaact ctaaggaatt ccgagatcac aagaaacgtg ctcagtccta tattgactac    840
```

-continued

```
tacgttgata aggctcttta cgccacatct ttcgctgctg agaactctat tgcagagaag    900
gatgctgctg cagagtctag tggcatctat gtgttctcgc ttgagatggc taaagttacc    960
cgagacccag tgacgatacg tgatcaaatt ttcaacattc tcattgctgg tagagataca   1020
acagctgcta cgttgagctt cgctattcat ttccttgcca gaaatcctga cgtattcaac   1080
aaactacgtg aggaggtcct cgatcatttt ggaaccaagg aggagcaaag gcctttatca   1140
ttcgaacttc tgaagcaagc accttatttg aagcaagtta taaatgaagt cttgcgtctt   1200
gcgccggtat tgccattgaa cttccgtact gctgtgagag atacaactct acccataggt   1260
ggtggtcccg agcagaagga tccgatcttc gttcctaagg gcaccgcagt ttactattca   1320
atttacatgg tccacaggga catcaagtat tggggtcctg acgcccacga attcaatccc   1380
aatcgatggg agaacttgaa gctagataat gtgtgggcat tcttgccctt caatggcggt   1440
ccccgaattt gtctcggcca acaattcgcc ctgacagagc tttcgctaac tctggtgaga   1500
ctcttacagg agtattccaa gattgagatg ggtcccgact tcccagagtc ccctcgtttc   1560
tcaacaacgc ttacagctca acacgctcct cccggtgtgg ttgtgcggtt ttcttaa      1617
```

```
<210> SEQ ID NO 3
<211> LENGTH: 1392
<212> TYPE: DNA
<213> ORGANISM: Candida bombicola

<400> SEQUENCE: 3

atgagccctt catcacacaa acccctgatt ctcgcttgcg gcttgcctct ttcaggccat     60
ataatgcccg ttttgagtct ggtacacggc cttacggacg acggatacga agctactgtt    120
gtgacaggca gagcgtttga acaaaaagtt cgagatgtgg gtgcagactt tgttccttta    180
gaagggaacg cagattttga tgaccacacc ttagacgatc tggtcccggg ccgtaaagac    240
atggccccaa gcttcgatcg tacagttcaa gatgtggagc acatgatggt agctactctt    300
cctgagcagt ttgccgctat tcagagggct ttcaaaaagc tcagcgcaag cggccgccct    360
gtcgttcttg tcagtgaagt gctgttttc ggtgcacacc ctatcagcct cggtgctcct    420
ggtttcaaac ccgctggctg gatttgttta ggggttttgc ctcttttgat ccgcagtgat    480
cataccttag gacttgacaa cgacaggagc cccgaagcac atgcaaagaa actcgctatg    540
aaccacgctc ttgagcacca aattttcgtt aaagccactg ctaagcacaa ggaaatctgc    600
cgagagttag gttgcactga agatcccaaa tttatctggg agcacagtta cattgctgca    660
gacaagttcc tgcagctgtg cccgccttct cttgagttca gcagagacca tctgcctagc    720
aacttcaaat tcgccggctc aacgcccaag caccgaactc aattcacccc tccttcctgg    780
tggggggatg ttctgagtgc caagcgagtc atcatggtca ctcaaggaac ttttgctgtc    840
agttacaagc atcttattgt gcctactctt gaggccttga aggacgagcc tgacacttta    900
acagtagcca tattgggccg ccgcggtgcc aagctaccgg atgatgttgt ggttcctgag    960
aatgctcgcg tgatcgacta cttcaactac gatgctctac ttcctcacgt tgatgctctt   1020
gtctacaatg gtggatatgg cggacttcag cacagcttaa gccactctgt tccagttgtt   1080
attgctggtg actctgaaga caagccaatg gtggcatcga gagctgaggc cgctggcgtg   1140
gcaattgatt tgaaaactgg cttgcctaca gtggagcaaa tcaaagaagc tgttgattcg   1200
ataattggaa atccgaaatt ccacgaagcc tcgaagaagg ttcaaatgga gttggaaagc   1260
cacaactcct tgaaaattct tgaggaaagc atcgaggaaa tcgccagcca tgactttggt   1320
cttttgacca agagtgacga ggaaactgaa gatatacctg tcaaagggcc ggccttagcg   1380
```

```
gtgagttctt ag                                                     1392

<210> SEQ ID NO 4
<211> LENGTH: 780
<212> TYPE: DNA
<213> ORGANISM: Candida bombicola

<400> SEQUENCE: 4

atggttgtaa actcctcgaa ggaccctcaa aacaaaggaa tgactcctag aaaagaaatt    60

gaccaggaaa tggtctcttg ggccaaaaaa aacctcaaaa acacccctgg caatgaaaac   120

tatgagaaga tggtctcagg agttccttac aatccatacg atccagatct tatgtttaga   180

gccctggcta ctagtgagaa agttagggag ttcaatacca ttgcaagtga aagtcgtact   240

tttgagtcaa atcacgctgc ttatatcaag aaggtcgaga ttctcaaaga cacttttggt   300

caaacaaagg atattgtctg gctgaccgct ccattctcag ttgattttgg attcaacatc   360

agcgtaggcg agcactttta cgccaacttc aacgtttgct tcttggactc ggctccaata   420

atctttggtg atgaggtgat tgtagggccc aatacaacgt tcgtgactgc gactcatcct   480

attagccccg agaaacgtgc gaggagaatt gtgtatgctc ttcctatcaa ggtggggaat   540

aatgtatgga ttggtgcgaa tgtgactgtc ctgccgggtg ttacgattgg agatggctca   600

acaattgcgg ctggtgctgt cgttcgagaa gatgttcctc ctcgtactgt ggtgggagga   660

gtccctgcgc gaatcctcaa gcatattcca gaggaggatc ccgacgaggc tgaaggagag   720

gaactggaat tccttcttcc agttgaaatg aacgtcaata ccgctaacca gaaggtctag   780

<210> SEQ ID NO 5
<211> LENGTH: 3900
<212> TYPE: DNA
<213> ORGANISM: Candida bombicola

<400> SEQUENCE: 5

atggtggatg atatacaggt agagaagcgt gagaaactca tcgagactaa ggacaagctt    60

ctcgaggaga agctctctgc gttagatcca catgaggcca atgtattgcg aagtcagctt   120

gaaacaaaga gagtcgccac aagctttttc aggttgttca gattttgcac tccccttgac   180

gttttcttgg agatacttgc gctttttttt gcagcggtgc atggagccgc gcttccaatg   240

ttcacgttag tagtgggcgc catcttcaac acattcagag acttcacttc atatgacctc   300

aagggcaatg agttccagca taaggtgaat cacctgtctc tctattttgt ctatattggc   360

attggtatgc tcggcagtgc gtttctcgag agcttcctgc ttgtggacag aggcgaagtg   420

ttggcaggac gttaccgaaa gcattatctg agtgctgtta ttcgccagaa tatcgcgttt   480

tacgacaaac taggtggtgg cgaggtcagc accagaatca ttaacgatac caactcaatt   540

caggaagcga tcagcgacaa gcttggaaac gtcgtacagg gaatagcttc cttcattgcg   600

gccaccgtta taagttttgc ttcgcaatgg aaactggctt gcatcctcct gagtgctgta   660

gggttcatgg taatcacaat gggaactggc gccaccttca tggccaaata tcagctcaga   720

tctgacgcga tatattcgca gtctggagct accgttgcgg aggaggctct cagtgctgtc   780

aggactacag tagcatttgg cgctcaacct catctcgccg tcaagtatga aaaggtactt   840

gatcgtgttg tgaaggaatc gaagcggagc agttactcat tgggggtcat gttagcgtgc   900

atatgggcta gtactttttg ggtgtatgcc ttagctctgt ggcagggttc cagagaaatc   960

gttagtggga gtgctgacgt tggaaagata atagttgtaa tcacagctat gttacttgga  1020
```

```
agcttccagc ttgggaatat cgcgccaaac gtgaggtttc ttgtcaaggg tctcactgcc   1080

gcgagcattc tcaatgaggc cattgatcgt gtcccagtca tcgatggcca gtccatagat   1140

aaaggaattg tcccccaaac taaggccgtt ggcagaattg agctcaaaaa tgtcaagttc   1200

cgatatccta gtcgcccaga cgttttggtc ctctccgatt ttagccttga agttcctgct   1260

ggatctactg tggcactggt aggtgcctcg ggatcaggga agtctacaat tgtaggtatt   1320

cttgagaggt tctatttacc tctcgaagga agcgttactc tggatggcca ggagattagc   1380

gacctgaaca caagatggct ccgtcaacaa attggttatg ttcagcagga accagtactc   1440

ttttcagagt caatatatga gaatatcagc tatggtttga ttggcactga cattgagttc   1500

gctgacgagc atgttaagga agctaaaatc attcaagctt gtaaagatgc caatgcctgg   1560

gatttcattc agactctctc agaaggcatc caaaccaatg ttggagatcg aggatttctt   1620

ctcagcggtg gtcagaaaca acgcattgca atagcaagag caatcgtctc agaccctaaa   1680

attctgctgc tcgatgaagc gacttctgct ctggatacca aatctgaagg tatcgttcaa   1740

gatgcgctcg acaaagcggc cgaaggtcgt accactatag tcgttgcaca cagactctct   1800

acgatcaagg atgccaacaa gatagttgtc atgtctaaag gtaacgtcat agagcagggt   1860

actcacaatg agctcataca gcgagaaggg ccttataaag ctttggttga tgctcaaaga   1920

gtaactaaag caaagagcac taacgttgag gtcctcgata ttgaagctct agacatttcg   1980

cctctggact cactgaacga aaagttcaat cccaaggatg tgagcacatt gagtgttcac   2040

agtgcaggta ctcagaccac tcaacctcct gaatatcaag aaaatgacat ccctggtgtg   2100

cgcaaccccc cacatagcac gttgatgacc aataccaaac tggtttgggg gctgaatagg   2160

aaagaatggg gttacattct cattggtagt ttagcctcca ttatttttggg ctattgctat   2220

cctgcaatgg caataataac tggccaaacc actggaagca tggttctacc tcccagtgaa   2280

tacggaaaaa tgcggcatgt ggtgaatatc atgggatggt ggtatttttt cgtaggctgc   2340

atttcattca tgacggcttt tatcactata gctgctttat cacttgcatc tgataagttg   2400

gtcaaaaata tcagattagc tttgttccgc caattgatgc gaatggatat tgcattcttc   2460

gaccacaaaa acaacacgcc gggtgcgcta acctcaattt tggcgaagga agctaaaatg   2520

atcgagggtt tgagtggggc caccctcggt caaattcaac agagtctggt gaccttgatt   2580

ggcggcatag ttactggtat acctttcaat tggagaattg gactcgtggc tacgtctgtt   2640

gttcctgtca tgttggtgtg tggcttcgtc agagtctggg ttcttaccca attatcggat   2700

cgtgcgagag aagtttacga acgaagtggc tccatggcat ctgagtatac aagtgctgtc   2760

cgcacagtcc agtccttaac tcgtgagtta gacgtggtcg taaaatacac aaagacagta   2820

gactctcaga ttttcagctc cagaattgcc attgcccgct cagcattgta ctacgcactc   2880

tcggaaggaa tgacaccctg ggtggtagcc ctcgtttttt ggtggggaag cactgtaatg   2940

agacgaggtg aagcttcggt cgcaggatat atgactgtct tcatggctat tattacaggt   3000

tctcaagccg ctggccaaat tttcagctat gctccaaaca tgaactcagc caaagatgca   3060

gcgcgtaaca tttacagaat cttgactgcc actccttcta tagatgtatg gagtgaggaa   3120

ggttacgttg ctcccgagga gtcggtgaga ggagatattg agttccgtca tgtgaatttc   3180

cgatatccta ctcgacctca agtaccagtt ttacaagatc tcaacttaac agtcaaaaag   3240

ggccaataca tcgctctagt tggagccagt ggatgcggta agtctactac tattggactg   3300

gtggaaagat tttatgatcc attagcaggt caagtacttt tcgatgggaa agatttacgc   3360

gaatataacc tgaatgcatt gagatcacac attgctttag tccagcaaga accaatgctt   3420
```

```
tattcaggca cgctacgtga gaatattcta atgggatggt ctggccctga gtctgaagta   3480

acgcaggaga tgattgagga tgccgctcgc aaagcgaaca ttcacgaatt catcatgtcg   3540

ttgcctgatg gctacgaaac gctcagcgga tctaggggat cgttgctatc tggggggcaa   3600

aagcagcgaa ttgcaattgc aagggccctg atcagaaatc caaaggtact cctcctcgat   3660

gaggccacct cagctctgga ttccgaatct gagaaagtag ttcaagcagc actcgacgca   3720

gcagcgaagg gccgtactac aatcgccgtt gcgcatagat tatcaacaat tcagaaagca   3780

gatgtcatat atgtgttctc aggagggcgc atcgtggagc agggcgacca tcagagcctc   3840

cttgaactca atggatggta cgctgaattg gtgaacttgc aaggtctcgg agagatttga   3900
```

<210> SEQ ID NO 6
<211> LENGTH: 1299
<212> TYPE: DNA
<213> ORGANISM: Candida bombicola

<400> SEQUENCE: 6

```
atggccatcg agaaaccagt gatagttgct tgtgcctgcc cactagcggg gcacgtgggc     60

ccagtgctca gcctggtccg cggtctactc aatagaggat atgaggtgac tttcgtaaca    120

gggaacgcat tcaaggagaa agttattgag gcaggatgca ctttcgtccc tctccaagga    180

cgagctgact accatgaata caatctccct gaaatcgctc caggattgct cacgattcct    240

ccaggccttg agcagaccgg ttactcaatg aatgagattt ttgtgaaggc gattcctgag    300

cagtacgatg cacttcaaac tgctctaaaa caggttgagg ctgaaaataa atcagctgtg    360

gtgattggcg agaccatgtt tctaggggtg catccgatat cactgggtgc cccaggtctc    420

aagccccaag gcgtaatcac gttaggaact attccgtgca tgctgaaagc agagaaggcg    480

cctggagttc ctagtcttga gccaatgatt gatactttag tgcggcaaca agtatttcaa    540

ccaggaactg actctgagaa ggagatcatg aagacgctcg gggccacgaa ggagcccgaa    600

tttctcctgg agaatatata cagcagccct gacagatttt tgcaactgtg ccctccatct    660

cttgaatttc acttgacttc gcctcctcct ggcttctcgt tcgctggtag tgcaccgcat    720

gtaaagtctg ctggattagc aactccacct cacctgccgt cttggtggcc tgatgtgctg    780

agtgcgaagc gtctgattgt tgttacacaa ggaacagcag ccatcaacta tgaagatctg    840

ctcattccag cattgcaggc ctttgctgac gaagaagaca ctctcgtagt tggtatattg    900

ggcgtcaaag gggcgtcact tcctgatagc gttaaagttc ctgcaaacgc tcgaattgtt    960

gattattttc cttacgatga gctactaccg catgcctctg ttttcatata caacggtgga   1020

tacggaggtc tgcagcacag tttgagccat ggcgttcccg tcatcatcgg aggaggaatg   1080

ttggtagaca agccagctgt tgcttcacga gctgtatggg ctggtgttgg ttatgatctt   1140

caaaccttgc aggcaacttc tgagctagtc tccacggccg ttaaggaggt gttggctact   1200

ccctcgtatc acgagaaagc catggcagtc aagaaagagc ttgaaaaata caagtctctt   1260

gatattctag agtcggcaat tagtgaatta gcttcttaa                          1299
```

<210> SEQ ID NO 7
<211> LENGTH: 538
<212> TYPE: PRT
<213> ORGANISM: Candida bombicola

<400> SEQUENCE: 7

```
Met Leu Ile Lys Asp Ile Ile Leu Thr Pro Met Ser Leu Ser Ala Val
1               5                   10                  15
```

```
Ala Gly Leu Leu Pro Leu Leu Phe Val Ala Phe Leu Val Leu His Glu
            20                  25                  30

Pro Ile Trp Leu Leu Trp Tyr Arg Tyr Ala Ala Arg Arg His Lys Cys
        35                  40                  45

Ser Met Pro Arg Phe Ile Glu Lys Ser Phe Pro Leu Gly Ile Gln Arg
    50                  55                  60

Thr Met Asp Met Ile Lys Thr Ala Lys Ser Tyr Thr Leu Leu Glu Val
65                  70                  75                  80

Gln Tyr Asp Arg Val Phe Asn Lys Phe Lys Ala Arg Thr Tyr Leu Arg
                85                  90                  95

Gln Ala Pro Leu Gln Tyr Gln Ile Phe Thr Ile Glu Pro Glu Asn Ile
            100                 105                 110

Lys Thr Ile Leu Ala Thr Lys Phe Asn Asp Phe Gly Leu Gly Ala Arg
        115                 120                 125

Phe His Thr Val Gly Lys Val Phe Gly Gln Gly Ile Phe Thr Leu Ser
    130                 135                 140

Gly Asn Gly Trp Lys Gln Ser Arg Ser Met Leu Arg Pro Gln Phe Thr
145                 150                 155                 160

Lys Asp Gln Val Cys Arg Ile Asp Gln Ile Ser Ser His Ala Ala Glu
                165                 170                 175

Leu Ile Lys Glu Met Asn Arg Ala Met Lys Val Asp Gln Phe Ile Asp
            180                 185                 190

Val Gln His Tyr Phe His Lys Leu Thr Leu Asp Thr Ala Thr Glu Phe
        195                 200                 205

Leu Phe Gly Glu Ser Cys Glu Ser Leu Asn Pro Glu Asn Gln Ser Cys
    210                 215                 220

Ile Val Ala Arg Asp Gly Ser Glu Ile Thr Ala Glu Gln Phe Val Glu
225                 230                 235                 240

Ser Tyr Asn Phe Leu Leu Asn Tyr Ala Phe Lys Arg Thr Leu Ser Ser
                245                 250                 255

Lys Val Tyr Trp Leu Phe Asn Ser Lys Glu Phe Arg Asp His Lys Lys
            260                 265                 270

Arg Ala Gln Ser Tyr Ile Asp Tyr Tyr Val Asp Lys Ala Leu Tyr Ala
        275                 280                 285

Thr Ser Phe Ala Ala Glu Asn Ser Ile Ala Glu Lys Asp Ala Ala Ala
    290                 295                 300

Glu Ser Ser Gly Ile Tyr Val Phe Ser Leu Glu Met Ala Lys Val Thr
305                 310                 315                 320

Arg Asp Pro Val Thr Ile Arg Asp Gln Ile Phe Asn Ile Leu Ile Ala
                325                 330                 335

Gly Arg Asp Thr Thr Ala Ala Thr Leu Ser Phe Ala Ile His Phe Leu
            340                 345                 350

Ala Arg Asn Pro Asp Val Phe Asn Lys Leu Arg Glu Glu Val Leu Asp
        355                 360                 365

His Phe Gly Thr Lys Glu Glu Gln Arg Pro Leu Ser Phe Glu Leu Leu
    370                 375                 380

Lys Gln Ala Pro Tyr Leu Lys Gln Val Ile Asn Glu Val Leu Arg Leu
385                 390                 395                 400

Ala Pro Val Leu Pro Leu Asn Phe Arg Thr Ala Val Arg Asp Thr Thr
                405                 410                 415

Leu Pro Ile Gly Gly Gly Pro Glu Gln Lys Asp Pro Ile Phe Val Pro
            420                 425                 430
```

```
Lys Gly Thr Ala Val Tyr Tyr Ser Ile Tyr Met Val His Arg Asp Ile
        435                 440                 445

Lys Tyr Trp Gly Pro Asp Ala His Glu Phe Asn Pro Asn Arg Trp Glu
    450                 455                 460

Asn Leu Lys Leu Asp Asn Val Trp Ala Phe Leu Pro Phe Asn Gly Gly
465                 470                 475                 480

Pro Arg Ile Cys Leu Gly Gln Gln Phe Ala Leu Thr Glu Leu Ser Leu
                485                 490                 495

Thr Leu Val Arg Leu Leu Gln Glu Tyr Ser Lys Ile Glu Met Gly Pro
            500                 505                 510

Asp Phe Pro Glu Ser Pro Arg Phe Ser Thr Thr Leu Thr Ala Gln His
        515                 520                 525

Ala Pro Pro Gly Val Val Val Arg Phe Ser
    530                 535


<210> SEQ ID NO 8
<211> LENGTH: 463
<212> TYPE: PRT
<213> ORGANISM: Candida bombicola

<400> SEQUENCE: 8

Met Ser Pro Ser Ser His Lys Pro Leu Ile Leu Ala Cys Gly Leu Pro
1               5                   10                  15

Leu Ser Gly His Ile Met Pro Val Leu Ser Leu Val His Gly Leu Thr
            20                  25                  30

Asp Asp Gly Tyr Glu Ala Thr Val Val Thr Gly Arg Ala Phe Glu Gln
        35                  40                  45

Lys Val Arg Asp Val Gly Ala Asp Phe Val Pro Leu Glu Gly Asn Ala
    50                  55                  60

Asp Phe Asp Asp His Thr Leu Asp Asp Leu Val Pro Gly Arg Lys Asp
65                  70                  75                  80

Met Ala Pro Ser Phe Asp Arg Thr Val Gln Asp Val Glu His Met Met
                85                  90                  95

Val Ala Thr Leu Pro Glu Gln Phe Ala Ala Ile Gln Arg Ala Phe Lys
            100                 105                 110

Lys Leu Ser Ala Ser Gly Arg Pro Val Val Leu Val Ser Glu Val Leu
        115                 120                 125

Phe Phe Gly Ala His Pro Ile Ser Leu Gly Ala Pro Gly Phe Lys Pro
    130                 135                 140

Ala Gly Trp Ile Cys Leu Gly Val Leu Pro Leu Leu Ile Arg Ser Asp
145                 150                 155                 160

His Thr Leu Gly Leu Asp Asn Asp Arg Ser Pro Glu Ala His Ala Lys
                165                 170                 175

Lys Leu Ala Met Asn His Ala Leu Glu His Gln Ile Phe Val Lys Ala
            180                 185                 190

Thr Ala Lys His Lys Glu Ile Cys Arg Glu Leu Gly Cys Thr Glu Asp
        195                 200                 205

Pro Lys Phe Ile Trp Glu His Ser Tyr Ile Ala Ala Asp Lys Phe Leu
    210                 215                 220

Gln Leu Cys Pro Pro Ser Leu Glu Phe Ser Arg Asp His Leu Pro Ser
225                 230                 235                 240

Asn Phe Lys Phe Ala Gly Ser Thr Pro Lys His Arg Thr Gln Phe Thr
                245                 250                 255

Pro Pro Ser Trp Trp Gly Asp Val Leu Ser Ala Lys Arg Val Ile Met
            260                 265                 270
```

```
Val Thr Gln Gly Thr Phe Ala Val Ser Tyr Lys His Leu Ile Val Pro
        275                 280                 285

Thr Leu Glu Ala Leu Lys Asp Glu Pro Asp Thr Leu Thr Val Ala Ile
    290                 295                 300

Leu Gly Arg Arg Gly Ala Lys Leu Pro Asp Asp Val Val Val Pro Glu
305                 310                 315                 320

Asn Ala Arg Val Ile Asp Tyr Phe Asn Tyr Asp Ala Leu Leu Pro His
                325                 330                 335

Val Asp Ala Leu Val Tyr Asn Gly Gly Tyr Gly Gly Leu Gln His Ser
            340                 345                 350

Leu Ser His Ser Val Pro Val Val Ile Ala Gly Asp Ser Glu Asp Lys
        355                 360                 365

Pro Met Val Ala Ser Arg Ala Glu Ala Ala Gly Val Ala Ile Asp Leu
    370                 375                 380

Lys Thr Gly Leu Pro Thr Val Glu Gln Ile Lys Glu Ala Val Asp Ser
385                 390                 395                 400

Ile Ile Gly Asn Pro Lys Phe His Glu Ala Ser Lys Lys Val Gln Met
                405                 410                 415

Glu Leu Glu Ser His Asn Ser Leu Lys Ile Leu Glu Glu Ser Ile Glu
            420                 425                 430

Glu Ile Ala Ser His Asp Phe Gly Leu Leu Thr Lys Ser Asp Glu Glu
        435                 440                 445

Thr Glu Asp Ile Pro Val Lys Gly Pro Ala Leu Ala Val Ser Ser
    450                 455                 460


<210> SEQ ID NO 9
<211> LENGTH: 259
<212> TYPE: PRT
<213> ORGANISM: Candida bombicola

<400> SEQUENCE: 9

Met Val Val Asn Ser Ser Lys Asp Pro Gln Asn Lys Gly Met Thr Pro
1               5                   10                  15

Arg Lys Glu Ile Asp Gln Glu Met Val Ser Trp Ala Lys Lys Asn Leu
            20                  25                  30

Lys Asn Thr Pro Gly Asn Glu Asn Tyr Glu Lys Met Val Ser Gly Val
        35                  40                  45

Pro Tyr Asn Pro Tyr Asp Pro Asp Leu Met Phe Arg Ala Leu Ala Thr
    50                  55                  60

Ser Glu Lys Val Arg Glu Phe Asn Thr Ile Ala Ser Glu Ser Arg Thr
65                  70                  75                  80

Phe Glu Ser Asn His Ala Ala Tyr Ile Lys Lys Val Glu Ile Leu Lys
                85                  90                  95

Asp Thr Phe Gly Gln Thr Lys Asp Ile Val Trp Leu Thr Ala Pro Phe
            100                 105                 110

Ser Val Asp Phe Gly Phe Asn Ile Ser Val Gly Glu His Phe Tyr Ala
        115                 120                 125

Asn Phe Asn Val Cys Phe Leu Asp Ser Ala Pro Ile Ile Phe Gly Asp
    130                 135                 140

Glu Val Ile Val Gly Pro Asn Thr Thr Phe Val Thr Ala Thr His Pro
145                 150                 155                 160

Ile Ser Pro Glu Lys Arg Ala Arg Arg Ile Val Tyr Ala Leu Pro Ile
                165                 170                 175

Lys Val Gly Asn Asn Val Trp Ile Gly Ala Asn Val Thr Val Leu Pro
```

```
            180                 185                 190

Gly Val Thr Ile Gly Asp Gly Ser Thr Ile Ala Ala Gly Ala Val Val
        195                 200                 205

Arg Glu Asp Val Pro Pro Arg Thr Val Val Gly Gly Val Pro Ala Arg
    210                 215                 220

Ile Leu Lys His Ile Pro Glu Glu Asp Pro Asp Glu Ala Glu Gly Glu
225                 230                 235                 240

Glu Leu Glu Phe Leu Leu Pro Val Glu Met Asn Val Asn Thr Ala Asn
                245                 250                 255

Gln Lys Val


<210> SEQ ID NO 10
<211> LENGTH: 1299
<212> TYPE: PRT
<213> ORGANISM: Candida bombicola

<400> SEQUENCE: 10

Met Val Asp Asp Ile Gln Val Glu Lys Arg Glu Lys Leu Ile Glu Thr
1               5                   10                  15

Lys Asp Lys Leu Leu Glu Glu Lys Leu Ser Ala Leu Asp Pro His Glu
            20                  25                  30

Ala Asn Val Leu Arg Ser Gln Leu Glu Thr Lys Arg Val Ala Thr Ser
        35                  40                  45

Phe Phe Arg Leu Phe Arg Phe Cys Thr Pro Leu Asp Val Phe Leu Glu
    50                  55                  60

Ile Leu Ala Leu Phe Phe Ala Ala Val His Gly Ala Ala Leu Pro Met
65                  70                  75                  80

Phe Thr Leu Val Val Gly Ala Ile Phe Asn Thr Phe Arg Asp Phe Thr
                85                  90                  95

Ser Tyr Asp Leu Lys Gly Asn Glu Phe Gln His Lys Val Asn His Leu
            100                 105                 110

Ser Leu Tyr Phe Val Tyr Ile Gly Ile Gly Met Leu Gly Ser Ala Phe
        115                 120                 125

Leu Glu Ser Phe Leu Leu Val Asp Arg Gly Glu Val Leu Ala Gly Arg
    130                 135                 140

Tyr Arg Lys His Tyr Leu Ser Ala Val Ile Arg Gln Asn Ile Ala Phe
145                 150                 155                 160

Tyr Asp Lys Leu Gly Gly Gly Glu Val Ser Thr Arg Ile Ile Asn Asp
                165                 170                 175

Thr Asn Ser Ile Gln Glu Ala Ile Ser Asp Lys Leu Gly Asn Val Val
            180                 185                 190

Gln Gly Ile Ala Ser Phe Ile Ala Ala Thr Val Ile Ser Phe Ala Ser
        195                 200                 205

Gln Trp Lys Leu Ala Cys Ile Leu Leu Ser Ala Val Gly Phe Met Val
    210                 215                 220

Ile Thr Met Gly Thr Gly Ala Thr Phe Met Ala Lys Tyr Gln Leu Arg
225                 230                 235                 240

Ser Asp Ala Ile Tyr Ser Gln Ser Gly Ala Thr Val Ala Glu Glu Ala
                245                 250                 255

Leu Ser Ala Val Arg Thr Thr Val Ala Phe Gly Ala Gln Pro His Leu
            260                 265                 270

Ala Val Lys Tyr Glu Lys Val Leu Asp Arg Val Val Lys Glu Ser Lys
        275                 280                 285

Arg Ser Ser Tyr Ser Leu Gly Val Met Leu Ala Cys Ile Trp Ala Ser
```

```
    290                 295                 300

Thr Phe Trp Val Tyr Ala Leu Ala Leu Trp Gln Gly Ser Arg Glu Ile
305                 310                 315                 320

Val Ser Gly Ser Ala Asp Val Gly Lys Ile Ile Val Val Ile Thr Ala
                325                 330                 335

Met Leu Leu Gly Ser Phe Gln Leu Gly Asn Ile Ala Pro Asn Val Arg
            340                 345                 350

Phe Leu Val Lys Gly Leu Thr Ala Ala Ser Ile Leu Asn Glu Ala Ile
        355                 360                 365

Asp Arg Val Pro Val Ile Asp Gly Gln Ser Ile Asp Lys Gly Ile Val
    370                 375                 380

Pro Gln Thr Lys Ala Val Gly Arg Ile Glu Leu Lys Asn Val Lys Phe
385                 390                 395                 400

Arg Tyr Pro Ser Arg Pro Asp Val Leu Val Leu Ser Asp Phe Ser Leu
                405                 410                 415

Glu Val Pro Ala Gly Ser Thr Val Ala Leu Val Gly Ala Ser Gly Ser
            420                 425                 430

Gly Lys Ser Thr Ile Val Gly Ile Leu Glu Arg Phe Tyr Leu Pro Leu
        435                 440                 445

Glu Gly Ser Val Thr Leu Asp Gly Gln Glu Ile Ser Asp Leu Asn Thr
    450                 455                 460

Arg Trp Leu Arg Gln Gln Ile Gly Tyr Val Gln Gln Glu Pro Val Leu
465                 470                 475                 480

Phe Ser Glu Ser Ile Tyr Glu Asn Ile Ser Tyr Gly Leu Ile Gly Thr
                485                 490                 495

Asp Ile Glu Phe Ala Asp Glu His Val Lys Glu Ala Lys Ile Ile Gln
            500                 505                 510

Ala Cys Lys Asp Ala Asn Ala Trp Asp Phe Ile Gln Thr Leu Ser Glu
        515                 520                 525

Gly Ile Gln Thr Asn Val Gly Asp Arg Gly Phe Leu Leu Ser Gly Gly
    530                 535                 540

Gln Lys Gln Arg Ile Ala Ile Ala Arg Ala Ile Val Ser Asp Pro Lys
545                 550                 555                 560

Ile Leu Leu Leu Asp Glu Ala Thr Ser Ala Leu Asp Thr Lys Ser Glu
                565                 570                 575

Gly Ile Val Gln Asp Ala Leu Asp Lys Ala Ala Glu Gly Arg Thr Thr
            580                 585                 590

Ile Val Val Ala His Arg Leu Ser Thr Ile Lys Asp Ala Asn Lys Ile
        595                 600                 605

Val Val Met Ser Lys Gly Asn Val Ile Glu Gln Gly Thr His Asn Glu
    610                 615                 620

Leu Ile Gln Arg Glu Gly Pro Tyr Lys Ala Leu Val Asp Ala Gln Arg
625                 630                 635                 640

Val Thr Lys Ala Lys Ser Thr Asn Val Glu Val Leu Asp Ile Glu Ala
                645                 650                 655

Leu Asp Ile Ser Pro Leu Asp Ser Leu Asn Glu Lys Phe Asn Pro Lys
            660                 665                 670

Asp Val Ser Thr Leu Ser Val His Ser Ala Gly Thr Gln Thr Thr Gln
        675                 680                 685

Pro Pro Glu Tyr Gln Glu Asn Asp Ile Pro Gly Val Arg Asn Pro Pro
    690                 695                 700

His Ser Thr Leu Met Thr Asn Thr Lys Leu Val Trp Gly Leu Asn Arg
705                 710                 715                 720
```

```
Lys Glu Trp Gly Tyr Ile Leu Ile Gly Ser Leu Ala Ser Ile Ile Leu
                725                 730                 735

Gly Tyr Cys Tyr Pro Ala Met Ala Ile Ile Thr Gly Gln Thr Thr Gly
            740                 745                 750

Ser Met Val Leu Pro Pro Ser Glu Tyr Gly Lys Met Arg His Val Val
        755                 760                 765

Asn Ile Met Gly Trp Trp Tyr Phe Phe Val Gly Cys Ile Ser Phe Met
    770                 775                 780

Thr Ala Phe Ile Thr Ile Ala Ala Leu Ser Leu Ala Ser Asp Lys Leu
785                 790                 795                 800

Val Lys Asn Ile Arg Leu Ala Leu Phe Arg Gln Leu Met Arg Met Asp
                805                 810                 815

Ile Ala Phe Phe Asp His Lys Asn Asn Thr Pro Gly Ala Leu Thr Ser
            820                 825                 830

Ile Leu Ala Lys Glu Ala Lys Met Ile Glu Gly Leu Ser Gly Ala Thr
        835                 840                 845

Leu Gly Gln Ile Gln Gln Ser Leu Val Thr Leu Ile Gly Gly Ile Val
    850                 855                 860

Thr Gly Ile Pro Phe Asn Trp Arg Ile Gly Leu Val Ala Thr Ser Val
865                 870                 875                 880

Val Pro Val Met Leu Val Cys Gly Phe Val Arg Val Trp Val Leu Thr
                885                 890                 895

Gln Leu Ser Asp Arg Ala Arg Glu Val Tyr Glu Arg Ser Gly Ser Met
            900                 905                 910

Ala Ser Glu Tyr Thr Ser Ala Val Arg Thr Val Gln Ser Leu Thr Arg
        915                 920                 925

Glu Leu Asp Val Val Val Lys Tyr Thr Lys Thr Val Asp Ser Gln Ile
    930                 935                 940

Phe Ser Ser Arg Ile Ala Ile Ala Arg Ser Ala Leu Tyr Tyr Ala Leu
945                 950                 955                 960

Ser Glu Gly Met Thr Pro Trp Val Val Ala Leu Val Phe Trp Trp Gly
                965                 970                 975

Ser Thr Val Met Arg Arg Gly Glu Ala Ser Val Ala Gly Tyr Met Thr
            980                 985                 990

Val Phe Met Ala Ile Ile Thr Gly  Ser Gln Ala Ala Gly  Gln Ile Phe
        995                 1000                 1005

Ser Tyr  Ala Pro Asn Met Asn  Ser Ala Lys Asp Ala  Ala Arg Asn
    1010                 1015                 1020

Ile Tyr  Arg Ile Leu Thr Ala  Thr Pro Ser Ile Asp  Val Trp Ser
    1025                 1030                 1035

Glu Glu  Gly Tyr Val Ala Pro  Glu Glu Ser Val Arg  Gly Asp Ile
    1040                 1045                 1050

Glu Phe  Arg His Val Asn Phe  Arg Tyr Pro Thr Arg  Pro Gln Val
    1055                 1060                 1065

Pro Val  Leu Gln Asp Leu Asn  Leu Thr Val Lys Lys  Gly Gln Tyr
    1070                 1075                 1080

Ile Ala  Leu Val Gly Ala Ser  Gly Cys Gly Lys Ser  Thr Thr Ile
    1085                 1090                 1095

Gly Leu  Val Glu Arg Phe Tyr  Asp Pro Leu Ala Gly  Gln Val Leu
    1100                 1105                 1110

Phe Asp  Gly Lys Asp Leu Arg  Glu Tyr Asn Leu Asn  Ala Leu Arg
    1115                 1120                 1125
```

```
Ser His  Ile Ala Leu Val Gln  Gln Glu Pro Met Leu  Tyr Ser Gly
    1130                 1135                 1140

Thr Leu  Arg Glu Asn Ile Leu  Met Gly Trp Ser Gly  Pro Glu Ser
    1145                 1150                 1155

Glu Val  Thr Gln Glu Met Ile  Glu Asp Ala Ala Arg  Lys Ala Asn
    1160                 1165                 1170

Ile His  Glu Phe Ile Met Ser  Leu Pro Asp Gly Tyr  Glu Thr Leu
    1175                 1180                 1185

Ser Gly  Ser Arg Gly Ser Leu  Leu Ser Gly Gly Gln  Lys Gln Arg
    1190                 1195                 1200

Ile Ala  Ile Ala Arg Ala Leu  Ile Arg Asn Pro Lys  Val Leu Leu
    1205                 1210                 1215

Leu Asp  Glu Ala Thr Ser Ala  Leu Asp Ser Glu Ser  Glu Lys Val
    1220                 1225                 1230

Val Gln  Ala Ala Leu Asp Ala  Ala Ala Lys Gly Arg  Thr Thr Ile
    1235                 1240                 1245

Ala Val  Ala His Arg Leu Ser  Thr Ile Gln Lys Ala  Asp Val Ile
    1250                 1255                 1260

Tyr Val  Phe Ser Gly Gly Arg  Ile Val Glu Gln Gly  Asp His Gln
    1265                 1270                 1275

Ser Leu  Leu Glu Leu Asn Gly  Trp Tyr Ala Glu Leu  Val Asn Leu
    1280                 1285                 1290

Gln Gly  Leu Gly Glu Ile
    1295


<210> SEQ ID NO 11
<211> LENGTH: 432
<212> TYPE: PRT
<213> ORGANISM: Candida bombicola

<400> SEQUENCE: 11

Met Ala Ile Glu Lys Pro Val Ile Val Ala Cys Ala Cys Pro Leu Ala
1               5                   10                  15

Gly His Val Gly Pro Val Leu Ser Leu Val Arg Gly Leu Leu Asn Arg
            20                  25                  30

Gly Tyr Glu Val Thr Phe Val Thr Gly Asn Ala Phe Lys Glu Lys Val
        35                  40                  45

Ile Glu Ala Gly Cys Thr Phe Val Pro Leu Gln Gly Arg Ala Asp Tyr
    50                  55                  60

His Glu Tyr Asn Leu Pro Glu Ile Ala Pro Gly Leu Leu Thr Ile Pro
65                  70                  75                  80

Pro Gly Leu Glu Gln Thr Gly Tyr Ser Met Asn Glu Ile Phe Val Lys
                85                  90                  95

Ala Ile Pro Glu Gln Tyr Asp Ala Leu Gln Thr Ala Leu Lys Gln Val
            100                 105                 110

Glu Ala Glu Asn Lys Ser Ala Val Val Ile Gly Glu Thr Met Phe Leu
        115                 120                 125

Gly Val His Pro Ile Ser Leu Gly Ala Pro Gly Leu Lys Pro Gln Gly
    130                 135                 140

Val Ile Thr Leu Gly Thr Ile Pro Cys Met Leu Lys Ala Glu Lys Ala
145                 150                 155                 160

Pro Gly Val Pro Ser Leu Glu Pro Met Ile Asp Thr Leu Val Arg Gln
                165                 170                 175

Gln Val Phe Gln Pro Gly Thr Asp Ser Glu Lys Glu Ile Met Lys Thr
            180                 185                 190
```

```
Leu Gly Ala Thr Lys Glu Pro Glu Phe Leu Leu Glu Asn Ile Tyr Ser
        195                 200                 205

Ser Pro Asp Arg Phe Leu Gln Leu Cys Pro Pro Ser Leu Glu Phe His
    210                 215                 220

Leu Thr Ser Pro Pro Pro Gly Phe Ser Phe Ala Gly Ser Ala Pro His
225                 230                 235                 240

Val Lys Ser Ala Gly Leu Ala Thr Pro Pro His Leu Pro Ser Trp Trp
                245                 250                 255

Pro Asp Val Leu Ser Ala Lys Arg Leu Ile Val Val Thr Gln Gly Thr
            260                 265                 270

Ala Ala Ile Asn Tyr Glu Asp Leu Leu Ile Pro Ala Leu Gln Ala Phe
        275                 280                 285

Ala Asp Glu Glu Asp Thr Leu Val Val Gly Ile Leu Gly Val Lys Gly
    290                 295                 300

Ala Ser Leu Pro Asp Ser Val Lys Val Pro Ala Asn Ala Arg Ile Val
305                 310                 315                 320

Asp Tyr Phe Pro Tyr Asp Glu Leu Leu Pro His Ala Ser Val Phe Ile
                325                 330                 335

Tyr Asn Gly Gly Tyr Gly Gly Leu Gln His Ser Leu Ser His Gly Val
            340                 345                 350

Pro Val Ile Ile Gly Gly Gly Met Leu Val Asp Lys Pro Ala Val Ala
        355                 360                 365

Ser Arg Ala Val Trp Ala Gly Val Gly Tyr Asp Leu Gln Thr Leu Gln
    370                 375                 380

Ala Thr Ser Glu Leu Val Ser Thr Ala Val Lys Glu Val Leu Ala Thr
385                 390                 395                 400

Pro Ser Tyr His Glu Lys Ala Met Ala Val Lys Lys Glu Leu Glu Lys
                405                 410                 415

Tyr Lys Ser Leu Asp Ile Leu Glu Ser Ala Ile Ser Glu Leu Ala Ser
            420                 425                 430
```

<210> SEQ ID NO 12
<211> LENGTH: 4143
<212> TYPE: DNA
<213> ORGANISM: Artificial
<220> FEATURE:
<223> OTHER INFORMATION: IntegrationConstruct

<400> SEQUENCE: 12

```
aattgttcga tggatagctt tggagtctgt cccatcatga tacgaaaagc gtgaagctcc     60

tctgacaatc aaaactttgt ttcaatgggg tgtaggatgg accccggatc caaacgaccg    120

cgagtcaaaa aacctacggg tgcatttacc cgtagttgat ctggaaagtc gagatcaact    180

ttttgtagtt tagttacatt catttcacgg tcgaaaaact cacacacaac gattgcagta    240

tatttaccaa aatcgtctga agagaagcat ctgattgaga gttcaccatg acgaatccca    300

taaacgacta ctccactgga cacaccgaca gacgccctgg ggatagtgaa actgaatttg    360

tcggtataat ggcccgtctc acaggccggg cagaacactt tcatgtcctt tcgcaggtct    420

cgacattgga caagtatgtt gtcgtgggtg acgacaaatt ggtcctcatc cttgaataag    480

atgctccctt tgttctcagg aactggcacc attccattat gggcgaataa tttctgctca    540

tcttcgggac tgatgccata ttcttctaac agaagacggc gctcacatgg gacctggtgc    600

tctcgccggc ctctcaaatc gccggtgcat ctccacacgc aaattcacgg gtgtataccc    660

ctgatcaaac gtatcttgcg cgttctgtta ttcattggag cgagggcccg atcctgtcct    720
```

```
atcaaatgat ttcatgtggg aataatccat caattgttct ggattgaggt atacttcgag    780
ctgtaaagat gtcgcttcta tgtcaagaat agtcggttaa acgcactcct tcaagattta    840
catgatttac atgattcttc ataaagagca taaataaaga actgcagcca ttcttgagta    900
aagtgctcag aataataaaa aggttgccac aggttgagtt aacatgggtt gattgaacca    960
attaaggagg gaacgtttct tccatgggag gctaagaaac ttaataactt cgtataatgt   1020
atgctatacg aagttattaa ttaactgacg ggcggatagt acaggctttg ccaaaagcct   1080
ataaggctaa agaaagtaaa caagtgaggt tgaaccatga tggcagtgtt cgaattctga   1140
tcaatgaagt acactgcgaa gggaatcccc gaaacggcga acaaaaagaa catcagagga   1200
ggaacgccct cgcaatcccg aacataccag tttcgcagaa cctggggtat caactggatg   1260
caccagcata ctgttcccac tgttgccaat gctgtagacg ctccattgtt gtcagtcatt   1320
ttagcatttt acagtaacca actccaaaaa acagcccgct ctgctgggaa gacttcgcaa   1380
ttatttatcc actactgctg cggttatata cttctcgatc tcagtctcgg ttataattgc   1440
cgcttgacag cctggagaaa ttcggatact ccacgtgata attgccatag ggcataattt   1500
tcgaaacagc tcgcaacgat ctcggctagt tttccccttt tttgacccat atcgacgctg   1560
agactcactc acttgatgcc taccgttagg gtaaattttt caagcctgca gaatatcgcg   1620
ggacgcagtc tcctgcacgc gcgtgacttc atcttactta catcaaacag cccgattaat   1680
ttgaaaagtc ctagctgatc gagggcacgg gcactactgt agagaaataa tatgaagctg   1740
agctatgagg agcgccgaga gaggctgccg gctgtagcag cccggctatt cgacatcatt   1800
gtgagcaagc aaacaaatct ttgcgcaagc ttggatgtgc gaactacctc tgagttactg   1860
agtatcctgg accgcattgg accttacatt tgtatggtta agacccacat tgacataatt   1920
gacgacttcg aatacgacac aactgtcagc ggtttgaaac agctttcaac gaagcacaat   1980
tttctcattt ttgaagaccg aaagttcgca gacatcggtt ccactgttaa ggcccaatat   2040
gcaggtggag tgtttaagat cgctcaatgg gctgatataa caaatgctca cggtgttcct   2100
gggccgggaa ttgtgagcgg actagaagag gctgcgaagg aaactacgga tgaacctcgc   2160
ggccttgtca tgcttgcaga actgagttcg aagggcacac tggctcacgg cgaatactcg   2220
caagcgacag tagacatcgc tcgcagtaac cgcgcatttg tgtttggttt catcgctcag   2280
caaaaagtcg gaaagccaga ggaagactgg gtcattatga ctcctggggt gggcctggac   2340
gacaaaggtg atggattggg gcagcagtat cgtactgtgg acgacgtcat agagaccggc   2400
acagacgtta ttatcgtcgg acgcgggctc tatagcaagg gacgagatcc tgtgcacgaa   2460
gctcagcgtt accaaaaggc gggctggaat gcatatctga gaaaagttca gtcaagatga   2520
ttttctcaaa cagttccttc aatgcaactt gcacatgaat acctataaaa tctgattaaa   2580
ttaccataaa aggtacagat taaaatatat atgccttcaa tggcatcctt cgcgattctg   2640
attcgtcagc acacttcaac cttcctacta tgagtgacag tgatgatgat ctgctggcat   2700
tggccgacgt tggctccgac tccgaagagg aaatctcgct gccgtcgccg ccaagcaatg   2760
aggtcgtcaa tccctatcct ctagaaggca aatatctcga tgctgaagac agggcgaagt   2820
tggacgcgct gccagagatt gagcgagaag agatcttgta tgaccgagct caggagatgc   2880
agcggtacga ggagagaagg tatcttgctc agcgaaggaa gcagatgacg cgggttgctg   2940
acgaggacga agcccccctcc gccaagcgtc aacggggtac aacaggcgtc tcttcgggta   3000
cgaagtcatc tcttgaggca ttaaagaaac gaagggccca gcagtctcgg aagtcctcac   3060
```

```
gccatggagt tgatgacgat gtgtatagtg acgatgatgt taattaataa cttcgtataa   3120

tgtatgctat acgaagttat atatgtactt ttcaatatga taaacggaga aataacgccc   3180

ggctctatat gcaagctgca tcaaccctaa tatatattag cgagtttctc atgcaggctg   3240

tagtttgagt cgctgtaacc tcagcctcaa gactcttaca ccataggtag agtttcgtca   3300

ctgggaaact cagttactat ctaaaccaaa ctgtgctaat gctcaaacct atcactcaga   3360

atttagattg aatcaatcta agtctgttga gaaacagata tgcatcaggg gcacagacta   3420

aaagctgctc tcagcgagta cccttacctc ttgagaaccc tcaaaattta cccagcctgc   3480

agcatatcat gcaccatggt taaattcgga aatgaattta ccggtggcct tgaaccacgt   3540

tcctccaatt atttaaggca ataacctgcc actctcttga tttgattaag aaagactttc   3600

aatttagctt ctccctacga atattcaatg agcccttcat cacacaaacc cctgattctc   3660

gcttgcggct tgcctctttc aggccatata atgcccgttt tgagtctggt acacggcctt   3720

acggacgacg gatacgaagc tactgttgtg acaggcagag cgtttgaaca aaaagttcga   3780

gatgtgggtg cagactttgt tcctttagaa gggaacgcag attttgatga ccacacctta   3840

gacgatctgg tcccgggccg taaagacatg gccccaagct tcgatcgtac agttcaagat   3900

gtggagcaca tgatggtagc tactcttcct gagcagtttg ccgctattca gagggctttc   3960

aaaaagctca gcgcaagcgg ccgccctgtc gttcttgtca gtgaagtgct gtttttcggt   4020

gcacacccta tcagcctcgg tgctcctggt ttcaaacccg ctggctggat ttgtttaggg   4080

gttttgcctc ttttgatccg cagtgatcat accttaggac ttgacaacga caggagcccc   4140

gaa                                                                 4143
```

<210> SEQ ID NO 13
<211> LENGTH: 4143
<212> TYPE: DNA
<213> ORGANISM: Artificial
<220> FEATURE:
<223> OTHER INFORMATION: IntegrationConstruct

<400> SEQUENCE: 13

```
gaaatctgat caattctgca aacctgatct ttagtgaact gaggtctcaa catcgatcga     60

gactgtttcc atccatttcc gctgagtgta aatatccctt ggccaaacac ttttcccact    120

gtgtggaaac gtgctccaag accaaaatca ttgaatttgg ttgccaggat tgtcttaatg    180

ttttctggct cgattgtgaa gatttggtat tgaaggggag cttgtcgaag atacgtccgt    240

gctttgaact tattgaagac tctgtcgtat tgaacttcca gtaaggtgta tgacttggcc    300

gtcttgatca tgtccatggt tctttgtatt cccagtggga acgatttctc aatgaagcga    360

ggcatactac acttgtgcct acgtgctgca tagcggtacc ataggagcca gataggctcg    420

tgtagaacta agaaagctac gaagagcagt ggcaacaagc cagcaacagc ggataaactc    480

attggagtta gaataatgtc tttgattaac atatatgtac ttttcaatat gataaacgga    540

gaaataacgc ccggctctat atgcaagctg catcaaccct aatatatatt agcgagtttc    600

tcatgcaggc tgtagtttga gtcgctgtaa cctcagcctc aagactctta caccataggt    660

agagtttcgt cactgggaaa ctcagttact atctaaacca aactgtgcta atgctcaaac    720

ctatcactca gaatttagat tgaatcaatc taagtctgtt gagaaacaga tatgcatcag    780

gggcacagac taaaagctgc tctcagcgag tacccttacc tcttgagaac cctcaaaatt    840

tacccagcct gcagcatatc atgcaccatg gttaaattcg gaaatgaatt taccggtggc    900

cttgaaccac gttcctccaa ttatttaagg caataacctg ccactctctt gatttgatta    960
```

```
agaaagactt tcaatttagc ttctccctac gaatattcaa taacttcgta taatgtatgc   1020
tatacgaagt tattaattaa ctgacgggcg gatagtacag gctttgccaa aagcctataa   1080
ggctaaagaa agtaaacaag tgaggttgaa ccatgatggc agtgttcgaa ttctgatcaa   1140
tgaagtacac tgcgaaggga atccccgaaa cggcgaacaa aaagaacatc agaggaggaa   1200
cgccctcgca atcccgaaca taccagtttc gcagaacctg ggtatcaac tggatgcacc   1260
agcatactgt tcccactgtt gccaatgctg tagacgctcc attgttgtca gtcattttag   1320
cattttacag taaccaactc caaaaaacag cccgctctgc tgggaagact tcgcaattat   1380
ttatccacta ctgctgcggt tatatacttc tcgatctcag tctcggttat aattgccgct   1440
tgacagcctg gagaaattcg gatactccac gtgataattg ccatagggca taattttcga   1500
aacagctcgc aacgatctcg gctagttttc cccttttttg acccatatcg acgctgagac   1560
tcactcactt gatgcctacc gttagggtaa atttttcaag cctgcagaat atcgcgggac   1620
gcagtctcct gcacgcgcgt gacttcatct tacttacatc aaacagcccg attaatttga   1680
aaagtcctag ctgatcgagg gcacgggcac tactgtagag aaataatatg aagctgagct   1740
atgaggagcg ccgagagagg ctgccggctg tagcagcccg gctattcgac atcattgtga   1800
gcaagcaaac aaatctttgc gcaagcttgg atgtgcgaac tacctctgag ttactgagta   1860
tcctggaccg cattggacct tacatttgta tggttaagac ccacattgac ataattgacg   1920
acttcgaata cgacacaact gtcagcggtt tgaaacagct ttcaacgaag cacaattttc   1980
tcatttttga agaccgaaag ttcgcagaca tcggttccac tgttaaggcc caatatgcag   2040
gtggagtgtt taagatcgct caatgggctg atataacaaa tgctcacggt gttcctgggc   2100
cgggaattgt gagcggacta gaagaggctg cgaaggaaac tacggatgaa cctcgcggcc   2160
ttgtcatgct tgcagaactg agttcgaagg gcacactggc tcacggcgaa tactcgcaag   2220
cgacagtaga catcgctcgc agtaaccgcg catttgtgtt tggtttcatc gctcagcaaa   2280
aagtcggaaa gccagaggaa gactgggtca ttatgactcc tggggtgggc ctggacgaca   2340
aaggtgatgg attggggcag cagtatcgta ctgtggacga cgtcatagag accggcacag   2400
acgttattat cgtcggacgc gggctctata gcaagggacg agatcctgtg cacgaagctc   2460
agcgttacca aaaggcgggc tggaatgcat atctgagaaa agttcagtca agatgatttt   2520
ctcaaacagt tccttcaatg caacttgcac atgaatacct ataaaatctg attaaattac   2580
cataaaaggt acagattaaa atatatatgc cttcaatggc atccttcgcg attctgattc   2640
gtcagcacac ttcaaccttc ctactatgag tgacagtgat gatgatctgc tggcattggc   2700
cgacgttggc tccgactccg aagaggaaat ctcgctgccg tcgccgccaa gcaatgaggt   2760
cgtcaatccc tatcctctag aaggcaaata tctcgatgct gaagacaggg cgaagttgga   2820
cgcgctgcca gagattgagc gagaagagat cttgtatgac cgagctcagg agatgcagcg   2880
gtacgaggag agaaggtatc ttgctcagcg aaggaagcag atgacgcggg ttgctgacga   2940
ggacgaagcc ccctccgcca agcgtcaacg gggtacaaca ggcgtctctt cgggtacgaa   3000
gtcatctctt gaggcattaa agaaacgaag ggcccagcag tctcggaagt cctcacgcca   3060
tggagttgat gacgatgtgt atagtgacga tgatgttaat taataacttc gtataatgta   3120
tgctatacga agttattaga atcgtacgat caaatcagat cagggaagag aggtagggtt   3180
tttttatttt atgtctttgt ttttattgat tgaaatttac aatacaacaa ccatcaaatt   3240
aatttgaaca aacaacaaca cacacacaca ctgcaacttt caaaaaaata agtaaaagga   3300
```

```
agagaggagt ttgccaatat atttaccttc ttctaattct gttatttttt ttaattgttt   3360

tgtggaaaga aagaagaaaa ggctgtcatg aatttagttt acctagacct tctggttagc   3420

ggtattgacg ttcatttcaa ctggaagaag gaattccagt tcctctcctt cagcctcgtc   3480

gggatcctcc tctggaatat gcttgaggat tcgcgcaggg actcctccca ccacagtacg   3540

aggaggaaca tcttctcgaa cgacagcacc agccgcaatt gttgagccat ctccaatcgt   3600

aacacccggc aggacagtca cattcgcacc aatccataca ttattcccca ccttgatagg   3660

aagagcatac acaattctcc tcgcacgttt ctcggggcta ataggatgag tcgcagtcac   3720

gaacgttgta ttgggcccta caatcacctc atcaccaaag attattggag ccgagtccaa   3780

gaagcaaacg ttgaagttgg cgtaaaagtg ctcgcctacg ctgatgttga atccaaaatc   3840

aactgagaat ggagcggtca gccagacaat atcctttgtt tgaccaaaag tgtctttgag   3900

aatctcgacc ttcttgatat aagcagcgtg atttgactca aaagtacgac tttcacttgc   3960

aatggtattg aactccctaa ctttctcact agtagccagg gctctaaaca taagatctgg   4020

atcgtatgga ttgtaaggaa ctcctgagac catcttctca tagttttcat tgccaggggt   4080

gtttttgagg ttttttttgg cccaagagac catttcctgg tcaatttctt ttctaggagt   4140

cat                                                                 4143
```

<210> SEQ ID NO 14
<211> LENGTH: 4140
<212> TYPE: DNA
<213> ORGANISM: Artificial
<220> FEATURE:
<223> OTHER INFORMATION: IntegrationConstruct

<400> SEQUENCE: 14

```
tgcagacaag ttcctgcagc tgtgcccgcc ttctcttgag ttcagcagag accatctgcc     60

tagcaacttc aaattcgccg gctcaacgcc caagcaccga actcaattca cccctccttc    120

ctggtggggg gatgttctga gtgccaagcg agtcatcatg gtcactcaag gaacttttgc    180

tgtcagttac aagcatctta ttgtgcctac tcttgaggcc ttgaaggacg agcctgacac    240

tttaacagta gccatattgg gccgccgcgg tgccaagcta ccggatgatg ttgtggttcc    300

tgagaatgct cgcgtgatcg actacttcaa ctacgatgct ctacttcctc acgttgatgc    360

tcttgtctac aatggtggat atggcggact tcagcacagc ttaagccact ctgttccagt    420

tgttattgct ggtgactctg aagacaagcc aatggtggca tcgagagctg aggccgctgg    480

cgtggcaatt gatttgaaaa ctggcttgcc tacagtggag caaatcaaag aagctgttga    540

ttcgataatt ggaaatccga aattccacga agcctcgaag aaggttcaaa tggagttgga    600

aagccacaac tccttgaaaa ttcttgagga aagcatcgag gaaatcgcca gccatgactt    660

tggtcttttg accaagagtg acgaggaaac tgaagatata cctgtcaaag ggccggcctt    720

agcggtgagt tcttagaatc gtacgatcaa atcagatcag ggaagagagg tagggttttt    780

tttatttatg tctttgtttt tattgattga aatttacaat acaacaacca tcaaattaat    840

ttgaacaaac aacaacacac acacacactg caactttcaa aaaaataagt aaaaggaaga    900

gaggagtttg ccaatatatt taccttcttc taattctgtt attttttta attgttttgt    960

ggaaagaaag aagaaaaggc tgtcatgaat ttagtttacc taataacttc gtataatgta   1020

tgctatacga agttattaat taactgacgg gcggatagta caggctttgc caaaagccta   1080

taaggctaaa gaaagtaaac aagtgaggtt gaaccatgat ggcagtgttc gaattctgat   1140

caatgaagta cactgcgaag ggaatccccg aaacggcgaa caaaaagaac atcagaggag   1200
```

```
gaacgccctc gcaatcccga acataccagt ttcgcagaac ctggggtatc aactggatgc   1260
accagcatac tgttcccact gttgccaatg ctgtagacgc tccattgttg tcagtcattt   1320
tagcatttta cagtaaccaa ctccaaaaaa cagcccgctc tgctgggaag acttcgcaat   1380
tatttatcca ctactgctgc ggttatatac ttctcgatct cagtctcggt tataattgcc   1440
gcttgacagc ctggagaaat tcggatactc cacgtgataa ttgccatagg gcataatttt   1500
cgaaacagct cgcaacgatc tcggctagtt ttcccctttt ttgacccata tcgacgctga   1560
gactcactca cttgatgcct accgttaggg taaatttttc aagcctgcag aatatcgcgg   1620
gacgcagtct cctgcacgcg cgtgacttca tcttacttac atcaaacagc ccgattaatt   1680
tgaaaagtcc tagctgatcg agggcacggg cactactgta gagaaataat atgaagctga   1740
gctatgagga gcgccgagag aggctgccgg ctgtagcagc ccggctattc gacatcattg   1800
tgagcaagca aacaaatctt tgcgcaagct tggatgtgcg aactacctct gagttactga   1860
gtatcctgga ccgcattgga ccttacattt gtatggttaa gacccacatt gacataattg   1920
acgacttcga atacgacaca actgtcagcg gtttgaaaca gctttcaacg aagcacaatt   1980
ttctcatttt tgaagaccga aagttcgcag acatcggttc cactgttaag gcccaatatg   2040
caggtggagt gtttaagatc gctcaatggg ctgatataac aaatgctcac ggtgttcctg   2100
ggccgggaat tgtgagcgga ctagaagagg ctgcgaagga aactacggat gaacctcgcg   2160
gccttgtcat gcttgcagaa ctgagttcga agggcacact ggctcacggc gaatactcgc   2220
aagcgacagt agacatcgct cgcagtaacc gcgcatttgt gtttggtttc atcgctcagc   2280
aaaaagtcgg aaagccagag gaagactggg tcattatgac tcctggggtg ggcctggacg   2340
acaaaggtga tggattgggg cagcagtatc gtactgtgga cgacgtcata gagaccggca   2400
cagacgttat tatcgtcgga cgcgggctct atagcaaggg acgagatcct gtgcacgaag   2460
ctcagcgtta ccaaaaggcg ggctggaatg catatctgag aaaagttcag tcaagatgat   2520
tttctcaaac agttccttca atgcaacttg cacatgaata cctataaaat ctgattaaat   2580
taccataaaa ggtacagatt aaaatatata tgccttcaat ggcatccttc gcgattctga   2640
ttcgtcagca cacttcaacc ttcctactat gagtgacagt gatgatgatc tgctggcatt   2700
ggccgacgtt ggctccgact ccgaagagga aatctcgctg ccgtcgccgc caagcaatga   2760
ggtcgtcaat ccctatcctc tagaaggcaa atatctcgat gctgaagaca gggcgaagtt   2820
ggacgcgctg ccagagattg agcgagaaga gatcttgtat gaccgagctc aggagatgca   2880
gcggtacgag gagagaaggt atcttgctca gcgaaggaag cagatgacgc gggttgctga   2940
cgaggacgaa gccccctccg ccaagcgtca acggggtaca acaggcgtct cttcgggtac   3000
gaagtcatct cttgaggcat taaagaaacg aagggcccag cagtctcgga agtcctcacg   3060
ccatggagtt gatgacgatg tgtatagtga cgatgatgtt aattaataac ttcgtataat   3120
gtatgctata cgaagttatt gaattctaga atgtgaggtg gaatgaggca aggaaggagg   3180
aacgtattga gttgtacctt aagatatctc aaagtgctta tctccgacta ccggaatatg   3240
ctccgggtaa tgcaagtcag tgtgcatatg ggtaaggtga tgcaagctaa ccctcagggc   3300
atatctaatt cgcgtgaggg ttattattgg tctacattac ctcagtcata gcccgtcaaa   3360
gcaaaagccc aaaatcagca cgaaatccca gagatagatt gttgctgtct cttcaagtac   3420
tacgacagtt ccctatatct acagattatc gtcacgagtg aattatgcag gataggtgac   3480
tcaggggtca taatcagagg aatccaatgt gctatttcaa ttaacgagtc cctttaatca   3540
```

```
gacaatgtat ggtgactcag gggccataac tagagaaatt cgatatgcta tttcaattaa   3600

tgagtgcctt taatcaaata atgtatgcaa gcagtggcca aaaataaatg aacgtcaaat   3660

ctctccgaga ccttgcaagt tcaccaattc agcgtaccat ccattgagtt caaggaggct   3720

ctgatggtcg ccctgctcca cgatgcgccc tcctgagaac acatatatga catctgcttt   3780

ctgaattgtt gataatctat gcgcaacggc gattgtagta cggcccttcg ctgctgcgtc   3840

gagtgctgct tgaactactt tctcagattc ggaatccaga gctgaggtgg cctcatcgag   3900

gaggagtacc tttggatttc tgatcagggc ccttgcaatt gcaattcgct gcttttgccc   3960

cccagatagc aacgatcccc tagatccgct gagcgtttcg tagccatcag gcaacgacat   4020

gatgaattcg tgaatgttcg ctttgcgagc ggcatcctca atcatctcct gcgttacttc   4080

agactcaggg ccagaccatc ccattagaat attctcacgt agcgtgcctg aataaagcat   4140
```

<210> SEQ ID NO 15
<211> LENGTH: 4130
<212> TYPE: DNA
<213> ORGANISM: Artificial
<220> FEATURE:
<223> OTHER INFORMATION: IntegrationConstruct

<400> SEQUENCE: 15

```
ggatgagtcg cagtcacgaa cgttgtattg ggccctacaa tcacctcatc accaaagatt     60

attggagccg agtccaagaa gcaaacgttg aagttggcgt aaaagtgctc gcctacgctg    120

atgttgaatc caaaatcaac tgagaatgga gcggtcagcc agacaatatc ctttgtttga    180

ccaaaagtgt ctttgagaat ctcgaccttc ttgatataag cagcgtgatt tgactcaaaa    240

gtacgacttt cacttgcaat ggtattgaac tccctaactt tctcactagt agccagggct    300

ctaaacataa gatctggatc gtatggattg taaggaactc ctgagaccat cttctcatag    360

ttttcattgc caggggtgtt tttgaggttt tttttggccc aagagaccat ttcctggtca    420

atttcttttc taggagtcat tcctttgttt tgagggtcct tcgaggagtt tacaaccatt    480

gaattctaga atgtgaggtg gaatgaggca aggaaggagg aacgtattga gttgtacctt    540

aagatatctc aaagtgctta tctccgacta ccggaatatg ctccgggtaa tgcaagtcag    600

tgtgcatatg ggtaaggtga tgcaagctaa ccctcagggc atatctaatt cgcgtgaggg    660

ttattattgg tctacattac ctcagtcata gcccgtcaaa gcaaaagccc aaaatcagca    720

cgaaatccca gagatagatt gttgctgtct cttcaagtac tacgacagtt ccctatatct    780

acagattatc gtcacgagtg aattatgcag gataggtgac tcaggggtca taatcagagg    840

aatccaatgt gctatttcaa ttaacgagtc cctttaatca gacaatgtat ggtgactcag    900

gggccataac tagagaaatt cgatatgcta tttcaattaa tgagtgcctt taatcaaata    960

atgtatgcaa gcagtggcca aaaataaatg aacgtcaata acttcgtata atgtatgcta   1020

tacgaagtta ttaattaact gacgggcgga tagtacaggc tttgccaaaa gcctataagg   1080

ctaaagaaag taaacaagtg aggttgaacc atgatggcag tgttcgaatt ctgatcaatg   1140

aagtacactg cgaagggaat ccccgaaacg gcgaacaaaa agaacatcag aggaggaacg   1200

ccctcgcaat cccgaacata ccagtttcgc agaacctggg gtatcaactg gatgcaccag   1260

catactgttc ccactgttgc caatgctgta gacgctccat tgttgtcagt cattttagca   1320

ttttacagta accaactcca aaaaacagcc cgctctgctg ggaagacttc gcaattattt   1380

atccactact gctgcggtta tatacttctc gatctcagtc tcggttataa ttgccgcttg   1440

acagcctgga gaaattcgga tactccacgt gataattgcc atagggcata attttcgaaa   1500
```

```
cagctcgcaa cgatctcggc tagttttccc ctttttttgac ccatatcgac gctgagactc   1560
actcacttga tgcctaccgt tagggtaaat ttttcaagcc tgcagaatat cgcgggacgc   1620
agtctcctgc acgcgcgtga cttcatctta cttacatcaa acagcccgat taatttgaaa   1680
agtcctagct gatcgagggc acgggcacta ctgtagagaa ataatatgaa gctgagctat   1740
gaggagcgcc gagagaggct gccggctgta gcagcccggc tattcgacat cattgtgagc   1800
aagcaaacaa atctttgcgc aagcttggat gtgcgaacta cctctgagtt actgagtatc   1860
ctggaccgca ttggacctta catttgtatg gttaagaccc acattgacat aattgacgac   1920
ttcgaatacg acacaactgt cagcggtttg aaacagcttt caacgaagca caattttctc   1980
atttttgaag accgaaagtt cgcagacatc ggttccactg ttaaggccca atatgcaggt   2040
ggagtgttta agatcgctca atgggctgat ataacaaatg ctcacggtgt tcctgggccg   2100
ggaattgtga gcggactaga agaggctgcg aaggaaacta cggatgaacc tcgcggcctt   2160
gtcatgcttg cagaactgag ttcgaagggc acactggctc acggcgaata ctcgcaagcg   2220
acagtagaca tcgctcgcag taaccgcgca tttgtgtttg gtttcatcgc tcagcaaaaa   2280
gtcggaaagc cagaggaaga ctgggtcatt atgactcctg ggtgggcct ggacgacaaa   2340
ggtgatggat tggggcagca gtatcgtact gtggacgacg tcatagagac cggcacagac   2400
gttattatcg tcggacgcgg gctctatagc aagggacgag atcctgtgca cgaagctcag   2460
cgttaccaaa aggcgggctg gaatgcatat ctgagaaaag ttcagtcaag atgatttct   2520
caaacagttc cttcaatgca acttgcacat gaatacctat aaaatctgat taaattacca   2580
taaaaggtac agattaaaat atatatgcct tcaatggcat ccttcgcgat tctgattcgt   2640
cagcacactt caaccttcct actatgagtg acagtgatga tgatctgctg gcattggccg   2700
acgttggctc cgactccgaa gaggaaatct cgctgccgtc gccgccaagc aatgaggtcg   2760
tcaatcccta tcctctagaa ggcaaatatc tcgatgctga agacagggcg aagttggacg   2820
cgctgccaga gattgagcga gaagagatct tgtatgaccg agctcaggag atgcagcggt   2880
acgaggagag aaggtatctt gctcagcgaa ggaagcagat gacgcgggtt gctgacgagg   2940
acgaagcccc ctccgccaag cgtcaacggg gtacaacagg cgtctcttcg ggtacgaagt   3000
catctcttga ggcattaaag aaacgaaggg cccagcagtc tcggaagtcc tcacgccatg   3060
gagttgatga cgatgtgtat agtgacgatg atgttaatta ataacttcgt ataatgtatg   3120
ctatacgaag ttataagcca aaatcagaga gtgggacctg attcagaatc acacggaccc   3180
gtatatataa caatcacttt ccaacaatat agcgagtatt aatatatttc cgggtaaggg   3240
ttgttccgga cttatgcatt taatcacagg ttgcatcagc taaatatgtc agggccgacg   3300
gcgtaaattt agaaggttag gtcaagatcc atcggtcagg ccaatggagc tctactatga   3360
taggcagctg aagcgagaca agatatactt cagttgcgct ctctgaaaaa attattttgt   3420
gattctcact cagtggatgt ggcgacacac ggaaccaata atctcgccgg aaaggcggct   3480
gaacatcagt cttgcataag tgtgcaagtg gcctgagcac agcgtgcatt acccttacca   3540
tacattcggg gcaagttaaa tccagcatta tataaacttg attgacacaa atgggcataa   3600
aacaataaag tctcctatat ggccatcgag aaaccagtga tagttgcttg tgcctgccca   3660
ctagcggggc acgtgggccc agtgctcagc ctggtccgcg gtctactcaa tagaggatat   3720
gaggtgactt tcgtaacagg gaacgcattc aaggagaaag ttattgaggc aggatgcact   3780
ttcgtccctc tccaaggacg agctgactac catgaataca atctccctga aatcgctcca   3840
```

```
ggattgctca cgattcctcc aggccttgag cagaccggtt actcaatgaa tgagattttt   3900

gtgaaggcga ttcctgagca gtacgatgca cttcaaactg ctctaaaaca ggttgaggct   3960

gaaaataaat cagctgtggt gattggcgag accatgtttc taggggtgca tccgatatca   4020

ctgggtgccc caggtctcaa gccccaaggc gtaatcacgt taggaactat tccgtgcatg   4080

ctgaaagcag agaaggcgcc tggagttcct agtcttgagc caatgattga              4130


<210> SEQ ID NO 16
<211> LENGTH: 4141
<212> TYPE: DNA
<213> ORGANISM: Artificial
<220> FEATURE:
<223> OTHER INFORMATION: IntegrationConstruct

<400> SEQUENCE: 16

attctggtgc tgacctcgcc accacctagt ttgtcgtaaa acgcgatatt ctggcgaata     60

acagcactca gataatgctt tcggtaacgt cctgccaaca cttcgcctct gtccacaagc    120

aggaagctct cgagaaacgc actgccgagc ataccaatgc caatatagac aaaatagaga    180

gacaggtgat tcaccttatg ctggaactca ttgcccttga ggtcatatga agtgaagtct    240

ctgaatgtgt tgaagatggc gcccactact aacgtgaaca ttggaagcgc ggctccatgc    300

accgctgcaa aaaaaagcgc aagtatctcc aagaaaacgt caaggggagt gcaaaatctg    360

aacaacctga aaaagcttgt ggcgactctc tttgtttcaa gctgacttcg caatacattg    420

gcctcatgtg gatctaacgc agagagcttc tcctcgagaa gcttgtcctt agtctcgatg    480

agtttctcac gcttctctac ctgtatatca tccaccataa gccaaaatca gagagtggga    540

cctgattcag aatcacacgg acccgtatat ataacaatca ctttccaaca atatagcgag    600

tattaatata tttccgggta agggttgttc cggacttatg catttaatca caggttgcat    660

cagctaaata tgtcagggcc gacggcgtaa atttagaagg ttaggtcaag atccatcggt    720

caggccaatg gagctctact atgataggca gctgaagcga gacaagatat acttcagttg    780

cgctctctga aaaaattatt ttgtgattct cactcagtgg atgtggcgac acacggaacc    840

aataatctcg ccggaaaggc ggctgaacat cagtcttgca taagtgtgca agtggcctga    900

gcacagcgtg cattaccctt accatacatt cggggcaagt taaatccagc attatataaa    960

cttgattgac acaaatgggc ataaaacaat aaagtctcct atataacttc gtataatgta   1020

tgctatacga agttattaat taactgacgg gcggatagta caggctttgc caaaagccta   1080

taaggctaaa gaaagtaaac aagtgaggtt gaaccatgat ggcagtgttc gaattctgat   1140

caatgaagta cactgcgaag ggaatccccg aaacggcgaa caaaaagaac atcagaggag   1200

gaacgccctc gcaatcccga acataccagt ttcgcagaac ctggggtatc aactggatgc   1260

accagcatac tgttcccact gttgccaatg ctgtagacgc tccattgttg tcagtcattt   1320

tagcatttta cagtaaccaa ctccaaaaaa cagcccgctc tgctgggaag acttcgcaat   1380

tatttatcca ctactgctgc ggttatatac ttctcgatct cagtctcggt tataattgcc   1440

gcttgacagc ctggagaaat tcggatactc cacgtgataa ttgccatagg gcataatttt   1500

cgaaacagct cgcaacgatc tcggctagtt ttcccctttt ttgacccata tcgacgctga   1560

gactcactca cttgatgcct accgttaggg taaatttttc aagcctgcag aatatcgcgg   1620

gacgcagtct cctgcacgcg cgtgacttca tcttacttac atcaaacagc ccgattaatt   1680

tgaaaagtcc tagctgatcg agggcacggg cactactgta gagaaataat atgaagctga   1740

gctatgagga gcgccgagag aggctgccgg ctgtagcagc ccggctattc gacatcattg   1800
```

```
tgagcaagca aacaaatctt tgcgcaagct tggatgtgcg aactacctct gagttactga   1860
gtatcctgga ccgcattgga ccttacattt gtatggttaa gacccacatt gacataattg   1920
acgacttcga atacgacaca actgtcagcg gtttgaaaca gctttcaacg aagcacaatt   1980
ttctcatttt tgaagaccga aagttcgcag acatcggttc cactgttaag gcccaatatg   2040
caggtggagt gtttaagatc gctcaatggg ctgatataac aaatgctcac ggtgttcctg   2100
ggccgggaat tgtgagcgga ctagaagagg ctgcgaagga aactacggat gaacctcgcg   2160
gccttgtcat gcttgcagaa ctgagttcga agggcacact ggctcacggc gaatactcgc   2220
aagcgacagt agacatcgct cgcagtaacc gcgcatttgt gtttggtttc atcgctcagc   2280
aaaaagtcgg aaagccagag gaagactggg tcattatgac tcctggggtg ggcctggacg   2340
acaaaggtga tggattgggg cagcagtatc gtactgtgga cgacgtcata gagaccggca   2400
cagacgttat tatcgtcgga cgcgggctct atagcaaggg acgagatcct gtgcacgaag   2460
ctcagcgtta ccaaaaggcg ggctggaatg catatctgag aaaagttcag tcaagatgat   2520
tttctcaaac agttccttca atgcaacttg cacatgaata cctataaaat ctgattaaat   2580
taccataaaa ggtacagatt aaaatatata tgccttcaat ggcatccttc gcgattctga   2640
ttcgtcagca cacttcaacc ttcctactat gagtgacagt gatgatgatc tgctggcatt   2700
ggccgacgtt ggctccgact ccgaagagga aatctcgctg ccgtcgccgc caagcaatga   2760
ggtcgtcaat ccctatcctc tagaaggcaa atatctcgat gctgaagaca gggcgaagtt   2820
ggacgcgctg ccagagattg agcgagaaga gatcttgtat gaccgagctc aggagatgca   2880
gcggtacgag gagagaaggt atcttgctca gcgaaggaag cagatgacgc gggttgctga   2940
cgaggacgaa gccccctccg ccaagcgtca acggggtaca acaggcgtct cttcgggtac   3000
gaagtcatct cttgaggcat taaagaaacg aagggcccag cagtctcgga agtcctcacg   3060
ccatggagtt gatgacgatg tgtatagtga cgatgatgtt aattaataac ttcgtataat   3120
gtatgctata cgaagttatt aacctggctc tttttctaga tatgtctgcg ccctgctcac   3180
tgcttactgg cctaagctgg tattacggac cttaatcaag tatcacccca aggcaatcga   3240
gagtcttatc gagtctctag gtagatagat acacgttttg atttttcggc ccactttgta   3300
gaaaaatctc agtgatttca tggaattcag ttacaaatac taatctgata aaccaagaac   3360
tacactcggt gttgagagca gaattaaagg gacttggcgt ctagcacaaa acgatacttg   3420
acgtcaccac tgtgaacgcg cttccaagct tcggcgatat agctgtactc aatcagctca   3480
acatcacagg tgatgttatt ttcaccacag aagtccagca tctcctgagt ctctggcaag   3540
ccaccaatgt ttgagtaagt gatagattta tttccagcca aatgagaggt cagaaccttg   3600
aggggtccaa tttgaccaac aacaacgaga cacccaccaa tatcaaggga cttgaggtat   3660
ggctcgaagt cgtgttcaaa gggaatggtg tcgatgatca ggtcaaatgt gccagcgacc   3720
gcctcgagct cattcggatc agaggaagca actacgcggc tagcaccttg tgctttcgct   3780
cctgcggctt tggcgtgact cctgctgaac agtgtgactt cagagcccat ggctgaggca   3840
aatttgatag ccatggaacc aaggcctccg agaccaacta caccgactct ttttccaggt   3900
ccggcgccgt gagccctcag aggagagtag gtagtgatac cagcacagag aaggggcgca   3960
gaagctgcca agtcgaggtt ggaggggatt ttgagcacaa actcctcgcg agcaagaatg   4020
tgttgcgaat accctccctt cgtgacttcc ccgttctttc cgctggaatt gtaagtttga   4080
gtgcgtgaaa cacaccaatt ttctttgcct aatttacagt tcttgcaagt acgacatgag   4140
```

t 4141

<210> SEQ ID NO 17
<211> LENGTH: 27
<212> TYPE: DNA
<213> ORGANISM: Artificial
<220> FEATURE:
<223> OTHER INFORMATION: Primer

<400> SEQUENCE: 17
aattgttcga tggatagctt tggagtc 27

<210> SEQ ID NO 18
<211> LENGTH: 21
<212> TYPE: DNA
<213> ORGANISM: Artificial
<220> FEATURE:
<223> OTHER INFORMATION: Primer

<400> SEQUENCE: 18
ttcggggctc ctgtcgttgt c 21

<210> SEQ ID NO 19
<211> LENGTH: 26
<212> TYPE: DNA
<213> ORGANISM: Artificial
<220> FEATURE:
<223> OTHER INFORMATION: Primer

<400> SEQUENCE: 19
gaaatctgat caattctgca aacctg 26

<210> SEQ ID NO 20
<211> LENGTH: 27
<212> TYPE: DNA
<213> ORGANISM: Artificial
<220> FEATURE:
<223> OTHER INFORMATION: Primer

<400> SEQUENCE: 20
atgactccta gaaaagaaat tgaccag 27

<210> SEQ ID NO 21
<211> LENGTH: 22
<212> TYPE: DNA
<213> ORGANISM: Artificial
<220> FEATURE:
<223> OTHER INFORMATION: Primer

<400> SEQUENCE: 21
tgcagacaag ttcctgcagc tg 22

<210> SEQ ID NO 22
<211> LENGTH: 23
<212> TYPE: DNA
<213> ORGANISM: Artificial
<220> FEATURE:
<223> OTHER INFORMATION: Primer

<400> SEQUENCE: 22
atgctttatt caggcacgct acg 23

<210> SEQ ID NO 23
<211> LENGTH: 21
<212> TYPE: DNA
<213> ORGANISM: Artificial

<220> FEATURE:
<223> OTHER INFORMATION: Primer

<400> SEQUENCE: 23
ggatgagtcg cagtcacgaa c 21

<210> SEQ ID NO 24
<211> LENGTH: 26
<212> TYPE: DNA
<213> ORGANISM: Artificial
<220> FEATURE:
<223> OTHER INFORMATION: Primer

<400> SEQUENCE: 24
tcaatcattg gctcaagact aggaac 26

<210> SEQ ID NO 25
<211> LENGTH: 22
<212> TYPE: DNA
<213> ORGANISM: Artificial
<220> FEATURE:
<223> OTHER INFORMATION: Primer

<400> SEQUENCE: 25
attctggtgc tgacctcgcc ac 22

<210> SEQ ID NO 26
<211> LENGTH: 25
<212> TYPE: DNA
<213> ORGANISM: Artificial
<220> FEATURE:
<223> OTHER INFORMATION: Primer

<400> SEQUENCE: 26
actcatgtcg tacttgcaag aactg 25

<210> SEQ ID NO 27
<211> LENGTH: 27
<212> TYPE: DNA
<213> ORGANISM: Artificial
<220> FEATURE:
<223> OTHER INFORMATION: Primer

<400> SEQUENCE: 27
gtgtcgactc gccaaattcc atcggag 27

<210> SEQ ID NO 28
<211> LENGTH: 28
<212> TYPE: DNA
<213> ORGANISM: Artificial
<220> FEATURE:
<223> OTHER INFORMATION: Primer

<400> SEQUENCE: 28
ggttcatagc gagtttcttt gcatgtgc 28

<210> SEQ ID NO 29
<211> LENGTH: 28
<212> TYPE: DNA
<213> ORGANISM: Artificial
<220> FEATURE:
<223> OTHER INFORMATION: Primer

<400> SEQUENCE: 29
ctcctttatt aactccgcag catgactg 28

<210> SEQ ID NO 30
<211> LENGTH: 27
<212> TYPE: DNA
<213> ORGANISM: Artificial
<220> FEATURE:
<223> OTHER INFORMATION: Primer

<400> SEQUENCE: 30
ctcctcgaag gaccctcaaa acaaagg 27

<210> SEQ ID NO 31
<211> LENGTH: 30
<212> TYPE: DNA
<213> ORGANISM: Artificial
<220> FEATURE:
<223> OTHER INFORMATION: Primer

<400> SEQUENCE: 31
caaatttatc tgggagcaca gttacattgc 30

<210> SEQ ID NO 32
<211> LENGTH: 28
<212> TYPE: DNA
<213> ORGANISM: Artificial
<220> FEATURE:
<223> OTHER INFORMATION: Primer

<400> SEQUENCE: 32
cacacattgc tttagtccag caagaacc 28

<210> SEQ ID NO 33
<211> LENGTH: 25
<212> TYPE: DNA
<213> ORGANISM: Artificial
<220> FEATURE:
<223> OTHER INFORMATION: Primer

<400> SEQUENCE: 33
attctcctcg cacgtttctc ggggc 25

<210> SEQ ID NO 34
<211> LENGTH: 28
<212> TYPE: DNA
<213> ORGANISM: Artificial
<220> FEATURE:
<223> OTHER INFORMATION: Primer

<400> SEQUENCE: 34
ggttgaaata cttgttgccg cactaaag 28

<210> SEQ ID NO 35
<211> LENGTH: 31
<212> TYPE: DNA
<213> ORGANISM: Artificial
<220> FEATURE:
<223> OTHER INFORMATION: Primer

<400> SEQUENCE: 35
cgcttcctga attgagttgg tatcgttaat g 31

<210> SEQ ID NO 36
<211> LENGTH: 28
<212> TYPE: DNA
<213> ORGANISM: Artificial
<220> FEATURE:
<223> OTHER INFORMATION: Primer

<400> SEQUENCE: 36
gacattgttg gaattggctg cttagtgg 28

<210> SEQ ID NO 37
<211> LENGTH: 3107
<212> TYPE: DNA
<213> ORGANISM: Artificial
<220> FEATURE:
<223> OTHER INFORMATION: ExpressionCassette

<400> SEQUENCE: 37
acaaacgacc ccgccccacc cctcacacgg ccttaccagc ccaggaagca atggcccgaa 60
cctcgtgggc taccgcactc cgtttggaaa cccaatagga actgcagcag cagggaactc 120
agctgctact ccagctggaa accctctagg gaaggtaaga gcagactctt caacgagcct 180
tactactcag ggacagcgaa gggtccgcgt gcatgtccag ggcgacacat ttctcatttt 240
ggtgccaccg gacctgaagt ttgagcatct ttccaatcgt gttgagcgca agctccgact 300
atgtgggaaa atgccgcctt caggccaggc aggctcactc atttttgaat acatggatga 360
agacgaggac cgcgtgcgac tggagagcga cgaggaccta agtgtggcgt ttgaggctgt 420
gcccgaccac catgagctgt ccgtctacgt caaaaactga cgattatgat ctaatgatat 480
ttaaaagata tgtaaaacgg ttattttttg gacctgcgcc ctaaaatggg actttgtcaa 540
aaaaagaacg gcctcctgcg cgatggagag caatcaagaa ttcggagttc cgatgcgaat 600
ccatcaagaa aacggcccct aggcaatcta aaaccgtggc cgacatacta taagtcaatt 660
ccgctgtaca aataacaagc gatcaatcca taatctgagg ctcatttcat acggactttt 720
ctaagttcac ataattctat gatgcatact aacaaatacg atgcacaaat gggtacaagg 780
cctaaagagg gccacaatcg cgatttactc gatacggcaa atcagttcca caagtaattc 840
gctatcgtcg gtgttgttat acacctctcg gcttgagtca atatcgagca tgcaaggttg 900
acgcattctg ggaaatgta tccacgtgat cgccgatatc ggagcggata cgctgtgtag 960
tcttcagttg taagatttct tatacagcga cgcaaccatc atgtctgtgc aaacgaaaac 1020
aattgttctt cttcctggag accactgtgg cccagaagtc gttgccgaag cagtgaaagt 1080
actcaaagcc gtggaaactg ctttaccatc ggttaccttc gagtttcagc accatttgat 1140
tggcggtgct gccatagatg ctgctggtgt tcccattacg gaagagactc ttgctgcctc 1200
tagaaaggct gacgctgttt tgcttggtgc tgtaggaggg cccaagtggg gcactggctc 1260
agtgagaccc gaacagggtc tcctcaagat tcgcaaggag cttcaattgt acgcgaatct 1320
gcgtccctgt aacatcattg ctccaaagtt tgccaagctc agtcctctga aggaggagaa 1380
tgttttggga accgacatta tgattgtacg agaactcaca ggtggaatct acttcggaga 1440
tcgcgaagaa gccgatatga gcacggccga ccctcatgcc acagatactg agaagtacag 1500
cgttagtgaa attacgcgca tcgctcgtat ggcaggcttt ttggctctgc aggcccaacc 1560
tccgctacct gtttggagct tggacaaggc caatgtgctt gcttccagcc gtttgtggcg 1620
cgaaaccgtc accaaggtgt tcaaagagga attccctcag ctcaaattgg agcatcagct 1680
cattgattcg gcggccatga ttttggtgaa gaaccctcga cagctcaatg gtgtcgttat 1740
caccaccaac atgttcggag acattttcag cgacgaggcg agtgttattc ctggctctct 1800
gggtctgcta ccctcagctt cgctcagtgg actgcctgac acaaactctg cctttggtct 1860
gtacgagcct tgtcacggct ctgctcccga cctcgctgct aacaaggcaa atccagtcgc 1920

```
taccattctc agcgcagcaa tgatgcttcg tctttcacta ggtcttcctg aagctgctga   1980

tgctgttgag aaagctgttt ccaacgtttt gaactcagtc gcggccacgg cagacattgg   2040

tggaacagcc tccaccacag aggtaggcga tgcaattgcc gcagagacgt tgaagcttct   2100

caaatagtct gctataaatt gacggagttt cgtacagtgc gctcgtacag tgcgctgcca   2160

aatacaattt agtgtagcca gattggatgg ttgaattgct cttcacggtt gcacgctatt   2220

ggcaaaaaag agagagccgc tctgaactgg ttcatccgca gctgaccttc gaaactcttt   2280

aatatttaat aatattgcag caaaatctat agcttatgcc acatctatac ggaagaggta   2340

ttcaacatta gagcttgtgt cgcccattct ctacacgagc ccacgcatca gcagtgaggg   2400

gcttgtagct cgtgccctct aaccagtaga ttgtttgtcc tgctggggcg ggaatctgct   2460

ggtttcggaa ttctttcttc tgaactttgt tgttgccggt gatggtgacg gtgtcgacga   2520

acttaatgaa tatcggcacg gcatagcgtg gcagcctttc caaaagatgc ttgccgagtt   2580

tatccatatc cagctgtttt ctaggattgt tgagcttgat cacagcaaat ccggcacgac   2640

cctcatgctt gggaacctgc acacctacac agacacacag atcgactcca ccgaagtcca   2700

caactgcttc ctcgacttcg tttgtgctaa cgttctcgct cttccatcga aacgtatccc   2760

cgagtcgatc aacaaagtag acgctatgat ctttatcagc cctcagaagg tctccgctgc   2820

gcacccaggc atctcccttc ttgaaaacat caaacacaag cttctcatcc gtggctgatt   2880

ggttgccgac atagccctgg aaatcgagtt tgatattctt cgggtcgagt ttgaaaagga   2940

attcacccgg ctcgtccgag tgtgtctcac ggcacaggcc ggttttggga tcgcgccata   3000

aatcctgcgt gtcaacatca atcgcggcga tgttccacct ggtacgatgc agcacgcggg   3060

tggccacagt accataatgg ccacatgcac caacaccata tgcacct                 3107
```

```
<210> SEQ ID NO 38
<211> LENGTH: 45
<212> TYPE: DNA
<213> ORGANISM: Artificial
<220> FEATURE:
<223> OTHER INFORMATION: Primer

<400> SEQUENCE: 38

atatatatac atatgttaat caaagacatt attctaactc caatg                    45


<210> SEQ ID NO 39
<211> LENGTH: 42
<212> TYPE: DNA
<213> ORGANISM: Artificial
<220> FEATURE:
<223> OTHER INFORMATION: Primer

<400> SEQUENCE: 39

atatatggcc ggccaactta agaaaaccgc acaaccacac cg                       42


<210> SEQ ID NO 40
<211> LENGTH: 39
<212> TYPE: DNA
<213> ORGANISM: Artificial
<220> FEATURE:
<223> OTHER INFORMATION: Primer

<400> SEQUENCE: 40

atatatatac atatgagccc ttcatcacac aaaccccctg                          39


<210> SEQ ID NO 41
<211> LENGTH: 39
```

<212> TYPE: DNA
<213> ORGANISM: Artificial
<220> FEATURE:
<223> OTHER INFORMATION: Primer

<400> SEQUENCE: 41
atatatggcc ggccattcta agaactcacc gctaaggcc 39

<210> SEQ ID NO 42
<211> LENGTH: 38
<212> TYPE: DNA
<213> ORGANISM: Artificial
<220> FEATURE:
<223> OTHER INFORMATION: Primer

<400> SEQUENCE: 42
atatatatac atatggttgt aaactcctcg aaggaccc 38

<210> SEQ ID NO 43
<211> LENGTH: 42
<212> TYPE: DNA
<213> ORGANISM: Artificial
<220> FEATURE:
<223> OTHER INFORMATION: Primer

<400> SEQUENCE: 43
atatatggcc ggcctaccta gaccttctgg ttagcggtat tg 42

<210> SEQ ID NO 44
<211> LENGTH: 40
<212> TYPE: DNA
<213> ORGANISM: Artificial
<220> FEATURE:
<223> OTHER INFORMATION: Primer

<400> SEQUENCE: 44
atatatatac atatggtgga tgatatacag gtagagaagc 40

<210> SEQ ID NO 45
<211> LENGTH: 42
<212> TYPE: DNA
<213> ORGANISM: Artificial
<220> FEATURE:
<223> OTHER INFORMATION: Primer

<400> SEQUENCE: 45
atatatggcc ggccacgtca aatctctccg agaccttgca ag 42

<210> SEQ ID NO 46
<211> LENGTH: 40
<212> TYPE: DNA
<213> ORGANISM: Artificial
<220> FEATURE:
<223> OTHER INFORMATION: Primer

<400> SEQUENCE: 46
atatatatac atatggccat cgagaaacca gtgatagttg 40

<210> SEQ ID NO 47
<211> LENGTH: 45
<212> TYPE: DNA
<213> ORGANISM: Artificial
<220> FEATURE:
<223> OTHER INFORMATION: Primer

<400> SEQUENCE: 47
atatatggcc ggccaggtta agaagctaat tcactaattg ccgac 45

<210> SEQ ID NO 48
<211> LENGTH: 23
<212> TYPE: DNA
<213> ORGANISM: Artificial
<220> FEATURE:
<223> OTHER INFORMATION: Primer

<400> SEQUENCE: 48
ggacctgcgc cctaaaatgg gac 23

<210> SEQ ID NO 49
<211> LENGTH: 30
<212> TYPE: DNA
<213> ORGANISM: Artificial
<220> FEATURE:
<223> OTHER INFORMATION: Primer

<400> SEQUENCE: 49
atcctagaaa acagctggat atggataaac 30

<210> SEQ ID NO 50
<211> LENGTH: 23
<212> TYPE: DNA
<213> ORGANISM: Artificial
<220> FEATURE:
<223> OTHER INFORMATION: Primer

<400> SEQUENCE: 50
gtgcccgacc accatgagct gtc 23

<210> SEQ ID NO 51
<211> LENGTH: 23
<212> TYPE: DNA
<213> ORGANISM: Artificial
<220> FEATURE:
<223> OTHER INFORMATION: Primer

<400> SEQUENCE: 51
cccaagcatg agggtcgtgc cgg 23

<210> SEQ ID NO 52
<211> LENGTH: 1572
<212> TYPE: DNA
<213> ORGANISM: Candida bombicola
<220> FEATURE:
<221> NAME/KEY: CDS
<222> LOCATION: (1)..(1572)

<400> SEQUENCE: 52

```
atg att ctt tat gct gtg ctg ggc gca ttc gcc gcc ttc ttg ctt tac       48
Met Ile Leu Tyr Ala Val Leu Gly Ala Phe Ala Ala Phe Leu Leu Tyr
1               5                   10                  15

atg gat gta ctt tac cct ttc gtg att tac cct ctg aga gcg cga tgg       96
Met Asp Val Leu Tyr Pro Phe Val Ile Tyr Pro Leu Arg Ala Arg Trp
            20                  25                  30

cac aaa tgt ggt tac atc cct aga gat ttg agc tgg cca ttg ggg att      144
His Lys Cys Gly Tyr Ile Pro Arg Asp Leu Ser Trp Pro Leu Gly Ile
        35                  40                  45

cca ctc acc ctg gta gtt ctc tcg aag ttg agg aaa gat atg ctg ctg      192
Pro Leu Thr Leu Val Val Leu Ser Lys Leu Arg Lys Asp Met Leu Leu
    50                  55                  60

caa ttc atg gca gcg caa gac ctt agt cgc cct tac aag aca tcc tta      240
Gln Phe Met Ala Ala Gln Asp Leu Ser Arg Pro Tyr Lys Thr Ser Leu
```

```
65                  70                  75                  80

cgt caa ttt ctg ggt aaa tgg gta atc gcc act aga gat cct gag aac      288
Arg Gln Phe Leu Gly Lys Trp Val Ile Ala Thr Arg Asp Pro Glu Asn
                85                  90                  95

atc aag gct gtt cta tcc acc aag ttc aat gac ttc tcg ctg aaa gaa      336
Ile Lys Ala Val Leu Ser Thr Lys Phe Asn Asp Phe Ser Leu Lys Glu
            100                 105                 110

aga ggg aat agg atg agg cat gta atc ggt gat gga att ttt acc caa      384
Arg Gly Asn Arg Met Arg His Val Ile Gly Asp Gly Ile Phe Thr Gln
        115                 120                 125

gat ggc gca cca tgg aag cac tcg cga gat atg ctc agg cct cag ttc      432
Asp Gly Ala Pro Trp Lys His Ser Arg Asp Met Leu Arg Pro Gln Phe
    130                 135                 140

acc aag gat caa atc agc cga gtg gaa ttg ttg agc cac cac atc gac      480
Thr Lys Asp Gln Ile Ser Arg Val Glu Leu Leu Ser His His Ile Asp
145                 150                 155                 160

gtt ttg att cgt gaa atc agg aag tcg gga ggt aac gtc gag ttg caa      528
Val Leu Ile Arg Glu Ile Arg Lys Ser Gly Gly Asn Val Glu Leu Gln
                165                 170                 175

cgt tta ttc cac ctc atg act atg gac acc gcc act cac ttt cta ttc      576
Arg Leu Phe His Leu Met Thr Met Asp Thr Ala Thr His Phe Leu Phe
            180                 185                 190

ggc gag tcc gtt ggc tcg ttg gag gtc agt ggc gaa agc aag ggc att      624
Gly Glu Ser Val Gly Ser Leu Glu Val Ser Gly Glu Ser Lys Gly Ile
        195                 200                 205

gag atc acc gac cca aag act gga gag att gtg aac acc gtt gat ttt      672
Glu Ile Thr Asp Pro Lys Thr Gly Glu Ile Val Asn Thr Val Asp Phe
    210                 215                 220

gtt gag tct tat act ttt gca aac aag ttt gct ctc aag aag att atc      720
Val Glu Ser Tyr Thr Phe Ala Asn Lys Phe Ala Leu Lys Lys Ile Ile
225                 230                 235                 240

ctc aac gac ttg gag ttt tta gcc gac ttg acg gag ccc tcg tat aag      768
Leu Asn Asp Leu Glu Phe Leu Ala Asp Leu Thr Glu Pro Ser Tyr Lys
                245                 250                 255

tgg cat ctg cgc cgt gtc cac aca gtc atg gat cac tac gtt cag ctg      816
Trp His Leu Arg Arg Val His Thr Val Met Asp His Tyr Val Gln Leu
            260                 265                 270

gct ttg aag gct act gag aag tat gat cct gat gat gat agc gag aag      864
Ala Leu Lys Ala Thr Glu Lys Tyr Asp Pro Asp Asp Asp Ser Glu Lys
        275                 280                 285

gga gaa tac tac ttt agc cat gag ctg gcg aaa ctc acg aga gac ccc      912
Gly Glu Tyr Tyr Phe Ser His Glu Leu Ala Lys Leu Thr Arg Asp Pro
    290                 295                 300

ttg tcg ttg aga gat cag ctt ttc aat att ctc att gct ggc cgc gac      960
Leu Ser Leu Arg Asp Gln Leu Phe Asn Ile Leu Ile Ala Gly Arg Asp
305                 310                 315                 320

act acc gca gca act ttg tcc tat gcc ttc cac tat cta acg aag aat     1008
Thr Thr Ala Ala Thr Leu Ser Tyr Ala Phe His Tyr Leu Thr Lys Asn
                325                 330                 335

ccc gct atc tac gcc aag gtc cgc gaa gat gtg ctc acg gtc ttc cct     1056
Pro Ala Ile Tyr Ala Lys Val Arg Glu Asp Val Leu Thr Val Phe Pro
            340                 345                 350

aat gga gac gca tca ttg gcg act tac gag gac ttg cga aag gct aag     1104
Asn Gly Asp Ala Ser Leu Ala Thr Tyr Glu Asp Leu Arg Lys Ala Lys
        355                 360                 365

tat ctc caa atg gtg atc aag gag gta ttg cgt ctt gcg cct gcg gtt     1152
Tyr Leu Gln Met Val Ile Lys Glu Val Leu Arg Leu Ala Pro Ala Val
    370                 375                 380

ccc ttg aac acg cgt gcc gcg gtt cgt gac aca tat ctg cca cgg ggc     1200
```

-continued

```
Pro Leu Asn Thr Arg Ala Ala Val Arg Asp Thr Tyr Leu Pro Arg Gly
385                 390                 395                 400

gga ggc cca gcc gga aac ctg ccc gtt ttt gtt ccc aag ggc act gct     1248
Gly Gly Pro Ala Gly Asn Leu Pro Val Phe Val Pro Lys Gly Thr Ala
                405                 410                 415

gtc aac tac cct aca tat att ttg cac cgc gat cca gat atc tat ggt     1296
Val Asn Tyr Pro Thr Tyr Ile Leu His Arg Asp Pro Asp Ile Tyr Gly
            420                 425                 430

gcc gac gcg tac gag ttc aac ccc gag aga tgg agg cct gag aat aag     1344
Ala Asp Ala Tyr Glu Phe Asn Pro Glu Arg Trp Arg Pro Glu Asn Lys
        435                 440                 445

ctt ccg aat agc cca atg tac tct tgg gga tac att ccc ttc aat ggt     1392
Leu Pro Asn Ser Pro Met Tyr Ser Trp Gly Tyr Ile Pro Phe Asn Gly
    450                 455                 460

ggc cct cgc atc tgc att gga cag cag ttc gcc ttg act gag atc gct     1440
Gly Pro Arg Ile Cys Ile Gly Gln Gln Phe Ala Leu Thr Glu Ile Ala
465                 470                 475                 480

ttg acg atg atc aag ctg gtt ctg gaa ttt gag agg ctg gag cct gcc     1488
Leu Thr Met Ile Lys Leu Val Leu Glu Phe Glu Arg Leu Glu Pro Ala
                485                 490                 495

gac gac ttt gag ccc aat ctt caa gac aag tcc tct tta act gtc atg     1536
Asp Asp Phe Glu Pro Asn Leu Gln Asp Lys Ser Ser Leu Thr Val Met
            500                 505                 510

gtc gga ggg tcg ggc gtc cga gtg aaa ctg agt taa                     1572
Val Gly Gly Ser Gly Val Arg Val Lys Leu Ser
        515                 520


<210> SEQ ID NO 53
<211> LENGTH: 523
<212> TYPE: PRT
<213> ORGANISM: Candida bombicola

<400> SEQUENCE: 53

Met Ile Leu Tyr Ala Val Leu Gly Ala Phe Ala Ala Phe Leu Leu Tyr
1               5                   10                  15

Met Asp Val Leu Tyr Pro Phe Val Ile Tyr Pro Leu Arg Ala Arg Trp
            20                  25                  30

His Lys Cys Gly Tyr Ile Pro Arg Asp Leu Ser Trp Pro Leu Gly Ile
        35                  40                  45

Pro Leu Thr Leu Val Val Leu Ser Lys Leu Arg Lys Asp Met Leu Leu
    50                  55                  60

Gln Phe Met Ala Ala Gln Asp Leu Ser Arg Pro Tyr Lys Thr Ser Leu
65                  70                  75                  80

Arg Gln Phe Leu Gly Lys Trp Val Ile Ala Thr Arg Asp Pro Glu Asn
                85                  90                  95

Ile Lys Ala Val Leu Ser Thr Lys Phe Asn Asp Phe Ser Leu Lys Glu
            100                 105                 110

Arg Gly Asn Arg Met Arg His Val Ile Gly Asp Gly Ile Phe Thr Gln
        115                 120                 125

Asp Gly Ala Pro Trp Lys His Ser Arg Asp Met Leu Arg Pro Gln Phe
    130                 135                 140

Thr Lys Asp Gln Ile Ser Arg Val Glu Leu Leu Ser His His Ile Asp
145                 150                 155                 160

Val Leu Ile Arg Glu Ile Arg Lys Ser Gly Gly Asn Val Glu Leu Gln
                165                 170                 175

Arg Leu Phe His Leu Met Thr Met Asp Thr Ala Thr His Phe Leu Phe
            180                 185                 190
```

```
Gly Glu Ser Val Gly Ser Leu Glu Val Ser Gly Glu Ser Lys Gly Ile
        195                 200                 205

Glu Ile Thr Asp Pro Lys Thr Gly Glu Ile Val Asn Thr Val Asp Phe
    210                 215                 220

Val Glu Ser Tyr Thr Phe Ala Asn Lys Phe Ala Leu Lys Lys Ile Ile
225                 230                 235                 240

Leu Asn Asp Leu Glu Phe Leu Ala Asp Leu Thr Glu Pro Ser Tyr Lys
                245                 250                 255

Trp His Leu Arg Arg Val His Thr Val Met Asp His Tyr Val Gln Leu
            260                 265                 270

Ala Leu Lys Ala Thr Glu Lys Tyr Asp Pro Asp Asp Asp Ser Glu Lys
        275                 280                 285

Gly Glu Tyr Tyr Phe Ser His Glu Leu Ala Lys Leu Thr Arg Asp Pro
    290                 295                 300

Leu Ser Leu Arg Asp Gln Leu Phe Asn Ile Leu Ile Ala Gly Arg Asp
305                 310                 315                 320

Thr Thr Ala Ala Thr Leu Ser Tyr Ala Phe His Tyr Leu Thr Lys Asn
                325                 330                 335

Pro Ala Ile Tyr Ala Lys Val Arg Glu Asp Val Leu Thr Val Phe Pro
            340                 345                 350

Asn Gly Asp Ala Ser Leu Ala Thr Tyr Glu Asp Leu Arg Lys Ala Lys
        355                 360                 365

Tyr Leu Gln Met Val Ile Lys Glu Val Leu Arg Leu Ala Pro Ala Val
    370                 375                 380

Pro Leu Asn Thr Arg Ala Ala Val Arg Asp Thr Tyr Leu Pro Arg Gly
385                 390                 395                 400

Gly Gly Pro Ala Gly Asn Leu Pro Val Phe Val Pro Lys Gly Thr Ala
                405                 410                 415

Val Asn Tyr Pro Thr Tyr Ile Leu His Arg Asp Pro Asp Ile Tyr Gly
            420                 425                 430

Ala Asp Ala Tyr Glu Phe Asn Pro Glu Arg Trp Arg Pro Glu Asn Lys
        435                 440                 445

Leu Pro Asn Ser Pro Met Tyr Ser Trp Gly Tyr Ile Pro Phe Asn Gly
    450                 455                 460

Gly Pro Arg Ile Cys Ile Gly Gln Gln Phe Ala Leu Thr Glu Ile Ala
465                 470                 475                 480

Leu Thr Met Ile Lys Leu Val Leu Glu Phe Glu Arg Leu Glu Pro Ala
                485                 490                 495

Asp Asp Phe Glu Pro Asn Leu Gln Asp Lys Ser Ser Leu Thr Val Met
            500                 505                 510

Val Gly Gly Ser Gly Val Arg Val Lys Leu Ser
        515                 520


<210> SEQ ID NO 54
<211> LENGTH: 1671
<212> TYPE: DNA
<213> ORGANISM: Candida bombicola
<220> FEATURE:
<221> NAME/KEY: CDS
<222> LOCATION: (1)..(1671)

<400> SEQUENCE: 54

atg agg ccc ctg ttg cgg gaa caa gac aca tca cac cca gag cta ttg       48
Met Arg Pro Leu Leu Arg Glu Gln Asp Thr Ser His Pro Glu Leu Leu
1               5                   10                  15

ttg gca agc aat act att ttt aac ccc ctt tcc aag agt gtc caa act       96
```

-continued

```
Leu Ala Ser Asn Thr Ile Phe Asn Pro Leu Ser Lys Ser Val Gln Thr
            20                  25                  30

gtt caa tac ggc ctc atg aac att aat ttc tct gac gtg ctc gtg cta         144
Val Gln Tyr Gly Leu Met Asn Ile Asn Phe Ser Asp Val Leu Val Leu
        35                  40                  45

gga ggc atc agc gtg agc ttt ttg ctc gcc tac cag gcg att tac ttt         192
Gly Gly Ile Ser Val Ser Phe Leu Leu Ala Tyr Gln Ala Ile Tyr Phe
    50                  55                  60

tat ttc att tac tcg cca cga gcc aaa aag ctc ggt tgc gct ctt cca         240
Tyr Phe Ile Tyr Ser Pro Arg Ala Lys Lys Leu Gly Cys Ala Leu Pro
65                  70                  75                  80

ccg gtc ttc ttc tct ttc cca ctc gga ata ccg gag gtc ata cgt ctt         288
Pro Val Phe Phe Ser Phe Pro Leu Gly Ile Pro Glu Val Ile Arg Leu
                85                  90                  95

gtg aac gcc tgg ttc aac gat gat ctc ctt gag tat ttc acc ttc aaa         336
Val Asn Ala Trp Phe Asn Asp Asp Leu Leu Glu Tyr Phe Thr Phe Lys
            100                 105                 110

ttc gag gag ttc cag cgc aaa acc gga ttc caa tca gtc gct ggg caa         384
Phe Glu Glu Phe Gln Arg Lys Thr Gly Phe Gln Ser Val Ala Gly Gln
        115                 120                 125

cta tgg att ggg act att gag ccc gag aac atc aag act atg ctc gct         432
Leu Trp Ile Gly Thr Ile Glu Pro Glu Asn Ile Lys Thr Met Leu Ala
    130                 135                 140

act tca ttt aaa gac tac tcc cta ggc ttc cgt tac gag gcc atg tac         480
Thr Ser Phe Lys Asp Tyr Ser Leu Gly Phe Arg Tyr Glu Ala Met Tyr
145                 150                 155                 160

ggc ctt ctc gga aat ggc att ttc act ctc agt ggt gag ggc tgg aag         528
Gly Leu Leu Gly Asn Gly Ile Phe Thr Leu Ser Gly Glu Gly Trp Lys
                165                 170                 175

cac agc cgc gct ttg ttg cgt ccg caa ttt agt cgt gag caa gtc tct         576
His Ser Arg Ala Leu Leu Arg Pro Gln Phe Ser Arg Glu Gln Val Ser
            180                 185                 190

cac ctt gaa tca atg cgc aca cac atc aat atg ttg atc aac aac cac         624
His Leu Glu Ser Met Arg Thr His Ile Asn Met Leu Ile Asn Asn His
        195                 200                 205

ttc aag ggt ggc aaa gtc gtc gat gct cag gtt ttg ttc cac aat cta         672
Phe Lys Gly Gly Lys Val Val Asp Ala Gln Val Leu Phe His Asn Leu
    210                 215                 220

acc att gat act gct acc gaa ttc cta ttc gga gag agc acc aac act         720
Thr Ile Asp Thr Ala Thr Glu Phe Leu Phe Gly Glu Ser Thr Asn Thr
225                 230                 235                 240

ctt gac cct gct ctt gct cag cat gga ttc cct gga cct aag ggt ctt         768
Leu Asp Pro Ala Leu Ala Gln His Gly Phe Pro Gly Pro Lys Gly Leu
                245                 250                 255

gta acc ggt gag cag ttt gct gag gct ttt acc tct gct ctc gaa ttg         816
Val Thr Gly Glu Gln Phe Ala Glu Ala Phe Thr Ser Ala Leu Glu Leu
            260                 265                 270

ctt tct gtg cga gtt atg gcc ggc gcc gca tgg ttc ctc gtt tgg acc         864
Leu Ser Val Arg Val Met Ala Gly Ala Ala Trp Phe Leu Val Trp Thr
        275                 280                 285

ccc aaa ttc tgg cgc tca tgc aaa gtc tgc cac aac ttc att gat tac         912
Pro Lys Phe Trp Arg Ser Cys Lys Val Cys His Asn Phe Ile Asp Tyr
    290                 295                 300

ttc gtt ttc aag gct ctg gcc act cct atg gag aag gac cag gaa gct         960
Phe Val Phe Lys Ala Leu Ala Thr Pro Met Glu Lys Asp Gln Glu Ala
305                 310                 315                 320

gat cgc tac gtc ttt att cga gaa ctc aca aag gag acc tct gac cca        1008
Asp Arg Tyr Val Phe Ile Arg Glu Leu Thr Lys Glu Thr Ser Asp Pro
                325                 330                 335
```

```
cgg gtc atc cgc gac cag gcc ctc aac atc ctc ttg gct ggt cgt gat      1056
Arg Val Ile Arg Asp Gln Ala Leu Asn Ile Leu Leu Ala Gly Arg Asp
            340                 345                 350

acc act gcg gca ctt ctc agc ttc acc acc tac tac ctt ggt gcc tac      1104
Thr Thr Ala Ala Leu Leu Ser Phe Thr Thr Tyr Tyr Leu Gly Ala Tyr
        355                 360                 365

cct gag gtc tac gat gag ctt cgc gag gct gtt att gcg gac ttc ggc      1152
Pro Glu Val Tyr Asp Glu Leu Arg Glu Ala Val Ile Ala Asp Phe Gly
    370                 375                 380

aag gaa gat gct gag ccc cct acg ttt gag cag ctt aag cag tgc aag      1200
Lys Glu Asp Ala Glu Pro Pro Thr Phe Glu Gln Leu Lys Gln Cys Lys
385                 390                 395                 400

gtg cta cag aac gtc att cgg gaa gtt ttg cga ttg cac ccg aat gtg      1248
Val Leu Gln Asn Val Ile Arg Glu Val Leu Arg Leu His Pro Asn Val
                405                 410                 415

ccc ctc aac ttc cgc gag gcc att acc gat act aag ttc ccc aca gga      1296
Pro Leu Asn Phe Arg Glu Ala Ile Thr Asp Thr Lys Phe Pro Thr Gly
            420                 425                 430

ggc ggc ccg aat gga gac cag ccc gtt ttc gtt ccc aag gga cag aaa      1344
Gly Gly Pro Asn Gly Asp Gln Pro Val Phe Val Pro Lys Gly Gln Lys
        435                 440                 445

gtg ttt tac gcc acc tac gtc atg cag cga aat gag ggt ctc tgg ggt      1392
Val Phe Tyr Ala Thr Tyr Val Met Gln Arg Asn Glu Gly Leu Trp Gly
    450                 455                 460

cct gac tcc aca aca ttc cgc cct gac cgc tgg aac gag tca aga gag      1440
Pro Asp Ser Thr Thr Phe Arg Pro Asp Arg Trp Asn Glu Ser Arg Glu
465                 470                 475                 480

gcc atc gca tcc gga tgg gac tac att cct ttc aac ggc ggc cct cgt      1488
Ala Ile Ala Ser Gly Trp Asp Tyr Ile Pro Phe Asn Gly Gly Pro Arg
                485                 490                 495

att tgc ctg ggt cag cag ttc gct ctc aca gag gcg agc tac acg ctc      1536
Ile Cys Leu Gly Gln Gln Phe Ala Leu Thr Glu Ala Ser Tyr Thr Leu
            500                 505                 510

gtg cgt atc tgc caa gag ttc tcc agg att gag gtt ctc cac cct gat      1584
Val Arg Ile Cys Gln Glu Phe Ser Arg Ile Glu Val Leu His Pro Asp
        515                 520                 525

gtt att acc tcc agg aac gtg atg aaa cag cgc atg cgt ttg acc aac      1632
Val Ile Thr Ser Arg Asn Val Met Lys Gln Arg Met Arg Leu Thr Asn
    530                 535                 540

tct tcc agc ggc ggc gtc ata gcg aag ttc att cgc tag                  1671
Ser Ser Ser Gly Gly Val Ile Ala Lys Phe Ile Arg
545                 550                 555


<210> SEQ ID NO 55
<211> LENGTH: 556
<212> TYPE: PRT
<213> ORGANISM: Candida bombicola

<400> SEQUENCE: 55

Met Arg Pro Leu Leu Arg Glu Gln Asp Thr Ser His Pro Glu Leu Leu
1               5                   10                  15

Leu Ala Ser Asn Thr Ile Phe Asn Pro Leu Ser Lys Ser Val Gln Thr
            20                  25                  30

Val Gln Tyr Gly Leu Met Asn Ile Asn Phe Ser Asp Val Leu Val Leu
        35                  40                  45

Gly Gly Ile Ser Val Ser Phe Leu Leu Ala Tyr Gln Ala Ile Tyr Phe
    50                  55                  60

Tyr Phe Ile Tyr Ser Pro Arg Ala Lys Lys Leu Gly Cys Ala Leu Pro
65                  70                  75                  80
```

-continued

```
Pro Val Phe Phe Ser Phe Pro Leu Gly Ile Pro Glu Val Ile Arg Leu
                85                  90                  95

Val Asn Ala Trp Phe Asn Asp Asp Leu Leu Glu Tyr Phe Thr Phe Lys
            100                 105                 110

Phe Glu Glu Phe Gln Arg Lys Thr Gly Phe Gln Ser Val Ala Gly Gln
        115                 120                 125

Leu Trp Ile Gly Thr Ile Glu Pro Glu Asn Ile Lys Thr Met Leu Ala
    130                 135                 140

Thr Ser Phe Lys Asp Tyr Ser Leu Gly Phe Arg Tyr Glu Ala Met Tyr
145                 150                 155                 160

Gly Leu Leu Gly Asn Gly Ile Phe Thr Leu Ser Gly Glu Gly Trp Lys
                165                 170                 175

His Ser Arg Ala Leu Leu Arg Pro Gln Phe Ser Arg Glu Gln Val Ser
            180                 185                 190

His Leu Glu Ser Met Arg Thr His Ile Asn Met Leu Ile Asn Asn His
        195                 200                 205

Phe Lys Gly Gly Lys Val Val Asp Ala Gln Val Leu Phe His Asn Leu
    210                 215                 220

Thr Ile Asp Thr Ala Thr Glu Phe Leu Phe Gly Glu Ser Thr Asn Thr
225                 230                 235                 240

Leu Asp Pro Ala Leu Ala Gln His Gly Phe Pro Gly Pro Lys Gly Leu
                245                 250                 255

Val Thr Gly Glu Gln Phe Ala Glu Ala Phe Thr Ser Ala Leu Glu Leu
            260                 265                 270

Leu Ser Val Arg Val Met Ala Gly Ala Ala Trp Phe Leu Val Trp Thr
        275                 280                 285

Pro Lys Phe Trp Arg Ser Cys Lys Val Cys His Asn Phe Ile Asp Tyr
    290                 295                 300

Phe Val Phe Lys Ala Leu Ala Thr Pro Met Glu Lys Asp Gln Glu Ala
305                 310                 315                 320

Asp Arg Tyr Val Phe Ile Arg Glu Leu Thr Lys Glu Thr Ser Asp Pro
                325                 330                 335

Arg Val Ile Arg Asp Gln Ala Leu Asn Ile Leu Leu Ala Gly Arg Asp
            340                 345                 350

Thr Thr Ala Ala Leu Leu Ser Phe Thr Thr Tyr Tyr Leu Gly Ala Tyr
        355                 360                 365

Pro Glu Val Tyr Asp Glu Leu Arg Glu Ala Val Ile Ala Asp Phe Gly
    370                 375                 380

Lys Glu Asp Ala Glu Pro Pro Thr Phe Glu Gln Leu Lys Gln Cys Lys
385                 390                 395                 400

Val Leu Gln Asn Val Ile Arg Glu Val Leu Arg Leu His Pro Asn Val
                405                 410                 415

Pro Leu Asn Phe Arg Glu Ala Ile Thr Asp Thr Lys Phe Pro Thr Gly
            420                 425                 430

Gly Gly Pro Asn Gly Asp Gln Pro Val Phe Val Pro Lys Gly Gln Lys
        435                 440                 445

Val Phe Tyr Ala Thr Tyr Val Met Gln Arg Asn Glu Gly Leu Trp Gly
    450                 455                 460

Pro Asp Ser Thr Thr Phe Arg Pro Asp Arg Trp Asn Glu Ser Arg Glu
465                 470                 475                 480

Ala Ile Ala Ser Gly Trp Asp Tyr Ile Pro Phe Asn Gly Gly Pro Arg
                485                 490                 495

Ile Cys Leu Gly Gln Gln Phe Ala Leu Thr Glu Ala Ser Tyr Thr Leu
```

```
            500                 505                 510

Val Arg Ile Cys Gln Glu Phe Ser Arg Ile Glu Val Leu His Pro Asp
        515                 520                 525

Val Ile Thr Ser Arg Asn Val Met Lys Gln Arg Met Arg Leu Thr Asn
    530                 535                 540

Ser Ser Ser Gly Gly Val Ile Ala Lys Phe Ile Arg
545                 550                 555


<210> SEQ ID NO 56
<211> LENGTH: 1560
<212> TYPE: DNA
<213> ORGANISM: Candida bombicola
<220> FEATURE:
<221> NAME/KEY: CDS
<222> LOCATION: (1)..(1560)

<400> SEQUENCE: 56

atg att att gat ctt tca gac gcg ctg ata ata gga ggc atc gcc ctg       48
Met Ile Ile Asp Leu Ser Asp Ala Leu Ile Ile Gly Gly Ile Ala Leu
1               5                   10                  15

tgc ttc ttg ctc tcc tac cag gcg atc tac ttt tac ttt att tac tcg       96
Cys Phe Leu Leu Ser Tyr Gln Ala Ile Tyr Phe Tyr Phe Ile Tyr Ser
            20                  25                  30

cca cgg gcc aag aag ctt gga tgc gct cct cct ctc att gtg cac gct      144
Pro Arg Ala Lys Lys Leu Gly Cys Ala Pro Pro Leu Ile Val His Ala
        35                  40                  45

ttc cca ctg ggt ttg ccg aca att ttc gga ctt ata aga gct tgg cgc      192
Phe Pro Leu Gly Leu Pro Thr Ile Phe Gly Leu Ile Arg Ala Trp Arg
    50                  55                  60

aac gac gat ctt ctc cag tac ttg agc gac aac ttc gct aga atc agg      240
Asn Asp Asp Leu Leu Gln Tyr Leu Ser Asp Asn Phe Ala Arg Ile Arg
65                  70                  75                  80

acc aga acc gga atg caa gta atg gcc ggt cag ctg tgg ctc aac acc      288
Thr Arg Thr Gly Met Gln Val Met Ala Gly Gln Leu Trp Leu Asn Thr
                85                  90                  95

att gag cca gaa aac atc aag gcc atg ctt gcc act tcg ttc aag gat      336
Ile Glu Pro Glu Asn Ile Lys Ala Met Leu Ala Thr Ser Phe Lys Asp
            100                 105                 110

ttc tcg ctt ggg ttc cgc tat gaa gtc atg cat ggc ctc ctc gga gat      384
Phe Ser Leu Gly Phe Arg Tyr Glu Val Met His Gly Leu Leu Gly Asp
        115                 120                 125

ggt atc ttc act ctc agt ggt gag ggc tgg aaa cac agc cgt gcc ttg      432
Gly Ile Phe Thr Leu Ser Gly Glu Gly Trp Lys His Ser Arg Ala Leu
    130                 135                 140

cta cgt cca cag ttc agc cgt gag caa gtc tct cac ttg gac tca atg      480
Leu Arg Pro Gln Phe Ser Arg Glu Gln Val Ser His Leu Asp Ser Met
145                 150                 155                 160

cgc aca cac atc aat ttg atg atc aac aac cac ttc aaa ggt ggc cag      528
Arg Thr His Ile Asn Leu Met Ile Asn Asn His Phe Lys Gly Gly Gln
                165                 170                 175

gtc gtc gac gct cag gtt cta tac cat aac ctg aca atc gac act gcc      576
Val Val Asp Ala Gln Val Leu Tyr His Asn Leu Thr Ile Asp Thr Ala
            180                 185                 190

act gaa ttc ctg ttc ggt gag agc acc aac act ctt gac cct gtt ctt      624
Thr Glu Phe Leu Phe Gly Glu Ser Thr Asn Thr Leu Asp Pro Val Leu
        195                 200                 205

gca cag cag gga cta ccg ggt cct agg ggc gtt gtt act ggt gag cag      672
Ala Gln Gln Gly Leu Pro Gly Pro Arg Gly Val Val Thr Gly Glu Gln
    210                 215                 220

ttc gct aac gct ttc acc tac gct caa gag ttg ctc agt att cga gtc      720
```

```
Phe Ala Asn Ala Phe Thr Tyr Ala Gln Glu Leu Leu Ser Ile Arg Val
225                 230                 235                 240

atg gcc ggc tca gca tgg ttc ctc gtc tgg act cct aag ttc agg cgc      768
Met Ala Gly Ser Ala Trp Phe Leu Val Trp Thr Pro Lys Phe Arg Arg
                245                 250                 255

tcg tgc aag gtg tgc cac aac ttt att gac tac ttc gtc ttt aag gct      816
Ser Cys Lys Val Cys His Asn Phe Ile Asp Tyr Phe Val Phe Lys Ala
            260                 265                 270

ctg gcc act cct atg gag aaa gac cag gag gct gat cgc tat gta ttc      864
Leu Ala Thr Pro Met Glu Lys Asp Gln Glu Ala Asp Arg Tyr Val Phe
        275                 280                 285

atc cga gaa ctc act aag gag act tct gac cca aag gtt ata cgt gac      912
Ile Arg Glu Leu Thr Lys Glu Thr Ser Asp Pro Lys Val Ile Arg Asp
    290                 295                 300

cag gct ctc aac atc ctt tta gct ggc cgc gat acc act gca gca ctc      960
Gln Ala Leu Asn Ile Leu Leu Ala Gly Arg Asp Thr Thr Ala Ala Leu
305                 310                 315                 320

ctc agc ttc acc act tac tac ctt ggc gca tat cct gag gtc tac gac     1008
Leu Ser Phe Thr Thr Tyr Tyr Leu Gly Ala Tyr Pro Glu Val Tyr Asp
                325                 330                 335

gag ctt cgc gag gca gtt ctt gca gac ttc ggc cct gcc gat tct gag     1056
Glu Leu Arg Glu Ala Val Leu Ala Asp Phe Gly Pro Ala Asp Ser Glu
            340                 345                 350

ccc cct acc ttt gag agg ctc aag cag tgc aag gtg ttg cag aat gtc     1104
Pro Pro Thr Phe Glu Arg Leu Lys Gln Cys Lys Val Leu Gln Asn Val
        355                 360                 365

atc cgc gag gtt ctg cga ttg cac ccg aat gtg ccc ctc aac ttc cgc     1152
Ile Arg Glu Val Leu Arg Leu His Pro Asn Val Pro Leu Asn Phe Arg
    370                 375                 380

cag gcc atc gtt gat act aag ttc cct act ggt ggt ggc ccg aat aga     1200
Gln Ala Ile Val Asp Thr Lys Phe Pro Thr Gly Gly Gly Pro Asn Arg
385                 390                 395                 400

gac cag ccc atc ttt gtt cca aaa gga cag aag gtg ttc tac tcc acg     1248
Asp Gln Pro Ile Phe Val Pro Lys Gly Gln Lys Val Phe Tyr Ser Thr
                405                 410                 415

tac gtc atg cag cga agc aag gac atc tgg ggc gct gac tcc aca tcg     1296
Tyr Val Met Gln Arg Ser Lys Asp Ile Trp Gly Ala Asp Ser Thr Ser
            420                 425                 430

ttc cga cca gaa cgc tgg aac gag ccc aga gaa gct ctt gca tca ggt     1344
Phe Arg Pro Glu Arg Trp Asn Glu Pro Arg Glu Ala Leu Ala Ser Gly
        435                 440                 445

tgg gat tac att cct ttc aat ggt ggc cct cgc att tgt atc ggt cag     1392
Trp Asp Tyr Ile Pro Phe Asn Gly Gly Pro Arg Ile Cys Ile Gly Gln
    450                 455                 460

cag ttc gct ctc act gag gct agc tac acg ctt gtc cgt att tgc cag     1440
Gln Phe Ala Leu Thr Glu Ala Ser Tyr Thr Leu Val Arg Ile Cys Gln
465                 470                 475                 480

gag ttt acc aga att gag gtt ctt cat ccc gat gtc att act tct agg     1488
Glu Phe Thr Arg Ile Glu Val Leu His Pro Asp Val Ile Thr Ser Arg
                485                 490                 495

aaa gag atg aag cag cgc atg cgc ttg acc aac tcg gct agc ggt ggc     1536
Lys Glu Met Lys Gln Arg Met Arg Leu Thr Asn Ser Ala Ser Gly Gly
            500                 505                 510

gtg atg gcg aga ttc att cgt tag                                     1560
Val Met Ala Arg Phe Ile Arg
        515

<210> SEQ ID NO 57
<211> LENGTH: 519
<212> TYPE: PRT
```

<213> ORGANISM: Candida bombicola

<400> SEQUENCE: 57

```
Met Ile Ile Asp Leu Ser Asp Ala Leu Ile Ile Gly Gly Ile Ala Leu
1               5                   10                  15

Cys Phe Leu Leu Ser Tyr Gln Ala Ile Tyr Phe Tyr Phe Ile Tyr Ser
            20                  25                  30

Pro Arg Ala Lys Lys Leu Gly Cys Ala Pro Pro Leu Ile Val His Ala
        35                  40                  45

Phe Pro Leu Gly Leu Pro Thr Ile Phe Gly Leu Ile Arg Ala Trp Arg
    50                  55                  60

Asn Asp Asp Leu Leu Gln Tyr Leu Ser Asp Asn Phe Ala Arg Ile Arg
65                  70                  75                  80

Thr Arg Thr Gly Met Gln Val Met Ala Gly Gln Leu Trp Leu Asn Thr
                85                  90                  95

Ile Glu Pro Glu Asn Ile Lys Ala Met Leu Ala Thr Ser Phe Lys Asp
            100                 105                 110

Phe Ser Leu Gly Phe Arg Tyr Glu Val Met His Gly Leu Leu Gly Asp
        115                 120                 125

Gly Ile Phe Thr Leu Ser Gly Glu Gly Trp Lys His Ser Arg Ala Leu
    130                 135                 140

Leu Arg Pro Gln Phe Ser Arg Glu Gln Val Ser His Leu Asp Ser Met
145                 150                 155                 160

Arg Thr His Ile Asn Leu Met Ile Asn Asn His Phe Lys Gly Gly Gln
                165                 170                 175

Val Val Asp Ala Gln Val Leu Tyr His Asn Leu Thr Ile Asp Thr Ala
            180                 185                 190

Thr Glu Phe Leu Phe Gly Glu Ser Thr Asn Thr Leu Asp Pro Val Leu
        195                 200                 205

Ala Gln Gln Gly Leu Pro Gly Pro Arg Gly Val Val Thr Gly Glu Gln
    210                 215                 220

Phe Ala Asn Ala Phe Thr Tyr Ala Gln Glu Leu Leu Ser Ile Arg Val
225                 230                 235                 240

Met Ala Gly Ser Ala Trp Phe Leu Val Trp Thr Pro Lys Phe Arg Arg
                245                 250                 255

Ser Cys Lys Val Cys His Asn Phe Ile Asp Tyr Phe Val Phe Lys Ala
            260                 265                 270

Leu Ala Thr Pro Met Glu Lys Asp Gln Glu Ala Asp Arg Tyr Val Phe
        275                 280                 285

Ile Arg Glu Leu Thr Lys Glu Thr Ser Asp Pro Lys Val Ile Arg Asp
    290                 295                 300

Gln Ala Leu Asn Ile Leu Leu Ala Gly Arg Asp Thr Thr Ala Ala Leu
305                 310                 315                 320

Leu Ser Phe Thr Thr Tyr Tyr Leu Gly Ala Tyr Pro Glu Val Tyr Asp
                325                 330                 335

Glu Leu Arg Glu Ala Val Leu Ala Asp Phe Gly Pro Ala Asp Ser Glu
            340                 345                 350

Pro Pro Thr Phe Glu Arg Leu Lys Gln Cys Lys Val Leu Gln Asn Val
        355                 360                 365

Ile Arg Glu Val Leu Arg Leu His Pro Asn Val Pro Leu Asn Phe Arg
    370                 375                 380

Gln Ala Ile Val Asp Thr Lys Phe Pro Thr Gly Gly Gly Pro Asn Arg
385                 390                 395                 400
```

```
Asp Gln Pro Ile Phe Val Pro Lys Gly Gln Lys Val Phe Tyr Ser Thr
                405                 410                 415

Tyr Val Met Gln Arg Ser Lys Asp Ile Trp Gly Ala Asp Ser Thr Ser
            420                 425                 430

Phe Arg Pro Glu Arg Trp Asn Glu Pro Arg Glu Ala Leu Ala Ser Gly
        435                 440                 445

Trp Asp Tyr Ile Pro Phe Asn Gly Gly Pro Arg Ile Cys Ile Gly Gln
    450                 455                 460

Gln Phe Ala Leu Thr Glu Ala Ser Tyr Thr Leu Val Arg Ile Cys Gln
465                 470                 475                 480

Glu Phe Thr Arg Ile Glu Val Leu His Pro Asp Val Ile Thr Ser Arg
                485                 490                 495

Lys Glu Met Lys Gln Arg Met Arg Leu Thr Asn Ser Ala Ser Gly Gly
            500                 505                 510

Val Met Ala Arg Phe Ile Arg
        515


<210> SEQ ID NO 58
<211> LENGTH: 1572
<212> TYPE: DNA
<213> ORGANISM: Candida bombicola
<220> FEATURE:
<221> NAME/KEY: CDS
<222> LOCATION: (1)..(1572)

<400> SEQUENCE: 58

atg att ttt tat gct gtg ctt ggc gct gtg gtc acc ttc tta ctt tac       48
Met Ile Phe Tyr Ala Val Leu Gly Ala Val Val Thr Phe Leu Leu Tyr
1               5                   10                  15

gta gat gtg atc tac cct ttc gtg ata tat cct tta aaa gca cga tgg       96
Val Asp Val Ile Tyr Pro Phe Val Ile Tyr Pro Leu Lys Ala Arg Trp
            20                  25                  30

cac aaa tgt ggc tcc gta cct cga gag ctt agc tgg cca ttg ggg att      144
His Lys Cys Gly Ser Val Pro Arg Glu Leu Ser Trp Pro Leu Gly Ile
        35                  40                  45

cca acc acc ata gga gtt ttt tcg aac ata aag aag gat cta cat ctt      192
Pro Thr Thr Ile Gly Val Phe Ser Asn Ile Lys Lys Asp Leu His Leu
    50                  55                  60

caa gtc ctg gca gcg tac gac ctc agc cgg tct tat aag aca agc ttg      240
Gln Val Leu Ala Ala Tyr Asp Leu Ser Arg Ser Tyr Lys Thr Ser Leu
65                  70                  75                  80

cgt caa agt ctc ggc aca tgg gta gtt gct acg cgg gat cct gag aac      288
Arg Gln Ser Leu Gly Thr Trp Val Val Ala Thr Arg Asp Pro Glu Asn
                85                  90                  95

atc aag gcc gtt ttg tct acc aag ttc aat gac ttt tca ctg aaa gag      336
Ile Lys Ala Val Leu Ser Thr Lys Phe Asn Asp Phe Ser Leu Lys Glu
            100                 105                 110

aga gga att cgg tta agg cat gta att ggt gat ggt atc ttt acc caa      384
Arg Gly Ile Arg Leu Arg His Val Ile Gly Asp Gly Ile Phe Thr Gln
        115                 120                 125

gat ggt gca ccg tgg aag cac tcg cga gat atg ctc aga cct caa ttc      432
Asp Gly Ala Pro Trp Lys His Ser Arg Asp Met Leu Arg Pro Gln Phe
    130                 135                 140

agt agg gaa caa atc agc cgc gtg gag gtg ttg agt cac cac atc gat      480
Ser Arg Glu Gln Ile Ser Arg Val Glu Val Leu Ser His His Ile Asp
145                 150                 155                 160

gtt ttg att cgt gag atc aaa aag tcg gga ggt aat gtt gag ttg caa      528
Val Leu Ile Arg Glu Ile Lys Lys Ser Gly Gly Asn Val Glu Leu Gln
                165                 170                 175
```

```
cga cta ttc cac ctc atg act atg gac acc gcc aca cag ttt ctt ttc      576
Arg Leu Phe His Leu Met Thr Met Asp Thr Ala Thr Gln Phe Leu Phe
            180                 185                 190

ggc gaa tca att ggc tcg cta gaa gtc agt ggc gac agc aag ggc att      624
Gly Glu Ser Ile Gly Ser Leu Glu Val Ser Gly Asp Ser Lys Gly Ile
        195                 200                 205

gag att act gac cca aat act gga gat att gtg agt acc gtt gac ttc      672
Glu Ile Thr Asp Pro Asn Thr Gly Asp Ile Val Ser Thr Val Asp Phe
    210                 215                 220

gtt gag tct tat act ttc aca aac aga ttt gct atg aag aag gta ttc      720
Val Glu Ser Tyr Thr Phe Thr Asn Arg Phe Ala Met Lys Lys Val Phe
225                 230                 235                 240

ctg aac aaa tgg gaa ttc ttg gca aac ttg tcg aac ccc tca tat gag      768
Leu Asn Lys Trp Glu Phe Leu Ala Asn Leu Ser Asn Pro Ser Tyr Glu
                245                 250                 255

agg cat atg cgg cgt gtc cac aca gtc ctg gat cac tac gtt cag ctg      816
Arg His Met Arg Arg Val His Thr Val Leu Asp His Tyr Val Gln Leu
            260                 265                 270

gct ttg aag gct act gag aag tat gat cct gaa gat gac agc gag aaa      864
Ala Leu Lys Ala Thr Glu Lys Tyr Asp Pro Glu Asp Asp Ser Glu Lys
        275                 280                 285

gga gaa tac tac ttt agc cat gag ctg gct aaa ctc acg aga gac ccc      912
Gly Glu Tyr Tyr Phe Ser His Glu Leu Ala Lys Leu Thr Arg Asp Pro
    290                 295                 300

ttg tcg ttg cgc aat cag ctt ttt aat atc ctg att gct ggc cgc gac      960
Leu Ser Leu Arg Asn Gln Leu Phe Asn Ile Leu Ile Ala Gly Arg Asp
305                 310                 315                 320

act acc gca gca aca ttg tcc tat gcc ttc cat tac tta acg aag aac     1008
Thr Thr Ala Ala Thr Leu Ser Tyr Ala Phe His Tyr Leu Thr Lys Asn
                325                 330                 335

cca gcc atc tac gcc aag gtt cgc gaa gat gtg ctc acc gtc ttc ccc     1056
Pro Ala Ile Tyr Ala Lys Val Arg Glu Asp Val Leu Thr Val Phe Pro
            340                 345                 350

gat gga gac gcc tca ttg gcg acc ttt gag gac ttg cga aag gcc aag     1104
Asp Gly Asp Ala Ser Leu Ala Thr Phe Glu Asp Leu Arg Lys Ala Lys
        355                 360                 365

tat ctc caa atg gta atc aag gag gta ttg cgc ctt gcg cct gcg gtt     1152
Tyr Leu Gln Met Val Ile Lys Glu Val Leu Arg Leu Ala Pro Ala Val
    370                 375                 380

ccc aca aat tcg cgt act gcg gtt cgt gac acc tat ctg cca cgg ggt     1200
Pro Thr Asn Ser Arg Thr Ala Val Arg Asp Thr Tyr Leu Pro Arg Gly
385                 390                 395                 400

gga ggc cca gct gga aac cta ccc gtt ttc gtt ccc aag ggc act att     1248
Gly Gly Pro Ala Gly Asn Leu Pro Val Phe Val Pro Lys Gly Thr Ile
                405                 410                 415

atc agg tat cct gca tat atc ttg cac cgc gat cct gat ata tat ggt     1296
Ile Arg Tyr Pro Ala Tyr Ile Leu His Arg Asp Pro Asp Ile Tyr Gly
            420                 425                 430

gcc gac tcg tat gac ttc aac cct gag agg tgg aga ccc gag aat aag     1344
Ala Asp Ser Tyr Asp Phe Asn Pro Glu Arg Trp Arg Pro Glu Asn Lys
        435                 440                 445

ctc cca ggt agc cca atg tac tca tgg ggc tat att ccc ttt aat ggc     1392
Leu Pro Gly Ser Pro Met Tyr Ser Trp Gly Tyr Ile Pro Phe Asn Gly
    450                 455                 460

ggc cct cgc att tgc gtt gga cag cag ttt gcc ttg act gaa atc gct     1440
Gly Pro Arg Ile Cys Val Gly Gln Gln Phe Ala Leu Thr Glu Ile Ala
465                 470                 475                 480

ttg aca atg atc aag ctg gtt ttg gaa ttt gag agg ctg gag cct gct     1488
Leu Thr Met Ile Lys Leu Val Leu Glu Phe Glu Arg Leu Glu Pro Ala
                485                 490                 495
```

```
gat gac ttt gag ccc aat ctt cga gat agg acc tca tta act tcc atg     1536
Asp Asp Phe Glu Pro Asn Leu Arg Asp Arg Thr Ser Leu Thr Ser Met
            500                 505                 510

gtc gga ggg tcg ggc gtc cga gta aaa ctg agt taa                     1572
Val Gly Gly Ser Gly Val Arg Val Lys Leu Ser
        515                 520


<210> SEQ ID NO 59
<211> LENGTH: 523
<212> TYPE: PRT
<213> ORGANISM: Candida bombicola

<400> SEQUENCE: 59

Met Ile Phe Tyr Ala Val Leu Gly Ala Val Val Thr Phe Leu Leu Tyr
1               5                   10                  15

Val Asp Val Ile Tyr Pro Phe Val Ile Tyr Pro Leu Lys Ala Arg Trp
            20                  25                  30

His Lys Cys Gly Ser Val Pro Arg Glu Leu Ser Trp Pro Leu Gly Ile
        35                  40                  45

Pro Thr Thr Ile Gly Val Phe Ser Asn Ile Lys Lys Asp Leu His Leu
    50                  55                  60

Gln Val Leu Ala Ala Tyr Asp Leu Ser Arg Ser Tyr Lys Thr Ser Leu
65                  70                  75                  80

Arg Gln Ser Leu Gly Thr Trp Val Val Ala Thr Arg Asp Pro Glu Asn
                85                  90                  95

Ile Lys Ala Val Leu Ser Thr Lys Phe Asn Asp Phe Ser Leu Lys Glu
            100                 105                 110

Arg Gly Ile Arg Leu Arg His Val Ile Gly Asp Gly Ile Phe Thr Gln
        115                 120                 125

Asp Gly Ala Pro Trp Lys His Ser Arg Asp Met Leu Arg Pro Gln Phe
    130                 135                 140

Ser Arg Glu Gln Ile Ser Arg Val Glu Val Leu Ser His His Ile Asp
145                 150                 155                 160

Val Leu Ile Arg Glu Ile Lys Lys Ser Gly Gly Asn Val Glu Leu Gln
                165                 170                 175

Arg Leu Phe His Leu Met Thr Met Asp Thr Ala Thr Gln Phe Leu Phe
            180                 185                 190

Gly Glu Ser Ile Gly Ser Leu Glu Val Ser Gly Asp Ser Lys Gly Ile
        195                 200                 205

Glu Ile Thr Asp Pro Asn Thr Gly Asp Ile Val Ser Thr Val Asp Phe
    210                 215                 220

Val Glu Ser Tyr Thr Phe Thr Asn Arg Phe Ala Met Lys Lys Val Phe
225                 230                 235                 240

Leu Asn Lys Trp Glu Phe Leu Ala Asn Leu Ser Asn Pro Ser Tyr Glu
                245                 250                 255

Arg His Met Arg Arg Val His Thr Val Leu Asp His Tyr Val Gln Leu
            260                 265                 270

Ala Leu Lys Ala Thr Glu Lys Tyr Asp Pro Glu Asp Asp Ser Glu Lys
        275                 280                 285

Gly Glu Tyr Tyr Phe Ser His Glu Leu Ala Lys Leu Thr Arg Asp Pro
    290                 295                 300

Leu Ser Leu Arg Asn Gln Leu Phe Asn Ile Leu Ile Ala Gly Arg Asp
305                 310                 315                 320

Thr Thr Ala Ala Thr Leu Ser Tyr Ala Phe His Tyr Leu Thr Lys Asn
                325                 330                 335
```

```
Pro Ala Ile Tyr Ala Lys Val Arg Glu Asp Val Leu Thr Val Phe Pro
            340                 345                 350

Asp Gly Asp Ala Ser Leu Ala Thr Phe Glu Asp Leu Arg Lys Ala Lys
        355                 360                 365

Tyr Leu Gln Met Val Ile Lys Glu Val Leu Arg Leu Ala Pro Ala Val
    370                 375                 380

Pro Thr Asn Ser Arg Thr Ala Val Arg Asp Thr Tyr Leu Pro Arg Gly
385                 390                 395                 400

Gly Gly Pro Ala Gly Asn Leu Pro Val Phe Val Pro Lys Gly Thr Ile
                405                 410                 415

Ile Arg Tyr Pro Ala Tyr Ile Leu His Arg Asp Pro Asp Ile Tyr Gly
            420                 425                 430

Ala Asp Ser Tyr Asp Phe Asn Pro Glu Arg Trp Arg Pro Glu Asn Lys
        435                 440                 445

Leu Pro Gly Ser Pro Met Tyr Ser Trp Gly Tyr Ile Pro Phe Asn Gly
    450                 455                 460

Gly Pro Arg Ile Cys Val Gly Gln Gln Phe Ala Leu Thr Glu Ile Ala
465                 470                 475                 480

Leu Thr Met Ile Lys Leu Val Leu Glu Phe Glu Arg Leu Glu Pro Ala
                485                 490                 495

Asp Asp Phe Glu Pro Asn Leu Arg Asp Arg Thr Ser Leu Thr Ser Met
            500                 505                 510

Val Gly Gly Ser Gly Val Arg Val Lys Leu Ser
        515                 520


<210> SEQ ID NO 60
<211> LENGTH: 1572
<212> TYPE: DNA
<213> ORGANISM: Candida bombicola
<220> FEATURE:
<221> NAME/KEY: CDS
<222> LOCATION: (1)..(1572)

<400> SEQUENCE: 60

atg att ttt tat gct gtg ctt ggc act gtg gtc gcc ttc tta ctt tac       48
Met Ile Phe Tyr Ala Val Leu Gly Thr Val Val Ala Phe Leu Leu Tyr
1               5                   10                  15

gta gat gtg atc tac cct ttc gtg ata tat cct tta aag gca cga tgg       96
Val Asp Val Ile Tyr Pro Phe Val Ile Tyr Pro Leu Lys Ala Arg Trp
            20                  25                  30

cac aaa tgt ggc ttc gtc cct cga gag ctg agc tgg cca ttg ggg att      144
His Lys Cys Gly Phe Val Pro Arg Glu Leu Ser Trp Pro Leu Gly Ile
        35                  40                  45

cca gac acc ata gca gtt ttt tcg agg ata aag aag gat cta cat ctt      192
Pro Asp Thr Ile Ala Val Phe Ser Arg Ile Lys Lys Asp Leu His Leu
    50                  55                  60

caa ttc ctg gca gcg cac gac ctc agc cgg tct tat aag aca agc ttg      240
Gln Phe Leu Ala Ala His Asp Leu Ser Arg Ser Tyr Lys Thr Ser Leu
65                  70                  75                  80

cgt caa act ctc ggc aca tgg gta gtt gat acg cga gat cct gag aat      288
Arg Gln Thr Leu Gly Thr Trp Val Val Asp Thr Arg Asp Pro Glu Asn
                85                  90                  95

atc aag gcc gtt ttg tct acc aag ttc aat gac ttt tca ctg aaa gat      336
Ile Lys Ala Val Leu Ser Thr Lys Phe Asn Asp Phe Ser Leu Lys Asp
            100                 105                 110

aga gga att cgg tta agg caa gta att ggt gat ggt att ttt acc caa      384
Arg Gly Ile Arg Leu Arg Gln Val Ile Gly Asp Gly Ile Phe Thr Gln
        115                 120                 125
```

```
gat ggt gca ccg tgg aag cac tcg cga gat atg ctc aga cct caa ttc      432
Asp Gly Ala Pro Trp Lys His Ser Arg Asp Met Leu Arg Pro Gln Phe
    130                 135                 140

agt agg gaa caa att agc cgc gtg gag gtg ttg agt cac cac atc gat      480
Ser Arg Glu Gln Ile Ser Arg Val Glu Val Leu Ser His His Ile Asp
145                 150                 155                 160

gtt ttg att cgt gag atc aaa aag tcg gga ggt aat gtt gag ttg caa      528
Val Leu Ile Arg Glu Ile Lys Lys Ser Gly Gly Asn Val Glu Leu Gln
                165                 170                 175

cga cta ttc cac ctc atg act atg gac act gct aca cag ttt ctt ttc      576
Arg Leu Phe His Leu Met Thr Met Asp Thr Ala Thr Gln Phe Leu Phe
            180                 185                 190

ggc gaa tca att ggc tcg cta gaa gtc agt ggc gac agc aag ggc att      624
Gly Glu Ser Ile Gly Ser Leu Glu Val Ser Gly Asp Ser Lys Gly Ile
        195                 200                 205

gag att act gac cca aat act gga gat att gtg aat acc gtt gac ttc      672
Glu Ile Thr Asp Pro Asn Thr Gly Asp Ile Val Asn Thr Val Asp Phe
    210                 215                 220

gtt gag tct tat act ttt gca aac aga ttt gct atg aaa aag ata tta      720
Val Glu Ser Tyr Thr Phe Ala Asn Arg Phe Ala Met Lys Lys Ile Leu
225                 230                 235                 240

ctg aac aaa tgg gaa ttc gtg gta aac ttg tcg aac ccc tca tat gag      768
Leu Asn Lys Trp Glu Phe Val Val Asn Leu Ser Asn Pro Ser Tyr Glu
                245                 250                 255

agg cat atg cga cgt gtc cac aca gtc ctg gat cac tac gtt cag ctg      816
Arg His Met Arg Arg Val His Thr Val Leu Asp His Tyr Val Gln Leu
            260                 265                 270

gct ttg aag gct act gag aag tat gat cct gaa gat gac tgc gag aaa      864
Ala Leu Lys Ala Thr Glu Lys Tyr Asp Pro Glu Asp Asp Cys Glu Lys
        275                 280                 285

gga gaa tac tac ttt agc cat gag ctg gct aaa ctc acg aga gac ccc      912
Gly Glu Tyr Tyr Phe Ser His Glu Leu Ala Lys Leu Thr Arg Asp Pro
    290                 295                 300

ttg tgc ttg cgc aat cag ctt ttt aat atc ctg att gct ggc cgc gac      960
Leu Cys Leu Arg Asn Gln Leu Phe Asn Ile Leu Ile Ala Gly Arg Asp
305                 310                 315                 320

act acc gca gca aca ttg gcc tat gcc ttc cat tac ttg acg aag aac     1008
Thr Thr Ala Ala Thr Leu Ala Tyr Ala Phe His Tyr Leu Thr Lys Asn
                325                 330                 335

cca gcc atc tac gcc aag gtg cgc gaa gat gtg ctc acc gtc ttc ccc     1056
Pro Ala Ile Tyr Ala Lys Val Arg Glu Asp Val Leu Thr Val Phe Pro
            340                 345                 350

aat gga gat gcc tca ttg gcg acc ttt gag gac ttg cga aag gcc aag     1104
Asn Gly Asp Ala Ser Leu Ala Thr Phe Glu Asp Leu Arg Lys Ala Lys
        355                 360                 365

tat ctc caa atg gta atc aag gag gta ttg cgc ctt gcg cct gtg gtt     1152
Tyr Leu Gln Met Val Ile Lys Glu Val Leu Arg Leu Ala Pro Val Val
    370                 375                 380

ccc aca aat tcg cgt act gcg gtt cgt gac acc tat ctg cca cgg ggt     1200
Pro Thr Asn Ser Arg Thr Ala Val Arg Asp Thr Tyr Leu Pro Arg Gly
385                 390                 395                 400

gga ggc cca gct gga aac cta ccc gtt ttc gtt ccc aag ggc aca aat     1248
Gly Gly Pro Ala Gly Asn Leu Pro Val Phe Val Pro Lys Gly Thr Asn
                405                 410                 415

gtc agg tat tct gca tat gtc ttg cac cgc gat cct gat ata tat ggt     1296
Val Arg Tyr Ser Ala Tyr Val Leu His Arg Asp Pro Asp Ile Tyr Gly
            420                 425                 430

gcc gac tcg tat gac ttc aac cct gag agg tgg aga ccc gag aat aag     1344
Ala Asp Ser Tyr Asp Phe Asn Pro Glu Arg Trp Arg Pro Glu Asn Lys
```

```
        435                 440                 445

ctc cca ggt agc cca atg tac tca tgg ggc tat att ccc ttt aat ggc     1392
Leu Pro Gly Ser Pro Met Tyr Ser Trp Gly Tyr Ile Pro Phe Asn Gly
    450                 455                 460

ggc cct cgc att tgc gtt gga cag cag ttt gcc ttg act gaa ttc gct     1440
Gly Pro Arg Ile Cys Val Gly Gln Gln Phe Ala Leu Thr Glu Phe Ala
465                 470                 475                 480

ttg aca atg atc aag ctg gtt tta gaa ttt gag agg ctg gag cct gct     1488
Leu Thr Met Ile Lys Leu Val Leu Glu Phe Glu Arg Leu Glu Pro Ala
                485                 490                 495

gat gac ttt gag ccc aat ctt cta gat agg acc tca tta act gcc atg     1536
Asp Asp Phe Glu Pro Asn Leu Leu Asp Arg Thr Ser Leu Thr Ala Met
            500                 505                 510

gtc gga ggg tcg ggc gtc cga gta aaa ctg agt taa                     1572
Val Gly Gly Ser Gly Val Arg Val Lys Leu Ser
        515                 520


<210> SEQ ID NO 61
<211> LENGTH: 523
<212> TYPE: PRT
<213> ORGANISM: Candida bombicola

<400> SEQUENCE: 61

Met Ile Phe Tyr Ala Val Leu Gly Thr Val Val Ala Phe Leu Leu Tyr
1               5                   10                  15

Val Asp Val Ile Tyr Pro Phe Val Ile Tyr Pro Leu Lys Ala Arg Trp
            20                  25                  30

His Lys Cys Gly Phe Val Pro Arg Glu Leu Ser Trp Pro Leu Gly Ile
        35                  40                  45

Pro Asp Thr Ile Ala Val Phe Ser Arg Ile Lys Lys Asp Leu His Leu
    50                  55                  60

Gln Phe Leu Ala Ala His Asp Leu Ser Arg Ser Tyr Lys Thr Ser Leu
65                  70                  75                  80

Arg Gln Thr Leu Gly Thr Trp Val Val Asp Thr Arg Asp Pro Glu Asn
                85                  90                  95

Ile Lys Ala Val Leu Ser Thr Lys Phe Asn Asp Phe Ser Leu Lys Asp
            100                 105                 110

Arg Gly Ile Arg Leu Arg Gln Val Ile Gly Asp Gly Ile Phe Thr Gln
        115                 120                 125

Asp Gly Ala Pro Trp Lys His Ser Arg Asp Met Leu Arg Pro Gln Phe
    130                 135                 140

Ser Arg Glu Gln Ile Ser Arg Val Glu Val Leu Ser His His Ile Asp
145                 150                 155                 160

Val Leu Ile Arg Glu Ile Lys Lys Ser Gly Gly Asn Val Glu Leu Gln
                165                 170                 175

Arg Leu Phe His Leu Met Thr Met Asp Thr Ala Thr Gln Phe Leu Phe
            180                 185                 190

Gly Glu Ser Ile Gly Ser Leu Glu Val Ser Gly Asp Ser Lys Gly Ile
        195                 200                 205

Glu Ile Thr Asp Pro Asn Thr Gly Asp Ile Val Asn Thr Val Asp Phe
    210                 215                 220

Val Glu Ser Tyr Thr Phe Ala Asn Arg Phe Ala Met Lys Lys Ile Leu
225                 230                 235                 240

Leu Asn Lys Trp Glu Phe Val Val Asn Leu Ser Asn Pro Ser Tyr Glu
                245                 250                 255

Arg His Met Arg Arg Val His Thr Val Leu Asp His Tyr Val Gln Leu
```

```
            260                 265                 270

Ala Leu Lys Ala Thr Glu Lys Tyr Asp Pro Glu Asp Asp Cys Glu Lys
        275                 280                 285

Gly Glu Tyr Tyr Phe Ser His Glu Leu Ala Lys Leu Thr Arg Asp Pro
    290                 295                 300

Leu Cys Leu Arg Asn Gln Leu Phe Asn Ile Leu Ile Ala Gly Arg Asp
305                 310                 315                 320

Thr Thr Ala Ala Thr Leu Ala Tyr Ala Phe His Tyr Leu Thr Lys Asn
                325                 330                 335

Pro Ala Ile Tyr Ala Lys Val Arg Glu Asp Val Leu Thr Val Phe Pro
            340                 345                 350

Asn Gly Asp Ala Ser Leu Ala Thr Phe Glu Asp Leu Arg Lys Ala Lys
        355                 360                 365

Tyr Leu Gln Met Val Ile Lys Glu Val Leu Arg Leu Ala Pro Val Val
    370                 375                 380

Pro Thr Asn Ser Arg Thr Ala Val Arg Asp Thr Tyr Leu Pro Arg Gly
385                 390                 395                 400

Gly Gly Pro Ala Gly Asn Leu Pro Val Phe Val Pro Lys Gly Thr Asn
                405                 410                 415

Val Arg Tyr Ser Ala Tyr Val Leu His Arg Asp Pro Asp Ile Tyr Gly
            420                 425                 430

Ala Asp Ser Tyr Asp Phe Asn Pro Glu Arg Trp Arg Pro Glu Asn Lys
        435                 440                 445

Leu Pro Gly Ser Pro Met Tyr Ser Trp Gly Tyr Ile Pro Phe Asn Gly
    450                 455                 460

Gly Pro Arg Ile Cys Val Gly Gln Gln Phe Ala Leu Thr Glu Phe Ala
465                 470                 475                 480

Leu Thr Met Ile Lys Leu Val Leu Glu Phe Glu Arg Leu Glu Pro Ala
                485                 490                 495

Asp Asp Phe Glu Pro Asn Leu Leu Asp Arg Thr Ser Leu Thr Ala Met
            500                 505                 510

Val Gly Gly Ser Gly Val Arg Val Lys Leu Ser
        515                 520


<210> SEQ ID NO 62
<211> LENGTH: 1206
<212> TYPE: DNA
<213> ORGANISM: Candida bombicola
<220> FEATURE:
<221> NAME/KEY: CDS
<222> LOCATION: (1)..(1206)

<400> SEQUENCE: 62

atg ttt gcg aaa gct tta tgg gag gat gat gtt ttg gag tac gcc tgc       48
Met Phe Ala Lys Ala Leu Trp Glu Asp Asp Val Leu Glu Tyr Ala Cys
1               5                   10                  15

cgc agg ttt gca ggc atg aag gtc aga act ggg ctt caa act gtc gct       96
Arg Arg Phe Ala Gly Met Lys Val Arg Thr Gly Leu Gln Thr Val Ala
            20                  25                  30

ggc cag cta tgg ata gca act atc gag ccg gag aac atc aag acc gta      144
Gly Gln Leu Trp Ile Ala Thr Ile Glu Pro Glu Asn Ile Lys Thr Val
        35                  40                  45

ctt gcc acc tcg ttc aat gac tac tcc ctt ggc ttc cgt tat aat gcc      192
Leu Ala Thr Ser Phe Asn Asp Tyr Ser Leu Gly Phe Arg Tyr Asn Ala
    50                  55                  60

cta tac ggc ctt ctc gga aat ggt att ttc acc ctt agt ggt gat ggc      240
Leu Tyr Gly Leu Leu Gly Asn Gly Ile Phe Thr Leu Ser Gly Asp Gly
```

-continued

```
65                  70                  75                  80

tgg aag cac agt cgt gct ttg ttg cgt ccg cag ttc agt cgt gag caa      288
Trp Lys His Ser Arg Ala Leu Leu Arg Pro Gln Phe Ser Arg Glu Gln
                85                  90                  95

gtt tct cac ttg gac tcc atg cgt aca cac atc aac ttg atg atc aac      336
Val Ser His Leu Asp Ser Met Arg Thr His Ile Asn Leu Met Ile Asn
            100                 105                 110

aac cat ttc aaa ggc ggc cac gtc gtt gac gca cag gct cga tac cac      384
Asn His Phe Lys Gly Gly His Val Val Asp Ala Gln Ala Arg Tyr His
        115                 120                 125

aat ttg acc atc gat act gcg act gaa ttc ctt ttc ggt gag agc act      432
Asn Leu Thr Ile Asp Thr Ala Thr Glu Phe Leu Phe Gly Glu Ser Thr
    130                 135                 140

aac aca ctc gac cct gtt ctt gca cag caa gga ctc cct ggt cct aag      480
Asn Thr Leu Asp Pro Val Leu Ala Gln Gln Gly Leu Pro Gly Pro Lys
145                 150                 155                 160

ggc acc gtt acc gga gag cag ttt gct gaa gct ttc acc tcc gct ctt      528
Gly Thr Val Thr Gly Glu Gln Phe Ala Glu Ala Phe Thr Ser Ala Leu
                165                 170                 175

caa gtg ctg agt gtc cga gtt atg gcc ggc tcc gca tgg ttc ctc att      576
Gln Val Leu Ser Val Arg Val Met Ala Gly Ser Ala Trp Phe Leu Ile
            180                 185                 190

tgg act cct aaa ttc tgg cgc tcg tgc aag gtg tgc cac aac ttc att      624
Trp Thr Pro Lys Phe Trp Arg Ser Cys Lys Val Cys His Asn Phe Ile
        195                 200                 205

gac tac ttc gta tac aag gcc ttg gcc act ccg atg gag aag ggc caa      672
Asp Tyr Phe Val Tyr Lys Ala Leu Ala Thr Pro Met Glu Lys Gly Gln
    210                 215                 220

gag gct gat cgc tat gtt ttt att cga gag ctc aca aag gag act tct      720
Glu Ala Asp Arg Tyr Val Phe Ile Arg Glu Leu Thr Lys Glu Thr Ser
225                 230                 235                 240

gac cca aga gtc atc cgt gac cag gct cta aat atc ctg ctg gct ggt      768
Asp Pro Arg Val Ile Arg Asp Gln Ala Leu Asn Ile Leu Leu Ala Gly
                245                 250                 255

cgt gat acc act gcg gca ctc ctc atc att gcg gac ttt ggc tct gag      816
Arg Asp Thr Thr Ala Ala Leu Leu Ile Ile Ala Asp Phe Gly Ser Glu
            260                 265                 270

gac gct gag ccc cct acc ttt gag cag ctc aag cag tgc aag gta ctg      864
Asp Ala Glu Pro Pro Thr Phe Glu Gln Leu Lys Gln Cys Lys Val Leu
        275                 280                 285

cag aat gtc att cgc gag gtt tta cgt ttg cac cct aat gtg ccg ctc      912
Gln Asn Val Ile Arg Glu Val Leu Arg Leu His Pro Asn Val Pro Leu
    290                 295                 300

aac ttc cgc cag gct ata act gat act aag ctc ccc act ggt ggt ggc      960
Asn Phe Arg Gln Ala Ile Thr Asp Thr Lys Leu Pro Thr Gly Gly Gly
305                 310                 315                 320

ccg aac aga gac cag cct gtc ttt gtt cca aag gga cag aaa gtg ttc     1008
Pro Asn Arg Asp Gln Pro Val Phe Val Pro Lys Gly Gln Lys Val Phe
                325                 330                 335

tac gcc acc tac gtc atg cag cga gat ccg gaa ata tgg ggc ccc gac     1056
Tyr Ala Thr Tyr Val Met Gln Arg Asp Pro Glu Ile Trp Gly Pro Asp
            340                 345                 350

tct aca agc ttc cgc cct gat cga tgg aat gag ccg aga gag gct ctt     1104
Ser Thr Ser Phe Arg Pro Asp Arg Trp Asn Glu Pro Arg Glu Ala Leu
        355                 360                 365

gca tca ggt tgg gat tat att cct ttc aat ggc ggc cct cgc att tgt     1152
Ala Ser Gly Trp Asp Tyr Ile Pro Phe Asn Gly Gly Pro Arg Ile Cys
    370                 375                 380

atc ggt cag cag ttc gct ctc act gag gct agc tac aca ctt gtc cgt     1200
```

```
Ile Gly Gln Gln Phe Ala Leu Thr Glu Ala Ser Tyr Thr Leu Val Arg
385                 390                 395                 400

atc tag                                                           1206
Ile


<210> SEQ ID NO 63
<211> LENGTH: 401
<212> TYPE: PRT
<213> ORGANISM: Candida bombicola

<400> SEQUENCE: 63

Met Phe Ala Lys Ala Leu Trp Glu Asp Asp Val Leu Glu Tyr Ala Cys
1               5                   10                  15

Arg Arg Phe Ala Gly Met Lys Val Arg Thr Gly Leu Gln Thr Val Ala
            20                  25                  30

Gly Gln Leu Trp Ile Ala Thr Ile Glu Pro Glu Asn Ile Lys Thr Val
        35                  40                  45

Leu Ala Thr Ser Phe Asn Asp Tyr Ser Leu Gly Phe Arg Tyr Asn Ala
    50                  55                  60

Leu Tyr Gly Leu Leu Gly Asn Gly Ile Phe Thr Leu Ser Gly Asp Gly
65                  70                  75                  80

Trp Lys His Ser Arg Ala Leu Leu Arg Pro Gln Phe Ser Arg Glu Gln
                85                  90                  95

Val Ser His Leu Asp Ser Met Arg Thr His Ile Asn Leu Met Ile Asn
            100                 105                 110

Asn His Phe Lys Gly Gly His Val Val Asp Ala Gln Ala Arg Tyr His
        115                 120                 125

Asn Leu Thr Ile Asp Thr Ala Thr Glu Phe Leu Phe Gly Glu Ser Thr
    130                 135                 140

Asn Thr Leu Asp Pro Val Leu Ala Gln Gln Gly Leu Pro Gly Pro Lys
145                 150                 155                 160

Gly Thr Val Thr Gly Glu Gln Phe Ala Glu Ala Phe Thr Ser Ala Leu
                165                 170                 175

Gln Val Leu Ser Val Arg Val Met Ala Gly Ser Ala Trp Phe Leu Ile
            180                 185                 190

Trp Thr Pro Lys Phe Trp Arg Ser Cys Lys Val Cys His Asn Phe Ile
        195                 200                 205

Asp Tyr Phe Val Tyr Lys Ala Leu Ala Thr Pro Met Glu Lys Gly Gln
    210                 215                 220

Glu Ala Asp Arg Tyr Val Phe Ile Arg Glu Leu Thr Lys Glu Thr Ser
225                 230                 235                 240

Asp Pro Arg Val Ile Arg Asp Gln Ala Leu Asn Ile Leu Leu Ala Gly
                245                 250                 255

Arg Asp Thr Thr Ala Ala Leu Leu Ile Ile Ala Asp Phe Gly Ser Glu
            260                 265                 270

Asp Ala Glu Pro Pro Thr Phe Glu Gln Leu Lys Gln Cys Lys Val Leu
        275                 280                 285

Gln Asn Val Ile Arg Glu Val Leu Arg Leu His Pro Asn Val Pro Leu
    290                 295                 300

Asn Phe Arg Gln Ala Ile Thr Asp Thr Lys Leu Pro Thr Gly Gly Gly
305                 310                 315                 320

Pro Asn Arg Asp Gln Pro Val Phe Val Pro Lys Gly Gln Lys Val Phe
                325                 330                 335

Tyr Ala Thr Tyr Val Met Gln Arg Asp Pro Glu Ile Trp Gly Pro Asp
            340                 345                 350
```

```
Ser Thr Ser Phe Arg Pro Asp Arg Trp Asn Glu Pro Arg Glu Ala Leu
        355                 360                 365

Ala Ser Gly Trp Asp Tyr Ile Pro Phe Asn Gly Gly Pro Arg Ile Cys
    370                 375                 380

Ile Gly Gln Gln Phe Ala Leu Thr Glu Ala Ser Tyr Thr Leu Val Arg
385                 390                 395                 400

Ile


<210> SEQ ID NO 64
<211> LENGTH: 6084
<212> TYPE: DNA
<213> ORGANISM: Artificial
<220> FEATURE:
<223> OTHER INFORMATION: Vector

<400> SEQUENCE: 64

ctaaattgta agcgttaata ttttgttaaa attcgcgtta aatttttgtt aaatcagctc     60

atttttaac caataggccg aaatcggcaa aatcccttat aaatcaaaag aatagaccga    120

gatagggttg agtggccgct acagggcgct cccattcgcc attcaggctg cgcaactgtt    180

gggaagggcg tttcggtgcg ggcctcttcg ctattacgcc agctggcgaa agggggatgt    240

gctgcaaggc gattaagttg ggtaacgcca gggttttccc agtcacgacg ttgtaaaacg    300

acggccagtg agcgcgacgt aatacgactc actatagggc gaattggcgg aaggccgtca    360

aggcctaggc gcgcctgcag gatcctagaa aacagctgga tatggataaa ctcggcaagc    420

atcttttgga aaggctgcca cgctatgccg tgccgatatt cattaagttc gtcgacaccg    480

tcaccatcac cggcaacaac aaagttcaga agaaagaatt ccgaaaccag cagattcccg    540

ccccagcagg acaaacaatc tactggttag agggcacgag ctacaagccc ctcactgctg    600

atgcgtgggc tcgtgtagag aatgggcgac acaagctcta atgttgaata cctcttccgt    660

atagatgtgg cataagctat agattttgct gcaatattat taaatattaa agagtttcga    720

aggtcagctg cggatgaacc agttcagagc ggctctctct tttttgccaa tagcgtgcaa    780

ccgtgaagag caattcaacc atccaatctg gctacactaa attgtatttg gcagcgcact    840

gtacgagcgc actgtacgaa actccgtcaa tttatagcag aacgcgtgcg atcgcgggcc    900

ccagcgatat gacgagaatc aggcaataat agcttaagct gaagtgtttt tagatttagt    960

tcggagtgcg cttctcaaaa gtgctgggat caacaagttt ttaacatggg ttttgattta   1020

tattgtttta tatgagcgcc tcagatatgc gctgacagcc tattaggaga aatggccggc   1080

ctacaagtcc atatgtgtag agttgttttt gttgttaagt ctttctttaa gagcttgacc   1140

gactataacc gttcaacggc gcattatata ctttgggtat cggccagtgc tgacaactca   1200

cacgttgcga ccccttaccc agaagcatac ccagcgcgat gtcgatcgtg ttatatcgta   1260

gacgcacacc ctgcaatgac gggtaggctc taaatcggga tgcgaaaaag aggttgcctt   1320

gctttttgcc ctggtagatg gcatgctgag cgtgcgcttg ccgcctaatt tttgtgtgtc   1380

gcctgctatt tattgctgaa gctagcccgc cgcatctttc cccaaggctt cgattgctcg   1440

tattggggca gggattggta ctcaaccttg cagatgagac tccagcaaca acgtcgtact   1500

gcttagcgat cgcacatgtt tcatcatcgt cactatacac atcgtcatca actccatggc   1560

gtgaggactt ccgagactgc tgggcccttc gtttctttaa tgcctcaaga gatgacttcg   1620

tacccgaaga gacgcctgtt gtaccccgtt gacgcttggc ggagggggct tcgtcctcgt   1680

cagcaacccg cgtcatctgc ttccttcgct gagcaagata ccttctctcc tcgtaccgct   1740
```

```
gcatctcctg agctcggtca tacaagatct cttctcgctc aatctctggc agcgcgtcca   1800
acttcgccct gtcttcagca tcgagatatt tgccttctag aggataggga ttgacgacct   1860
cattgcttgg cggcgacggc agcgagattt cctcttcgga gtcggagcca acgtcggcca   1920
atgccagcag atcatcatca ctgtcactca tagtaggaag gttgaagtgt gctgacgaat   1980
cagaatcgcg aaggatgcca ttgaaggcat atatatttta atctgtacct tttatggtaa   2040
tttaatcaga ttttataggt attcatgtgc aagttgcatt gaaggaactg tttgagaaaa   2100
tcatcttgac tgaacttttc tcagatatgc attccagccc gccttttggt aacgctgagc   2160
ttcgtgcaca ggatctcgtc ccttgctata gagcccgcgt ccgacgataa taacgtctgt   2220
gccggtctct atgacgtcgt ccacagtacg atactgctgc cccaatccat cacctttgtc   2280
gtccaggccc accccaggag tcataatgac ccagtcttcc tctggctttc cgactttttg   2340
ctgagcgatg aaaccaaaca caaatgcgcg gttactgcga gcgatgtcta ctgtcgcttg   2400
cgagtattcg ccgtgagcca gtgtgccctt cgaactcagt tctgcaagca tgacaaggcc   2460
gcgaggttca tccgtagttt ccttcgcagc ctcttctagt ccgctcacaa ttcccggccc   2520
aggaacaccg tgagcatttg ttatatcagc ccattgagcg atcttaaaca ctccacctgc   2580
atattgggcc ttaacagtgg aaccgatgtc tgcgaacttt cggtcttcaa aaatgagaaa   2640
attgtgcttc gttgaaagct gtttcaaacc gctgacagtt gtgtcgtatt cgaagtcgtc   2700
aattatgtca atgtgggtct taaccataca aatgtaaggt ccaatgcggt ccaggatact   2760
cagtaactca gaggtagttc gcacatccaa gcttgcgcaa agatttgttt gcttgctcac   2820
aatgatgtcg aatagccggg ctgctacagc cggcagcctc tctcggcgct cctcatagct   2880
cagcttcata ttatttctct acagtagtgc ccgtgccctc gatcagctag gacttttcaa   2940
attaatcggg ctgtttgatg taagtaagat gaagtcacgc gcgtgcagga gactgcgtcc   3000
cgcgatattc tgcaggcttg aaaaatttac cctaacggta ggcatcaagt gagtgagtct   3060
cagcgtcgat atgggtcaaa aaaggggaaa actagccgag atcgttgcga gctgtttcga   3120
aaattatgcc ctatggcaat tatcacgtgg agtatccgaa tttctccagg ctgtcaagcg   3180
gcaattataa ccgagactga gatcgagaag tatataaccg cagcagtagt ggataaataa   3240
ttgcgaagtc ttcccagcag agcgggctgt tttttggagt tggttactgt aaaatgctaa   3300
aatgactgac aacaatggag cgtctacagc attggcaaca gtgggaacag tatgctggtg   3360
catccagttg ataccccagg ttctgcgaaa ctggtatgtt cgggattgcg agggcgttcc   3420
tcctctgatg ttctttttgt tcgccgtttc ggggattccc ttcgcagtgt acttcattga   3480
tcagaattcg aacactgcca tcatggttca acctcacttg tttactttct ttagccttat   3540
aggcttttgg caaagcctgt actatccgcc cgtcagacca gcacgggccg tcacatgtat   3600
ggttgcgtcg ctgtataaga aatcttacaa ctgaagacta cacagcgtat ccgctccgat   3660
atcggcgatc acgtggatac atttccccag aatgcgtcaa ccttgcatgc tcgatattga   3720
ctcaagccga gaggtgtata acaacaccga cgatagcgaa ttacttgtgg aactgatttg   3780
ccgtatcgag taaatcgcga ttgtggccct ctttaggcct tgtacccatt tgtgcatcgt   3840
atttgttagt atgcatcata gaattatgtg aacttagaaa agtccgtatg aaatgagcct   3900
cagattatgg attgatcgct tgttatttgt acagcggaat tgacttatag tatgtcggcc   3960
acggttttag attgcctagg ggccgttttc ttgatggatt cgcatcggaa ctccgaattc   4020
ttgattgctc tccatcgcgc aggaggccgt tctttttttg acaaagtccc atttttagggc  4080
```

```
gcaggtccaa aaaataagcg gccgcttaat taactggcct catgggcctt ccgctcactg   4140

cccgctttcc agtcgggaaa cctgtcgtgc cagctgcatt aacatggtca tagctgtttc   4200

cttgcgtatt gggcgctctc cgcttcctcg ctcactgact cgctgcgctc ggtcgttcgg   4260

gtaaagcctg gggtgcctaa tgagcaaaag gccagcaaaa ggccaggaac cgtaaaaagg   4320

ccgcgttgct ggcgtttttc cataggctcc gcccccctga cgagcatcac aaaaatcgac   4380

gctcaagtca gaggtggcga aacccgacag gactataaag ataccaggcg tttccccctg   4440

gaagctccct cgtgcgctct cctgttccga ccctgccgct taccggatac ctgtccgcct   4500

ttctcccttc gggaagcgtg gcgctttctc atagctcacg ctgtaggtat ctcagttcgg   4560

tgtaggtcgt tcgctccaag ctgggctgtg tgcacgaacc ccccgttcag cccgaccgct   4620

gcgccttatc cggtaactat cgtcttgagt ccaacccggt aagacacgac ttatcgccac   4680

tggcagcagc cactggtaac aggattagca gagcgaggta tgtaggcggt gctacagagt   4740

tcttgaagtg gtggcctaac tacggctaca ctagaagaac agtatttggt atctgcgctc   4800

tgctgaagcc agttaccttc ggaaaaagag ttggtagctc ttgatccggc aaacaaacca   4860

ccgctggtag cggtggtttt tttgtttgca agcagcagat tacgcgcaga aaaaaaggat   4920

ctcaagaaga tcctttgatc ttttctacgg ggtctgacgc tcagtggaac gaaaactcac   4980

gttaagggat tttggtcatg agattatcaa aaaggatctt cacctagatc cttttaaatt   5040

aaaaatgaag ttttaaatca atctaaagta tatatgagta aacttggtct gacagttacc   5100

aatgcttaat cagtgaggca cctatctcag cgatctgtct atttcgttca tccatagttg   5160

cctgactccc cgtcgtgtag ataactacga tacgggaggg cttaccatct ggccccagtg   5220

ctgcaatgat accgcgagaa ccacgctcac cggctccaga tttatcagca ataaaccagc   5280

cagccggaag ggccgagcgc agaagtggtc ctgcaacttt atccgcctcc atccagtcta   5340

ttaattgttg ccgggaagct agagtaagta gttcgccagt taatagtttg cgcaacgttg   5400

ttgccattgc tacaggcatc gtggtgtcac gctcgtcgtt tggtatggct tcattcagct   5460

ccggttccca acgatcaagg cgagttacat gatcccccat gttgtgcaaa aaagcggtta   5520

gctccttcgg tcctccgatc gttgtcagaa gtaagttggc cgcagtgtta tcactcatgg   5580

ttatggcagc actgcataat tctcttactg tcatgccatc cgtaagatgc ttttctgtga   5640

ctggtgagta ctcaaccaag tcattctgag aatagtgtat gcggcgaccg agttgctctt   5700

gcccggcgtc aatacgggat aataccgcgc cacatagcag aactttaaaa gtgctcatca   5760

ttggaaaacg ttcttcgggg cgaaaactct caaggatctt accgctgttg agatccagtt   5820

cgatgtaacc cactcgtgca cccaactgat cttcagcatc ttttactttc accagcgttt   5880

ctgggtgagc aaaaacagga aggcaaaatg ccgcaaaaaa gggaataagg gcgacacgga   5940

aatgttgaat actcatactc ttcctttttc aatattattg aagcatttat cagggttatt   6000

gtctcatgag cggatacata tttgaatgta tttagaaaaa taaacaaata ggggttccgc   6060

gcacatttcc ccgaaaagtg ccac                                          6084
```

<210> SEQ ID NO 65
<211> LENGTH: 7693
<212> TYPE: DNA
<213> ORGANISM: Artificial
<220> FEATURE:
<223> OTHER INFORMATION: Vector

<400> SEQUENCE: 65

```
ctaaattgta agcgttaata ttttgttaaa attcgcgtta aatttttgtt aaatcagctc     60
```

```
atttttttaac caataggccg aaatcggcaa aatcccttat aaatcaaaag aatagaccga    120
gatagggttg agtggccgct acagggcgct cccattcgcc attcaggctg cgcaactgtt    180
gggaagggcg tttcggtgcg ggcctcttcg ctattacgcc agctggcgaa agggggatgt    240
gctgcaaggc gattaagttg ggtaacgcca gggttttccc agtcacgacg ttgtaaaacg    300
acggccagtg agcgcgacgt aatacgactc actatagggc gaattggcgg aaggccgtca    360
aggcctaggc gcgcctgcag gatcctagaa aacagctgga tatggataaa ctcggcaagc    420
atcttttgga aaggctgcca cgctatgccg tgccgatatt cattaagttc gtcgacaccg    480
tcaccatcac cggcaacaac aaagttcaga agaaagaatt ccgaaaccag cagattcccg    540
ccccagcagg acaaacaatc tactggttag agggcacgag ctacaagccc ctcactgctg    600
atgcgtgggc tcgtgtagag aatgggcgac acaagctcta atgttgaata cctcttccgt    660
atagatgtgg cataagctat agattttgct gcaatattat taaatattaa agagtttcga    720
aggtcagctg cggatgaacc agttcagagc ggctctctct tttttgccaa tagcgtgcaa    780
ccgtgaagag caattcaacc atccaatctg gctacactaa attgtatttg gcagcgcact    840
gtacgagcgc actgtacgaa actccgtcaa tttatagcag aacgcgtgcg atcgcgggcc    900
ccagcgatat gacgagaatc aggcaataat agcttaagct gaagtgtttt tagatttagt    960
tcggagtgcg cttctcaaaa gtgctgggat caacaagttt ttaacatggg ttttgattta   1020
tattgtttta tatgagcgcc tcagatatgc gctgacagcc tattaggaga aatggccggc   1080
caacttaaga aaaccgcaca accacaccgg gaggagcgtg ttgagctgta agcgttgttg   1140
agaaacgagg ggactctggg aagtcgggac ccatctcaat cttggaatac tcctgtaaga   1200
gtctcaccag agttagcgaa agctctgtca gggcgaattg ttggccgaga caaattcggg   1260
gaccgccatt gaagggcaag aatgcccaca cattatctag cttcaagttc tcccatcgat   1320
tgggattgaa ttcgtgggcg tcaggacccc aatacttgat gtccctgtgg accatgtaaa   1380
ttgaatagta aactgcggtg cccttaggaa cgaagatcgg atccttctgc tcgggaccac   1440
cacctatggg tagagttgta tctctcacag cagtacggaa gttcaatggc aataccggcg   1500
caagacgcaa gacttcattt ataacttgct tcaaataagg tgcttgcttc agaagttcga   1560
atgataaagg cctttgctcc tccttggttc caaaatgatc gaggacctcc tcacgtagtt   1620
tgttgaatac gtcaggattt ctggcaagga aatgaatagc gaagctcaac gtagcagctg   1680
ttgtatctct accagcaatg agaatgttga aaatttgatc acgtatcgtc actgggtctc   1740
gggtaacttt agccatctca agcgagaaca catagatgcc actagactct gcagcagcat   1800
ccttctctgc aatagagttc tcagcagcga aagatgtggc gtaaagagcc ttatcaacgt   1860
agtagtcaat ataggactga gcacgtttct tgtgatctcg gaattcctta gagttgaaca   1920
accagtagac tttgcttgat agggtccgtt tgaaagcgta attcagtaga aagttgtagg   1980
actccacgaa ttgttcggca gtaatctccg aaccatcacg ggctacaata catgactgat   2040
tctcagggtt caagctctcg caggactccc caaataggaa ttcagtcgct gtatccagcg   2100
taagtttgtg gaaataatgt tgaacatcaa taaattggtc cactttcatt gcacggttca   2160
tctcctttat taactccgca gcatgactgg aaatctgatc aattctgcaa acctgatctt   2220
tagtgaactg aggtctcaac atcgatcgag actgtttcca tccatttccg ctgagtgtaa   2280
atatcccttg gccaaacact tttcccactg tgtggaaacg tgctccaaga ccaaaatcat   2340
tgaatttggt tgccaggatt gtcttaatgt tttctggctc gattgtgaag atttggtatt   2400
```

```
gaaggggagc ttgtcgaaga tacgtccgtg ctttgaactt attgaagact ctgtcgtatt   2460
gaacttccag taaggtgtat gacttggccg tcttgatcat gtccatggtt ctttgtattc   2520
ccagtgggaa cgatttctca atgaagcgag gcatactaca cttgtgccta cgtgctgcat   2580
agcggtacca taggagccag ataggctcgt gtagaactaa gaaagctacg aagagcagtg   2640
gcaacaagcc agcaacagcg gataaactca ttggagttag aataatgtct ttgattaaca   2700
tatgtgtaga gttgttttg ttgttaagtc tttctttaag agcttgaccg actataaccg    2760
ttcaacggcg cattatatac tttgggtatc ggccagtgct gacaactcac acgttgcgac   2820
cccttaccca gaagcatacc cagcgcgatg tcgatcgtgt tatatcgtag acgcacaccc   2880
tgcaatgacg ggtaggctct aaatcgggat gcgaaaaaga ggttgccttg ctttttgccc   2940
tggtagatgg catgctgagc gtgcgcttgc cgcctaattt ttgtgtgtcg cctgctattt   3000
attgctgaag ctagcccgcc gcatctttcc ccaaggcttc gattgctcgt attggggcag   3060
ggattggtac tcaaccttgc agatgagact ccagcaacaa cgtcgtactg cttagcgatc   3120
gcacatgttt catcatcgtc actatacaca tcgtcatcaa ctccatggcg tgaggacttc   3180
cgagactgct gggcccttcg tttctttaat gcctcaagag atgacttcgt acccgaagag   3240
acgcctgttg taccccgttg acgcttggcg gagggggctt cgtcctcgtc agcaacccgc   3300
gtcatctgct tccttcgctg agcaagatac cttctctcct cgtaccgctg catctcctga   3360
gctcggtcat acaagatctc ttctcgctca atctctggca gcgcgtccaa cttcgccctg   3420
tcttcagcat cgagatattt gccttctaga ggatagggat tgacgacctc attgcttggc   3480
ggcgacggca gcgagatttc ctcttcggag tcggagccaa cgtcggccaa tgccagcaga   3540
tcatcatcac tgtcactcat agtaggaagg ttgaagtgtg ctgacgaatc agaatcgcga   3600
aggatgccat tgaaggcata tatattttaa tctgtacctt ttatggtaat ttaatcagat   3660
tttataggta ttcatgtgca agttgcattg aaggaactgt ttgagaaaat catcttgact   3720
gaacttttct cagatatgca ttccagcccg ccttttggta acgctgagct tcgtgcacag   3780
gatctcgtcc cttgctatag agcccgcgtc cgacgataat aacgtctgtg ccggtctcta   3840
tgacgtcgtc cacagtacga tactgctgcc ccaatccatc acctttgtcg tccaggccca   3900
ccccaggagt cataatgacc cagtcttcct ctggctttcc gactttttgc tgagcgatga   3960
aaccaaacac aaatgcgcgg ttactgcgag cgatgtctac tgtcgcttgc gagtattcgc   4020
cgtgagccag tgtgcccttc gaactcagtt ctgcaagcat gacaaggccg cgaggttcat   4080
ccgtagtttc cttcgcagcc tcttctagtc cgctcacaat tcccggccca ggaacaccgt   4140
gagcatttgt tatatcagcc cattgagcga tcttaaacac tccacctgca tattgggcct   4200
taacagtgga accgatgtct gcgaactttc ggtcttcaaa aatgagaaaa ttgtgcttcg   4260
ttgaaagctg tttcaaaccg ctgacagttg tgtcgtattc gaagtcgtca attatgtcaa   4320
tgtgggtctt aaccatacaa atgtaaggtc caatgcggtc caggatactc agtaactcag   4380
aggtagttcg cacatccaag cttgcgcaaa gatttgtttg cttgctcaca atgatgtcga   4440
atagccgggc tgctacagcc ggcagcctct ctcggcgctc ctcatagctc agcttcatat   4500
tatttctcta cagtagtgcc cgtgccctcg atcagctagg acttttcaaa ttaatcgggc   4560
tgtttgatgt aagtaagatg aagtcacgcg cgtgcaggag actgcgtccc gcgatattct   4620
gcaggcttga aaaatttacc ctaacggtag gcatcaagtg agtgagtctc agcgtcgata   4680
tgggtcaaaa aaggggaaaa ctagccgaga tcgttgcgag ctgtttcgaa aattatgccc   4740
tatggcaatt atcacgtgga gtatccgaat ttctccaggc tgtcaagcgg caattataac   4800
```

```
cgagactgag atcgagaagt atataaccgc agcagtagtg gataaataat tgcgaagtct   4860
tcccagcaga gcgggctgtt ttttggagtt ggttactgta aaatgctaaa atgactgaca   4920
acaatggagc gtctacagca ttggcaacag tgggaacagt atgctggtgc atccagttga   4980
taccccaggt tctgcgaaac tggtatgttc gggattgcga gggcgttcct cctctgatgt   5040
tctttttgtt cgccgtttcg ggattccct tcgcagtgta cttcattgat cagaattcga   5100
acactgccat catggttcaa cctcacttgt ttactttctt tagccttata ggcttttggc   5160
aaagcctgta ctatccgccc gtcagaccag cacgggccgt cacatgtatg gttgcgtcgc   5220
tgtataagaa atcttacaac tgaagactac acagcgtatc cgctccgata tcggcgatca   5280
cgtggataca tttccccaga atgcgtcaac cttgcatgct cgatattgac tcaagccgag   5340
aggtgtataa caacaccgac gatagcgaat tacttgtgga actgatttgc cgtatcgagt   5400
aaatcgcgat tgtggccctc tttaggcctt gtacccattt gtgcatcgta tttgttagta   5460
tgcatcatag aattatgtga acttagaaaa gtccgtatga aatgagcctc agattatgga   5520
ttgatcgctt gttatttgta cagcggaatt gacttatagt atgtcggcca cggttttaga   5580
ttgcctaggg gccgtttct tgatggattc gcatcggaac tccgaattct tgattgctct   5640
ccatcgcgca ggaggccgtt ctttttttga caaagtccca ttttagggcg caggtccaaa   5700
aaataagcgg ccgcttaatt aactggcctc atgggccttc cgctcactgc ccgctttcca   5760
gtcgggaaac ctgtcgtgcc agctgcatta acatggtcat agctgtttcc ttgcgtattg   5820
ggcgctctcc gcttcctcgc tcactgactc gctgcgctcg gtcgttcggg taaagcctgg   5880
ggtgcctaat gagcaaaagg ccagcaaaag gccaggaacc gtaaaaaggc cgcgttgctg   5940
gcgtttttcc ataggctccg cccccctgac gagcatcaca aaaatcgacg ctcaagtcag   6000
aggtggcgaa acccgacagg actataaaga taccaggcgt ttccccctgg aagctccctc   6060
gtgcgctctc ctgttccgac cctgccgctt accggatacc tgtccgcctt tctcccttcg   6120
ggaagcgtgg cgctttctca tagctcacgc tgtaggtatc tcagttcggt gtaggtcgtt   6180
cgctccaagc tgggctgtgt gcacgaaccc cccgttcagc ccgaccgctg cgccttatcc   6240
ggtaactatc gtcttgagtc caacccggta agacacgact tatcgccact ggcagcagcc   6300
actggtaaca ggattagcag agcgaggtat gtaggcggtg ctacagagtt cttgaagtgg   6360
tggcctaact acggctacac tagaagaaca gtatttggta tctgcgctct gctgaagcca   6420
gttaccttcg gaaaaagagt tggtagctct tgatccggca aacaaaccac cgctggtagc   6480
ggtggttttt ttgtttgcaa gcagcagatt acgcgcagaa aaaaaggatc tcaagaagat   6540
cctttgatct tttctacggg gtctgacgct cagtggaacg aaaactcacg ttaagggatt   6600
ttggtcatga gattatcaaa aaggatcttc acctagatcc ttttaaatta aaaatgaagt   6660
tttaaatcaa tctaaagtat atatgagtaa acttggtctg acagttacca atgcttaatc   6720
agtgaggcac ctatctcagc gatctgtcta tttcgttcat ccatagttgc ctgactcccc   6780
gtcgtgtaga taactacgat acgggagggc ttaccatctg gccccagtgc tgcaatgata   6840
ccgcgagaac cacgctcacc ggctccagat ttatcagcaa taaaccagcc agccggaagg   6900
gccgagcgca gaagtggtcc tgcaacttta tccgcctcca tccagtctat taattgttgc   6960
cgggaagcta gagtaagtag ttcgccagtt aatagtttgc gcaacgttgt tgccattgct   7020
acaggcatcg tggtgtcacg ctcgtcgttt ggtatggctt cattcagctc cggttcccaa   7080
cgatcaaggc gagttacatg atcccccatg ttgtgcaaaa aagcggttag ctccttcggt   7140
```

```
cctccgatcg ttgtcagaag taagttggcc gcagtgttat cactcatggt tatggcagca   7200

ctgcataatt ctcttactgt catgccatcc gtaagatgct tttctgtgac tggtgagtac   7260

tcaaccaagt cattctgaga atagtgtatg cggcgaccga gttgctcttg cccggcgtca   7320

atacgggata ataccgcgcc acatagcaga actttaaaag tgctcatcat tggaaaacgt   7380

tcttcggggc gaaaactctc aaggatctta ccgctgttga gatccagttc gatgtaaccc   7440

actcgtgcac ccaactgatc ttcagcatct tttactttca ccagcgtttc tgggtgagca   7500

aaaacaggaa ggcaaaatgc cgcaaaaaag ggaataaggg cgacacggaa atgttgaata   7560

ctcatactct tcctttttca atattattga agcatttatc agggttattg tctcatgagc   7620

ggatacatat ttgaatgtat ttagaaaaat aaacaaatag gggttccgcg cacatttccc   7680

cgaaaagtgc cac                                                      7693
```

<210> SEQ ID NO 66
<211> LENGTH: 7465
<212> TYPE: DNA
<213> ORGANISM: Artificial
<220> FEATURE:
<223> OTHER INFORMATION: Vector

<400> SEQUENCE: 66

```
ctaaattgta agcgttaata ttttgttaaa attcgcgtta aatttttgtt aaatcagctc     60

atttttaac caataggccg aaatcggcaa aatcccttat aaatcaaaag aatagaccga    120

gatagggttg agtggccgct acagggcgct cccattcgcc attcaggctg cgcaactgtt    180

gggaagggcg tttcggtgcg ggcctcttcg ctattacgcc agctggcgaa agggggatgt    240

gctgcaaggc gattaagttg ggtaacgcca gggttttccc agtcacgacg ttgtaaaacg    300

acggccagtg agcgcgacgt aatacgactc actatagggc gaattggcgg aaggccgtca    360

aggcctaggc gcgcctgcag gatcctagaa aacagctgga tatggataaa ctcggcaagc    420

atcttttgga aaggctgcca cgctatgccg tgccgatatt cattaagttc gtcgacaccg    480

tcaccatcac cggcaacaac aaagttcaga agaaagaatt ccgaaaccag cagattcccg    540

ccccagcagg acaaacaatc tactggttag agggcacgag ctacaagccc ctcactgctg    600

atgcgtgggc tcgtgtagag aatgggcgac acaagctcta atgttgaata cctcttccgt    660

atagatgtgg cataagctat agattttgct gcaatattat taaatattaa agagtttcga    720

aggtcagctg cggatgaacc agttcagagc ggctctctct tttttgccaa tagcgtgcaa    780

ccgtgaagag caattcaacc atccaatctg gctacactaa attgtatttg gcagcgcact    840

gtacgagcgc actgtacgaa actccgtcaa tttatagcag aacgcgtgcg atcgcgggcc    900

ccagcgatat gacgagaatc aggcaataat agcttaagct gaagtgtttt tagatttagt    960

tcggagtgcg cttctcaaaa gtgctgggat caacaagttt ttaacatggg ttttgattta   1020

tattgtttta tatgagcgcc tcagatatgc gctgacagcc tattaggaga aatggccggc   1080

cctaagaact caccgctaag gccggacctt tgacaggtat atcttcagtt tcctcgtcac   1140

tcttggtcaa aagaccaaag tcatggctgg cgatttcctc gatgctttcc tcaagaattt   1200

tcaaggagtt gtggctttcc aactccattt gaaccttctt cgaggcttcg tggaatttcg   1260

gatttccaat tatcgaatca acagcttctt tgatttgctc cactgtaggc aagccagttt   1320

tcaaatcaat tgccacgcca gcggcctcag ctctcgatgc caccattggc ttgtcttcag   1380

agtcaccagc aataacaact ggaacagagt ggcttaagct gtgctgaagt ccgccatatc   1440

caccattgta gacaagagca tcaacgtgag gaagtagagc atcgtagttg aagtagtcga   1500
```

-continued

```
tcacgcgagc attctcagga accacaacat catccggtag cttggcaccg cggcggccca   1560
atatggctac tgttaaagtg tcaggctcgt ccttcaaggc ctcaagagta ggcacaataa   1620
gatgcttgta actgacagca aaagttcctt gagtgaccat gatgactcgc ttggcactca   1680
gaacatcccc ccaccaggaa ggaggggtga attgagttcg gtgcttgggc gttgagccgg   1740
cgaatttgaa gttgctaggc agatggtctc tgctgaactc aagagaaggc gggcacagct   1800
gcaggaactt gtctgcagca atgtaactgt gctcccagat aaatttggga tcttcagtgc   1860
aacctaactc tcggcagatt tccttgtgct tagcagtggc tttaacgaaa atttggtgct   1920
caagagcgtg gttcatagcg agtttctttg catgtgcttc ggggctcctg tcgttgtcaa   1980
gtcctaaggt atgatcactg cggatcaaaa gaggcaaaac ccctaaacaa atccagccag   2040
cgggtttgaa accaggagca ccgaggctga tagggtgtgc accgaaaaac agcacttcac   2100
tgacaagaac gacagggcga ccgcttgcgc tgagcttttt gaaagccctc tgaatagcgg   2160
caaactgctc aggaagagta gctaccatca tgtgctccac atcttgaact gtacgatcga   2220
agcttggggc catgtcttta cggcccggga ccagatcgtc taaggtgtgg tcatcaaaat   2280
ctgcgttccc ttctaaagga acaaagtctg cacccacatc tcgaactttt tgttcaaacg   2340
ctctgcctgt cacaacagta gcttcgtatc cgtcgtccgt aaggccgtgt accagactca   2400
aaacgggcat tatatggcct gaaagaggca agccgcaagc gagaatcagg ggtttgtgtg   2460
atgaagggct catatgtgta gagttgtttt tgttgttaag tctttcttta agagcttgac   2520
cgactataac cgttcaacgg cgcattatat actttgggta tcggccagtg ctgacaactc   2580
acacgttgcg accccttacc cagaagcata cccagcgcga tgtcgatcgt gttatatcgt   2640
agacgcacac cctgcaatga cgggtaggct ctaaatcggg atgcgaaaaa gaggttgcct   2700
tgctttttgc cctggtagat ggcatgctga gcgtgcgctt gccgcctaat ttttgtgtgt   2760
cgcctgctat ttattgctga agctagcccg ccgcatcttt ccccaaggct tcgattgctc   2820
gtattggggc agggattggt actcaacctt gcagatgaga ctccagcaac aacgtcgtac   2880
tgcttagcga tcgcacatgt ttcatcatcg tcactataca catcgtcatc aactccatgg   2940
cgtgaggact tccgagactg ctgggccctt cgtttcttta atgcctcaag agatgacttc   3000
gtacccgaag agacgcctgt tgtaccccgt tgacgcttgg cggagggggc ttcgtcctcg   3060
tcagcaaccc gcgtcatctg cttccttcgc tgagcaagat accttctctc ctcgtaccgc   3120
tgcatctcct gagctcggtc atacaagatc tcttctcgct caatctctgg cagcgcgtcc   3180
aacttcgccc tgtcttcagc atcgagatat ttgccttcta gaggataggg attgacgacc   3240
tcattgcttg gcggcgacgg cagcgagatt tcctcttcgg agtcggagcc aacgtcggcc   3300
aatgccagca gatcatcatc actgtcactc atagtaggaa ggttgaagtg tgctgacgaa   3360
tcagaatcgc gaaggatgcc attgaaggca tatatatttt aatctgtacc ttttatggta   3420
atttaatcag attttatagg tattcatgtg caagttgcat tgaaggaact gtttgagaaa   3480
atcatcttga ctgaactttt ctcagatatg cattccagcc cgccttttgg taacgctgag   3540
cttcgtgcac aggatctcgt cccttgctat agagcccgcg tccgacgata ataacgtctg   3600
tgccggtctc tatgacgtcg tccacagtac gatactgctg ccccaatcca tcacctttgt   3660
cgtccaggcc caccccagga gtcataatga cccagtcttc ctctggcttt ccgacttttt   3720
gctgagcgat gaaaccaaac acaaatgcgc ggttactgcg agcgatgtct actgtcgctt   3780
gcgagtattc gccgtgagcc agtgtgccct tcgaactcag ttctgcaagc atgacaaggc   3840
```

-continued

```
cgcgaggttc atccgtagtt tccttcgcag cctcttctag tccgctcaca attcccggcc   3900
caggaacacc gtgagcattt gttatatcag cccattgagc gatcttaaac actccacctg   3960
catattgggc cttaacagtg gaaccgatgt ctgcgaactt tcggtcttca aaaatgagaa   4020
aattgtgctt cgttgaaagc tgtttcaaac cgctgacagt tgtgtcgtat tcgaagtcgt   4080
caattatgtc aatgtgggtc ttaaccatac aaatgtaagg tccaatgcgg tccaggatac   4140
tcagtaactc agaggtagtt cgcacatcca agcttgcgca aagatttgtt tgcttgctca   4200
caatgatgtc gaatagccgg gctgctacag ccggcagcct ctctcggcgc tcctcatagc   4260
tcagcttcat attatttctc tacagtagtg cccgtgccct cgatcagcta ggacttttca   4320
aattaatcgg gctgtttgat gtaagtaaga tgaagtcacg cgcgtgcagg agactgcgtc   4380
ccgcgatatt ctgcaggctt gaaaaattta ccctaacggt aggcatcaag tgagtgagtc   4440
tcagcgtcga tatgggtcaa aaaaggggaa aactagccga gatcgttgcg agctgtttcg   4500
aaaattatgc cctatggcaa ttatcacgtg gagtatccga atttctccag gctgtcaagc   4560
ggcaattata accgagactg agatcgagaa gtatataacc gcagcagtag tggataaata   4620
attgcgaagt cttcccagca gagcgggctg tttttggag ttggttactg taaaatgcta   4680
aaatgactga caacaatgga gcgtctacag cattggcaac agtgggaaca gtatgctggt   4740
gcatccagtt gataccccag gttctgcgaa actggtatgt tcgggattgc gagggcgttc   4800
ctcctctgat gttcttttg ttcgccgttt cggggattcc cttcgcagtg tacttcattg   4860
atcagaattc gaacactgcc atcatggttc aacctcactt gtttactttc tttagcctta   4920
taggcttttg gcaaagcctg tactatccgc ccgtcagacc agcacgggcc gtcacatgta   4980
tggttgcgtc gctgtataag aaatcttaca actgaagact acacagcgta tccgctccga   5040
tatcggcgat cacgtggata catttcccca gaatgcgtca accttgcatg ctcgatattg   5100
actcaagccg agaggtgtat aacaacaccg acgatagcga attacttgtg gaactgattt   5160
gccgtatcga gtaaatcgcg attgtggccc tctttaggcc ttgtacccat ttgtgcatcg   5220
tatttgttag tatgcatcat agaattatgt gaacttagaa aagtccgtat gaaatgagcc   5280
tcagattatg gattgatcgc ttgttatttg tacagcggaa ttgacttata gtatgtcggc   5340
cacggtttta gattgcctag gggccgtttt cttgatggat tcgcatcgga actccgaatt   5400
cttgattgct ctccatcgcg caggaggccg ttcttttttt gacaaagtcc catttttaggg   5460
cgcaggtcca aaaaataagc ggccgcttaa ttaactggcc tcatgggcct tccgctcact   5520
gcccgctttc cagtcgggaa acctgtcgtg ccagctgcat taacatggtc atagctgttt   5580
ccttgcgtat tgggcgctct ccgcttcctc gctcactgac tcgctgcgct cggtcgttcg   5640
ggtaaagcct ggggtgccta atgagcaaaa ggccagcaaa aggccaggaa ccgtaaaaag   5700
gccgcgttgc tggcgttttt ccataggctc cgcccccctg acgagcatca caaaaatcga   5760
cgctcaagtc agaggtggcg aaacccgaca ggactataaa gataccaggc gtttccccct   5820
ggaagctccc tcgtgcgctc tcctgttccg accctgccgc ttaccggata cctgtccgcc   5880
tttctccctt cgggaagcgt ggcgctttct catagctcac gctgtaggta tctcagttcg   5940
gtgtaggtcg ttcgctccaa gctgggctgt gtgcacgaac cccccgttca gcccgaccgc   6000
tgcgccttat ccggtaacta tcgtcttgag tccaacccgg taagacacga cttatcgcca   6060
ctggcagcag ccactggtaa caggattagc agagcgaggt atgtaggcgg tgctacagag   6120
ttcttgaagt ggtggcctaa ctacggctac actagaagaa cagtatttgg tatctgcgct   6180
ctgctgaagc cagttacctt cggaaaaaga gttggtagct cttgatccgg caaacaaacc   6240
```

```
accgctggta gcggtggttt ttttgtttgc aagcagcaga ttacgcgcag aaaaaaagga   6300

tctcaagaag atcctttgat cttttctacg gggtctgacg ctcagtggaa cgaaaactca   6360

cgttaaggga ttttggtcat gagattatca aaaaggatct tcacctagat ccttttaaat   6420

taaaaatgaa gttttaaatc aatctaaagt atatatgagt aaacttggtc tgacagttac   6480

caatgcttaa tcagtgaggc acctatctca gcgatctgtc tatttcgttc atccatagtt   6540

gcctgactcc ccgtcgtgta gataactacg atacgggagg gcttaccatc tggccccagt   6600

gctgcaatga taccgcgaga cccacgctca ccggctccag atttatcagc aataaaccag   6660

ccagccggaa gggccgagcg cagaagtggt cctgcaactt tatccgcctc catccagtct   6720

attaattgtt gccgggaagc tagagtaagt agttcgccag ttaatagttt gcgcaacgtt   6780

gttgccattg ctacaggcat cgtggtgtca cgctcgtcgt ttggtatggc ttcattcagc   6840

tccggttccc aacgatcaag gcgagttaca tgatccccca tgttgtgcaa aaaagcggtt   6900

agctccttcg gtcctccgat cgttgtcaga agtaagttgg ccgcagtgtt atcactcatg   6960

gttatggcag cactgcataa ttctcttact gtcatgccat ccgtaagatg cttttctgtg   7020

actggtgagt actcaaccaa gtcattctga gaatagtgta tgcggcgacc gagttgctct   7080

tgcccggcgt caatacggga taataccgcg ccacatagca gaactttaaa agtgctcatc   7140

attggaaaac gttcttcggg gcgaaaactc tcaaggatct taccgctgtt gagatccagt   7200

tcgatgtaac ccactcgtgc acccaactga tcttcagcat cttttacttt caccagcgtt   7260

tctgggtgag caaaaacagg aaggcaaaat gccgcaaaaa agggaataag ggcgacacgg   7320

aaatgttgaa tactcatact cttccttttt caatattatt gaagcattta tcagggttat   7380

tgtctcatga gcggatacat atttgaatgt atttagaaaa ataaacaaat aggggttccg   7440

cgcacatttc cccgaaaagt gccac                                         7465
```

<210> SEQ ID NO 67
<211> LENGTH: 6856
<212> TYPE: DNA
<213> ORGANISM: Artificial
<220> FEATURE:
<223> OTHER INFORMATION: Vector

<400> SEQUENCE: 67

```
ctaaattgta agcgttaata ttttgttaaa attcgcgtta aatttttgtt aaatcagctc     60

atttttaac caataggccg aaatcggcaa aatcccttat aaatcaaaag aatagaccga    120

gatagggttg agtggccgct acagggcgct cccattcgcc attcaggctg cgcaactgtt    180

gggaagggcg tttcggtgcg ggcctcttcg ctattacgcc agctggcgaa agggggatgt    240

gctgcaaggc gattaagttg ggtaacgcca gggttttccc agtcacgacg ttgtaaaacg    300

acggccagtg agcgcgacgt aatacgactc actatagggc gaattggcgg aaggccgtca    360

aggcctaggc gcgcctgcag gatcctagaa aacagctgga tatggataaa ctcggcaagc    420

atcttttgga aaggctgcca cgctatgccg tgccgatatt cattaagttc gtcgacaccg    480

tcaccatcac cggcaacaac aaagttcaga agaaagaatt ccgaaaccag cagattcccg    540

ccccagcagg acaaacaatc tactggttag agggcacgag ctacaagccc ctcactgctg    600

atgcgtgggc tcgtgtagag aatgggcgac acaagctcta atgttgaata cctcttccgt    660

atagatgtgg cataagctat agattttgct gcaatattat taaatattaa agagtttcga    720

aggtcagctg cggatgaacc agttcagagc ggctctctct tttttgccaa tagcgtgcaa    780
```

```
ccgtgaagag caattcaacc atccaatctg gctacactaa attgtatttg gcagcgcact    840

gtacgagcgc actgtacgaa actccgtcaa tttatagcag aacgcgtgcg atcgcgggcc    900

ccagcgatat gacgagaatc aggcaataat agcttaagct gaagtgtttt tagatttagt    960

tcggagtgcg cttctcaaaa gtgctgggat caacaagttt ttaacatggg ttttgattta   1020

tattgtttta tatgagcgcc tcagatatgc gctgacagcc tattaggaga aatggccggc   1080

ctacctagac cttctggtta gcggtattga cgttcatttc aactggaaga aggaattcca   1140

gttcctctcc ttcagcctcg tcgggatcct cctctggaat atgcttgagg attcgcgcag   1200

ggactcctcc caccacagta cgaggaggaa catcttctcg aacgacagca ccagccgcaa   1260

ttgttgagcc atctccaatc gtaacacccg gcaggacagt cacattcgca ccaatccata   1320

cattattccc caccttgata ggaagagcat acacaattct cctcgcacgt ttctcggggc   1380

taataggatg agtcgcagtc acgaacgttg tattgggccc tacaatcacc tcatcaccaa   1440

agattattgg agccgagtcc aagaagcaaa cgttgaagtt ggcgtaaaag tgctcgccta   1500

cgctgatgtt gaatccaaaa tcaactgaga atggagcggt cagccagaca atatcctttg   1560

tttgaccaaa agtgtctttg agaatctcga ccttcttgat ataagcagcg tgatttgact   1620

caaaagtacg actttcactt gcaatggtat tgaactccct aactttctca ctagtagcca   1680

gggctctaaa cataagatct ggatcgtatg gattgtaagg aactcctgag accatcttct   1740

catagttttc attgccaggg gtgtttttga ggtttttttt ggcccaagag accatttcct   1800

ggtcaatttc ttttctagga gtcattcctt tgttttgagg gtccttcgag gagtttacaa   1860

ccatatgtgt agagttgttt ttgttgttaa gtctttcttt aagagcttga ccgactataa   1920

ccgttcaacg gcgcattata tactttgggt atcggccagt gctgacaact cacacgttgc   1980

gaccccttac ccagaagcat acccagcgcg atgtcgatcg tgttatatcg tagacgcaca   2040

ccctgcaatg acgggtaggc tctaaatcgg gatgcgaaaa agaggttgcc ttgctttttg   2100

ccctggtaga tggcatgctg agcgtgcgct tgccgcctaa tttttgtgtg tcgcctgcta   2160

tttattgctg aagctagccc gccgcatctt tccccaaggc ttcgattgct cgtattgggg   2220

cagggattgg tactcaacct tgcagatgag actccagcaa caacgtcgta ctgcttagcg   2280

atcgcacatg tttcatcatc gtcactatac acatcgtcat caactccatg gcgtgaggac   2340

ttccgagact gctgggccct tcgtttcttt aatgcctcaa gagatgactt cgtacccgaa   2400

gagacgcctg ttgtaccccg ttgacgcttg gcggaggggg cttcgtcctc gtcagcaacc   2460

cgcgtcatct gcttccttcg ctgagcaaga taccttctct cctcgtaccg ctgcatctcc   2520

tgagctcggt catacaagat ctcttctcgc tcaatctctg gcagcgcgtc caacttcgcc   2580

ctgtcttcag catcgagata tttgccttct agaggatagg gattgacgac ctcattgctt   2640

ggcggcgacg gcagcgagat ttcctcttcg gagtcggagc caacgtcggc caatgccagc   2700

agatcatcat cactgtcact catagtagga aggttgaagt gtgctgacga atcagaatcg   2760

cgaaggatgc cattgaaggc atatatattt taatctgtac cttttatggt aatttaatca   2820

gattttatag gtattcatgt gcaagttgca ttgaaggaac tgtttgagaa aatcatcttg   2880

actgaacttt tctcagatat gcattccagc ccgccttttg gtaacgctga gcttcgtgca   2940

caggatctcg tcccttgcta tagagcccgc gtccgacgat aataacgtct gtgccggtct   3000

ctatgacgtc gtccacagta cgatactgct gccccaatcc atcacctttg tcgtccaggc   3060

ccaccccagg agtcataatg acccagtctt cctctggctt tccgactttt tgctgagcga   3120

tgaaaccaaa cacaaatgcg cggttactgc gagcgatgtc tactgtcgct tgcgagtatt   3180
```

```
cgccgtgagc cagtgtgccc ttcgaactca gttctgcaag catgacaagg ccgcgaggtt   3240
catccgtagt ttccttcgca gcctcttcta gtccgctcac aattcccggc ccaggaacac   3300
cgtgagcatt tgttatatca gcccattgag cgatcttaaa cactccacct gcatattggg   3360
ccttaacagt ggaaccgatg tctgcgaact ttcggtcttc aaaaatgaga aaattgtgct   3420
tcgttgaaag ctgtttcaaa ccgctgacag ttgtgtcgta ttcgaagtcg tcaattatgt   3480
caatgtgggt cttaaccata caaatgtaag gtccaatgcg gtccaggata ctcagtaact   3540
cagaggtagt tcgcacatcc aagcttgcgc aaagatttgt ttgcttgctc acaatgatgt   3600
cgaatagccg ggctgctaca gccggcagcc tctctcggcg ctcctcatag ctcagcttca   3660
tattatttct ctacagtagt gcccgtgccc tcgatcagct aggacttttc aaattaatcg   3720
ggctgtttga tgtaagtaag atgaagtcac gcgcgtgcag gagactgcgt cccgcgatat   3780
tctgcaggct tgaaaaattt accctaacgg taggcatcaa gtgagtgagt ctcagcgtcg   3840
atatgggtca aaaaagggga aaactagccg agatcgttgc gagctgtttc gaaaattatg   3900
ccctatggca attatcacgt ggagtatccg aatttctcca ggctgtcaag cggcaattat   3960
aaccgagact gagatcgaga agtatataac cgcagcagta gtggataaat aattgcgaag   4020
tcttcccagc agagcgggct gttttttgga gttggttact gtaaaatgct aaaatgactg   4080
acaacaatgg agcgtctaca gcattggcaa cagtgggaac agtatgctgg tgcatccagt   4140
tgatacccca ggttctgcga aactggtatg ttcgggattg cgagggcgtt cctcctctga   4200
tgttcttttt gttcgccgtt tcggggattc ccttcgcagt gtacttcatt gatcagaatt   4260
cgaacactgc catcatggtt caacctcact tgtttacttt ctttagcctt ataggctttt   4320
ggcaaagcct gtactatccg cccgtcagac cagcacgggc cgtcacatgt atggttgcgt   4380
cgctgtataa gaaatcttac aactgaagac tacacagcgt atccgctccg atatcggcga   4440
tcacgtggat acatttcccc agaatgcgtc aaccttgcat gctcgatatt gactcaagcc   4500
gagaggtgta taacaacacc gacgatagcg aattacttgt ggaactgatt tgccgtatcg   4560
agtaaatcgc gattgtggcc ctctttaggc cttgtaccca tttgtgcatc gtatttgtta   4620
gtatgcatca tagaattatg tgaacttaga aaagtccgta tgaaatgagc ctcagattat   4680
ggattgatcg cttgttattt gtacagcgga attgacttat agtatgtcgg ccacggtttt   4740
agattgccta ggggccgttt tcttgatgga ttcgcatcgg aactccgaat tcttgattgc   4800
tctccatcgc gcaggaggcc gttctttttt tgacaaagtc ccattttagg gcgcaggtcc   4860
aaaaaataag cggccgctta attaactggc ctcatgggcc ttccgctcac tgcccgcttt   4920
ccagtcggga aacctgtcgt gccagctgca ttaacatggt catagctgtt tccttgcgta   4980
ttgggcgctc tccgcttcct cgctcactga ctcgctgcgc tcggtcgttc gggtaaagcc   5040
tggggtgcct aatgagcaaa aggccagcaa aaggccagga accgtaaaaa ggccgcgttg   5100
ctggcgtttt tccataggct ccgcccccct gacgagcatc acaaaaatcg acgctcaagt   5160
cagaggtggc gaaacccgac aggactataa agataccagg cgtttccccc tggaagctcc   5220
ctcgtgcgct ctcctgttcc gaccctgccg cttaccggat acctgtccgc ctttctccct   5280
tcgggaagcg tggcgctttc tcatagctca cgctgtaggt atctcagttc ggtgtaggtc   5340
gttcgctcca agctgggctg tgtgcacgaa ccccccgttc agcccgaccg ctgcgcctta   5400
tccggtaact atcgtcttga gtccaacccg gtaagacacg acttatcgcc actggcagca   5460
gccactggta acaggattag cagagcgagg tatgtaggcg gtgctacaga gttcttgaag   5520
```

```
tggtggccta actacggcta cactagaaga acagtatttg gtatctgcgc tctgctgaag   5580
ccagttacct tcggaaaaag agttggtagc tcttgatccg gcaaacaaac caccgctggt   5640
agcggtggtt tttttgtttg caagcagcag attacgcgca gaaaaaaagg atctcaagaa   5700
gatcctttga tcttttctac ggggtctgac gctcagtgga acgaaaactc acgttaaggg   5760
attttggtca tgagattatc aaaaaggatc ttcacctaga tccttttaaa ttaaaaatga   5820
agttttaaat caatctaaag tatatatgag taaacttggt ctgacagtta ccaatgctta   5880
atcagtgagg cacctatctc agcgatctgt ctatttcgtt catccatagt tgcctgactc   5940
cccgtcgtgt agataactac gatacgggag ggcttaccat ctggccccag tgctgcaatg   6000
ataccgcgag aaccacgctc accggctcca gatttatcag caataaacca gccagccgga   6060
agggccgagc gcagaagtgg tcctgcaact ttatccgcct ccatccagtc tattaattgt   6120
tgccgggaag ctagagtaag tagttcgcca gttaatagtt tgcgcaacgt tgttgccatt   6180
gctacaggca tcgtggtgtc acgctcgtcg tttggtatgg cttcattcag ctccggttcc   6240
caacgatcaa ggcgagttac atgatccccc atgttgtgca aaaaagcggt tagctccttc   6300
ggtcctccga tcgttgtcag aagtaagttg gccgcagtgt tatcactcat ggttatggca   6360
gcactgcata attctcttac tgtcatgcca tccgtaagat gcttttctgt gactggtgag   6420
tactcaacca agtcattctg agaatagtgt atgcggcgac cgagttgctc ttgcccggcg   6480
tcaatacggg ataataccgc gccacatagc agaactttaa aagtgctcat cattggaaaa   6540
cgttcttcgg ggcgaaaact ctcaaggatc ttaccgctgt tgagatccag ttcgatgtaa   6600
cccactcgtg cacccaactg atcttcagca tcttttactt tcaccagcgt ttctgggtga   6660
gcaaaaacag gaaggcaaaa tgccgcaaaa aagggaataa gggcgacacg gaaatgttga   6720
atactcatac tcttcctttt tcaatattat tgaagcattt atcagggtta ttgtctcatg   6780
agcggataca tatttgaatg tatttagaaa aataaacaaa taggggttcc gcgcacattt   6840
ccccgaaaag tgccac                                                   6856
```

```
<210> SEQ ID NO 68
<211> LENGTH: 9973
<212> TYPE: DNA
<213> ORGANISM: Artificial
<220> FEATURE:
<223> OTHER INFORMATION: Vector

<400> SEQUENCE: 68
```

```
ctaaattgta agcgttaata ttttgttaaa attcgcgtta aatttttgtt aaatcagctc     60
atttttaac caataggccg aaatcggcaa aatcccttat aaatcaaaag aatagaccga     120
gatagggttg agtggccgct acagggcgct cccattcgcc attcaggctg cgcaactgtt   180
gggaagggcg tttcggtgcg ggcctcttcg ctattacgcc agctggcgaa agggggatgt   240
gctgcaaggc gattaagttg ggtaacgcca gggttttccc agtcacgacg ttgtaaaacg   300
acggccagtg agcgcgacgt aatacgactc actatagggc gaattggcgg aaggccgtca   360
aggcctaggc gcgcctgcag gatcctagaa aacagctgga tatggataaa ctcggcaagc   420
atcttttgga aaggctgcca cgctatgccg tgccgatatt cattaagttc gtcgacaccg   480
tcaccatcac cggcaacaac aaagttcaga agaaagaatt ccgaaaccag cagattcccg   540
ccccagcagg acaaacaatc tactggttag agggcacgag ctacaagccc ctcactgctg   600
atgcgtgggc tcgtgtagag aatgggcgac acaagctcta atgttgaata cctcttccgt   660
atagatgtgg cataagctat agattttgct gcaatattat taaatattaa agagtttcga   720
```

```
aggtcagctg cggatgaacc agttcagagc ggctctctct tttttgccaa tagcgtgcaa    780
ccgtgaagag caattcaacc atccaatctg gctacactaa attgtatttg gcagcgcact    840
gtacgagcgc actgtacgaa actccgtcaa tttatagcag aacgcgtgcg atcgcgggcc    900
ccagcgatat gacgagaatc aggcaataat agcttaagct gaagtgtttt tagatttagt    960
tcggagtgcg cttctcaaaa gtgctgggat caacaagttt ttaacatggg ttttgattta   1020
tattgtttta tatgagcgcc tcagatatgc gctgacagcc tattaggaga aatggccggc   1080
ctcaaatctc tccgagacct tgcaagttca ccaattcagc gtaccatcca ttgagttcaa   1140
ggaggctctg atggtcgccc tgctccacga tgcgccctcc tgagaacaca tatatgacat   1200
ctgctttctg aattgttgat aatctatgcg caacggcgat tgtagtacgg cccttcgctg   1260
ctgcgtcgag tgctgcttga actactttct cagattcgga atccagagct gaggtggcct   1320
catcgaggag gagtaccttt ggatttctga tcagggccct tgcaattgca attcgctgct   1380
tttgcccccc agatagcaac gatcccctag atccgctgag cgtttcgtag ccatcaggca   1440
acgacatgat gaattcgtga atgttcgctt tgcgagcggc atcctcaatc atctcctgcg   1500
ttacttcaga ctcagggcca gaccatccca ttagaatatt ctcacgtagc gtgcctgaat   1560
aaagcattgg ttcttgctgg actaaagcaa tgtgtgatct caatgcattc aggttatatt   1620
cgcgtaaatc tttcccatcg aaaagtactt gacctgctaa tggatcataa aatctttcca   1680
ccagtccaat agtagtagac ttaccgcatc cactggctcc aactagagcg atgtattggc   1740
ccttttttgac tgttaagttg agatcttgta aaactggtac ttgaggtcga gtaggatatc   1800
ggaaattcac atgacggaac tcaatatctc ctctcaccga ctcctcggga gcaacgtaac   1860
cttcctcact ccatacatct atagaaggag tggcagtcaa gattctgtaa atgttacgcg   1920
ctgcatcttt ggctgagttc atgtttggag catagctgaa aatttggcca gcggcttgag   1980
aacctgtaat aatagccatg aagacagtca tatatcctgc gaccgaagct tcacctcgtc   2040
tcattacagt gcttccccac caaaaaacga gggctaccac ccagggtgtc attccttccg   2100
agagtgcgta gtacaatgct gagcgggcaa tggcaattct ggagctgaaa atctgagagt   2160
ctactgtctt tgtgtatttt acgaccacgt ctaactcacg agttaaggac tggactgtgc   2220
ggacagcact tgtatactca gatgccatgg agccacttcg ttcgtaaact tctctcgcac   2280
gatccgataa ttgggtaaga acccagactc tgacgaagcc acacaccaac atgacaggaa   2340
caacagacgt agccacgagt ccaattctcc aattgaaagg tataccagta actatgccgc   2400
caatcaaggt caccagactc tgttgaattt gaccgagggt ggccccactc aaaccctcga   2460
tcattttagc ttccttcgcc aaaattgagg ttagcgcacc cggcgtgttg tttttgtggt   2520
cgaagaatgc aatatccatt cgcatcaatt ggcggaacaa agctaatctg atatttttga   2580
ccaacttatc agatgcaagt gataaagcag ctatagtgat aaaagccgtc atgaatgaaa   2640
tgcagcctac gaaaaaatac caccatccca tgatattcac cacatgccgc atttttccgt   2700
attcactggg aggtagaacc atgcttccag tggtttggcc agttattatt gccattgcag   2760
gatagcaata gcccaaaata atggaggcta aactaccaat gagaatgtaa ccccattctt   2820
tcctattcag cccccaaacc agtttggtat tggtcatcaa cgtgctatgt ggggggttgc   2880
gcacaccagg gatgtcattt tcttgatatt caggaggttg agtggtctga gtacctgcac   2940
tgtgaacact caatgtgctc acatccttgg gattgaactt ttcgttcagt gagtccagag   3000
gcgaaatgtc tagagcttca atatcgagga cctcaacgtt agtgctcttt gctttagtta   3060
```

```
ctctttgagc atcaaccaaa gctttataag gcccttctcg ctgtatgagc tcattgtgag   3120
taccctgctc tatgacgtta cctttagaca tgacaactat cttgttggca tccttgatcg   3180
tagagagtct gtgtgcaacg actatagtgg tacgaccttc ggccgctttg tcgagcgcat   3240
cttgaacgat accttcagat ttggtatcca gagcagaagt cgcttcatcg agcagcagaa   3300
ttttagggtc tgagacgatt gctcttgcta ttgcaatgcg ttgtttctga ccaccgctga   3360
gaagaaatcc tcgatctcca acattggttt ggatgccttc tgagagagtc tgaatgaaat   3420
cccaggcatt ggcatcttta caagcttgaa tgattttagc ttccttaaca tgctcgtcag   3480
cgaactcaat gtcagtgcca atcaaaccat agctgatatt ctcatatatt gactctgaaa   3540
agagtactgg ttcctgctga acataaccaa tttgttgacg gagccatctt gtgttcaggt   3600
cgctaatctc ctggccatcc agagtaacgc ttccttcgag aggtaaatag aacctctcaa   3660
gaatacctac aattgtagac ttccctgatc ccgaggcacc taccagtgcc acagtagatc   3720
cagcaggaac ttcaaggcta aaatcggaga ggaccaaaac gtctgggcga ctaggatatc   3780
ggaacttgac atttttgagc tcaattctgc caacggcctt agtttggggg acaattcctt   3840
tatctatgga ctggccatcg atgactggga cacgatcaat ggcctcattg agaatgctcg   3900
cggcagtgag acccttgaca agaaacctca cgtttggcgc gatattccca agctggaagc   3960
ttccaagtaa catagctgtg attacaacta ttatctttcc aacgtcagca ctcccactaa   4020
cgatttctct ggaaccctgc cacagagcta aggcatacac ccaaaaagta ctagcccaaa   4080
tgcacgctaa catgaccccc aatgagtaac tgctccgctt cgattccttc acaacacgat   4140
caagtacctt ttcatacttg acggcgagat gaggttgagc gccaaatgct actgtagtcc   4200
tgacagcact gagagcctcc tccgcaacgg tagctccaga ctgcgaatat atcgcgtcag   4260
atctgagctg atatttggcc atgaaggtgg cgccagttcc cattgtgatt accatgaacc   4320
ctacagcact caggaggatg caagccagtt tccattgcga agcaaaactt ataacggtgg   4380
ccgcaatgaa ggaagctatt ccctgtacga cgtttccaag cttgtcgctg atcgcttcct   4440
gaattgagtt ggtatcgtta atgattctgg tgctgacctc gccaccacct agtttgtcgt   4500
aaaacgcgat attctggcga ataacagcac tcagataatg ctttcggtaa cgtcctgcca   4560
acacttcgcc tctgtccaca agcaggaagc tctcgagaaa cgcactgccg agcataccaa   4620
tgccaatata gacaaaatag agagacaggt gattcacctt atgctggaac tcattgccct   4680
tgaggtcata gctagtgaag tctctgaatg tgttgaagat ggcgcccact actaacgtga   4740
acattggaag cgcggctcca tgcaccgctg caaaaaaaag cgcaagtatc tccaagaaaa   4800
cgtcaagggg agtgcaaaat ctgaacaacc tgaaaaagct tgtggcgact ctctttgttt   4860
caagctgact tcgcaataca ttggcctcat gtggatctaa cgcagagagc ttctcctcga   4920
gaagcttgtc cttagtctcg atgagtttct cacgcttctc tacctgtata tcatccacca   4980
tatgtgtaga gttgtttttg ttgttaagtc tttctttaag agcttgaccg actataaccg   5040
ttcaacggcg cattatatac tttgggtatc ggccagtgct gacaactcac acgttgcgac   5100
cccttaccca gaagcatacc cagcgcgatg tcgatcgtgt tatatcgtag acgcacaccc   5160
tgcaatgacg ggtaggctct aaatcgggat gcgaaaaaga ggttgccttg ctttttgccc   5220
tggtagatgg catgctgagc gtgcgcttgc cgcctaattt ttgtgtgtcg cctgctattt   5280
attgctgaag ctagcccgcc gcatctttcc ccaaggcttc gattgctcgt attggggcag   5340
ggattggtac tcaaccttgc agatgagact ccagcaacaa cgtcgtactg cttagcgatc   5400
gcacatgttt catcatcgtc actatacaca tcgtcatcaa ctccatggcg tgaggacttc   5460
```

```
cgagactgct gggcccttcg tttctttaat gcctcaagag atgacttcgt acccgaagag   5520
acgcctgttg taccccgttg acgcttggcg gagggggctt cgtcctcgtc agcaacccgc   5580
gtcatctgct tccttcgctg agcaagatac cttctctcct cgtaccgctg catctcctga   5640
gctcggtcat acaagatctc ttctcgctca atctctggca gcgcgtccaa cttcgccctg   5700
tcttcagcat cgagatattt gccttctaga ggatagggat tgacgacctc attgcttggc   5760
ggcgacggca gcgagatttc ctcttcggag tcggagccaa cgtcggccaa tgccagcaga   5820
tcatcatcac tgtcactcat agtaggaagg ttgaagtgtg ctgacgaatc agaatcgcga   5880
aggatgccat tgaaggcata tatattttaa tctgtacctt ttatggtaat ttaatcagat   5940
tttataggta ttcatgtgca agttgcattg aaggaactgt ttgagaaaat catcttgact   6000
gaacttttct cagatatgca ttccagcccg ccttttggta acgctgagct tcgtgcacag   6060
gatctcgtcc cttgctatag agcccgcgtc cgacgataat aacgtctgtg ccggtctcta   6120
tgacgtcgtc cacagtacga tactgctgcc ccaatccatc acctttgtcg tccaggccca   6180
ccccaggagt cataatgacc cagtcttcct ctggctttcc gactttttgc tgagcgatga   6240
aaccaaacac aaatgcgcgg ttactgcgag cgatgtctac tgtcgcttgc gagtattcgc   6300
cgtgagccag tgtgcccttc gaactcagtt ctgcaagcat gacaaggccg cgaggttcat   6360
ccgtagtttc cttcgcagcc tcttctagtc cgctcacaat tcccggccca ggaacaccgt   6420
gagcatttgt tatatcagcc cattgagcga tcttaaacac tccacctgca tattgggcct   6480
taacagtgga accgatgtct gcgaactttc ggtcttcaaa aatgagaaaa ttgtgcttcg   6540
ttgaaagctg tttcaaaccg ctgacagttg tgtcgtattc gaagtcgtca attatgtcaa   6600
tgtgggtctt aaccatacaa atgtaaggtc caatgcggtc caggatactc agtaactcag   6660
aggtagttcg cacatccaag cttgcgcaaa gatttgtttg cttgctcaca atgatgtcga   6720
atagccgggc tgctacagcc ggcagcctct ctcggcgctc ctcatagctc agcttcatat   6780
tatttctcta cagtagtgcc cgtgccctcg atcagctagg acttttcaaa ttaatcgggc   6840
tgtttgatgt aagtaagatg aagtcacgcg cgtgcaggag actgcgtccc gcgatattct   6900
gcaggcttga aaaatttacc ctaacggtag gcatcaagtg agtgagtctc agcgtcgata   6960
tgggtcaaaa aaggggaaaa ctagccgaga tcgttgcgag ctgtttcgaa aattatgccc   7020
tatggcaatt atcacgtgga gtatccgaat ttctccaggc tgtcaagcgg caattataac   7080
cgagactgag atcgagaagt atataaccgc agcagtagtg gataaataat tgcgaagtct   7140
tcccagcaga gcgggctgtt ttttggagtt ggttactgta aaatgctaaa atgactgaca   7200
acaatggagc gtctacagca ttggcaacag tgggaacagt atgctggtgc atccagttga   7260
taccccaggt tctgcgaaac tggtatgttc gggattgcga gggcgttcct cctctgatgt   7320
tctttttgtt cgccgtttcg gggattccct tcgcagtgta cttcattgat cagaattcga   7380
acactgccat catggttcaa cctcacttgt ttactttctt tagccttata ggcttttggc   7440
aaagcctgta ctatccgccc gtcagaccag cacgggccgt cacatgtatg gttgcgtcgc   7500
tgtataagaa atcttacaac tgaagactac acagcgtatc cgctccgata tcggcgatca   7560
cgtggataca tttccccaga atgcgtcaac cttgcatgct cgatattgac tcaagccgag   7620
aggtgtataa caacaccgac gatagcgaat tacttgtgga actgatttgc cgtatcgagt   7680
aaatcgcgat tgtggccctc tttaggcctt gtacccattt gtgcatcgta tttgttagta   7740
tgcatcatag aattatgtga acttagaaaa gtccgtatga aatgagcctc agattatgga   7800
```

```
ttgatcgctt gttatttgta cagcggaatt gacttatagt atgtcggcca cggttttaga   7860

ttgcctaggg gccgttttct tgatggattc gcatcggaac tccgaattct tgattgctct   7920

ccatcgcgca ggaggccgtt cttttttga caaagtccca ttttagggcg caggtccaaa   7980

aaataagcgg ccgcttaatt aactggcctc atgggccttc cgctcactgc ccgctttcca   8040

gtcgggaaac ctgtcgtgcc agctgcatta acatggtcat agctgtttcc ttgcgtattg   8100

ggcgctctcc gcttcctcgc tcactgactc gctgcgctcg gtcgttcggg taaagcctgg   8160

ggtgcctaat gagcaaaagg ccagcaaaag gccaggaacc gtaaaaaggc cgcgttgctg   8220

gcgtttttcc ataggctccg cccccctgac gagcatcaca aaaatcgacg ctcaagtcag   8280

aggtggcgaa acccgacagg actataaaga taccaggcgt ttccccctgg aagctccctc   8340

gtgcgctctc ctgttccgac cctgccgctt accggatacc tgtccgcctt tctcccttcg   8400

ggaagcgtgg cgctttctca tagctcacgc tgtaggtatc tcagttcggt gtaggtcgtt   8460

cgctccaagc tgggctgtgt gcacgaaccc cccgttcagc ccgaccgctg cgccttatcc   8520

ggtaactatc gtcttgagtc caacccggta agacacgact tatcgccact ggcagcagcc   8580

actggtaaca ggattagcag agcgaggtat gtaggcggtg ctacagagtt cttgaagtgg   8640

tggcctaact acggctacac tagaagaaca gtatttggta tctgcgctct gctgaagcca   8700

gttaccttcg gaaaaagagt tggtagctct tgatccggca aacaaaccac cgctggtagc   8760

ggtggttttt ttgtttgcaa gcagcagatt acgcgcagaa aaaaaggatc tcaagaagat   8820

cctttgatct tttctacggg gtctgacgct cagtggaacg aaaactcacg ttaagggatt   8880

ttggtcatga gattatcaaa aaggatcttc acctagatcc ttttaaatta aaaatgaagt   8940

tttaaatcaa tctaaagtat atatgagtaa acttggtctg acagttacca atgcttaatc   9000

agtgaggcac ctatctcagc gatctgtcta tttcgttcat ccatagttgc ctgactcccc   9060

gtcgtgtaga taactacgat acgggagggc ttaccatctg gccccagtgc tgcaatgata   9120

ccgcgagaac cacgctcacc ggctccagat ttatcagcaa taaaccagcc agccggaagg   9180

gccgagcgca gaagtggtcc tgcaacttta tccgcctcca tccagtctat taattgttgc   9240

cgggaagcta gagtaagtag ttcgccagtt aatagtttgc gcaacgttgt tgccattgct   9300

acaggcatcg tggtgtcacg ctcgtcgttt ggtatggctt cattcagctc cggttcccaa   9360

cgatcaaggc gagttacatg atcccccatg ttgtgcaaaa aagcggttag ctccttcggt   9420

cctccgatcg ttgtcagaag taagttggcc gcagtgttat cactcatggt tatggcagca   9480

ctgcataatt ctcttactgt catgccatcc gtaagatgct tttctgtgac tggtgagtac   9540

tcaaccaagt cattctgaga atagtgtatg cggcgaccga gttgctcttg cccggcgtca   9600

atacgggata ataccgcgcc acatagcaga actttaaaag tgctcatcat tggaaaacgt   9660

tcttcggggc gaaaactctc aaggatctta ccgctgttga gatccagttc gatgtaaccc   9720

actcgtgcac ccaactgatc ttcagcatct tttactttca ccagcgtttc tgggtgagca   9780

aaaacaggaa ggcaaaatgc cgcaaaaaag ggaataaggg cgacacggaa atgttgaata   9840

ctcatactct tcctttttca atattattga agcatttatc agggttattg tctcatgagc   9900

ggatacatat ttgaatgtat ttagaaaaat aaacaaatag gggttccgcg cacatttccc   9960

cgaaaagtgc cac                                                      9973
```

<210> SEQ ID NO 69
<211> LENGTH: 7375
<212> TYPE: DNA
<213> ORGANISM: Artificial
<220> FEATURE:
<223> OTHER INFORMATION: Vector

<400> SEQUENCE: 69

```
ctaaattgta agcgttaata ttttgttaaa attcgcgtta aatttttgtt aaatcagctc     60
atttttaac caataggccg aaatcggcaa aatcccttat aaatcaaaag aatagaccga     120
gatagggttg agtggccgct acagggcgct cccattcgcc attcaggctg cgcaactgtt    180
gggaagggcg tttcggtgcg ggcctcttcg ctattacgcc agctggcgaa agggggatgt    240
gctgcaaggc gattaagttg ggtaacgcca gggttttccc agtcacgacg ttgtaaaacg    300
acggccagtg agcgcgacgt aatacgactc actatagggc gaattggcgg aaggccgtca    360
aggcctaggc gcgcctgcag gatcctagaa aacagctgga tatggataaa ctcggcaagc    420
atcttttgga aaggctgcca cgctatgccg tgccgatatt cattaagttc gtcgacaccg    480
tcaccatcac cggcaacaac aaagttcaga agaaagaatt ccgaaaccag cagattcccg    540
ccccagcagg acaaacaatc tactggttag agggcacgag ctacaagccc ctcactgctg    600
atgcgtgggc tcgtgtagag aatgggcgac acaagctcta atgttgaata cctcttccgt    660
atagatgtgg cataagctat agattttgct gcaatattat taaatattaa agagtttcga    720
aggtcagctg cggatgaacc agttcagagc ggctctctct tttttgccaa tagcgtgcaa    780
ccgtgaagag caattcaacc atccaatctg gctacactaa attgtatttg gcagcgcact    840
gtacgagcgc actgtacgaa actccgtcaa tttatagcag aacgcgtgcg atcgcgggcc    900
ccagcgatat gacgagaatc aggcaataat agcttaagct gaagtgtttt tagatttagt    960
tcggagtgcg cttctcaaaa gtgctgggat caacaagttt ttaacatggg ttttgattta   1020
tattgtttta tatgagcgcc tcagatatgc gctgacagcc tattaggaga aatggccggc   1080
caggttaaga agctaattca ctaattgccg actctagaat atcaagagac ttgtattttt   1140
caagctcttt cttgactgcc atggctttct cgtgatacga gggagtagcc aacacctcct   1200
taacggccgt ggagactagc tcagaagttg cctgcaaggt ttgaagatca taaccaacac   1260
cagcccatac agctcgtgaa gcaacagctg gcttgtctac caacattcct cctccgatga   1320
tgacgggaac gccatggctc aaactgtgct gcagacctcc gtatccaccg ttgtatatga   1380
aaacagaggc atgcggtagt agctcatcgt aaggaaaata atcaacaatt cgagcgtttg   1440
caggaacttt aacgctatca ggaagtgacg cccctttgac gcccaatata ccaactacga   1500
gagtgtcttc ttcgtcagca aaggcctgca atgctggaat gagcagatct tcatagttga   1560
tggctgctgt tccttgtgta acaacaatca gacgcttcgc actcagcaca tcaggccacc   1620
aagacggcag gtgaggtgga gttgctaatc cagcagactt tacatgcggt gcactaccag   1680
cgaacgagaa gccaggagga ggcgaagtca agtgaaattc aagagatgga gggcacagtt   1740
gcaaaaatct gtcagggctg ctgtatatat tctccaggag aaattcgggc tccttcgtgg   1800
ccccgagcgt cttcatgatc tccttctcag agtcagttcc tggttgaaat acttgttgcc   1860
gcactaaagt atcaatcatt ggctcaagac taggaactcc aggcgccttc tctgctttca   1920
gcatgcacgg aatagttcct aacgtgatta cgccttgggg cttgagacct ggggcaccca   1980
gtgatatcgg atgcacccct agaaacatgg tctcgccaat caccacagct gatttatttt   2040
cagcctcaac ctgttttaga gcagtttgaa gtgcatcgta ctgctcagga atcgccttca   2100
caaaaatctc attcattgag taaccggtct gctcaaggcc tggaggaatc gtgagcaatc   2160
ctggagcgat ttcagggaga ttgtattcat ggtagtcagc tcgtccttgg agagggacga   2220
```

```
aagtgcatcc tgcctcaata actttctcct tgaatgcgtt ccctgttacg aaagtcacct   2280
catatcctct attgagtaga ccgcggacca ggctgagcac tgggcccacg tgccccgcta   2340
gtgggcaggc acaagcaact atcactggtt tctcgatggc catatgtgta gagttgtttt   2400
tgttgttaag tctttcttta agagcttgac cgactataac cgttcaacgg cgcattatat   2460
actttgggta tcggccagtg ctgacaactc acacgttgcg accccttacc cagaagcata   2520
cccagcgcga tgtcgatcgt gttatatcgt agacgcacac cctgcaatga cgggtaggct   2580
ctaaatcggg atgcgaaaaa gaggttgcct tgctttttgc cctggtagat ggcatgctga   2640
gcgtgcgctt gccgcctaat ttttgtgtgt cgcctgctat ttattgctga agctagcccg   2700
ccgcatcttt ccccaaggct tcgattgctc gtattggggc agggattggt actcaacctt   2760
gcagatgaga ctccagcaac aacgtcgtac tgcttagcga tcgcacatgt ttcatcatcg   2820
tcactataca catcgtcatc aactccatgg cgtgaggact tccgagactg ctgggccctt   2880
cgtttcttta atgcctcaag agatgacttc gtacccgaag agacgcctgt tgtaccccgt   2940
tgacgcttgg cggagggggc ttcgtcctcg tcagcaaccc gcgtcatctg cttccttcgc   3000
tgagcaagat accttctctc ctcgtaccgc tgcatctcct gagctcggtc atacaagatc   3060
tcttctcgct caatctctgg cagcgcgtcc aacttcgccc tgtcttcagc atcgagatat   3120
ttgccttcta gaggataggg attgacgacc tcattgcttg gcggcgacgg cagcgagatt   3180
tcctcttcgg agtcggagcc aacgtcggcc aatgccagca gatcatcatc actgtcactc   3240
atagtaggaa ggttgaagtg tgctgacgaa tcagaatcgc gaaggatgcc attgaaggca   3300
tatatatttt aatctgtacc ttttatggta atttaatcag attttatagg tattcatgtg   3360
caagttgcat tgaaggaact gtttgagaaa atcatcttga ctgaactttt ctcagatatg   3420
cattccagcc cgccttttgg taacgctgag cttcgtgcac aggatctcgt cccttgctat   3480
agagcccgcg tccgacgata ataacgtctg tgccggtctc tatgacgtcg tccacagtac   3540
gatactgctg ccccaatcca tcacctttgt cgtccaggcc caccccagga gtcataatga   3600
cccagtcttc ctctggcttt ccgacttttt gctgagcgat gaaaccaaac acaaatgcgc   3660
ggttactgcg agcgatgtct actgtcgctt gcgagtattc gccgtgagcc agtgtgccct   3720
tcgaactcag ttctgcaagc atgacaaggc cgcgaggttc atccgtagtt tccttcgcag   3780
cctcttctag tccgctcaca attcccggcc caggaacacc gtgagcattt gttatatcag   3840
cccattgagc gatcttaaac actccacctg catattgggc cttaacagtg gaaccgatgt   3900
ctgcgaactt tcggtcttca aaaatgagaa aattgtgctt cgttgaaagc tgtttcaaac   3960
cgctgacagt tgtgtcgtat tcgaagtcgt caattatgtc aatgtgggtc ttaaccatac   4020
aaatgtaagg tccaatgcgg tccaggatac tcagtaactc agaggtagtt cgcacatcca   4080
agcttgcgca aagatttgtt tgcttgctca caatgatgtc gaatagccgg gctgctacag   4140
ccggcagcct ctctcggcgc tcctcatagc tcagcttcat attatttctc tacagtagtg   4200
cccgtgccct cgatcagcta ggacttttca aattaatcgg gctgtttgat gtaagtaaga   4260
tgaagtcacg cgcgtgcagg agactgcgtc ccgcgatatt ctgcaggctt gaaaaattta   4320
ccctaacggt aggcatcaag tgagtgagtc tcagcgtcga tatgggtcaa aaaaggggaa   4380
aactagccga gatcgttgcg agctgtttcg aaaattatgc cctatggcaa ttatcacgtg   4440
gagtatccga atttctccag gctgtcaagc ggcaattata accgagactg agatcgagaa   4500
gtatataacc gcagcagtag tggataaata attgcgaagt cttcccagca gagcgggctg   4560
tttttggag ttggttactg taaaatgcta aaatgactga caacaatgga gcgtctacag   4620
```

```
cattggcaac agtgggaaca gtatgctggt gcatccagtt gataccccag gttctgcgaa   4680

actggtatgt tcgggattgc gagggcgttc ctcctctgat gttctttttg ttcgccgttt   4740

cggggattcc cttcgcagtg tacttcattg atcagaattc gaacactgcc atcatggttc   4800

aacctcactt gtttactttc tttagcctta taggcttttg gcaaagcctg tactatccgc   4860

ccgtcagacc agcacgggcc gtcacatgta tggttgcgtc gctgtataag aaatcttaca   4920

actgaagact acacagcgta tccgctccga tatcggcgat cacgtggata catttcccca   4980

gaatgcgtca accttgcatg ctcgatattg actcaagccg agaggtgtat aacaacaccg   5040

acgatagcga attacttgtg gaactgattt gccgtatcga gtaaatcgcg attgtggccc   5100

tctttaggcc ttgtacccat ttgtgcatcg tatttgttag tatgcatcat agaattatgt   5160

gaacttagaa aagtccgtat gaaatgagcc tcagattatg gattgatcgc ttgttatttg   5220

tacagcggaa ttgacttata gtatgtcggc cacggtttta gattgcctag ggccgtttt   5280

cttgatggat tcgcatcgga actccgaatt cttgattgct ctccatcgcg caggaggccg   5340

ttcttttttt gacaaagtcc cattttaggg cgcaggtcca aaaaataagc ggccgcttaa   5400

ttaactggcc tcatgggcct tccgctcact gcccgctttc cagtcgggaa acctgtcgtg   5460

ccagctgcat taacatggtc atagctgttt ccttgcgtat tgggcgctct ccgcttcctc   5520

gctcactgac tcgctgcgct cggtcgttcg ggtaaagcct ggggtgccta atgagcaaaa   5580

ggccagcaaa aggccaggaa ccgtaaaaag gccgcgttgc tggcgttttt ccataggctc   5640

cgcccccctg acgagcatca caaaaatcga cgctcaagtc agaggtggcg aaacccgaca   5700

ggactataaa gataccaggc gtttccccct ggaagctccc tcgtgcgctc tcctgttccg   5760

accctgccgc ttaccggata cctgtccgcc tttctccctt cgggaagcgt ggcgctttct   5820

catagctcac gctgtaggta tctcagttcg gtgtaggtcg ttcgctccaa gctgggctgt   5880

gtgcacgaac cccccgttca gcccgaccgc tgcgccttat ccggtaacta tcgtcttgag   5940

tccaacccgg taagacacga cttatcgcca ctggcagcag ccactggtaa caggattagc   6000

agagcgaggt atgtaggcgg tgctacagag ttcttgaagt ggtggcctaa ctacggctac   6060

actagaagaa cagtatttgg tatctgcgct ctgctgaagc cagttacctt cggaaaaaga   6120

gttggtagct cttgatccgg caaacaaacc accgctggta gcggtggttt ttttgtttgc   6180

aagcagcaga ttacgcgcag aaaaaaagga tctcaagaag atcctttgat cttttctacg   6240

gggtctgacg ctcagtggaa cgaaaactca cgttaaggga ttttggtcat gagattatca   6300

aaaaggatct tcacctagat ccttttaaat taaaaatgaa gttttaaatc aatctaaagt   6360

atatatgagt aaacttggtc tgacagttac caatgcttaa tcagtgaggc acctatctca   6420

gcgatctgtc tatttcgttc atccatagtt gcctgactcc ccgtcgtgta gataactacg   6480

atacgggagg gcttaccatc tggccccagt gctgcaatga taccgcgaga accacgctca   6540

ccggctccag atttatcagc aataaaccag ccagccggaa gggccgagcg cagaagtggt   6600

cctgcaactt tatccgcctc catccagtct attaattgtt gccgggaagc tagagtaagt   6660

agttcgccag ttaatagttt gcgcaacgtt gttgccattg ctacaggcat cgtggtgtca   6720

cgctcgtcgt ttggtatggc ttcattcagc tccggttccc aacgatcaag gcgagttaca   6780

tgatccccca tgttgtgcaa aaaagcggtt agctccttcg gtcctccgat cgttgtcaga   6840

agtaagttgg ccgcagtgtt atcactcatg gttatggcag cactgcataa ttctcttact   6900

gtcatgccat ccgtaagatg cttttctgtg actggtgagt actcaaccaa gtcattctga   6960
```

-continued

```
gaatagtgta tgcggcgacc gagttgctct tgcccggcgt caatacggga taataccgcg   7020

ccacatagca gaactttaaa agtgctcatc attggaaaac gttcttcggg gcgaaaactc   7080

tcaaggatct taccgctgtt gagatccagt tcgatgtaac ccactcgtgc acccaactga   7140

tcttcagcat cttttacttt caccagcgtt tctgggtgag caaaaacagg aaggcaaaat   7200

gccgcaaaaa agggaataag ggcgacacgg aaatgttgaa tactcatact cttccttttt   7260

caatattatt gaagcattta tcagggttat tgtctcatga gcggatacat atttgaatgt   7320

atttagaaaa ataaacaaat aggggttccg cgcacatttc cccgaaaagt gccac        7375
```

<210> SEQ ID NO 70
<211> LENGTH: 5316
<212> TYPE: DNA
<213> ORGANISM: Artificial
<220> FEATURE:
<223> OTHER INFORMATION: koCasssette

<400> SEQUENCE: 70

```
ggacctgcgc cctaaaatgg gactttgtca aaaaaagaac ggcctcctgc gcgatggaga     60

gcaatcaaga attcggagtt ccgatgcgaa tccatcaaga aaacggcccc taggcaatct    120

aaaaccgtgg ccgacatact ataagtcaat tccgctgtac aaataacaag cgatcaatcc    180

ataatctgag gctcatttca tacggacttt tctaagttca cataattcta tgatgcatac    240

taacaaatac gatgcacaaa tgggtacaag gcctaaagag ggccacaatc gcgatttact    300

cgatacggca aatcagttcc acaagtaatt cgctatcgtc ggtgttgtta tacacctctc    360

ggcttgagtc aatatcgagc atgcaaggtt gacgcattct ggggaaatgt atccacgtga    420

tcgccgatat cggagcggat acgctgtgta gtcttcagtt gtaagatttc ttatacagcg    480

acgcaaccat acatgtgacg gcccgtgctg gtctgacggg cggatagtac aggctttgcc    540

aaaagcctat aaggctaaag aaagtaaaca agtgaggttg aaccatgatg gcagtgttcg    600

aattctgatc aatgaagtac actgcgaagg gaatccccga aacggcgaac aaaaagaaca    660

tcagaggagg aacgccctcg caatcccgaa cataccagtt tcgcagaacc tggggtatca    720

actggatgca ccagcatact gttcccactg ttgccaatgc tgtagacgct ccattgttgt    780

cagtcatttt agcattttac agtaaccaac tccaaaaaac agcccgctct gctgggaaga    840

cttcgcaatt atttatccac tactgctgcg gttatatact tctcgatctc agtctcggtt    900

ataattgccg cttgacagcc tggagaaatt cggatactcc acgtgataat tgccataggg    960

cataattttc gaaacagctc gcaacgatct cggctagttt tcccctttttt tgacccatat   1020

cgacgctgag actcactcac ttgatgccta ccgttagggt aaatttttca agcctgcaga   1080

atatcgcggg acgcagtctc ctgcacgcgc gtgacttcat cttacttaca tcaaacagcc   1140

cgattaattt gaaaagtcct agctgatcga gggcacgggc actactgtag agaaataata   1200

tgaagctgag ctatgaggag cgccgagaga ggctgccggc tgtagcagcc cggctattcg   1260

acatcattgt gagcaagcaa acaaatcttt gcgcaagctt ggatgtgcga actacctctg   1320

agttactgag tatcctggac cgcattggac cttacatttg tatggttaag acccacattg   1380

acataattga cgacttcgaa tacgacacaa ctgtcagcgg tttgaaacag ctttcaacga   1440

agcacaattt tctcattttt gaagaccgaa agttcgcaga catcggttcc actgttaagg   1500

cccaatatgc aggtggagtg tttaagatcg ctcaatgggc tgatataaca aatgctcacg   1560

gtgttcctgg gccgggaatt gtgagcggac tagaagaggc tgcgaaggaa actacggatg   1620

aacctcgcgg ccttgtcatg cttgcagaac tgagttcgaa gggcacactg gctcacggcg   1680
```

```
aatactcgca agcgacagta gacatcgctc gcagtaaccg cgcatttgtg tttggtttca   1740
tcgctcagca aaaagtcgga aagccagagg aagactgggt cattatgact cctggggtgg   1800
gcctggacga caaaggtgat ggattggggc agcagtatcg tactgtggac gacgtcatag   1860
agaccggcac agacgttatt atcgtcggac gcgggctcta tagcaaggga cgagatcctg   1920
tgcacgaagc tcagcgttac caaaaggcgg gctggaatgc atatctgaga aaagttcagt   1980
caagatgatt ttctcaaaca gttccttcaa tgcaacttgc acatgaatac ctataaaatc   2040
tgattaaatt accataaaag gtacagatta aaatatatat gccttcaatg gcatccttcg   2100
cgattctgat tcgtcagcac acttcaacct tcctactatg agtgacagtg atgatgatct   2160
gctggcattg gccgacgttg gctccgactc cgaagaggaa atctcgctgc cgtcgccgcc   2220
aagcaatgag gtcgtcaatc cctatcctct agaaggcaaa tatctcgatg ctgaagacag   2280
ggcgaagttg gacgcgctgc cagagattga gcgagaagag atcttgtatg accgagctca   2340
ggagatgcag cggtacgagg agagaaggta tcttgctcag cgaaggaagc agatgacgcg   2400
ggttgctgac gaggacgaag ccccctccgc caagcgtcaa cggggtacaa caggcgtctc   2460
ttcgggtacg aagtcatctc ttgaggcatt aaagaaacga agggcccagc agtctcggaa   2520
gtcctcacgc catggagttg atgacgatgt gtatagtgac gatgatgaaa catgtgcgat   2580
cgctaagcag tacgacgttg ttgctggagt ctcatctgca aggttgagta ccaatccctg   2640
ccccaatacg agcaatcgaa gccttgggga aagatgcggc gggctagctt cagcaataaa   2700
tagcaggcga cacacaaaaa ttaggcggca agcgcacgct cagcatgcca tctaccaggg   2760
caaaaagcaa ggcaacctct ttttcgcatc ccgatttaga gcctacccgt cattgcaggg   2820
tgtgcgtcta cgatataaca cgatcgacat cgcgctgggt atgcttctgg gtaaggggtc   2880
gcaacgtgtg agttgtcagc actggccgat acccaaagta tataatgcgc cgttgaacgg   2940
ttatagtcgg tcaagctctt aaagaaagac ttaacaacaa aaacaactct acacatatgt   3000
taatcaaaga cattattcta actccaatga gtttatccgc tgttgctggc ttgttgccac   3060
tgctcttcgt agctttctta gttctacacg agcctatctg gctcctatgg taccgctatg   3120
cagcacgtag gcacaagtgt agtatgcctc gcttcattga gaaatcgttc ccactgggaa   3180
tacaaagaac catggacatg atcaagacgg ccaagtcata caccttactg gaagttcaat   3240
acgacagagt cttcaataag ttcaaagcac ggacgtatct tcgacaagct ccccttcaat   3300
accaaatctt cacaatcgag ccagaaaaca ttaagacaat cctggcaacc aaattcaatg   3360
attttggtct tggagcacgt ttccacacag tgggaaaagt gtttggccaa gggatattta   3420
cactcagcgg aaatggatgg aaacagtctc gatcgatgtt gagacctcag ttcactaaag   3480
atcaggtttg cagaattgat cagatttcca gtcatgctgc ggagttaata aaggagatga   3540
accgtgcaat gaaagtggac caatttattg atgttcaaca ttatttccac aaacttacgc   3600
tggatacagc gactgaattc ctatttgggg agtcctgcga gagcttgaac cctgagaatc   3660
agtcatgtat tgtagcccgt gatggttcgg agattactgc cgaacaattc gtggagtcct   3720
acaactttct actgaattac gctttcaaac ggaccctatc aagcaaagtc tactggttgt   3780
tcaactctaa ggaattccga gatcacaaga aacgtgctca gtcctatatt gactactacg   3840
ttgataaggc tctttacgcc acatctttcg ctgctgagaa ctctattgca gagaaggatg   3900
ctgctgcaga gtctagtggc atctatgtgt tctcgcttga gatggctaaa gttacccgag   3960
acccagtgac gatacgtgat caaattttca acattctcat tgctggtaga gatacaacag   4020
```

```
ctgctacgtt gagcttcgct attcatttcc ttgccagaaa tcctgacgta ttcaacaaac   4080

tacgtgagga ggtcctcgat cattttggaa ccaaggagga gcaaaggcct ttatcattcg   4140

aacttctgaa gcaagcacct tatttgaagc aagttataaa tgaagtcttg cgtcttgcgc   4200

cggtattgcc attgaacttc cgtactgctg tgagagatac aactctaccc ataggtggtg   4260

gtcccgagca gaaggatccg atcttcgttc ctaagggcac cgcagtttac tattcaattt   4320

acatggtcca cagggacatc aagtattggg gtcctgacgc ccacgaattc aatcccaatc   4380

gatgggagaa cttgaagcta gataatgtgt gggcattctt gcccttcaat ggcggtcccc   4440

gaatttgtct cggccaacaa ttcgccctga cagagctttc gctaactctg gtgagactct   4500

tacaggagta ttccaagatt gagatgggtc ccgacttccc agagtcccct cgtttctcaa   4560

caacgcttac agctcaacac gctcctcccg gtgtggttgt gcggttttct taagttggcc   4620

ggccatttct cctaataggc tgtcagcgca tatctgaggc gctcatataa aacaatataa   4680

atcaaaaccc atgttaaaaa cttgttgatc ccagcacttt tgagaagcgc actccgaact   4740

aaatctaaaa acacttcagc ttaagctatt attgcctgat tctcgtcata tcgctggggc   4800

ccgcgatcgc acgcgttctg ctataaattg acggagtttc gtacagtgcg ctcgtacagt   4860

gcgctgccaa atacaattta gtgtagccag attggatggt tgaattgctc ttcacggttg   4920

cacgctattg gcaaaaaaga gagagccgct ctgaactggt tcatccgcag ctgaccttcg   4980

aaactcttta atatttaata atattgcagc aaaatctata gcttatgcca catctatacg   5040

gaagaggtat tcaacattag agcttgtgtc gcccattctc tacacgagcc cacgcatcag   5100

cagtgagggg cttgtagctc gtgccctcta accagtagat tgtttgtcct gctggggcgg   5160

gaatctgctg gtttcggaat tctttcttct gaactttgtt gttgccggtg atggtgacgg   5220

tgtcgacgaa cttaatgaat atcggcacgg catagcgtgg cagcctttcc aaaagatgct   5280

tgccgagttt atccatatcc agctgttttc taggat                             5316
```

<210> SEQ ID NO 71
<211> LENGTH: 5088
<212> TYPE: DNA
<213> ORGANISM: Artificial
<220> FEATURE:
<223> OTHER INFORMATION: koCassette

<400> SEQUENCE: 71

```
ggacctgcgc cctaaaatgg gactttgtca aaaaaagaac ggcctcctgc gcgatggaga     60

gcaatcaaga attcggagtt ccgatgcgaa tccatcaaga aaacggcccc taggcaatct    120

aaaaccgtgg ccgacatact ataagtcaat tccgctgtac aaataacaag cgatcaatcc    180

ataatctgag gctcatttca tacggacttt tctaagttca cataattcta tgatgcatac    240

taacaaatac gatgcacaaa tgggtacaag gcctaaagag ggccacaatc gcgatttact    300

cgatacggca aatcagttcc acaagtaatt cgctatcgtc ggtgttgtta tacacctctc    360

ggcttgagtc aatatcgagc atgcaaggtt gacgcattct ggggaaatgt atccacgtga    420

tcgccgatat cggagcggat acgctgtgta gtcttcagtt gtaagatttc ttatacagcg    480

acgcaaccat acatgtgacg gcccgtgctg gtctgacggg cggatagtac aggctttgcc    540

aaaagcctat aaggctaaag aaagtaaaca agtgaggttg aaccatgatg gcagtgttcg    600

aattctgatc aatgaagtac actgcgaagg gaatccccga aacggcgaac aaaaagaaca    660

tcagaggagg aacgccctcg caatcccgaa cataccagtt tcgcagaacc tggggtatca    720

actggatgca ccagcatact gttcccactg ttgccaatgc tgtagacgct ccattgttgt    780
```

```
cagtcatttt agcattttac agtaaccaac tccaaaaaac agcccgctct gctgggaaga    840
cttcgcaatt atttatccac tactgctgcg gttatatact tctcgatctc agtctcggtt    900
ataattgccg cttgacagcc tggagaaatt cggatactcc acgtgataat tgccataggg    960
cataattttc gaaacagctc gcaacgatct cggctagttt tccccttttt tgacccatat   1020
cgacgctgag actcactcac ttgatgccta ccgttagggt aaatttttca agcctgcaga   1080
atatcgcggg acgcagtctc ctgcacgcgc gtgacttcat cttacttaca tcaaacagcc   1140
cgattaattt gaaaagtcct agctgatcga gggcacgggc actactgtag agaaataata   1200
tgaagctgag ctatgaggag cgccgagaga ggctgccggc tgtagcagcc cggctattcg   1260
acatcattgt gagcaagcaa acaaatcttt gcgcaagctt ggatgtgcga actacctctg   1320
agttactgag tatcctggac cgcattggac cttacatttg tatggttaag acccacattg   1380
acataattga cgacttcgaa tacgacacaa ctgtcagcgg tttgaaacag ctttcaacga   1440
agcacaattt tctcattttt gaagaccgaa agttcgcaga catcggttcc actgttaagg   1500
cccaatatgc aggtggagtg tttaagatcg ctcaatgggc tgatataaca aatgctcacg   1560
gtgttcctgg gccgggaatt gtgagcggac tagaagaggc tgcgaaggaa actacggatg   1620
aacctcgcgg ccttgtcatg cttgcagaac tgagttcgaa gggcacactg gctcacggcg   1680
aatactcgca agcgacagta gacatcgctc gcagtaaccg cgcatttgtg tttggtttca   1740
tcgctcagca aaaagtcgga aagccagagg aagactgggt cattatgact cctggggtgg   1800
gcctggacga caaaggtgat ggattggggc agcagtatcg tactgtggac gacgtcatag   1860
agaccggcac agacgttatt atcgtcggac gcgggctcta tagcaaggga cgagatcctg   1920
tgcacgaagc tcagcgttac caaaaggcgg gctggaatgc atatctgaga aaagttcagt   1980
caagatgatt ttctcaaaca gttccttcaa tgcaacttgc acatgaatac ctataaaatc   2040
tgattaaatt accataaaag gtacagatta aaatatatat gccttcaatg gcatccttcg   2100
cgattctgat tcgtcagcac acttcaacct tcctactatg agtgacagtg atgatgatct   2160
gctggcattg gccgacgttg gctccgactc cgaagaggaa atctcgctgc cgtcgccgcc   2220
aagcaatgag gtcgtcaatc cctatcctct agaaggcaaa tatctcgatg ctgaagacag   2280
ggcgaagttg gacgcgctgc cagagattga gcgagaagag atcttgtatg accgagctca   2340
ggagatgcag cggtacgagg agagaaggta tcttgctcag cgaaggaagc agatgacgcg   2400
ggttgctgac gaggacgaag ccccctccgc caagcgtcaa cggggtacaa caggcgtctc   2460
ttcgggtacg aagtcatctc ttgaggcatt aaagaaacga agggcccagc agtctcggaa   2520
gtcctcacgc catggagttg atgacgatgt gtatagtgac gatgatgaaa catgtgcgat   2580
cgctaagcag tacgacgttg ttgctggagt ctcatctgca aggttgagta ccaatccctg   2640
ccccaatacg agcaatcgaa gccttgggga aagatgcggc gggctagctt cagcaataaa   2700
tagcaggcga cacacaaaaa ttaggcggca agcgcacgct cagcatgcca tctaccaggg   2760
caaaaagcaa ggcaacctct ttttcgcatc ccgatttaga gcctacccgt cattgcaggg   2820
tgtgcgtcta cgatataaca cgatcgacat cgcgctgggt atgcttctgg gtaaggggtc   2880
gcaacgtgtg agttgtcagc actggccgat acccaaagta tataatgcgc cgttgaacgg   2940
ttatagtcgg tcaagctctt aaagaaagac ttaacaacaa aaacaactct acacatatga   3000
gcccttcatc acacaaaccc ctgattctcg cttgcggctt gcctctttca ggccatataa   3060
tgcccgtttt gagtctggta cacggcctta cggacgacgg atacgaagct actgttgtga   3120
```

```
caggcagagc gtttgaacaa aaagttcgag atgtgggtgc agactttgtt cctttagaag   3180

ggaacgcaga ttttgatgac cacaccttag acgatctggt cccgggccgt aaagacatgg   3240

ccccaagctt cgatcgtaca gttcaagatg tggagcacat gatggtagct actcttcctg   3300

agcagtttgc cgctattcag agggctttca aaaagctcag cgcaagcggt cgccctgtcg   3360

ttcttgtcag tgaagtgctg tttttcggtg cacaccctat cagcctcggt gctcctggtt   3420

tcaaacccgc tggctggatt tgtttagggg ttttgcctct tttgatccgc agtgatcata   3480

ccttaggact tgacaacgac aggagccccg aagcacatgc aaagaaactc gctatgaacc   3540

acgctcttga gcaccaaatt ttcgttaaag ccactgctaa gcacaaggaa atctgccgag   3600

agttaggttg cactgaagat cccaaattta tctgggagca cagttacatt gctgcagaca   3660

agttcctgca gctgtgcccg ccttctcttg agttcagcag agaccatctg cctagcaact   3720

tcaaattcgc cggctcaacg cccaagcacc gaactcaatt cacccctcct tcctggtggg   3780

gggatgttct gagtgccaag cgagtcatca tggtcactca aggaactttt gctgtcagtt   3840

acaagcatct tattgtgcct actcttgagg ccttgaagga cgagcctgac actttaacag   3900

tagccatatt gggccgccgc ggtgccaagc taccggatga tgttgtggtt cctgagaatg   3960

ctcgcgtgat cgactacttc aactacgatg ctctacttcc tcacgttgat gctcttgtct   4020

acaatggtgg atatggcgga cttcagcaca gcttaagcca ctctgttcca gttgttattg   4080

ctggtgactc tgaagacaag ccaatggtgg catcgagagc tgaggccgct ggcgtggcaa   4140

ttgatttgaa aactggcttg cctacagtgg agcaaatcaa agaagctgtt gattcgataa   4200

ttggaaatcc gaaattccac gaagcctcga agaaggttca aatggagttg gaaagccaca   4260

actccttgaa aattcttgag gaaagcatcg aggaaatcgc cagccatgac tttggtcttt   4320

tgaccaagag tgacgaggaa actgaagata tacctgtcaa aggtccggcc ttagcggtga   4380

gttcttaggg ccggccattt ctcctaatag gctgtcagcg catatctgag gcgctcatat   4440

aaaacaatat aaatcaaaac ccatgttaaa aacttgttga tcccagcact tttgagaagc   4500

gcactccgaa ctaaatctaa aaacacttca gcttaagcta ttattgcctg attctcgtca   4560

tatcgctggg gcccgcgatc gcacgcgttc tgctataaat tgacggagtt tcgtacagtg   4620

cgctcgtaca gtgcgctgcc aaatacaatt tagtgtagcc agattggatg gttgaattgc   4680

tcttcacggt tgcacgctat tggcaaaaaa gagagagccg ctctgaactg gttcatccgc   4740

agctgacctt cgaaactctt taatatttaa taatattgca gcaaaatcta tagcttatgc   4800

cacatctata cggaagaggt attcaacatt agagcttgtg tcgcccattc tctacacgag   4860

cccacgcatc agcagtgagg ggcttgtagc tcgtgccctc taaccagtag attgtttgtc   4920

ctgctggggc gggaatctgc tggtttcgga attctttctt ctgaactttg ttgttgccgg   4980

tgatggtgac ggtgtcgacg aacttaatga atatcggcac ggcatagcgt ggcagccttt   5040

ccaaaagatg cttgccgagt ttatccatat ccagctgttt tctaggat               5088
```

<210> SEQ ID NO 72
<211> LENGTH: 4479
<212> TYPE: DNA
<213> ORGANISM: Artificial
<220> FEATURE:
<223> OTHER INFORMATION: koCassette

<400> SEQUENCE: 72

```
ggacctgcgc cctaaaatgg gactttgtca aaaaaagaac ggcctcctgc gcgatggaga     60

gcaatcaaga attcggagtt ccgatgcgaa tccatcaaga aaacggcccc taggcaatct    120
```

```
aaaaccgtgg ccgacatact ataagtcaat tccgctgtac aaataacaag cgatcaatcc    180
ataatctgag gctcatttca tacggacttt tctaagttca cataattcta tgatgcatac    240
taacaaatac gatgcacaaa tgggtacaag gcctaaagag ggccacaatc gcgatttact    300
cgatacggca aatcagttcc acaagtaatt cgctatcgtc ggtgttgtta tacacctctc    360
ggcttgagtc aatatcgagc atgcaaggtt gacgcattct ggggaaatgt atccacgtga    420
tcgccgatat cggagcggat acgctgtgta gtcttcagtt gtaagatttc ttatacagcg    480
acgcaaccat acatgtgacg gcccgtgctg gtctgacggg cggatagtac aggctttgcc    540
aaaagcctat aaggctaaag aaagtaaaca agtgaggttg aaccatgatg gcagtgttcg    600
aattctgatc aatgaagtac actgcgaagg gaatccccga aacggcgaac aaaaagaaca    660
tcagaggagg aacgccctcg caatcccgaa cataccagtt tcgcagaacc tggggtatca    720
actggatgca ccagcatact gttcccactg ttgccaatgc tgtagacgct ccattgttgt    780
cagtcatttt agcattttac agtaaccaac tccaaaaaac agcccgctct gctgggaaga    840
cttcgcaatt atttatccac tactgctgcg gttatatact tctcgatctc agtctcggtt    900
ataattgccg cttgacagcc tggagaaatt cggatactcc acgtgataat tgccataggg    960
cataattttc gaaacagctc gcaacgatct cggctagttt tcccctttttt tgacccatat   1020
cgacgctgag actcactcac ttgatgccta ccgttagggt aaatttttca agcctgcaga   1080
atatcgcggg acgcagtctc ctgcacgcgc gtgacttcat cttacttaca tcaaacagcc   1140
cgattaattt gaaaagtcct agctgatcga gggcacgggc actactgtag agaaataata   1200
tgaagctgag ctatgaggag cgccgagaga ggctgccggc tgtagcagcc cggctattcg   1260
acatcattgt gagcaagcaa acaaatcttt gcgcaagctt ggatgtgcga actacctctg   1320
agttactgag tatcctggac cgcattggac cttacatttg tatggttaag acccacattg   1380
acataattga cgacttcgaa tacgacacaa ctgtcagcgg tttgaaacag ctttcaacga   1440
agcacaattt tctcattttt gaagaccgaa agttcgcaga catcggttcc actgttaagg   1500
cccaatatgc aggtggagtg tttaagatcg ctcaatgggc tgatataaca aatgctcacg   1560
gtgttcctgg gccgggaatt gtgagcggac tagaagaggc tgcgaaggaa actacggatg   1620
aacctcgcgg ccttgtcatg cttgcagaac tgagttcgaa gggcacactg gctcacggcg   1680
aatactcgca agcgacagta gacatcgctc gcagtaaccg cgcatttgtg tttggtttca   1740
tcgctcagca aaaagtcgga aagccagagg aagactgggt cattatgact cctggggtgg   1800
gcctggacga caaaggtgat ggattggggc agcagtatcg tactgtggac gacgtcatag   1860
agaccggcac agacgttatt atcgtcggac gcgggctcta tagcaaggga cgagatcctg   1920
tgcacgaagc tcagcgttac caaaaggcgg gctggaatgc atatctgaga aaagttcagt   1980
caagatgatt ttctcaaaca gttccttcaa tgcaacttgc acatgaatac ctataaaatc   2040
tgattaaatt accataaaag gtacagatta aaatatatat gccttcaatg gcatccttcg   2100
cgattctgat tcgtcagcac acttcaacct tcctactatg agtgacagtg atgatgatct   2160
gctggcattg gccgacgttg gctccgactc cgaagaggaa atctcgctgc cgtcgccgcc   2220
aagcaatgag gtcgtcaatc cctatcctct agaaggcaaa tatctcgatg ctgaagacag   2280
ggcgaagttg gacgcgctgc cagagattga gcgagaagag atcttgtatg accgagctca   2340
ggagatgcag cggtacgagg agagaaggta tcttgctcag cgaaggaagc agatgacgcg   2400
ggttgctgac gaggacgaag ccccctccgc caagcgtcaa cggggtacaa caggcgtctc   2460
```

```
ttcgggtacg aagtcatctc ttgaggcatt aaagaaacga agggcccagc agtctcggaa   2520
gtcctcacgc catggagttg atgacgatgt gtatagtgac gatgatgaaa catgtgcgat   2580
cgctaagcag tacgacgttg ttgctggagt ctcatctgca aggttgagta ccaatccctg   2640
ccccaatacg agcaatcgaa gccttgggga aagatgcggc gggctagctt cagcaataaa   2700
tagcaggcga cacacaaaaa ttaggcggca agcgcacgct cagcatgcca tctaccaggg   2760
caaaaagcaa ggcaacctct ttttcgcatc ccgatttaga gcctacccgt cattgcaggg   2820
tgtgcgtcta cgatataaca cgatcgacat cgcgctgggt atgcttctgg gtaaggggtc   2880
gcaacgtgtg agttgtcagc actggccgat acccaaagta tataatgcgc cgttgaacgg   2940
ttatagtcgg tcaagctctt aaagaaagac ttaacaacaa aaacaactct acacatatgg   3000
ttgtaaactc ctcgaaggac cctcaaaaca aaggaatgac tcctagaaaa gaaattgacc   3060
aggaaatggt ctcttgggcc aaaaaaaacc tcaaaaacac ccctggcaat gaaaactatg   3120
agaagatggt ctcaggagtt ccttacaatc catacgatcc agatcttatg tttagagccc   3180
tggctactag tgagaaagtt agggagttca ataccattgc aagtgaaagt cgtacttttg   3240
agtcaaatca cgctgcttat atcaagaagg tcgagattct caaagacact tttggtcaaa   3300
caaaggatat tgtctggctg accgctccat tctcagttga ttttggattc aacatcagcg   3360
taggcgagca cttttacgcc aacttcaacg tttgcttctt ggactcggct ccaataatct   3420
ttggtgatga ggtgattgta gggcccaata caacgttcgt gactgcgact catcctatta   3480
gccccgagaa acgtgcgagg agaattgtgt atgctcttcc tatcaaggtg gggaataatg   3540
tatggattgg tgcgaatgtg actgtcctgc cgggtgttac gattggagat ggctcaacaa   3600
ttgcggctgg tgctgtcgtt cgagaagatg ttcctcctcg tactgtggtg ggaggagtcc   3660
ctgcgcgaat cctcaagcat attccagagg aggatcccga cgaggctgaa ggagaggaac   3720
tggaattcct tcttccagtt gaaatgaacg tcaataccgc taaccagaag gtctaggtag   3780
gccggccatt tctcctaata ggctgtcagc gcatatctga ggcgctcata taaaacaata   3840
taaatcaaaa cccatgttaa aaacttgttg atcccagcac ttttgagaag cgcactccga   3900
actaaatcta aaaacacttc agcttaagct attattgcct gattctcgtc atatcgctgg   3960
ggcccgcgat cgcacgcgtt ctgctataaa ttgacggagt ttcgtacagt gcgctcgtac   4020
agtgcgctgc caaatacaat ttagtgtagc cagattggat ggttgaattg ctcttcacgg   4080
ttgcacgcta ttggcaaaaa agagagagcc gctctgaact ggttcatccg cagctgacct   4140
tcgaaactct ttaatattta ataatattgc agcaaaatct atagcttatg ccacatctat   4200
acggaagagg tattcaacat tagagcttgt gtcgcccatt ctctacacga gcccacgcat   4260
cagcagtgag ggcttgtag ctcgtgccct ctaaccagta gattgtttgt cctgctgggg   4320
cgggaatctg ctggtttcgg aattctttct tctgaacttt gttgttgccg gtgatggtga   4380
cggtgtcgac gaacttaatg aatatcggca cggcatagcg tggcagcctt tccaaaagat   4440
gcttgccgag tttatccata tccagctgtt ttctaggat                          4479
```

<210> SEQ ID NO 73
<211> LENGTH: 7596
<212> TYPE: DNA
<213> ORGANISM: Artificial
<220> FEATURE:
<223> OTHER INFORMATION: koCassette

<400> SEQUENCE: 73

```
ggacctgcgc cctaaaatgg gactttgtca aaaaaagaac ggcctcctgc gcgatggaga     60
```

-continued

```
gcaatcaaga attcggagtt ccgatgcgaa tccatcaaga aaacggcccc taggcaatct    120
aaaaccgtgg ccgacatact ataagtcaat tccgctgtac aaataacaag cgatcaatcc    180
ataatctgag gctcatttca tacggacttt tctaagttca cataattcta tgatgcatac    240
taacaaatac gatgcacaaa tgggtacaag gcctaaagag ggccacaatc gcgatttact    300
cgatacggca aatcagttcc acaagtaatt cgctatcgtc ggtgttgtta tacacctctc    360
ggcttgagtc aatatcgagc atgcaaggtt gacgcattct ggggaaatgt atccacgtga    420
tcgccgatat cggagcggat acgctgtgta gtcttcagtt gtaagatttc ttatacagcg    480
acgcaaccat acatgtgacg gcccgtgctg gtctgacggg cggatagtac aggctttgcc    540
aaaagcctat aaggctaaag aaagtaaaca agtgaggttg aaccatgatg gcagtgttcg    600
aattctgatc aatgaagtac actgcgaagg gaatccccga aacggcgaac aaaaagaaca    660
tcagaggagg aacgccctcg caatcccgaa cataccagtt tcgcagaacc tggggtatca    720
actggatgca ccagcatact gttcccactg ttgccaatgc tgtagacgct ccattgttgt    780
cagtcatttt agcattttac agtaaccaac tccaaaaaac agcccgctct gctgggaaga    840
cttcgcaatt atttatccac tactgctgcg gttatatact tctcgatctc agtctcggtt    900
ataattgccg cttgacagcc tggagaaatt cggatactcc acgtgataat tgccataggg    960
cataattttc gaaacagctc gcaacgatct cggctagttt tccccttttt tgacccatat   1020
cgacgctgag actcactcac ttgatgccta ccgttagggt aaatttttca agcctgcaga   1080
atatcgcggg acgcagtctc ctgcacgcgc gtgacttcat cttacttaca tcaaacagcc   1140
cgattaattt gaaaagtcct agctgatcga gggcacgggc actactgtag agaaataata   1200
tgaagctgag ctatgaggag cgccgagaga ggctgccggc tgtagcagcc cggctattcg   1260
acatcattgt gagcaagcaa acaaatcttt gcgcaagctt ggatgtgcga actacctctg   1320
agttactgag tatcctggac cgcattggac cttacattgg tatggttaag acccacattg   1380
acataattga cgacttcgaa tacgacacaa ctgtcagcgg tttgaaacag ctttcaacga   1440
agcacaattt tctcattttt gaagaccgaa agttcgcaga catcggttcc actgttaagg   1500
cccaatatgc aggtggagtg tttaagatcg ctcaatgggc tgatataaca aatgctcacg   1560
gtgttcctgg gccgggaatt gtgagcggac tagaagaggc tgcgaaggaa actacggatg   1620
aacctcgcgg ccttgtcatg cttgcagaac tgagttcgaa gggcacactg gctcacggcg   1680
aatactcgca agcgacagta gacatcgctc gcagtaaccg cgcatttgtg tttggtttca   1740
tcgctcagca aaaagtcgga aagccagagg aagactgggt cattatgact cctggggtgg   1800
gcctggacga caaaggtgat ggattggggc agcagtatcg tactgtggac gacgtcatag   1860
agaccggcac agacgttatt atcgtcggac gcgggctcta tagcaaggga cgagatcctg   1920
tgcacgaagc tcagcgttac caaaaggcgg gctggaatgc atatctgaga aaagttcagt   1980
caagatgatt ttctcaaaca gttccttcaa tgcaacttgc acatgaatac ctataaaatc   2040
tgattaaatt accataaaag gtacagatta aaatatatat gccttcaatg gcatccttcg   2100
cgattctgat tcgtcagcac acttcaacct tcctactatg agtgacagtg atgatgatct   2160
gctggcattg gccgacgttg gctccgactc cgaagaggaa atctcgctgc cgtcgccgcc   2220
aagcaatgag gtcgtcaatc cctatcctct agaaggcaaa tatctcgatg ctgaagacag   2280
ggcgaagttg gacgcgctgc cagagattga gcgagaagag atcttgtatg accgagctca   2340
ggagatgcag cggtacgagg agagaaggta tcttgctcag cgaaggaagc agatgacgcg   2400
```

```
ggttgctgac gaggacgaag ccccctccgc caagcgtcaa cggggtacaa caggcgtctc   2460
ttcgggtacg aagtcatctc ttgaggcatt aaagaaacga agggcccagc agtctcggaa   2520
gtcctcacgc catggagttg atgacgatgt gtatagtgac gatgatgaaa catgtgcgat   2580
cgctaagcag tacgacgttg ttgctggagt ctcatctgca aggttgagta ccaatccctg   2640
ccccaatacg agcaatcgaa gccttgggga aagatgcggc gggctagctt cagcaataaa   2700
tagcaggcga cacacaaaaa ttaggcggca agcgcacgct cagcatgcca tctaccaggg   2760
caaaaagcaa ggcaacctct ttttcgcatc ccgatttaga gcctacccgt cattgcaggg   2820
tgtgcgtcta cgatataaca cgatcgacat cgcgctgggt atgcttctgg gtaaggggtc   2880
gcaacgtgtg agttgtcagc actggccgat acccaaagta tataatgcgc cgttgaacgg   2940
ttatagtcgg tcaagctctt aaagaaagac ttaacaacaa aaacaactct acacatatgg   3000
tggatgatat acaggtagag aagcgtgaga aactcatcga gactaaggac aagcttctcg   3060
aggagaagct ctctgcgtta gatccacatg aggccaatgt attgcgaagt cagcttgaaa   3120
caaagagagt cgccacaagc tttttcaggt tgttcagatt ttgcactccc cttgacgttt   3180
tcttggagat acttgcgctt ttttttgcag cggtgcatgg agccgcgctt ccaatgttca   3240
cgttagtagt gggcgccatc ttcaacacat tcagagactt cactagctat gacctcaagg   3300
gcaatgagtt ccagcataag gtgaatcacc tgtctctcta ttttgtctat attggcattg   3360
gtatgctcgg cagtgcgttt ctcgagagct tcctgcttgt ggacagaggc gaagtgttgg   3420
caggacgtta ccgaaagcat tatctgagtg ctgttattcg ccagaatatc gcgttttacg   3480
acaaactagg tggtggcgag gtcagcacca gaatcattaa cgataccaac tcaattcagg   3540
aagcgatcag cgacaagctt ggaaacgtcg tacagggaat agcttccttc attgcggcca   3600
ccgttataag ttttgcttcg caatggaaac tggcttgcat cctcctgagt gctgtagggt   3660
tcatggtaat cacaatggga actggcgcca ccttcatggc caaatatcag ctcagatctg   3720
acgcgatata ttcgcagtct ggagctaccg ttgcggagga ggctctcagt gctgtcagga   3780
ctacagtagc atttggcgct caacctcatc tcgccgtcaa gtatgaaaag gtacttgatc   3840
gtgttgtgaa ggaatcgaag cggagcagtt actcattggg ggtcatgtta gcgtgcattt   3900
gggctagtac tttttgggtg tatgccttag ctctgtggca gggttccaga gaaatcgtta   3960
gtgggagtgc tgacgttgga aagataatag ttgtaatcac agctatgtta cttggaagct   4020
tccagcttgg gaatatcgcg ccaaacgtga ggtttcttgt caagggtctc actgccgcga   4080
gcattctcaa tgaggccatt gatcgtgtcc cagtcatcga tggccagtcc atagataaag   4140
gaattgtccc ccaaactaag gccgttggca gaattgagct caaaaatgtc aagttccgat   4200
atcctagtcg cccagacgtt ttggtcctct ccgattttag ccttgaagtt cctgctggat   4260
ctactgtggc actggtaggt gcctcgggat cagggaagtc tacaattgta ggtattcttg   4320
agaggttcta tttacctctc gaaggaagcg ttactctgga tggccaggag attagcgacc   4380
tgaacacaag atggctccgt caacaaattg gttatgttca gcaggaacca gtactctttt   4440
cagagtcaat atatgagaat atcagctatg gtttgattgg cactgacatt gagttcgctg   4500
acgagcatgt taaggaagct aaaatcattc aagcttgtaa agatgccaat gcctgggatt   4560
tcattcagac tctctcagaa ggcatccaaa ccaatgttgg agatcgagga tttcttctca   4620
gcggtggtca gaaacaacgc attgcaatag caagagcaat cgtctcagac cctaaaattc   4680
tgctgctcga tgaagcgact tctgctctgg ataccaaatc tgaaggtatc gttcaagatg   4740
cgctcgacaa agcggccgaa ggtcgtacca ctatagtcgt tgcacacaga ctctctacga   4800
```

```
tcaaggatgc caacaagata gttgtcatgt ctaaaggtaa cgtcatagag cagggtactc   4860
acaatgagct catacagcga gaagggcctt ataaagcttt ggttgatgct caaagagtaa   4920
ctaaagcaaa gagcactaac gttgaggtcc tcgatattga agctctagac atttcgcctc   4980
tggactcact gaacgaaaag ttcaatccca aggatgtgag cacattgagt gttcacagtg   5040
caggtactca gaccactcaa cctcctgaat atcaagaaaa tgacatccct ggtgtgcgca   5100
acccccccaca tagcacgttg atgaccaata ccaaactggt ttgggggctg aataggaaag   5160
aatggggtta cattctcatt ggtagtttag cctccattat tttgggctat tgctatcctg   5220
caatggcaat aataactggc caaaccactg gaagcatggt tctacctccc agtgaatacg   5280
gaaaaatgcg gcatgtggtg aatatcatgg gatggtggta tttttcgta ggctgcattt   5340
cattcatgac ggcttttatc actatagctg ctttatcact tgcatctgat aagttggtca   5400
aaaatatcag attagctttg ttccgccaat tgatgcgaat ggatattgca ttcttcgacc   5460
acaaaaacaa cacgccgggt gcgctaacct caattttggc gaaggaagct aaaatgatcg   5520
agggtttgag tggggccacc ctcggtcaaa ttcaacagag tctggtgacc ttgattggcg   5580
gcatagttac tggtatacct ttcaattgga gaattggact cgtggctacg tctgttgttc   5640
ctgtcatgtt ggtgtgtggc ttcgtcagag tctgggttct tacccaatta tcggatcgtg   5700
cgagagaagt ttacgaacga agtggctcca tggcatctga gtatacaagt gctgtccgca   5760
cagtccagtc cttaactcgt gagttagacg tggtcgtaaa atacacaaag acagtagact   5820
ctcagatttt cagctccaga attgccattg cccgctcagc attgtactac gcactctcgg   5880
aaggaatgac accctgggtg gtagccctcg tttttggtg gggaagcact gtaatgagac   5940
gaggtgaagc ttcggtcgca ggatatatga ctgtcttcat ggctattatt acaggttctc   6000
aagccgctgg ccaaattttc agctatgctc caaacatgaa ctcagccaaa gatgcagcgc   6060
gtaacattta cagaatcttg actgccactc cttctataga tgtatggagt gaggaaggtt   6120
acgttgctcc cgaggagtcg gtgagaggag atattgagtt ccgtcatgtg aatttccgat   6180
atcctactcg acctcaagta ccagttttac aagatctcaa cttaacagtc aaaaagggcc   6240
aatacatcgc tctagttgga gccagtggat gcggtaagtc tactactatt ggactggtgg   6300
aaagatttta tgatccatta gcaggtcaag tacttttcga tgggaaagat ttacgcgaat   6360
ataacctgaa tgcattgaga tcacacattg ctttagtcca gcaagaacca atgctttatt   6420
caggcacgct acgtgagaat attctaatgg gatggtctgg ccctgagtct gaagtaacgc   6480
aggagatgat tgaggatgcc gctcgcaaag cgaacattca cgaattcatc atgtcgttgc   6540
ctgatggcta cgaaacgctc agcggatcta ggggatcgtt gctatctggg gggcaaaagc   6600
agcgaattgc aattgcaagg gccctgatca gaaatccaaa ggtactcctc ctcgatgagg   6660
ccacctcagc tctggattcc gaatctgaga aagtagttca agcagcactc gacgcagcag   6720
cgaagggccg tactacaatc gccgttgcgc atagattatc aacaattcag aaagcagatg   6780
tcatatatgt gttctcagga gggcgcatcg tggagcaggg cgaccatcag agcctccttg   6840
aactcaatgg atggtacgct gaattggtga acttgcaagg tctcggagag atttgaggcc   6900
ggccatttct cctaataggc tgtcagcgca tatctgaggc gctcatataa aacaatataa   6960
atcaaaaccc atgttaaaaa cttgttgatc ccagcacttt tgagaagcgc actccgaact   7020
aaatctaaaa acacttcagc ttaagctatt attgcctgat tctcgtcata tcgctggggc   7080
ccgcgatcgc acgcgttctg ctataaattg acggagtttc gtacagtgcg ctcgtacagt   7140
```

gcgctgccaa atacaattta gtgtagccag attggatggt tgaattgctc ttcacggttg 7200
cacgctattg gcaaaaaaga gagagccgct ctgaactggt tcatccgcag ctgaccttcg 7260
aaactcttta atatttaata atattgcagc aaaatctata gcttatgcca catctatacg 7320
gaagaggtat tcaacattag agcttgtgtc gcccattctc tacacgagcc cacgcatcag 7380
cagtgagggg cttgtagctc gtgccctcta accagtagat tgtttgtcct gctggggcgg 7440
gaatctgctg gtttcggaat tctttcttct gaactttgtt gttgccggtg atggtgacgg 7500
tgtcgacgaa cttaatgaat atcggcacgg catagcgtgg cagcctttcc aaaagatgct 7560
tgccgagttt atccatatcc agctgttttc taggat 7596

<210> SEQ ID NO 74
<211> LENGTH: 4998
<212> TYPE: DNA
<213> ORGANISM: Artificial
<220> FEATURE:
<223> OTHER INFORMATION: koCassette

<400> SEQUENCE: 74
ggacctgcgc cctaaaatgg gactttgtca aaaaaagaac ggcctcctgc gcgatggaga 60
gcaatcaaga attcggagtt ccgatgcgaa tccatcaaga aaacggcccc taggcaatct 120
aaaaccgtgg ccgacatact ataagtcaat tccgctgtac aaataacaag cgatcaatcc 180
ataatctgag gctcatttca tacggacttt tctaagttca cataattcta tgatgcatac 240
taacaaatac gatgcacaaa tgggtacaag gcctaaagag ggccacaatc gcgatttact 300
cgatacggca aatcagttcc acaagtaatt cgctatcgtc ggtgttgtta tacacctctc 360
ggcttgagtc aatatcgagc atgcaaggtt gacgcattct ggggaaatgt atccacgtga 420
tcgccgatat cggagcggat acgctgtgta gtcttcagtt gtaagatttc ttatacagcg 480
acgcaaccat acatgtgacg gcccgtgctg gtctgacggg cggatagtac aggctttgcc 540
aaaagcctat aaggctaaag aaagtaaaca agtgaggttg aaccatgatg gcagtgttcg 600
aattctgatc aatgaagtac actgcgaagg gaatccccga aacggcgaac aaaaagaaca 660
tcagaggagg aacgccctcg caatcccgaa cataccagtt tcgcagaacc tggggtatca 720
actggatgca ccagcatact gttcccactg ttgccaatgc tgtagacgct ccattgttgt 780
cagtcatttt agcattttac agtaaccaac tccaaaaaac agcccgctct gctgggaaga 840
cttcgcaatt atttatccac tactgctgcg gttatatact tctcgatctc agtctcggtt 900
ataattgccg cttgacagcc tggagaaatt cggatactcc acgtgataat tgccataggg 960
cataattttc gaaacagctc gcaacgatct cggctagttt tccccttttt tgacccatat 1020
cgacgctgag actcactcac ttgatgccta ccgttagggt aaatttttca agcctgcaga 1080
atatcgcggg acgcagtctc ctgcacgcgc gtgacttcat cttacttaca tcaaacagcc 1140
cgattaattt gaaaagtcct agctgatcga gggcacgggc actactgtag agaaataata 1200
tgaagctgag ctatgaggag cgccgagaga ggctgccggc tgtagcagcc cggctattcg 1260
acatcattgt gagcaagcaa acaaatcttt gcgcaagctt ggatgtgcga actacctctg 1320
agttactgag tatcctggac cgcattggac cttacatttg tatggttaag acccacattg 1380
acataattga cgacttcgaa tacgacacaa ctgtcagcgg tttgaaacag ctttcaacga 1440
agcacaattt tctcattttt gaagaccgaa agttcgcaga catcggttcc actgttaagg 1500
cccaatatgc aggtggagtg tttaagatcg ctcaatgggc tgatataaca aatgctcacg 1560
gtgttcctgg gccgggaatt gtgagcggac tagaagaggc tgcgaaggaa actacggatg 1620

```
aacctcgcgg ccttgtcatg cttgcagaac tgagttcgaa gggcacactg gctcacggcg   1680
aatactcgca agcgacagta gacatcgctc gcagtaaccg cgcatttgtg tttggtttca   1740
tcgctcagca aaaagtcgga aagccagagg aagactgggt cattatgact cctggggtgg   1800
gcctggacga caaaggtgat ggattggggc agcagtatcg tactgtggac gacgtcatag   1860
agaccggcac agacgttatt atcgtcggac gcgggctcta tagcaaggga cgagatcctg   1920
tgcacgaagc tcagcgttac caaaaggcgg gctggaatgc atatctgaga aaagttcagt   1980
caagatgatt ttctcaaaca gttccttcaa tgcaacttgc acatgaatac ctataaaatc   2040
tgattaaatt accataaaag gtacagatta aaatatatat gccttcaatg gcatccttcg   2100
cgattctgat tcgtcagcac acttcaacct tcctactatg agtgacagtg atgatgatct   2160
gctggcattg gccgacgttg gctccgactc cgaagaggaa atctcgctgc cgtcgccgcc   2220
aagcaatgag gtcgtcaatc cctatcctct agaaggcaaa tatctcgatg ctgaagacag   2280
ggcgaagttg gacgcgctgc cagagattga gcgagaagag atcttgtatg accgagctca   2340
ggagatgcag cggtacgagg agagaaggta tcttgctcag cgaaggaagc agatgacgcg   2400
ggttgctgac gaggacgaag ccccctccgc caagcgtcaa cggggtacaa caggcgtctc   2460
ttcgggtacg aagtcatctc ttgaggcatt aaagaaacga agggcccagc agtctcggaa   2520
gtcctcacgc catggagttg atgacgatgt gtatagtgac gatgatgaaa catgtgcgat   2580
cgctaagcag tacgacgttg ttgctggagt ctcatctgca aggttgagta ccaatccctg   2640
ccccaatacg agcaatcgaa gccttgggga aagatgcggc gggctagctt cagcaataaa   2700
tagcaggcga cacacaaaaa ttaggcggca agcgcacgct cagcatgcca tctaccaggg   2760
caaaaagcaa ggcaacctct ttttcgcatc ccgatttaga gcctacccgt cattgcaggg   2820
tgtgcgtcta cgatataaca cgatcgacat cgcgctgggt atgcttctgg gtaaggggtc   2880
gcaacgtgtg agttgtcagc actggccgat acccaaagta tataatgcgc cgttgaacgg   2940
ttatagtcgg tcaagctctt aaagaaagac ttaacaacaa aaacaactct acacatatgg   3000
ccatcgagaa accagtgata gttgcttgtg cctgcccact agcggggcac gtgggcccag   3060
tgctcagcct ggtccgcggt ctactcaata gaggatatga ggtgactttc gtaacaggga   3120
acgcattcaa ggagaaagtt attgaggcag gatgcacttt cgtccctctc caaggacgag   3180
ctgactacca tgaatacaat ctccctgaaa tcgctccagg attgctcacg attcctccag   3240
gccttgagca gaccggttac tcaatgaatg agatttttgt gaaggcgatt cctgagcagt   3300
acgatgcact tcaaactgct ctaaaacagg ttgaggctga aaataaatca gctgtggtga   3360
ttggcgagac catgtttcta ggggtgcatc cgatatcact gggtgcccca ggtctcaagc   3420
cccaaggcgt aatcacgtta ggaactattc cgtgcatgct gaaagcagag aaggcgcctg   3480
gagttcctag tcttgagcca atgattgata ctttagtgcg gcaacaagta tttcaaccag   3540
gaactgactc tgagaaggag atcatgaaga cgctcggggc cacgaaggag cccgaatttc   3600
tcctggagaa tatatacagc agccctgaca gatttttgca actgtgccct ccatctcttg   3660
aatttcactt gacttcgcct cctcctggct tctcgttcgc tggtagtgca ccgcatgtaa   3720
agtctgctgg attagcaact ccacctcacc tgccgtcttg gtggcctgat gtgctgagtg   3780
cgaagcgtct gattgttgtt acacaaggaa cagcagccat caactatgaa gatctgctca   3840
ttccagcatt gcaggccttt gctgacgaag aagacactct cgtagttggt atattgggcg   3900
tcaaaggggc gtcacttcct gatagcgtta aagttcctgc aaacgctcga attgttgatt   3960
```

```
atttcctta cgatgagcta ctaccgcatg cctctgtttt catatacaac ggtggatacg   4020

gaggtctgca gcacagtttg agccatggcg ttcccgtcat catcggagga ggaatgttgg   4080

tagacaagcc agctgttgct tcacgagctg tatgggctgg tgttggttat gatcttcaaa   4140

ccttgcaggc aacttctgag ctagtctcca cggccgttaa ggaggtgttg gctactccct   4200

cgtatcacga gaaagccatg gcagtcaaga aagagcttga aaaatacaag tctcttgata   4260

ttctagagtc ggcaattagt gaattagctt cttaacctgg ccggccattt ctcctaatag   4320

gctgtcagcg catatctgag gcgctcatat aaaacaatat aaatcaaaac ccatgttaaa   4380

aacttgttga tcccagcact tttgagaagc gcactccgaa ctaaatctaa aaacacttca   4440

gcttaagcta ttattgcctg attctcgtca tatcgctggg gcccgcgatc gcacgcgttc   4500

tgctataaat tgacggagtt tcgtacagtg cgctcgtaca gtgcgctgcc aaatacaatt   4560

tagtgtagcc agattggatg gttgaattgc tcttcacggt tgcacgctat tggcaaaaaa   4620

gagagagccg ctctgaactg gttcatccgc agctgacctt cgaaactctt taatatttaa   4680

taatattgca gcaaaatcta tagcttatgc cacatctata cggaagaggt attcaacatt   4740

agagcttgtg tcgcccattc tctacacgag cccacgcatc agcagtgagg ggcttgtagc   4800

tcgtgccctc taaccagtag attgtttgtc ctgctggggc gggaatctgc tggtttcgga   4860

attctttctt ctgaactttg ttgttgccgg tgatggtgac ggtgtcgacg aacttaatga   4920

atatcggcac ggcatagcgt ggcagccttt ccaaaagatg cttgccgagt ttatccatat   4980

ccagctgttt tctaggat                                                4998
```

<210> SEQ ID NO 75
<211> LENGTH: 3732
<212> TYPE: DNA
<213> ORGANISM: Artificial
<220> FEATURE:
<223> OTHER INFORMATION: IntegrationCassette

<400> SEQUENCE: 75

```
gcggccgctt attttttgga cctgcgccct aaaatgggac tttgtcaaaa aaagaacggc     60

ctcctgcgcg atggagagca atcaagaatt cggagttccg atgcgaatcc atcaagaaaa    120

cggcccctag gcaatctaaa accgtggccg acatactata agtcaattcc gctgtacaaa    180

taacaagcga tcaatccata atctgaggct catttcatac ggacttttct aagttcacat    240

aattctatga tgcatactaa caaatacgat gcacaaatgg gtacaaggcc taaagagggc    300

cacaatcgcg atttactcga tacggcaaat cagttccaca agtaattcgc tatcgtcggt    360

gttgttatac acctctcggc ttgagtcaat atcgagcatg caaggttgac gcattctggg    420

gaaatgtatc cacgtgatcg ccgatatcgg agcggatacg ctgtgtagtc ttcagttgta    480

agatttctta tacagcgacg caaccataca tgtgacggcc cgtgctggtc tgacgggcgg    540

atagtacagg ctttgccaaa agcctataag gctaaagaaa gtaaacaagt gaggttgaac    600

catgatggca gtgttcgaat tctgatcaat gaagtacact gcgaagggaa tccccgaaac    660

ggcgaacaaa aagaacatca gaggaggaac gccctcgcaa tcccgaacat accagtttcg    720

cagaacctgg ggtatcaact ggatgcacca gcatactgtt cccactgttg ccaatgctgt    780

agacgctcca ttgttgtcag tcattttagc attttacagt aaccaactcc aaaaaacagc    840

ccgctctgct gggaagactt cgcaattatt tatccactac tgctgcggtt atatacttct    900

cgatctcagt ctcggttata attgccgctt gacagcctgg agaaattcgg atactccacg    960

tgataattgc catagggcat aattttcgaa acagctcgca acgatctcgg ctagttttcc   1020
```

cctttttga cccatatcga cgctgagact cactcacttg atgcctaccg ttagggtaaa 1080
tttttcaagc ctgcagaata tcgcgggacg cagtctcctg cacgcgcgtg acttcatctt 1140
acttacatca aacagcccga ttaatttgaa aagtcctagc tgatcgaggg cacgggcact 1200
actgtagaga aataatatga agctgagcta tgaggagcgc cgagagaggc tgccggctgt 1260
agcagcccgg ctattcgaca tcattgtgag caagcaaaca aatctttgcg caagcttgga 1320
tgtgcgaact acctctgagt tactgagtat cctggaccgc attggacctt acatttgtat 1380
ggttaagacc cacattgaca taattgacga cttcgaatac gacacaactg tcagcggttt 1440
gaaacagctt tcaacgaagc acaattttct catttttgaa gaccgaaagt tcgcagacat 1500
cggttccact gttaaggccc aatatgcagg tggagtgttt aagatcgctc aatgggctga 1560
tataacaaat gctcacggtg ttcctgggcc gggaattgtg agcggactag aagaggctgc 1620
gaaggaaact acggatgaac ctcgcggcct tgtcatgctt gcagaactga gttcgaaggg 1680
cacactggct cacggcgaat actcgcaagc gacagtagac atcgctcgca gtaaccgcgc 1740
atttgtgttt ggtttcatcg ctcagcaaaa agtcggaaag ccagaggaag actgggtcat 1800
tatgactcct ggggtgggcc tggacgacaa aggtgatgga ttggggcagc agtatcgtac 1860
tgtggacgac gtcatagaga ccggcacaga cgttattatc gtcggacgcg ggctctatag 1920
caagggacga gatcctgtgc acgaagctca gcgttaccaa aaggcgggct ggaatgcata 1980
tctgagaaaa gttcagtcaa gatgattttc tcaaacagtt ccttcaatgc aacttgcaca 2040
tgaataccta taaaatctga ttaaattacc ataaaaggta cagattaaaa tatatatgcc 2100
ttcaatggca tccttcgcga ttctgattcg tcagcacact tcaaccttcc tactatgagt 2160
gacagtgatg atgatctgct ggcattggcc gacgttggct ccgactccga agaggaaatc 2220
tcgctgccgt cgccgccaag caatgaggtc gtcaatccct atcctctaga aggcaaatat 2280
ctcgatgctg aagacagggc gaagttggac gcgctgccag agattgagcg agaagagatc 2340
ttgtatgacc gagctcagga gatgcagcgg tacgaggaga gaaggtatct tgctcagcga 2400
aggaagcaga tgacgcgggt tgctgacgag gacgaagccc cctccgccaa gcgtcaacgg 2460
ggtacaacag gcgtctcttc gggtacgaag tcatctcttg aggcattaaa gaaacgaagg 2520
gcccagcagt ctcggaagtc ctcacgccat ggagttgatg acgatgtgta tagtgacgat 2580
gatgaaacat gtgcgatcgc taagcagtac gacgttgttg ctggagtctc atctgcaagg 2640
ttgagtacca atccctgccc caatacgagc aatcgaagcc ttggggaaag atgcggcggg 2700
ctagcttcag caataaatag caggcgacac acaaaaatta ggcggcaagc gcacgctcag 2760
catgccatct accagggcaa aaagcaaggc aacctctttt tcgcatcccg atttagagcc 2820
tacccgtcat tgcagggtgt gcgtctacga tataacacga tcgacatcgc gctgggtatg 2880
cttctgggta aggggtcgca acgtgtgagt tgtcagcact ggccgatacc caaagtatat 2940
aatgcgccgt tgaacggtta tagtcggtca agctcttaaa gaaagactta acaacaaaaa 3000
caactctaca catatggact tgtaggccgg ccatttctcc taataggctg tcagcgcata 3060
tctgaggcgc tcatataaaa caatataaat caaaacccat gttaaaaact tgttgatccc 3120
agcacttttg agaagcgcac tccgaactaa atctaaaaac acttcagctt aagctattat 3180
tgcctgattc tcgtcatatc gctggggccc gcgatcgcac gcgttctgct ataaattgac 3240
ggagtttcgt acagtgcgct cgtacagtgc gctgccaaat acaatttagt gtagccagat 3300
tggatggttg aattgctctt cacggttgca cgctattggc aaaaaagaga gagccgctct 3360

```
gaactggttc atccgcagct gaccttcgaa actctttaat atttaataat attgcagcaa   3420

aatctatagc ttatgccaca tctatacgga agaggtattc aacattagag cttgtgtcgc   3480

ccattctcta cacgagccca cgcatcagca gtgaggggct tgtagctcgt gccctctaac   3540

cagtagattg tttgtcctgc tggggcggga atctgctggt ttcggaattc tttcttctga   3600

actttgttgt tgccggtgat ggtgacggtg tcgacgaact taatgaatat cggcacggca   3660

tagcgtggca gcctttccaa aagatgcttg ccgagtttat ccatatccag ctgttttcta   3720

ggatcctgca gg                                                       3732
```

<210> SEQ ID NO 76
<211> LENGTH: 50
<212> TYPE: DNA
<213> ORGANISM: Artificial
<220> FEATURE:
<223> OTHER INFORMATION: Primer

<400> SEQUENCE: 76

```
aaacgtctca gatgcaccac caccaccacc acatggttgt aaactcctcg                50
```

<210> SEQ ID NO 77
<211> LENGTH: 30
<212> TYPE: DNA
<213> ORGANISM: Artificial
<220> FEATURE:
<223> OTHER INFORMATION: Primer

<400> SEQUENCE: 77

```
aaaggcgcgc cctagacctt ctggttagcg                                      30
```

<210> SEQ ID NO 78
<211> LENGTH: 6700
<212> TYPE: DNA
<213> ORGANISM: Artificial
<220> FEATURE:
<223> OTHER INFORMATION: Vector

<400> SEQUENCE: 78

```
tggcgaatgg gacgcgccct gtagcggcgc attaagcgcg gcgggtgtgg tggttacgcg     60

cagcgtgacc gctacacttg ccagcgccct agcgcccgct cctttcgctt tcttcccttc    120

ctttctcgcc acgttcgccg gctttccccg tcaagctcta aatcgggggc tccctttagg    180

gttccgattt agtgctttac ggcacctcga ccccaaaaaa cttgattagg gtgatggttc    240

acgtagtggg ccatcgccct gatagacggt ttttcgccct ttgacgttgg agtccacgtt    300

ctttaatagt ggactcttgt tccaaactgg aacaacactc aaccctatct cggtctattc    360

ttttgattta taagggattt tgccgatttc ggcctattgg ttaaaaaatg agctgattta    420

acaaaaattt aacgcgaatt ttaacaaaat attaacgttt acaatttcag gtggcacttt    480

tcggggaaat gtgcgcggaa cccctatttg tttatttttc taaatacatt caaatatgta    540

tccgctcatg aattaattct tagaaaaact catcgagcat caaatgaaac tgcaatttat    600

tcatatcagg attatcaata ccatattttt gaaaaagccg tttctgtaat gaaggagaaa    660

actcaccgag gcagttccat aggatggcaa gatcctggta tcggtctgcg attccgactc    720

gtccaacatc aatacaacct attaatttcc cctcgtcaaa aataaggtta tcaagtgaga    780

aatcaccatg agtgacgact gaatccggtg agaatggcaa aagtttatgc atttctttcc    840

agacttgttc aacaggccag ccattacgct cgtcatcaaa atcactcgca tcaaccaaac    900

cgttattcat tcgtgattgc gcctgagcga gacgaaatac gcgatcgctg ttaaaaggac    960
```

```
aattacaaac aggaatcgaa tgcaaccggc gcaggaacac tgccagcgca tcaacaatat   1020
tttcacctga atcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg gcaacgctac   1200
ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa aatcccttaa   1440
cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actctttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100
gcctttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg gggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
```

-continued

```
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatatacg atgcaccacc accaccacca catgagccct   5100
tcatcacaca aacccctgat tctcgcttgc ggcttgcctc tttcaggcca tataatgccc   5160
gttttgagtc tggtacacgg ccttacggac gacggatacg aagctactgt tgtgacaggc   5220
agagcgtttg aacaaaaagt tcgagatgtg ggtgcagact ttgttccttt agaagggaac   5280
gcagattttg atgaccacac cttagacgat ctggtcccgg gccgtaaaga catggcccca   5340
agcttcgatc gtacagttca agatgtggag cacatgatgg tagctactct tcctgagcag   5400
tttgccgcta ttcagagggc tttcaaaaag ctcagcgcaa gcggtcgccc tgtcgttctt   5460
gtcagtgaag tgctgttttt cggtgcacac cctatcagcc tcggtgctcc tggtttcaaa   5520
cccgctggct ggatttgttt aggggttttg cctcttttga tccgcagtga tcatacctta   5580
ggacttgaca acgacaggag ccccgaagca catgcaaaga aactcgctat gaaccacgct   5640
cttgagcacc aaattttcgt taaagccact gctaagcaca aggaaatctg ccgagagtta   5700
```

ggttgcactg aagatcccaa atttatctgg gagcacagtt acattgctgc agacaagttc 5760
ctgcagctgt gcccgccttc tcttgagttc agcagagacc atctgcctag caacttcaaa 5820
ttcgccggct caacgcccaa gcaccgaact caattcaccc ctccttcctg gtggggggat 5880
gttctgagtg ccaagcgagt catcatggtc actcaaggaa cttttgctgt cagttacaag 5940
catcttattg tgcctactct tgaggccttg aaggacgagc ctgacacttt aacagtagcc 6000
atattgggcc gccgcggtgc caagctaccg gatgatgttg tggttcctga gaatgctcgc 6060
gtgatcgact acttcaacta cgatgctcta cttcctcacg ttgatgctct tgtctacaat 6120
ggtggatatg gcggacttca gcacagctta agccactctg ttccagttgt tattgctggt 6180
gactctgaag acaagccaat ggtggcatcg agagctgagg ccgctggcgt ggcaattgat 6240
ttgaaaactg gcttgcctac agtggagcaa atcaaagaag ctgttgattc gataattgga 6300
aatccgaaat tccacgaagc ctcgaagaag gttcaaatgg agttggaaag ccacaactcc 6360
ttgaaaattc ttgaggaaag catcgaggaa atcgccagcc atgactttgg tcttttgacc 6420
aagagtgacg aggaaactga agatatacct gtcaaaggtc cggccttagc ggtgagttct 6480
tagggcgcgc cctcgaggga tccgaattcg agctccgtcg acaagcttgc ggccgcactc 6540
gagcaccacc accaccacca ctgagatccg gctgctaaca aagcccgaaa ggaagctgag 6600
ttggctgctg ccaccgctga gcaataacta gcataacccc ttggggcctc taaacgggtc 6660
ttgaggggtt ttttgctgaa aggaggaact atatccggat 6700

<210> SEQ ID NO 79
<211> LENGTH: 51
<212> TYPE: DNA
<213> ORGANISM: Artificial
<220> FEATURE:
<223> OTHER INFORMATION: Primer

<400> SEQUENCE: 79
aaacgtctca gatgcaccac caccaccacc acatggccat cgagaaacca g 51

<210> SEQ ID NO 80
<211> LENGTH: 36
<212> TYPE: DNA
<213> ORGANISM: Artificial
<220> FEATURE:
<223> OTHER INFORMATION: Primer

<400> SEQUENCE: 80
aaaggcgcgc cttaagaagc taattcacta attgcc 36

<210> SEQ ID NO 81
<211> LENGTH: 6607
<212> TYPE: DNA
<213> ORGANISM: Artificial
<220> FEATURE:
<223> OTHER INFORMATION: Vector

<400> SEQUENCE: 81
tggcgaatgg gacgcgccct gtagcggcgc attaagcgcg gcgggtgtgg tggttacgcg 60
cagcgtgacc gctacacttg ccagcgccct agcgcccgct cctttcgctt tcttcccttc 120
ctttctcgcc acgttcgccg gctttccccg tcaagctcta aatcgggggc tccctttagg 180
gttccgattt agtgctttac ggcacctcga ccccaaaaaa cttgattagg gtgatggttc 240
acgtagtggg ccatcgccct gatagacggt ttttcgccct ttgacgttgg agtccacgtt 300

```
ctttaatagt ggactcttgt tccaaactgg aacaacactc aaccctatct cggtctattc    360
ttttgattta taagggattt tgccgatttc ggcctattgg ttaaaaaatg agctgattta    420
acaaaaattt aacgcgaatt ttaacaaaat attaacgttt acaatttcag gtggcacttt    480
tcggggaaat gtgcgcggaa cccctatttg tttatttttc taaatacatt caaatatgta    540
tccgctcatg aattaattct tagaaaaact catcgagcat caaatgaaac tgcaatttat    600
tcatatcagg attatcaata ccatattttt gaaaaagccg tttctgtaat gaaggagaaa    660
actcaccgag gcagttccat aggatggcaa gatcctggta tcggtctgcg attccgactc    720
gtccaacatc aatacaacct attaatttcc cctcgtcaaa aataaggtta tcaagtgaga    780
aatcaccatg agtgacgact gaatccggtg agaatggcaa aagtttatgc atttctttcc    840
agacttgttc aacaggccag ccattacgct cgtcatcaaa atcactcgca tcaaccaaac    900
cgttattcat tcgtgattgc gcctgagcga gacgaaatac gcgatcgctg ttaaaaggac    960
aattacaaac aggaatcgaa tgcaaccggc gcaggaacac tgccagcgca tcaacaatat   1020
tttcacctga atcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg gcaacgctac   1200
ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa aatcccttaa   1440
cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actctttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100
gcctttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
```

```
ggtcactgat gcctccgtgt aagggggatt tctgttcatg gggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
```

```
ttttgtttaa ctttaagaag gagatatacg atgcaccacc accaccacca catggccatc   5100

gagaaaccag tgatagttgc ttgtgcctgc ccactagcgg ggcacgtggg cccagtgctc   5160

agcctggtcc gcggtctact caatagagga tatgaggtga ctttcgtaac agggaacgca   5220

ttcaaggaga aagttattga ggcaggatgc actttcgtcc ctctccaagg acgagctgac   5280

taccatgaat acaatctccc tgaaatcgct ccaggattgc tcacgattcc tccaggcctt   5340

gagcagaccg gttactcaat gaatgagatt tttgtgaagg cgattcctga gcagtacgat   5400

gcacttcaaa ctgctctaaa acaggttgag gctgaaaata aatcagctgt ggtgattggc   5460

gagaccatgt ttctaggggt gcatccgata tcactgggtg ccccaggtct caagccccaa   5520

ggcgtaatca cgttaggaac tattccgtgc atgctgaaag cagagaaggc gcctggagtt   5580

cctagtcttg agccaatgat tgatacttta gtgcggcaac aagtatttca accaggaact   5640

gactctgaga aggagatcat gaagacgctc ggggccacga aggagcccga atttctcctg   5700

gagaatatat acagcagccc tgacagattt ttgcaactgt gccctccatc tcttgaattt   5760

cacttgactt cgcctcctcc tggcttctcg ttcgctggta gtgcaccgca tgtaaagtct   5820

gctggattag caactccacc tcacctgccg tcttggtggc ctgatgtgct gagtgcgaag   5880

cgtctgattg ttgttacaca aggaacagca gccatcaact atgaagatct gctcattcca   5940

gcattgcagg cctttgctga cgaagaagac actctcgtag ttggtatatt gggcgtcaaa   6000

ggggcgtcac ttcctgatag cgttaaagtt cctgcaaacg ctcgaattgt tgattatttt   6060

ccttacgatg agctactacc gcatgcctct gttttcatat acaacggtgg atacggaggt   6120

ctgcagcaca gtttgagcca tggcgttccc gtcatcatcg gaggaggaat gttggtagac   6180

aagccagctg ttgcttcacg agctgtatgg gctggtgttg gttatgatct tcaaaccttg   6240

caggcaactt ctgagctagt ctccacggcc gttaaggagg tgttggctac tccctcgtat   6300

cacgagaaag ccatggcagt caagaaagag cttgaaaaat acaagtctct tgatattcta   6360

gagtcggcaa ttagtgaatt agcttcttaa ggcgcgccct cgagggatcc gaattcgagc   6420

tccgtcgaca agcttgcggc cgcactcgag caccaccacc accaccactg agatccggct   6480

gctaacaaag cccgaaagga agctgagttg gctgctgcca ccgctgagca ataactagca   6540

taaccccttg gggcctctaa acgggtcttg aggggttttt tgctgaaagg aggaactata   6600

tccggat                                                             6607
```

<210> SEQ ID NO 82
<211> LENGTH: 50
<212> TYPE: DNA
<213> ORGANISM: Artificial
<220> FEATURE:
<223> OTHER INFORMATION: Primer

<400> SEQUENCE: 82

```
aaacgtctca gatgcaccac caccaccacc acatggttgt aaactcctcg                50
```

<210> SEQ ID NO 83
<211> LENGTH: 30
<212> TYPE: DNA
<213> ORGANISM: Artificial
<220> FEATURE:
<223> OTHER INFORMATION: Primer

<400> SEQUENCE: 83

```
aaaggcgcgc cctagacctt ctggttagcg                                      30
```

<210> SEQ ID NO 84
<211> LENGTH: 6088
<212> TYPE: DNA
<213> ORGANISM: Artificial
<220> FEATURE:
<223> OTHER INFORMATION: Vector

<400> SEQUENCE: 84

```
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta aatcgggggc tccctttagg     180
gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aaccctatct cggtctattc     360
ttttgattta taagggattt tgccgatttc ggcctattgg ttaaaaaatg agctgattta     420
acaaaaattt aacgcgaatt ttaacaaaat attaacgttt acaatttcag gtggcacttt     480
tcggggaaat gtgcgcggaa cccctatttg tttatttttc taaatacatt caaatatgta     540
tccgctcatg aattaattct tagaaaaact catcgagcat caaatgaaac tgcaatttat     600
tcatatcagg attatcaata ccatattttt gaaaaagccg tttctgtaat gaaggagaaa     660
actcaccgag gcagttccat aggatggcaa gatcctggta tcggtctgcg attccgactc     720
gtccaacatc aatacaacct attaatttcc cctcgtcaaa aataaggtta tcaagtgaga     780
aatcaccatg agtgacgact gaatccggtg agaatggcaa aagtttatgc atttctttcc     840
agacttgttc aacaggccag ccattacgct cgtcatcaaa atcactcgca tcaaccaaac     900
cgttattcat tcgtgattgc gcctgagcga gacgaaatac gcgatcgctg ttaaaaggac     960
aattacaaac aggaatcgaa tgcaaccggc gcaggaacac tgccagcgca tcaacaatat    1020
tttcacctga atcaggatat tcttctaata cctggaatgc tgttttcccg gggatcgcag    1080
tggtgagtaa ccatgcatca tcaggagtac ggataaaatg cttgatggtc ggaagaggca    1140
taaattccgt cagccagttt agtctgacca tctcatctgt aacatcattg gcaacgctac    1200
ctttgccatg tttcagaaac aactctggcg catcgggctt cccatacaat cgatagattg    1260
tcgcacctga ttgcccgaca ttatcgcgag cccatttata cccatataaa tcagcatcca    1320
tgttggaatt taatcgcggc ctagagcaag acgtttcccg ttgaatatgg ctcataacac    1380
cccttgtatt actgtttatg taagcagaca gttttattgt tcatgaccaa aatcccttaa    1440
cgtgagtttt cgttccactg agcgtcagac cccgtagaaa agatcaaagg atcttcttga    1500
gatccttttt ttctgcgcgt aatctgctgc ttgcaaacaa aaaaaccacc gctaccagcg    1560
gtggtttgtt tgccggatca agagctacca actctttttc cgaaggtaac tggcttcagc    1620
agagcgcaga taccaaatac tgtccttcta gtgtagccgt agttaggcca ccacttcaag    1680
aactctgtag caccgcctac atacctcgct ctgctaatcc tgttaccagt ggctgctgcc    1740
agtggcgata agtcgtgtct taccgggttg gactcaagac gatagttacc ggataaggcg    1800
cagcggtcgg gctgaacggg gggttcgtgc acacagccca gcttggagcg aacgacctac    1860
accgaactga gatacctaca gcgtgagcta tgagaaagcg ccacgcttcc cgaagggaga    1920
aaggcggaca ggtatccggt aagcggcagg gtcggaacag gagagcgcac gagggagctt    1980
ccagggggaa acgcctggta tctttatagt cctgtcgggt ttcgccacct ctgacttgag    2040
cgtcgatttt tgtgatgctc gtcagggggg cggagcctat ggaaaaacgc cagcaacgcg    2100
```

```
gcctttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg gggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
```

```
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatatacg atgcaccacc accaccacca catggttgta   5100
aactcctcga aggaccctca aaacaaagga atgactccta gaaaagaaat tgaccaggaa   5160
atggtctctt gggccaaaaa aaacctcaaa aacacccctg gcaatgaaaa ctatgagaag   5220
atggtctcag gagttcctta caatccatac gatccagatc ttatgtttag agccctggct   5280
actagtgaga aagttaggga gttcaatacc attgcaagtg aaagtcgtac ttttgagtca   5340
aatcacgctg cttatatcaa gaaggtcgag attctcaaag acacttttgg tcaaacaaag   5400
gatattgtct ggctgaccgc tccattctca gttgattttg gattcaacat cagcgtaggc   5460
gagcactttt acgccaactt caacgtttgc ttcttggact cggctccaat aatctttggt   5520
gatgaggtga ttgtagggcc caatacaacg ttcgtgactg cgactcatcc tattagcccc   5580
gagaaacgtg cgaggagaat tgtgtatgct cttcctatca aggtggggaa taatgtatgg   5640
attggtgcga atgtgactgt cctgccgggt gttacgattg gagatggctc aacaattgcg   5700
gctggtgctg tcgttcgaga agatgttcct cctcgtactg tggtgggagg agtccctgcg   5760
cgaatcctca agcatattcc agaggaggat cccgacgagg ctgaaggaga ggaactggaa   5820
ttccttcttc cagttgaaat gaacgtcaat accgctaacc agaaggtcta gggcgcgccc   5880
tcgagggatc cgaattcgag ctccgtcgac aagcttgcgg ccgcactcga gcaccaccac   5940
caccaccact gagatccggc tgctaacaaa gcccgaaagg aagctgagtt ggctgctgcc   6000
accgctgagc aataactagc ataacccctt ggggcctcta aacgggtctt gaggggtttt   6060
ttgctgaaag gaggaactat atccggat                                      6088
```

<210> SEQ ID NO 85
<211> LENGTH: 10065
<212> TYPE: DNA
<213> ORGANISM: Artificial
<220> FEATURE:
<223> OTHER INFORMATION: Vector
<220> FEATURE:
<221> NAME/KEY: misc_feature
<222> LOCATION: (3998)..(3998)
<223> OTHER INFORMATION: n is a, c, g, or t

<400> SEQUENCE: 85

```
gaattctcat gtttgacagc ttatcatcga taagctttaa tgcggtagtt tatcacagtt     60
aaattgctaa cgcagtcagg caccgtgtat gaaatctaac aatgcgctca tcgtcatcct    120
cggcaccgtc accctggatg ctgtaggcat aggcttggtt atgccggtac tgccgggcct    180
cttgcgggat atcgtccatt ccgacagcat cgccagtcac tatggcgtgc tgctagcgct    240
atatgcgttg atgcaatttc tatgcgcacc cgttctcgga gcactgtccg accgctttgg    300
```

```
ccgccgccca gtcctgctcg cttcgctact tggagccact atcgactacg cgatcatggc    360
gaccacaccc gtcctgtgga tccaggccgt tgagcaccgc cgccgcaagg aatggtgcat    420
gctgaggtgt ctcacaagtg ccgtgcagtc ccgcccccac ttgcttctct ttgtgtgtag    480
tgtacgtaca ttatcgagac cgttgttccc gcccacctcg atccggcatg ctgaggtgtc    540
tcacaagtgc cgtgcagtcc cgcccccact tgcttctctt tgtgtgtagt gtacgtacat    600
tatcgagacc gttgttcccg cccacctcga tccggcatgc tgaggtgtct cacaagtgcc    660
gtgcagtccc gcccccactt gcttctcttt gtgtgtagtg tacgtacatt atcgagaccg    720
ttgttcccgc ccacctcgat ccggcatgct gaggtgtctc acaagtgccg tgcagtcccg    780
cccccacttg cttctctttg tgtgtagtgt acgtacatta tcgagaccgt tgttcccgcc    840
cacctcgatc cggcatgcac tgatcacggg caaaagtgcg tatatataca agagcgtttg    900
ccagccacag attttcactc cacacaccac atcacacata caaccacaca catccacaat    960
gaaaaagcct gaactcaccg cgacgagcgt cgagaagttt ctgatcgaaa agttcgacag   1020
cgtctccgac ctgatgcagc tctcggaggg cgaagaatct cgtgctttca gcttcgatgt   1080
aggagggcgt ggatatgtcc tgcgggtaaa tagctgcgcc gatggtttct acaaagatcg   1140
ttatgtttat cggcactttg catcggccgc gctcccgatt ccggaagtgc ttgacattgg   1200
ggagttcagc gagagcctga cctattgcat ctcccgccgt gcacagggtg tcacgttgca   1260
agacctgcct gaaaccgaac tgcccgctgt tctgcagccg gtcgcggagg ccatggatgc   1320
gatcgctgcg gccgatctta gccagacgag cgggttcggc ccattcggac cgcaaggaat   1380
cggtcaatac actacatggc gtgatttcat atgcgcgatt gctgatcccc atgtgtatca   1440
ctggcaaact gtgatggacg acaccgtcag tgcgtccgtc gcgcaggctc tcgatgagct   1500
gatgctttgg gccgaggact gccccgaagt ccggcacctc gtgcacgcgg atttcggctc   1560
caacaatgtc ctgacggaca atggccgcat aacagcggtc attgactgga gcgaggcgat   1620
gttcggggat tcccaatacg aggtcgccaa catcttcttc tggaggccgt ggttggcttg   1680
tatggagcag cagacgcgct acttcgagcg gaggcatccg gagcttgcag gatcgccgcg   1740
gctccgggcg tatatgctcc gcattggtct tgaccaactc tatcagagct tggttgacgg   1800
caatttcgat gatgcagctt gggcgcaggg tcgatgcgac gcaatcgtcc gatccggagc   1860
cgggactgtc gggcgtacac aaatcgcccg cagaagcgcg gccgtctgga ccgatggctg   1920
tgtagaagta ctcgccgata gtggaaaccg acgccccagc actcgtccga gggcaaagga   1980
atagtcgacg ctctccctta tgcgactcct gcattaggaa gcagcccagt agtaggttga   2040
ggccgttgag caccgccgcc gcaaggaatg gtgcatgctg aggtgtctca caagtgccgt   2100
gcagtcccgc ccccacttgc ttctctttgt gtgtagtgta cgtacattat cgagaccgtt   2160
gttcccgccc acctcgatcc ggcatgctga ggtgtctcac aagtgccgtg cagtcccgcc   2220
cccacttgct tctctttgtg tgtagtgtac gtacattatc gagaccgttg ttcccgccca   2280
cctcgatccg gcatgctgag gtgtctcaca agtgccgtgc agtcccgccc ccacttgctt   2340
ctctttgtgt gtagtgtacg tacattatcg agaccgttgt tcccgcccac ctcgatccgg   2400
catgctgagg tgtctcacaa gtgccgtgca gtcccgcccc cacttgcttc tctttgtgtg   2460
tagtgtacgt acattatcga gaccgttgtt cccgcccacc tcgatccggc atgcactgat   2520
cacgggcaaa agtgcgtata tatacaagag cgtttgccag ccacagattt tcactccaca   2580
caccacatca cacatacaac cacacacatc cacgggctgc aggaattcga tatcaagctt   2640
atcgataccg tcgaggggca gagccgatcc tgtacacttt acttaaaacc attatctgag   2700
```

```
tgttaaatgt ccaatttact gaccgtacac caaaatttgc ctgcattacc ggtcgatgca   2760
acgagtgatg aggttcgcaa gaacctgatg gacatgttca gggatcgcca ggcgttttct   2820
gagcatacct ggaaaatgct tctgtccgtt tgccggtcgt gggcggcatg gtgcaagttg   2880
aataaccgga aatggtttcc cgcagaacct gaagatgttc gcgattatct tctatatctt   2940
caggcgcgcg gtctggcagt aaaaactatc cagcaacatt tgggccagct aaacatgctt   3000
catcgtcggt ccgggctgcc acgaccaagt gacagcaatg ctgtttcact ggttatgcgg   3060
cggatccgaa aagaaaacgt tgatgccggt gaacgtgcaa aacaggctct agcgttcgaa   3120
cgcactgatt tcgaccaggt tcgttcactc atggaaaata gcgatcgctg ccaggatata   3180
cgtaatctgg catttctggg gattgcttat aacaccctgt tacgtatagc cgaaattgcc   3240
aggatcaggg ttaaagatat ctcacgtact gacggtggga gaatgttaat ccatattggc   3300
agaacgaaaa cgctggttag caccgcaggt gtagagaagg cacttagcct gggggtaact   3360
aaactggtcg agcgatggat ttccgtctct ggtgtagctg atgatccgaa taactacctg   3420
ttttgccggg tcagaaaaaa tggtgttgcc gcgccatctg ccaccagcca gctatcaact   3480
cgcgccctgg aagggatttt tgaagcaact catcgattga tttacggcgc taaggatgac   3540
tctggtcaga gatacctggc ctggtctgga cacagtgccc gtgtcggagc cgcgcgagat   3600
atggcccgcg ctggagtttc aataccggag atcatgcaag ctggtggctg gaccaatgta   3660
aatattgtca tgaactatat ccgtaccctg gatagtgaaa caggggcaat ggtgcgcctg   3720
ctggaagatg gcgattagcc attaacgcgt aaatgattgc tataattatt tgatatttat   3780
ggtgacatat gagaaaggat ttcaacatcg acggaaaata tgtagtgctg tctgtaagca   3840
ctaatattca gtcgccagcc gtcattgtca ctgtaaagct gagcgataga atgcctgata   3900
ttgactcaat atccgttgcg tttcctgtca aaagtatgcg tagtgctgaa catttcgtga   3960
tgaatgccac cgaggaagaa gcacggcgcg gttttgcnta aagtgatgtc tgagtttggc   4020
gaactcttgg gtaaggttgg aattgtcgac cgatgccctt gagagccttc aacccagtca   4080
gctccttccg gtgggcgcgg ggcatgacta tcgtcgccgc acttatgact gtcttcttta   4140
tcatgcaact cgtaggacag gtgccggcag cgctctgggt cattttcggc gaggaccgct   4200
ttcgctggag cgcgacgatg atcggcctgt cgcttgcggt attcggaatc ttgcacgccc   4260
tcgctcaagc cttcgtcact ggtcccgcca ccaaacgttt cggcgagaag caggccatta   4320
tcgccggcat ggcggccgac gcgctgggct acgtcttgct ggcgttcgcg acgcgaggct   4380
ggatggcctt ccccattatg attcttctcg cttccggcgg catcgggatg cccgcgttgc   4440
aggccatgct gtccaggcag gtagatgacg accatcaggg acagcttcaa ggatcgctcg   4500
cggctcttac cagcctaact tcgatcactg gaccgctgat cgtcacggcg atttatgccg   4560
cctcggcgag cacatggaac gggttggcat ggattgtagg cgccgcccta taccttgtct   4620
gcctccccgc gttgcgtcgc ggtgcatgga gccgggccac ctcgacctga atggaagccg   4680
gcggcacctc gctaacggat tcaccactcc aagaattgga gccaatcaat tcttgcggag   4740
aactgtgaat gcgcaaacca acccttggca gaacatatcc atcgcgtccg ccatctccag   4800
cagccgcacg cggcgcatct cgggcagcgt tgggtcctgg ccacgggtgc gcatgatcgt   4860
gctcctgtcg ttgaggaccc ggctaggctg gcggggttgc cttactggtt agcagaatga   4920
atcaccgata cgcgagcgaa cgtgaagcga ctgctgctgc aaaacgtctg cgacctgagc   4980
aacaacatga atggtcttcg gtttccgtgt ttcgtaaagt ctggaaacgc ggaagtcagc   5040
```

```
gccctgcacc attatgttcc ggatctgcat cgcaggatgc tgctggctac cctgtggaac   5100
acctacatct gtattaacga agcgctggca ttgaccctga gtgatttttc tctggtcccg   5160
ccgcatccat accgccagtt gtttaccctc acaacgttcc agtaaccggg catgttcatc   5220
atcagtaacc cgtatcgtga gcatcctctc tcgtttcatc ggtatcatta cccccatgaa   5280
cagaaattcc cccttacacg gaggcatcaa gtgaccaaac aggaaaaaac cgcccttaac   5340
atggcccgct ttatcagaag ccagacatta acgcttctgg agaaactcaa cgagctggac   5400
gcggatgaac aggcagacat ctgtgaatcg cttcacgacc acgctgatga gctttaccgc   5460
agcagatctg tatatatata tatatatgca agccattttt tttctctcac catctatttt   5520
aatatataaa attagatcat ctatctaaac tttttcatta aataaattag atggcgaaaa   5580
taatggagac gtattccatt ataatatata aaaacctaaa actatgtttc attataacaa   5640
tttacttcct aatttggaaa attcgaagtt ggttattata tgtgcatata tactgaatgt   5700
tcataacttc tagtcaacag atataattta ttcctcgtag taacttgccc gcaaacattt   5760
tatatctaaa ttaatttcaa gggaagttct tgtaaatata tatttatctc aagtaaacag   5820
ttagaaatat cagccatgat gacattttcc aggatggcaa tgactcatga tcacactgag   5880
atttttaata gatatttcgt tagagatgat ggtatctcaa aacaaaacga ctgtagctct   5940
tttaccacct catttacaat ttcatctttc atcaaattta gggatgccat caactttcag   6000
ttcataatta atatcttacc aaattaggta atctgcaaaa gttcagactg tgaaatgtaa   6060
cattttatat atcaagctct atttaatgcc tcacagtagt taacataaag agatacagaa   6120
ttgtcgtgtc agtgtatact atccatgtgt atactctgga tatccatttg tattccatta   6180
tctacgaaaa gcacttagat aaatactaaa ttgttatttg gtatgtatcg tataagttga   6240
aagttttgag cccatcttgt tgttttcttt tattaaataa aataaaataa ctaacgttat   6300
gatactttga tgtgtttttt aatttaatta taccagtact tgtttgaaat ttttttctgc   6360
agaattttgg ccggctcatt tctatttgtt gtaagtacga gtatttgaac ttttagtcag   6420
atactggtag ttatatattt attttgtttt tgtttatttt gttgggtttt ttgtttgttg   6480
tttttttcg gggggttgtg ttccaacttc gtttttggaa ttttaattta gtttctcgat   6540
cttcgctttt ggaatttatt taatttatcc ctccccttga ggtgtgaata acttaaaaat   6600
gctagaagga gctacacagg tgtttgtaca gtaaaaacta tcagcaggat accatcgcaa   6660
gatgttcata tcgctttgtt gagtcactgc aggggaccgc tgaggtattc gctggttcgg   6720
tgagggcggc cgtccctgtg attcgtacga ataaattctt tgtacaagta ccagtgctac   6780
aattgtaggt ggtgctcata caggtacacc ccgtgtgtaa gtaaactcca attatgttat   6840
gtctgataaa aggatgtaac ataggcaagc tgctcgtgag tgttgagtac gaaccttaga   6900
tccaaatcac ccgcacccta cggatatact tgcttgaata tacttgtaat aaggctgtct   6960
gctgacatcg gtgcgcgtat gttctgggcg gcgactctct ccgaaccatc gaacagttcc   7020
tgaacacgac gagctagcta caacatgact cgcaagagct ctgtgcgtgt acacaacgag   7080
ccgtgcccgt gtaacagtct tcggttccga cccccaaaaa acccaccata caccgaaata   7140
gcacatcctt acgaccagta gcagcagagt gcgctacagt aagtattcgt caatacaagt   7200
aaatcacgag tacgacagtt gccgacacgg acagaaagga actacagatt taaatatacc   7260
aaacaataat tcattactaa tgtcaatcct tacagctgga taaaaaaact gggggatttt   7320
gttaacgagc tcattcgcaa atgaaacggg aaaagttctt cgatttagtg ttaaatctcc   7380
gttaaaaacc gcttatttgg atcgagctcg gaccttgcgg cgctttcgct tgagtcgtct   7440
```

```
gactctcttc tttctccact tagctctcat tctgggttag ttccatgttc tccgctggcg   7500
ggggcgacca ccgctaatcg agccgacttg tattgaaagg caggcaagaa ggtatcgaag   7560
gggaagaacc gttttgtggt tgctgcacca cggcttccaa tgctctccca atgaagaacc   7620
aaggtcggta attaatactc acttgaaaga tcaagacaag aacctgatga atgtgaggaa   7680
aaaaagacaa gaaggggaaa gtttgaccat ttttaagctg tgcgagccac aggccgggta   7740
acagataaat taggttctga aaattcggat ctgctgcctc gcgcgtttcg gtgatgacgg   7800
tgaaaacctc tgacacatgc agctcccgga gacggtcaca gcttgtctgt aagcggatgc   7860
cgggagcaga caagcccgtc agggcgcgtc agcgggtgtt ggcgggtgtc ggggcgcagc   7920
catgacccag tcacgtagcg atagcggagt gtatactggc ttaactatgc ggcatcagag   7980
cagattgtac tgagagtgca ccatatgcgg tgtgaaatac cgcacagatg cgtaaggaga   8040
aaataccgca tcaggcgctc ttccgcttcc tcgctcactg actcgctgcg ctcggtcgtt   8100
cggctgcggc gagcggtatc agctcactca aaggcggtaa tacggttatc cacagaatca   8160
ggggataacg caggaaagaa catgtgagca aaaggccagc aaaaggccag gaaccgtaaa   8220
aaggccgcgt tgctggcgtt tttccatagg ctccgccccc ctgacgagca tcacaaaaat   8280
cgacgctcaa gtcagaggtg gcgaaacccg acaggactat aaagatacca ggcgtttccc   8340
cctggaagct ccctcgtgcg ctctcctgtt ccgaccctgc cgcttaccgg atacctgtcc   8400
gcctttctcc cttcgggaag cgtggcgctt tctcatagct cacgctgtag gtatctcagt   8460
tcggtgtagg tcgttcgctc caagctgggc tgtgtgcacg aaccccccgt tcagcccgac   8520
cgctgcgcct tatccggtaa ctatcgtctt gagtccaacc cggtaagaca cgacttatcg   8580
ccactggcag cagccactgg taacaggatt agcagagcga ggtatgtagg cggtgctaca   8640
gagttcttga agtggtggcc taactacggc tacactagaa ggacagtatt tggtatctgc   8700
gctctgctga agccagttac cttcggaaaa agagttggta gctcttgatc cggcaaacaa   8760
accaccgctg gtagcggtgg tttttttgtt tgcaagcagc agattacgcg cagaaaaaaa   8820
ggatctcaag aagatccttt gatcttttct acggggtctg acgctcagtg gaacgaaaac   8880
tcacgttaag ggattttggt catgagatta tcaaaaagga tcttcaccta gatcctttta   8940
aattaaaaat gaagttttaa atcaatctaa agtatatatg agtaaacttg gtctgacagt   9000
taccaatgct taatcagtga ggcacctatc tcagcgatct gtctatttcg ttcatccata   9060
gttgcctgac tccccgtcgt gtagataact acgatacggg agggcttacc atctggcccc   9120
agtgctgcaa tgataccgcg agacccacgc tcaccggctc cagatttatc agcaataaac   9180
cagccagccg gaagggccga gcgcagaagt ggtcctgcaa ctttatccgc ctccatccag   9240
tctattaatt gttgccggga agctagagta agtagttcgc cagttaatag tttgcgcaac   9300
gttgttgcca ttgctgcagg catcgtggtg tcacgctcgt cgtttggtat ggcttcattc   9360
agctccggtt cccaacgatc aaggcgagtt acatgatccc ccatgttgtg caaaaaagcg   9420
gttagctcct tcggtcctcc gatcgttgtc agaagtaagt tggccgcagt gttatcactc   9480
atggttatgg cagcactgca taattctctt actgtcatgc catccgtaag atgcttttct   9540
gtgactggtg agtactcaac caagtcattc tgagaatagt gtatgcggcg accgagttgc   9600
tcttgcccgg cgtcaacacg ggataatacc gcgccacata gcagaacttt aaaagtgctc   9660
atcattggaa aacgttcttc ggggcgaaaa ctctcaagga tcttaccgct gttgagatcc   9720
agttcgatgt aacccactcg tgcacccaac tgatcttcag catcttttac tttcaccagc   9780
```

```
gtttctgggt gagcaaaaac aggaaggcaa aatgccgcaa aaaagggaat aagggcgaca   9840

cggaaatgtt gaatactcat actcttcctt tttcaatatt attgaagcat ttatcagggt   9900

tattgtctca tgagcggata catatttgaa tgtatttaga aaaataaaca aataggggtt   9960

ccgcgcacat ttccccgaaa agtgccacct gacgtctaag aaaccattat tatcatgaca  10020

ttaacctata aaaataggcg tatcacgagg ccctttcgtc ttcaa                  10065
```

<210> SEQ ID NO 86
<211> LENGTH: 28
<212> TYPE: DNA
<213> ORGANISM: Artificial
<220> FEATURE:
<223> OTHER INFORMATION: Primer

<400> SEQUENCE: 86

```
aaagatatct ctatgcgcac ccgttctc                                        28
```

<210> SEQ ID NO 87
<211> LENGTH: 39
<212> TYPE: DNA
<213> ORGANISM: Artificial
<220> FEATURE:
<223> OTHER INFORMATION: Primer

<400> SEQUENCE: 87

```
tttagatcta agcttgagac acctcagcat gcaccattc                            39
```

<210> SEQ ID NO 88
<211> LENGTH: 8114
<212> TYPE: DNA
<213> ORGANISM: Artificial
<220> FEATURE:
<223> OTHER INFORMATION: Vector

<400> SEQUENCE: 88

```
agcgcccaat acgcaaaccg cctctccccg cgcgttggcc gattcattaa tgcagctggc     60

acgacaggtt tcccgactgg aaagcgggca gtgagcgcaa cgcaattaat gtgagttagc    120

tcactcatta ggcaccccag gctttacact ttatgcttcc ggctcgtatg ttgtgtggaa    180

ttgtgagcgg ataacaattt cacacaggaa acagctatga ccatgattac gccaagctca    240

gaattaaccc tcactaaagg gactagtcct gcaggtttaa acgaattcgc cctttcatct    300

cgagatgctt tattcaggca cgctacgtga gaatattcta atgggatggt ctggccctga    360

gtctgaagta acgcaggaga tgattgagga tgccgctcgc aaagcgaaca ttcacgaatt    420

catcatgtcg ttgcctgatg gctacgaaac gctcagcgga tctaggggat cgttgctatc    480

tggggggcaa aagcagcgaa ttgcaattgc aagggccctg atcagaaatc caaaggtact    540

cctcctcgat gaggccacct cagctctgga ttccgaatct gagaaagtag ttcaagcagc    600

actcgacgca gcagcgaagg gccgtactac aatcgccgtt gcgcatagat tatcaacaat    660

tcagaaagca gatgtcatat atgtgttctc aggagggcgc atcgtggagc agggcgacca    720

tcagagcctc cttgaactca atggatggta cgctgaattg gtgaacttgc aaggtctcgg    780

agagatttga cgttcattta tttttggcca ctgcttgcat acattatttg attaaaggca    840

ctcattaatt gaaatagcat atcgaatttc tctagttatg gcccctgagt caccatacat    900

tgtctgatta aagggactcg ttaattgaaa tagcacattg gattcctctg attatgaccc    960

ctgagtcacc tatcctgcat aattcactcg tgacgataat ctgtagatat agggaactgt   1020

cgtagtactt gaagagacag caacaatcta tctctgggat ttcgtgctga ttttgggctt   1080
```

-continued

```
ttgctttgac gggctatgac tgaggtaatg tagaccaata ataaccctca cgcgaattag   1140
atatgccctg agggttagct tgcatcacct tacccatatg cacactgact tgcattaccc   1200
ggagcatatt ccggtagtcg gagataagca ctttgagata tcttaaggta caactcaata   1260
cgttcctcct tccttgcctc attccacctc acattctaga attcaataac ttcgtatagc   1320
atacattata cgaagttatt aattaacatc atcgtcacta tacacatcgt catcaactcc   1380
atggcgtgag gacttccgag actgctgggc ccttcgtttc tttaatgcct caagagatga   1440
cttcgtaccc gaagagacgc ctgttgtacc ccgttgacgc ttggcggagg gggcttcgtc   1500
ctcgtcagca acccgcgtca tctgcttcct tcgctgagca agataccttc tctcctcgta   1560
ccgctgcatc tcctgagctc ggtcatacaa gatctcttct cgctcaatct ctggcagcgc   1620
gtccaacttc gccctgtctt cagcatcgag atatttgcct tctagaggat agggattgac   1680
gacctcattg cttggcggcg acggcagcga gatttcctct tcggagtcgg agccaacgtc   1740
ggccaatgcc agcagatcat catcactgtc actcatagta ggaaggttga agtgtgctga   1800
cgaatcagaa tcgcgaagga tgccattgaa ggcatatata ttttaatctg taccttttat   1860
ggtaatttaa tcagatttta taggtattca tgtgcaagtt gcattgaagg aactgtttga   1920
gaaaatcatc ttgactgaac ttttctcaga tatgcattcc agcccgcctt ttggtaacgc   1980
tgagcttcgt gcacaggatc tcgtcccttg ctatagagcc cgcgtccgac gataataacg   2040
tctgtgccgg tctctatgac gtcgtccaca gtacgatact gctgccccaa tccatcacct   2100
ttgtcgtcca ggcccacccc aggagtcata atgacccagt cttcctctgg ctttccgact   2160
ttttgctgag cgatgaaacc aaacacaaat gcgcggttac tgcgagcgat gtctactgtc   2220
gcttgcgagt attcgccgtg agccagtgtg cccttcgaac tcagttctgc aagcatgaca   2280
aggccgcgag gttcatccgt agtttccttc gcagcctctt ctagtccgct cacaattccc   2340
ggcccaggaa caccgtgagc atttgttata tcagcccatt gagcgatctt aaacactcca   2400
cctgcatatt gggccttaac agtggaaccg atgtctgcga actttcggtc ttcaaaaatg   2460
agaaaattgt gcttcgttga aagctgtttc aaaccgctga cagttgtgtc gtattcgaag   2520
tcgtcaatta tgtcaatgtg ggtcttaacc atacaaatgt aaggtccaat gcggtccagg   2580
atactcagta actcagaggt agttcgcaca tccaagcttg cgcaaagatt tgtttgcttg   2640
ctcacaatga tgtcgaatag ccgggctgct acagccggca gcctctctcg gcgctcctca   2700
tagctcagct tcatattatt tctctacagt agtgcccgtg ccctcgatca gctaggactt   2760
ttcaaattaa tcgggctgtt tgatgtaagt aagatgaagt cacgcgcgtg caggagactg   2820
cgtcccgcga tattctgcag gcttgaaaaa tttaccctaa cggtaggcat caagtgagtg   2880
agtctcagcg tcgatatggg tcaaaaaagg ggaaaactag ccgagatcgt tgcgagctgt   2940
ttcgaaaatt atgccctatg gcaattatca cgtggagtat ccgaatttct ccaggctgtc   3000
aagcggcaat tataaccgag actgagatcg agaagtatat aaccgcagca gtagtggata   3060
aataattgcg aagtcttccc agcagagcgg gctgtttttt ggagttggtt actgtaaaat   3120
gctaaaatga ctgacaacaa tggagcgtct acagcattgg caacagtggg aacagtatgc   3180
tggtgcatcc agttgatacc ccaggttctg cgaaactggt atgttcggga ttgcgagggc   3240
gttcctcctc tgatgttctt tttgttcgcc gtttcgggga ttcccttcgc agtgtacttc   3300
attgatcaga attcgaacac tgccatcatg gttcaacctc acttgtttac tttctttagc   3360
cttataggct tttggcaaag cctgtactat ccgcccgtca gttaattaat aacttcgtat   3420
```

```
agcatacatt atacgaagtt attaggtaaa ctaaattcat gacagccttt tcttctttct   3480
ttccacaaaa caattaaaaa aaataacaga attagaagaa ggtaaatata ttggcaaact   3540
cctctcttcc ttttacttat ttttttgaaa gttgcagtgt gtgtgtgtgt tgttgtttgt   3600
tcaaattaat ttgatggttg ttgtattgta aatttcaatc aataaaaaca aagacataaa   3660
taaaaaaaac cctacctctc ttccctgatc tgatttgatc gtacgattct aagaactcac   3720
cgctaaggcc ggccctttga caggtatatc ttcagtttcc tcgtcactct tggtcaaaag   3780
accaaagtca tggctggcga tttcctcgat gctttcctca agaattttca aggagttgtg   3840
gctttccaac tccatttgaa ccttcttcga ggcttcgtgg aatttcggat ttccaattat   3900
cgaatcaaca gcttctttga tttgctccac tgtaggcaag ccagttttca aatcaattgc   3960
cacgccagcg gcctcagctc tcgatgccac cattggcttg tcttcagagt caccagcaat   4020
aacaactgga acagagtggc ttaagctgtg ctgaagtccg ccatatccac cattgtagac   4080
aagagcatca acgtgaggaa gtagagcatc gtagttgaag tagtcgatca cgcgagcatt   4140
ctcaggaacc acaacatcat ccggtagctt ggcaccgcgg cggcccaata tggctactgt   4200
taaagtgtca ggctcgtcct tcaaggcctc aagagtaggc acaataagat gcttgtaact   4260
gacagcaaaa gttccttgag tgaccatgat gactcgcttg gcactcagaa catccccccca   4320
ccaggaagga ggggtgaatt gagttcggtg cttgggcgtt gagccggcga atttgaagtt   4380
gctaggcaga tggtctctgc tgaactcaag agaaggcggg cacagctgca ggaacttgtc   4440
tgcaggtacc tcaagggcga attcgcggcc gctaaattca attcgcccta tagtgagtcg   4500
tattacaatt cactggccgt cgttttacaa cgtcgtgact gggaaaaccc tggcgttacc   4560
caacttaatc gccttgcagc acatccccct ttcgccagct ggcgtaatag cgaagaggcc   4620
cgcaccgatc gcccttccca acagttgcgc agcctatacg tacggcagtt taaggtttac   4680
acctataaaa gagagagccg ttatcgtctg tttgtggatg tacagagtga tattattgac   4740
acgccggggc gacggatggt gatccccctg gccagtgcac gtctgctgtc agataaagtc   4800
tcccgtgaac tttacccggt ggtgcatatc ggggatgaaa gctggcgcat gatgaccacc   4860
gatatggcca gtgtgccggt ctccgttatc ggggaagaag tggctgatct cagccaccgc   4920
gaaaatgaca tcaaaaacgc cattaacctg atgttctggg gaatataaat gtcaggcatg   4980
agattatcaa aaaggatctt cacctagatc cttttcacgt agaaagccag tccgcagaaa   5040
cggtgctgac cccggatgaa tgtcagctac tgggctatct ggacaaggga aaacgcaagc   5100
gcaaagagaa agcaggtagc ttgcagtggg cttacatggc gatagctaga ctgggcggtt   5160
ttatggacag caagcgaacc ggaattgcca gctggggcgc cctctggtaa ggttgggaag   5220
ccctgcaaag taaactggat ggctttcttg ccgccaagga tctgatggcg caggggatca   5280
agctctgatc aagagacagg atgaggatcg tttcgcatga ttgaacaaga tggattgcac   5340
gcaggttctc cggccgcttg ggtggagagg ctattcggct atgactgggc acaacagaca   5400
atcggctgct ctgatgccgc cgtgttccgg ctgtcagcgc aggggcgccc ggttcttttt   5460
gtcaagaccg acctgtccgg tgccctgaat gaactgcaag acgaggcagc gcggctatcg   5520
tggctggcca cgacgggcgt tccttgcgca gctgtgctcg acgttgtcac tgaagcggga   5580
agggactggc tgctattggg cgaagtgccg gggcaggatc tcctgtcatc tcaccttgct   5640
cctgccgaga aagtatccat catggctgat gcaatgcggc ggctgcatac gcttgatccg   5700
gctacctgcc cattcgacca ccaagcgaaa catcgcatcg agcgagcacg tactcggatg   5760
gaagccggtc ttgtcgatca ggatgatctg gacgaagagc atcaggggct cgcgccagcc   5820
```

```
gaactgttcg ccaggctcaa ggcgagcatg cccgacggcg aggatctcgt cgtgacccat   5880
ggcgatgcct gcttgccgaa tatcatggtg gaaaatggcc gcttttctgg attcatcgac   5940
tgtggccggc tgggtgtggc ggaccgctat caggacatag cgttggctac ccgtgatatt   6000
gctgaagagc ttggcggcga atgggctgac cgcttcctcg tgctttacgg tatcgccgct   6060
cccgattcgc agcgcatcgc cttctatcgc cttcttgacg agttcttctg aattattaac   6120
gcttacaatt tcctgatgcg gtattttctc cttacgcatc tgtgcggtat ttcacaccgc   6180
atcaggtggc acttttcggg gaaatgtgcg cggaacccct atttgtttat ttttctaaat   6240
acattcaaat atgtatccgc tcatgagatt atcaaaaagg atcttcacct agatcctttt   6300
aaattaaaaa tgaagtttta aatcaatcta aagtatatat gagtaaactt ggtctgacag   6360
ttaccaatgc ttaatcagtg aggcacctat ctcagcgatc tgtctatttc gttcatccat   6420
agttgcctga ctccccgtcg tgtagataac tacgatacgg gagggcttac catctggccc   6480
cagtgctgca atgataccgc gagacccacg ctcaccggct ccagatttat cagcaataaa   6540
ccagccagcc ggaagggccg agcgcagaag tggtcctgca actttatccg cctccatcca   6600
gtctattaat tgttgccggg aagctagagt aagtagttcg ccagttaata gtttgcgcaa   6660
cgttgttgcc attgctacag gcatcgtggt gtcacgctcg tcgtttggta tggcttcatt   6720
cagctccggt tcccaacgat caaggcgagt tacatgatcc cccatgttgt gcaaaaaagc   6780
ggttagctcc ttcggtcctc cgatcgttgt cagaagtaag ttggccgcag tgttatcact   6840
catggttatg gcagcactgc ataattctct tactgtcatg ccatccgtaa gatgcttttc   6900
tgtgactggt gagtactcaa ccaagtcatt ctgagaatag tgtatgcggc gaccgagttg   6960
ctcttgcccg gcgtcaatac gggataatac cgcgccacat agcagaactt taaaagtgct   7020
catcattgga aaacgttctt cggggcgaaa actctcaagg atcttaccgc tgttgagatc   7080
cagttcgatg taacccactc gtgcacccaa ctgatcttca gcatctttta ctttcaccag   7140
cgtttctggg tgagcaaaaa caggaaggca aaatgccgca aaaaagggaa taagggcgac   7200
acggaaatgt tgaatactca tactcttcct ttttcaatat tattgaagca tttatcaggg   7260
ttattgtctc atgaccaaaa tcccttaacg tgagttttcg ttccactgag cgtcagaccc   7320
cgtagaaaag atcaaaggat cttcttgaga tccttttttt ctgcgcgtaa tctgctgctt   7380
gcaaacaaaa aaaccaccgc taccagcggt ggtttgtttg ccggatcaag agctaccaac   7440
tctttttccg aaggtaactg gcttcagcag agcgcagata ccaaatactg ttcttctagt   7500
gtagccgtag ttaggccacc acttcaagaa ctctgtagca ccgcctacat acctcgctct   7560
gctaatcctg ttaccagtgg ctgctgccag tggcgataag tcgtgtctta ccgggttgga   7620
ctcaagacga tagttaccgg ataaggcgca gcggtcgggc tgaacggggg gttcgtgcac   7680
acagcccagc ttggagcgaa cgacctacac cgaactgaga tacctacagc gtgagctatg   7740
agaaagcgcc acgcttcccg aagggagaaa ggcggacagg tatccggtaa gcggcagggt   7800
cggaacagga gagcgcacga gggagcttcc agggggaaac gcctggtatc tttatagtcc   7860
tgtcgggttt cgccacctct gacttgagcg tcgatttttg tgatgctcgt caggggggcg   7920
gagcctatgg aaaaacgcca gcaacgcggc ctttttacgg ttcctggcct tttgctggcc   7980
ttttgctcac atgttctttc ctgcgttatc ccctgattct gtggataacc gtattaccgc   8040
ctttgagtga gctgataccg ctcgccgcag ccgaacgacc gagcgcagcg agtcagtgag   8100
cgaggaagcg gaag                                                       8114
```

<210> SEQ ID NO 89
<211> LENGTH: 8578
<212> TYPE: DNA
<213> ORGANISM: Artificial
<220> FEATURE:
<223> OTHER INFORMATION: Vector

<400> SEQUENCE: 89

```
agcgcccaat acgcaaaccg cctctccccg cgcgttggcc gattcattaa tgcagctggc     60
acgacaggtt tcccgactgg aaagcgggca gtgagcgcaa cgcaattaat gtgagttagc    120
tcactcatta ggcaccccag gctttacact ttatgcttcc ggctcgtatg ttgtgtggaa    180
ttgtgagcgg ataacaattt cacacaggaa acagctatga ccatgattac gccaagctca    240
gaattaaccc tcactaaagg gactagtcct gcaggtttaa acgaattcgc cctttcatct    300
cgagatgctt tattcaggca cgctacgtga gaatattcta atgggatggt ctggccctga    360
gtctgaagta acgcaggaga tgattgagga tgccgctcgc aaagcgaaca ttcacgaatt    420
catcatgtcg ttgcctgatg gctacgaaac gctcagcgga tctaggggat cgttgctatc    480
tgggggcaa aagcagcgaa ttgcaattgc aagggccctg atcagaaatc caaaggtact     540
cctcctcgat gaggccacct cagctctgga ttccgaatct gagaaagtag ttcaagcagc    600
actcgacgca gcagcgaagg gccgtactac aatcgccgtt gcgcatagat tatcaacaat    660
tcagaaagca gatgtcatat atgtgttctc aggagggcgc atcgtggagc agggcgacca    720
tcagagcctc cttgaactca atggatggta cgctgaattg gtgaacttgc aaggtctcgg    780
agagatttga cgttcattta tttttggcca ctgcttgcat acattatttg attaaaggca    840
ctcattaatt gaaatagcat atcgaatttc tctagttatg gcccctgagt caccatacat    900
tgtctgatta aagggactcg ttaattgaaa tagcacattg gattcctctg attatgaccc    960
ctgagtcacc tatcctgcat aattcactcg tgacgataat ctgtagatat agggaactgt   1020
cgtagtactt gaagagacag caacaatcta tctctgggat ttcgtgctga ttttgggctt   1080
ttgctttgac gggctatgac tgaggtaatg tagaccaata ataaccctca cgcgaattag   1140
atatgccctg agggttagct tgcatcacct tacccatatg cacactgact tgcattaccc   1200
ggagcatatt ccggtagtcg gagataagca ctttgagata tcttaaggta caactcaata   1260
cgttcctcct tccttgcctc attccacctc acattctaga attcaataac ttcgtatagc   1320
atacattata cgaagttatt aattaacatc atcgtcacta tacacatcgt catcaactcc   1380
atggcgtgag gacttccgag actgctgggc ccttcgtttc tttaatgcct caagagatga   1440
cttcgtaccc gaagagacgc ctgttgtacc ccgttgacgc ttggcggagg gggcttcgtc   1500
ctcgtcagca acccgcgtca tctgcttcct tcgctgagca agatacccttc tctcctcgta  1560
ccgctgcatc tcctgagctc ggtcatacaa gatctaagct tgagacacct cagcatgcac   1620
cattccttgc ggcggcggtg ctcaacggcc tcaacctact actgggctgc ttcctaatgc   1680
aggagtcgca taagggagag cgtcgactat tcctttgccc tcggacgagt gctggggcgt   1740
cggtttccac tatcggcgag tacttctaca cagccatcgg tccagacggc cgcgcttctg   1800
cgggcgattt gtgtacgccc gacagtcccg gctccggatc ggacgattgc gtcgcatcga   1860
ccctgcgccc aagctgcatc atcgaaattg ccgtcaacca agctctgata gagttggtca   1920
agaccaatgc ggagcatata cgcccggagc cgcggcgatc ctgcaagctc cggatgcctc   1980
cgctcgaagt agcgcgtctg ctgctccata caagccaacc acggcctcca gaagaagatg   2040
ttggcgacct cgtattggga atccccgaac atcgcctcgc tccagtcaat gaccgctgtt   2100
```

```
atgcggccat tgtccgtcag gacattgttg gagccgaaat ccgcgtgcac gaggtgccgg   2160
acttcggggc agtcctcggc ccaaagcatc agctcatcga gagcctgcgc gacggacgca   2220
ctgacggtgt cgtccatcac agtttgccag tgatacacat ggggatcagc aatcgcgcat   2280
atgaaatcac gccatgtagt gtattgaccg attccttgcg gtccgaatgg gccgaacccg   2340
ctcgtctggc taagatcggc cgcagcgatc gcatccatgg cctccgcgac cggctgcaga   2400
acagcgggca gttcggtttc aggcaggtct tgcaacgtga caccctgtgc acggcgggag   2460
atgcaatagg tcaggctctc gctaaattcc ccaatgtcaa gcacttccgg aatcgggagc   2520
gcggccgatg caaagtgccg ataaacataa cgatctttgt agaaaccatc ggcgcagcta   2580
tttacccgca ggacatatcc acgccctcct acatcgaagc tgaaagcacg agattcttcg   2640
ccctccgaga gctgcatcag gtcggagacg ctgtcgaact tttcgatcag aaacttctcg   2700
acagacgtgg cggtgagttc aggctttttc attgtggatg tgtgtggttg tatgtgtgat   2760
gtggtgtgtg gagtgaaaat ctgtggctgg caaacgctct tgtatatata cgcacttttg   2820
cccgtgatca gtgcatgccg gatcgaggtg ggcgggaaca acggtctcga taatgtacgt   2880
acactacaca caaagagaag caagtggggg cgggactgca cggcacttgt gagacacctc   2940
agcatgccgg atcgaggtgg gcgggaacaa cggtctcgat aatgtacgta cactacacac   3000
aaagagaagc aagtgggggc gggactgcac ggcacttgtg agacacctca gcatgccgga   3060
tcgaggtggg cgggaacaac ggtctcgata atgtacgtac actacacaca aagagaagca   3120
agtgggggcg ggactgcacg gcacttgtga gacacctcag catgccggat cgaggtgggc   3180
gggaacaacg gtctcgataa tgtacgtaca ctacacacaa agagaagcaa gtgggggcgg   3240
gactgcacgg cacttgtgag acacctcagc atgcaccatt ccttgcggcg gcggtgctca   3300
acggcctgga tccacaggac gggtgtggtc gccatgatcg cgtagtcgat agtggctcca   3360
agtagcgaag cgagcaggac tgggcggcgg ccaaagcggt cggacagtgc tccgagaacg   3420
ggtgcgcata gagatgtgga gtatccgaat ttctccaggc tgtcaagcgg caattataac   3480
cgagactgag atcgagaagt atataaccgc agcagtagtg gataaataat tgcgaagtct   3540
tcccagcaga gcgggctgtt ttttggagtt ggttactgta aaatgctaaa atgactgaca   3600
acaatggagc gtctacagca ttggcaacag tgggaacagt atgctggtgc atccagttga   3660
taccccaggt tctgcgaaac tggtatgttc gggattgcga gggcgttcct cctctgatgt   3720
tctttttgtt cgccgtttcg ggattccct tcgcagtgta cttcattgat cagaattcga   3780
acactgccat catggttcaa cctcacttgt ttactttctt tagccttata ggcttttggc   3840
aaagcctgta ctatccgccc gtcagttaat taataacttc gtatagcata cattatacga   3900
agttattagg taaactaaat tcatgacagc cttttcttct ttctttccac aaaacaatta   3960
aaaaaaataa cagaattaga agaaggtaaa tatattggca aactcctctc ttccttttac   4020
ttattttttt gaaagttgca gtgtgtgtgt gtgttgttgt ttgttcaaat taatttgatg   4080
gttgttgtat tgtaaatttc aatcaataaa aacaaagaca taaataaaaa aaaccctacc   4140
tctcttccct gatctgattt gatcgtacga ttctaagaac tcaccgctaa ggccggccct   4200
ttgacaggta tatcttcagt ttcctcgtca ctcttggtca aaagaccaaa gtcatggctg   4260
gcgatttcct cgatgctttc ctcaagaatt ttcaaggagt tgtggctttc caactccatt   4320
tgaaccttct tcgaggcttc gtggaatttc ggatttccaa ttatcgaatc aacagcttct   4380
ttgatttgct ccactgtagg caagccagtt ttcaaatcaa ttgccacgcc agcggcctca   4440
```

```
gctctcgatg ccaccattgg cttgtcttca gagtcaccag caataacaac tggaacagag   4500

tggcttaagc tgtgctgaag tccgccatat ccaccattgt agacaagagc atcaacgtga   4560

ggaagtagag catcgtagtt gaagtagtcg atcacgcgag cattctcagg aaccacaaca   4620

tcatccggta gcttggcacc gcggcggccc aatatggcta ctgttaaagt gtcaggctcg   4680

tccttcaagg cctcaagagt aggcacaata agatgcttgt aactgacagc aaaagttcct   4740

tgagtgacca tgatgactcg cttggcactc agaacatccc cccaccagga aggaggggtg   4800

aattgagttc ggtgcttggg cgttgagccg gcgaatttga agttgctagg cagatggtct   4860

ctgctgaact caagagaagg cgggcacagc tgcaggaact tgtctgcagg tacctcaagg   4920

gcgaattcgc ggccgctaaa ttcaattcgc cctatagtga gtcgtattac aattcactgg   4980

ccgtcgtttt acaacgtcgt gactgggaaa accctggcgt tacccaactt aatcgccttg   5040

cagcacatcc ccctttcgcc agctggcgta atagcgaaga ggcccgcacc gatcgccctt   5100

cccaacagtt gcgcagccta tacgtacggc agtttaaggt ttacacctat aaaagagaga   5160

gccgttatcg tctgtttgtg gatgtacaga gtgatattat tgacacgccg gggcgacgga   5220

tggtgatccc cctggccagt gcacgtctgc tgtcagataa agtctcccgt gaactttacc   5280

cggtggtgca tatcggggat gaaagctggc gcatgatgac caccgatatg gccagtgtgc   5340

cggtctccgt tatcggggaa gaagtggctg atctcagcca ccgcgaaaat gacatcaaaa   5400

acgccattaa cctgatgttc tggggaatat aaatgtcagg catgagatta tcaaaaagga   5460

tcttcaccta gatccttttc acgtagaaag ccagtccgca gaaacggtgc tgaccccgga   5520

tgaatgtcag ctactgggct atctggacaa gggaaaacgc aagcgcaaag agaaagcagg   5580

tagcttgcag tgggcttaca tggcgatagc tagactgggc ggttttatgg acagcaagcg   5640

aaccggaatt gccagctggg gcgccctctg gtaaggttgg gaagccctgc aaagtaaact   5700

ggatggcttt cttgccgcca aggatctgat ggcgcagggg atcaagctct gatcaagaga   5760

caggatgagg atcgtttcgc atgattgaac aagatggatt gcacgcaggt tctccggccg   5820

cttgggtgga gaggctattc ggctatgact gggcacaaca gacaatcggc tgctctgatg   5880

ccgccgtgtt ccggctgtca gcgcaggggc gcccggttct ttttgtcaag accgacctgt   5940

ccggtgccct gaatgaactg caagacgagg cagcgcggct atcgtggctg gccacgacgg   6000

gcgttccttg cgcagctgtg ctcgacgttg tcactgaagc gggaagggac tggctgctat   6060

tgggcgaagt gccggggcag gatctcctgt catctcacct tgctcctgcc gagaaagtat   6120

ccatcatggc tgatgcaatg cggcggctgc atacgcttga tccggctacc tgcccattcg   6180

accaccaagc gaaacatcgc atcgagcgag cacgtactcg gatggaagcc ggtcttgtcg   6240

atcaggatga tctggacgaa gagcatcagg ggctcgcgcc agccgaactg ttcgccaggc   6300

tcaaggcgag catgcccgac ggcgaggatc tcgtcgtgac ccatggcgat gcctgcttgc   6360

cgaatatcat ggtggaaaat ggccgctttt ctggattcat cgactgtggc cggctgggtg   6420

tggcggaccg ctatcaggac atagcgttgg ctacccgtga tattgctgaa gagcttggcg   6480

gcgaatgggc tgaccgcttc ctcgtgcttt acggtatcgc cgctcccgat tcgcagcgca   6540

tcgccttcta tcgccttctt gacgagttct tctgaattat taacgcttac aatttcctga   6600

tgcggtattt tctccttacg catctgtgcg gtatttcaca ccgcatcagg tggcactttt   6660

cggggaaatg tgcgcggaac ccctatttgt ttatttttct aaatacattc aaatatgtat   6720

ccgctcatga gattatcaaa aaggatcttc acctagatcc ttttaaatta aaaatgaagt   6780

tttaaatcaa tctaaagtat atatgagtaa acttggtctg acagttacca atgcttaatc   6840
```

```
agtgaggcac ctatctcagc gatctgtcta tttcgttcat ccatagttgc ctgactcccc   6900

gtcgtgtaga taactacgat acgggagggc ttaccatctg gccccagtgc tgcaatgata   6960

ccgcgagacc cacgctcacc ggctccagat ttatcagcaa taaaccagcc agccggaagg   7020

gccgagcgca gaagtggtcc tgcaacttta tccgcctcca tccagtctat taattgttgc   7080

cgggaagcta gagtaagtag ttcgccagtt aatagtttgc gcaacgttgt tgccattgct   7140

acaggcatcg tggtgtcacg ctcgtcgttt ggtatggctt cattcagctc cggttcccaa   7200

cgatcaaggc gagttacatg atcccccatg ttgtgcaaaa aagcggttag ctccttcggt   7260

cctccgatcg ttgtcagaag taagttggcc gcagtgttat cactcatggt tatggcagca   7320

ctgcataatt ctcttactgt catgccatcc gtaagatgct tttctgtgac tggtgagtac   7380

tcaaccaagt cattctgaga atagtgtatg cggcgaccga gttgctcttg cccggcgtca   7440

atacgggata ataccgcgcc acatagcaga actttaaaag tgctcatcat tggaaaacgt   7500

tcttcggggc gaaaactctc aaggatctta ccgctgttga gatccagttc gatgtaaccc   7560

actcgtgcac ccaactgatc ttcagcatct tttactttca ccagcgtttc tgggtgagca   7620

aaaacaggaa ggcaaaatgc cgcaaaaaag ggaataaggg cgacacggaa atgttgaata   7680

ctcatactct tcctttttca atattattga agcatttatc agggttattg tctcatgacc   7740

aaaatccctt aacgtgagtt ttcgttccac tgagcgtcag accccgtaga aaagatcaaa   7800

ggatcttctt gagatccttt ttttctgcgc gtaatctgct gcttgcaaac aaaaaaacca   7860

ccgctaccag cggtggtttg tttgccggat caagagctac caactctttt tccgaaggta   7920

actggcttca gcagagcgca gataccaaat actgttcttc tagtgtagcc gtagttaggc   7980

caccacttca agaactctgt agcaccgcct acatacctcg ctctgctaat cctgttacca   8040

gtggctgctg ccagtggcga taagtcgtgt cttaccgggt tggactcaag acgatagtta   8100

ccggataagg cgcagcggtc gggctgaacg gggggttcgt gcacacagcc cagcttggag   8160

cgaacgacct acaccgaact gagataccta cagcgtgagc tatgagaaag cgccacgctt   8220

cccgaaggga gaaaggcgga caggtatccg gtaagcggca gggtcggaac aggagagcgc   8280

acgagggagc ttccaggggg aaacgcctgg tatctttata gtcctgtcgg gtttcgccac   8340

ctctgacttg agcgtcgatt tttgtgatgc tcgtcagggg ggcggagcct atggaaaaac   8400

gccagcaacg cggccttttt acggttcctg gccttttgct ggccttttgc tcacatgttc   8460

tttcctgcgt tatcccctga ttctgtggat aaccgtatta ccgcctttga gtgagctgat   8520

accgctcgcc gcagccgaac gaccgagcgc agcgagtcag tgagcgagga agcggaag     8578
```

<210> SEQ ID NO 90
<211> LENGTH: 4657
<212> TYPE: DNA
<213> ORGANISM: Artificial
<220> FEATURE:
<223> OTHER INFORMATION: Vector

<400> SEQUENCE: 90

```
ggtttaaacg aattcgccct ttcatctcga gatgctttat tcaggcacgc tacgtgagaa     60

tattctaatg ggatggtctg gccctgagtc tgaagtaacg caggagatga ttgaggatgc    120

cgctcgcaaa gcgaacattc acgaattcat catgtcgttg cctgatggct acgaaacgct    180

cagcggatct aggggatcgt tgctatctgg ggggcaaaag cagcgaattg caattgcaag    240

ggccctgatc agaaatccaa aggtactcct cctcgatgag gccacctcag ctctggattc    300
```

-continued

```
cgaatctgag aaagtagttc aagcagcact cgacgcagca gcgaagggcc gtactacaat    360
cgccgttgcg catagattat caacaattca gaaagcagat gtcatatatg tgttctcagg    420
agggcgcatc gtggagcagg gcgaccatca gagcctcctt gaactcaatg gatggtacgc    480
tgaattggtg aacttgcaag gtctcggaga gatttgacgt tcatttattt ttggccactg    540
cttgcataca ttatttgatt aaaggcactc attaattgaa atagcatatc gaatttctct    600
agttatggcc cctgagtcac catacattgt ctgattaaag ggactcgtta attgaaatag    660
cacattggat tcctctgatt atgacccctg agtcacctat cctgcataat tcactcgtga    720
cgataatctg tagatatagg gaactgtcgt agtacttgaa gagacagcaa caatctatct    780
ctgggatttc gtgctgattt tgggcttttg ctttgacggg ctatgactga ggtaatgtag    840
accaataata accctcacgc gaattagata tgccctgagg gttagcttgc atcaccttac    900
ccatatgcac actgacttgc attacccgga gcatattccg gtagtcggag ataagcactt    960
tgagatatct taaggtacaa ctcaatacgt tcctccttcc ttgcctcatt ccacctcaca   1020
ttctagaatt caataacttc gtatagcata cattatacga agttattaat taacatcatc   1080
gtcactatac acatcgtcat caactccatg gcgtgaggac ttccgagact gctgggccct   1140
tcgtttcttt aatgcctcaa gagatgactt cgtacccgaa gagacgcctg ttgtaccccg   1200
ttgacgcttg gcggaggggg cttcgtcctc gtcagcaacc cgcgtcatct gcttccttcg   1260
ctgagcaaga taccttctct cctcgtaccg ctgcatctcc tgagctcggt catacaagat   1320
ctaagcttga gacacctcag catgcaccat tccttgcggc ggcggtgctc aacggcctca   1380
acctactact gggctgcttc ctaatgcagg agtcgcataa gggagagcgt cgactattcc   1440
tttgccctcg gacgagtgct ggggcgtcgg tttccactat cggcgagtac ttctacacag   1500
ccatcggtcc agacggccgc gcttctgcgg gcgatttgtg tacgcccgac agtcccggct   1560
ccggatcgga cgattgcgtc gcatcgaccc tgcgcccaag ctgcatcatc gaaattgccg   1620
tcaaccaagc tctgatagag ttggtcaaga ccaatgcgga gcatatacgc ccggagccgc   1680
ggcgatcctg caagctccgg atgcctccgc tcgaagtagc gcgtctgctg ctccatacaa   1740
gccaaccacg gcctccagaa gaagatgttg gcgacctcgt attgggaatc cccgaacatc   1800
gcctcgctcc agtcaatgac cgctgttatg cggccattgt ccgtcaggac attgttggag   1860
ccgaaatccg cgtgcacgag gtgccggact tcggggcagt cctcggccca aagcatcagc   1920
tcatcgagag cctgcgcgac ggacgcactg acggtgtcgt ccatcacagt ttgccagtga   1980
tacacatggg gatcagcaat cgcgcatatg aaatcacgcc atgtagtgta ttgaccgatt   2040
ccttgcggtc cgaatgggcc gaacccgctc gtctggctaa gatcggccgc agcgatcgca   2100
tccatggcct ccgcgaccgg ctgcagaaca gcgggcagtt cggtttcagg caggtcttgc   2160
aacgtgacac cctgtgcacg gcgggagatg caataggtca ggctctcgct aaattcccca   2220
atgtcaagca cttccggaat cgggagcgcg gccgatgcaa agtgccgata aacataacga   2280
tctttgtaga aaccatcggc gcagctattt acccgcagga catatccacg ccctcctaca   2340
tcgaagctga aagcacgaga ttcttcgccc tccgagagct gcatcaggtc ggagacgctg   2400
tcgaactttt cgatcagaaa cttctcgaca gacgtggcgg tgagttcagg ctttttcatt   2460
gtggatgtgt gtggttgtat gtgtgatgtg gtgtgtggag tgaaaatctg tggctggcaa   2520
acgctcttgt atatatacgc acttttgccc gtgatcagtg catgccggat cgaggtgggc   2580
gggaacaacg gtctcgataa tgtacgtaca ctacacacaa agagaagcaa gtgggggcgg   2640
gactgcacgg cacttgtgag acacctcagc atgccggatc gaggtgggcg ggaacaacgg   2700
```

-continued

```
tctcgataat gtacgtacac tacacacaaa gagaagcaag tgggggcggg actgcacggc   2760

acttgtgaga cacctcagca tgccggatcg aggtgggcgg gaacaacggt ctcgataatg   2820

tacgtacact acacacaaag agaagcaagt gggggcggga ctgcacggca cttgtgagac   2880

acctcagcat gccggatcga ggtgggcggg aacaacggtc tcgataatgt acgtacacta   2940

cacacaaaga gaagcaagtg ggggcgggac tgcacggcac ttgtgagaca cctcagcatg   3000

caccattcct tgcggcggcg gtgctcaacg gcctggatcc acaggacggg tgtggtcgcc   3060

atgatcgcgt agtcgatagt ggctccaagt agcgaagcga gcaggactgg gcggcggcca   3120

aagcggtcgg acagtgctcc gagaacgggt gcgcatagag atgtggagta tccgaatttc   3180

tccaggctgt caagcggcaa ttataaccga gactgagatc gagaagtata taaccgcagc   3240

agtagtggat aaataattgc gaagtcttcc cagcagagcg ggctgttttt tggagttggt   3300

tactgtaaaa tgctaaaatg actgacaaca atggagcgtc tacagcattg gcaacagtgg   3360

gaacagtatg ctggtgcatc cagttgatac cccaggttct gcgaaactgg tatgttcggg   3420

attgcgaggg cgttcctcct ctgatgttct ttttgttcgc cgtttcgggg attcccttcg   3480

cagtgtactt cattgatcag aattcgaaca ctgccatcat ggttcaacct cacttgttta   3540

ctttctttag ccttataggc ttttggcaaa gcctgtacta tccgcccgtc agttaattaa   3600

taacttcgta tagcatacat tatacgaagt tattaggtaa actaaattca tgacagcctt   3660

ttcttctttc tttccacaaa acaattaaaa aaaataacag aattagaaga aggtaaatat   3720

attggcaaac tcctctcttc cttttactta tttttttgaa agttgcagtg tgtgtgtgtg   3780

ttgttgtttg ttcaaattaa tttgatggtt gttgtattgt aaatttcaat caataaaaac   3840

aaagacataa ataaaaaaaa ccctacctct cttccctgat ctgatttgat cgtacgattc   3900

taagaactca ccgctaaggc cggccctttg acaggtatat cttcagtttc ctcgtcactc   3960

ttggtcaaaa gaccaaagtc atggctggcg atttcctcga tgctttcctc aagaattttc   4020

aaggagttgt ggctttccaa ctccatttga accttcttcg aggcttcgtg gaatttcgga   4080

tttccaatta tcgaatcaac agcttctttg atttgctcca ctgtaggcaa gccagttttc   4140

aaatcaattg ccacgccagc ggcctcagct ctcgatgcca ccattggctt gtcttcagag   4200

tcaccagcaa taacaactgg aacagagtgg cttaagctgt gctgaagtcc gccatatcca   4260

ccattgtaga caagagcatc aacgtgagga agtagagcat cgtagttgaa gtagtcgatc   4320

acgcgagcat tctcaggaac cacaacatca tccggtagct tggcaccgcg gcggcccaat   4380

atggctactg ttaaagtgtc aggctcgtcc ttcaaggcct caagagtagg cacaataaga   4440

tgcttgtaac tgacagcaaa agttccttga gtgaccatga tgactcgctt ggcactcaga   4500

acatcccccc accaggaagg aggggtgaat tgagttcggt gcttgggcgt tgagccggcg   4560

aatttgaagt tgctaggcag atggtctctg ctgaactcaa gagaaggcgg gcacagctgc   4620

aggaacttgt ctgcaggtac ctcaagggcg aattcgc                            4657
```

CELLS, NUCLEIC ACIDS, ENZYMES AND USE THEREOF, AND METHODS FOR THE PRODUCTION OF SOPHOROLIPIDS

This application is a Divisional and claims benefit under 35 U.S.C. §120 and §365 of U.S. application Ser. No. 13/509,716, filed May 14, 2012(now U.S. Patent No. 8,911,982), which is the U.S. national-stage of PCT/EP10/065713, filed Oct. 19, 2010. Priority is also claimed to Germany 10 2009 046 799.8, filed Nov. 18, 2009, and Germany 10 2010 014 680.3, filed Apr. 12, 2010.

FIELD OF THE INVENTION

The invention relates to nucleic acids, enzymes and cells and to their use for producing sophorolipids, and also to processes for producing sophorolipids.

PRIOR ART

Currently the production of surfactants is essentially based on the basis of petrochemical raw materials. The utilization of surfactants based on renewable raw materials is a suitable alternative due to the foreseeable shortage of petrochemical raw materials and the increasing demand for products which are based on renewable raw materials and/or which are biodegradable.

Sophorolipids have the surface-active properties required for use as a surfactant.

These lipids are currently produced using wild-type isolates of a variety of yeasts, in particular *Candida bombicola.*

Performance parameters of product formation, such as carbon yield, space-time yield, product concentration, product homogeneity (degree of acetylation, fatty acid species, lactone form vs. open-chain form) have to date been improved exclusively via the optimization of the process control (pH, oxygen supply, media composition, feeding strategies, nitrogen supply, temperature, choice of substrate and the like).

The only exception is the genetic modification of *Candida bombicola* in as far as β-oxidation has been eliminated so that triglycerides, fatty acids, fatty alcohols and the like which are fed by way of substrate can no longer be utilized as a carbon source, in other words degraded (Van Bogaert et al. FEMS Yeast Res. 2009 June; 9(4):610-7). In this manner, it should be possible, by choosing the substrate, specifically to control the fatty acid moiety of the sophorolipids in order to influence the product properties.

Since the improvement of performance parameters in the biotechnological production of sophorolipids via optimizing the process control is possible to a limited extent only, the cells also have to be subjected to genetic modification.

This comprises, firstly, the enhancement of the enzymes involved in sophorolipid synthesis: cytochrome P450 monooxygenase, glycosyltransferase I, glycosyltransferase II, acetyltransferase, sophorolipid exporter with the aim of improving the performance parameters of product formation such as carbon yield, space-time yield, product concentration, product homogeneity (degree of acetylation, fatty acid species) and the like.

This secondly comprises attenuating some of the enzymes involved in sophorolipid synthesis: glycosyltransferase II, acetyltransferase with the aim of modifying the structure and the properties of the sophorolipids produced: glycosyltransferase II: production of monoglycosyl-sophorolipids; acetyltransferase: production of nonacetylated sophorolipids.

If sophorolipids are to be employed on a large scale as surfactants in cleaning applications, cosmetic applications and other applications, they will have to compete with the currently employed surfactants. The latter are bulk chemicals which can be produced at very low cost. Therefore, sophorolipids must be produced at the lowest possible costs. This is not possible by merely optimizing the performance parameters via process optimization.

There is therefore an increasing demand for efficient productions of sophorolipids with high product yields.

The present invention was therefore based on the problem of providing tools and/or processes with the aid of which specific sophorolipids can be synthesized in a simple manner and in large amounts.

DESCRIPTION OF THE INVENTION

Surprisingly, it has been found that the cells, nucleic acids, polypeptides and processes described hereinbelow are capable of solving the above problem.

The subject matter of the present invention are, therefore, genetically modified cells with a modified enzymatic equipment for the synthesis of sophorolipids.

A further subject matter of the invention are novel nucleic acids and vectors as described in claims 11 and 12.

Yet another subject matter of the present invention are novel enzymes which are useful in sophorolipid biosynthesis.

The advantage of the present invention is that not only are the performance parameters of sophorolipid formation, such as carbon yield and space-time yield, improved, but also that the product homogeneity as regards for example the degree of acetylation and the fatty acid species can be improved.

A subject matter of the invention is a cell which is capable of forming sophorolipids, which cell has been genetically modified in such a way that it has an activity, as specified in each case hereinbelow, of at least one of the enzymes selected from the group hereafter, which activity is modified in comparison with its wild type:

at least one enzyme $E_1$ with the polypeptide sequence SEQ ID NO:7, SEQ ID NO:53, SEQ ID NO:55, SEQ ID NO:57, SEQ ID NO:59, SEQ ID NO:61 or SEQ ID NO:63, in particular SEQ ID NO:7, or with a polypeptide sequence where up to 25%, preferably up to 20%, especially preferably up to 15%, in particular up to 10, 9, 8, 7, 6, 5, 4, 3, 2, 1% of the amino acid residues are modified over the respective reference sequence SEQ ID NO:7, SEQ ID NO:53, SEQ ID NO:55, SEQ ID NO:57, SEQ ID NO:59, SEQ ID NO:61 or SEQ ID NO:63, in particular SEQ ID NO:7, by deletion, insertion, substitution or a combination of these and which retains at least 50%, preferably 65%, especially preferably 80%, in particular more than 90% of the enzymatic activity of the enzyme with the respective reference sequence SEQ ID NO:7, SEQ ID NO:53, SEQ ID NO:55, SEQ ID NO:57, SEQ ID NO:59, SEQ ID NO:61 or SEQ ID NO:63, where enzymatic activity for an enzyme $E_1$ is understood as meaning the ability to convert Z-9-octadecenoic acid into 17-hydroxy-Z-9-octadecenoic acid, at least one enzyme $E_2$ with the polypeptide sequence SEQ ID NO:8 or SEQ ID NO:11 or with a polypeptide sequence where up to 60%, preferably up to 25%, especially preferably up to 15%, in particular up to 10, 9, 8, 7, 6, 5, 4, 3, 2, 1% of the amino acid residues are modified over SEQ ID NO:8 or SEQ ID NO:11 by deletion, insertion, substitution or a combination of these and which retains at least 50%, preferably 65%, especially preferably 80%, in particular more than 90% of the enzymatic activity of the enzyme with the respective reference sequence SEQ ID NO:8 or SEQ ID NO:11, where enzymatic activity for an enzyme $E_2$ is understood as meaning the ability to convert UDP-glucose and 17-hydroxy-Z-9-octadecenoic acid into 17-(β-D-glucopyranosyloxy)-Z-9-octadecenoic acid, at least one enzyme $E_3$ with the polypeptide sequence SEQ ID NO:11 or with a polypeptide sequence where up to 60%, preferably up to 25%, especially preferably up to 15%, in particular up to 10, 9, 8, 7, 6, 5, 4, 3, 2, 1% of the amino acid residues are modified over SEQ ID NO:11 by deletion, insertion, substitution or a combination of these and which retains at least 50%, preferably 65%, especially preferably 80%, in particular more than 90% of the enzymatic activity of the enzyme with the reference sequence SEQ ID NO:11, where enzymatic activity for an enzyme $E_3$ is understood as meaning the ability to convert 17-(β-D-glucopyranosy-loxy)-Z-9-octadecenoic acid and UDP-glucose into 17-L-[(2'-O-β-D-glucopyranosyl-β-D-glucopyranosyl)oxy]-Z-9-octadecenoic acid, at least one enzyme $E_4$ with the polypeptide sequence SEQ ID NO:9 or with a polypeptide sequence where up to 50%, preferably up to 25%, especially preferably up to 15%, in particular up to 10, 9, 8, 7, 6, 5, 4, 3, 2, 1% of the amino acid residues are modified over SEQ ID NO:9 by deletion, insertion, substitution or a combination of these and which retains at least 50%, preferably 65%, especially preferably 80%, in particular more than 90% of the enzymatic activity of the enzyme with SEQ ID NO:9, where enzymatic activity for an enzyme $E_4$ is understood as meaning the ability to convert 17-L-[(2'-O-β-D-glucopyranosyl-β-D-glucopyranosyl)oxy]-Z-9-octadecenoic acid 1',4"-lactone and acetyl-coenzyme A into 17-L-[(2'-O-β-D-glucopyranosyl-β-D-glucopyranosyl)oxy]-Z-9-octadecenoic acid 1',4"-lactone monoacetate or 17-L-[(2'-O-β-D-glucopyranosyl-β-D-glucopyranosyl)oxy]-Z-9-octadecenoic acid 1',4"-lactone monoacetate and acetyl-coenzyme A into 17-L-[(2'-O-β-D-glucopyranosyl-β-D-glucopyranosyl)oxy]-Z-9-Octadecenoic acid 1',4"-lactone diacetate or 17-L-[(2'-O-β-D-glucopyranosyl-β-D-glucopyranosyl)oxy]-Z-9-octadecenoic acid 1',4"-lactone and acetyl-coenzyme A into 17-L-[(2'O-β-D-glucopyranosyl-β-D-glucopyranosyl)oxy]-Z-9-octadecenoic acid 1',4"-lactone diacetate, with the first option being preferred, at least one enzyme $E_5$ with the polypeptide sequence SEQ ID NO:10 or with a polypeptide sequence where up to 45%, preferably up to 25%, especially preferably up to 15% and in particular up to 10, 9, 8, 7, 6, 5, 4, 3, 2, 1% of the amino acid residues are modified over SEQ ID NO:10 by deletion, insertion, substitution or a combination of these and which retains at least 50%, preferably 65%, especially preferably 80%, in particular more than 90% of the enzymatic activity of the enzyme with SEQ ID NO:10, where enzymatic activity for an enzyme $E_5$ is understood as meaning the ability to transfer a sophorolipid out of a cell into the surrounding medium.

In the context of the present invention, the expression "sophorolipids" is understood as meaning compounds of the general formulae (Ia) and (Ib)

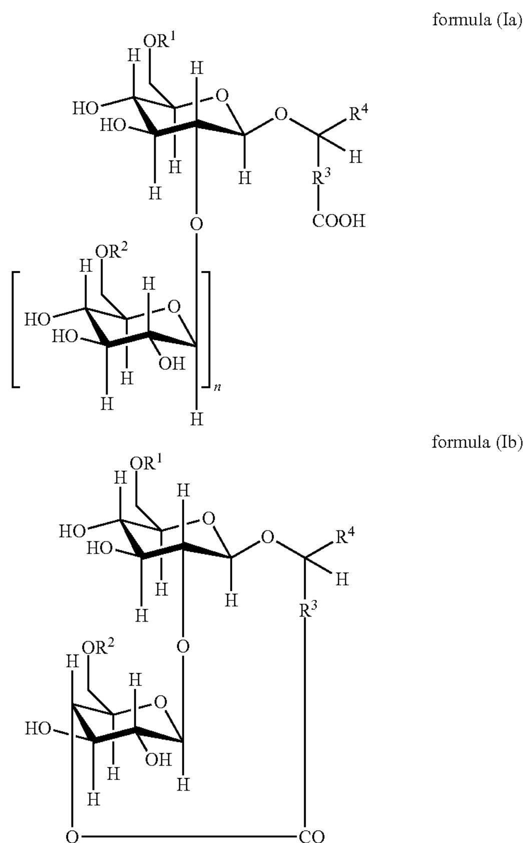

in which $R^1$=H or CO—$CH_3$, $R^2$=H or CO—$CH_3$, $R^3$=a divalent organic moiety which comprises 6 to 32 carbon atoms and which is unsubstituted or substituted by hydroxyl functions, is unbranched and optionally comprises one to three double or triple bonds, $R^4$=H, $CH_3$ or a monovalent organic radical which comprises 2 to 10 carbon atoms and which is unsubstituted or substituted by hydroxyl functions, which is unbranched and which optionally comprises one to three double or triple bonds, and n=1 or 0.

In connection with the present invention, a "wild type" of a cell is preferably understood as meaning the original strain from which the cell according to the invention has been developed as the result of recombinant manipulation of the genetic elements which are responsible for the activities of the enzymes of the abovementioned Seq ID Nos.

The expression "modified activity of an enzyme" is preferably understood as meaning modified intracellular activity.

Modifications of amino acid residues of a given polypeptide sequence which do not lead to any substantial modifications of the properties and function of the given polypeptide are known to a person skilled in the art. Thus, for example, it is possible to exchange what are known as conserved amino acids for each other; examples of such suitable amino acid substitutions are: Ala for Ser; Arg for Lys; Asn for Gln or His; Asp for Glu; Cys for Ser; Gln for Asn; Glu for Asp; Gly for Pro; His for Asn or Gln; Ile for Leu or Val; Leu for Met or Val; Lys for Arg or Gln or Glu; Met for Leu or Ile; Phe for Met or Leu or Tyr; Ser for Thr; Thr for Ser; Trp for Tyr; Tyr for Trp or Phe; Val for Ile or Leu. Likewise, it is known that modifications in particular at the N- or C-terminal end of a polypeptide in the form of, for example, amino acid insertions or deletions frequently have no substantial effect on the function of the polypeptide.

The activity of an enzyme $E_1$ can be determined by disrupting, in a manner known to the skilled worker, cells which comprise this activity, for example with the aid of a ball mill, a French press or an ultrasonic disintegrator, and intact cells, cell debris and disruption aids such as, for example, glass beads can subsequently be removed by centrifugation for 10 minutes at 13 000 rpm and 4° C. Then, enzyme assays followed by LC-ESI-MS detection of the products can be carried out with the resulting cell-free crude extract. As an alternative, the enzyme can be concentrated or else purified until homogeneous in a manner known to a person skilled in the art by chromatographic methods (such as nickel/nitrilotriacetic acid affinity chromatography, streptavidin affinity chromatography, gel filtration chromatography or ion-exchange chromatography). A standard assay can be carried out in a total volume of 200 μl of 200 mM sodium phosphate buffer (pH 7.4), 0.5 mM NADPH, 0.5 mM dithiothreitol, 3 mM glucose 6-phosphate and 0.5 U glucose-6-phosphate dehydrogenase and 50 μl of crude protein extract (approx. 1 mg of total protein) or purified protein in solution (10 μg of purified protein). The reaction is started by the addition of a) 5 μl of a 10 mM solution of the substrate (Z-9-octadecenoic acid) in ethanol or of b) 5 μl of a 10 mM solution of the substrate (Z-9-octadecenoic acid) in 0.1% Triton X-100 which had previously been pretreated by two sonication treatments for in each case 30 seconds, and incubated for 30 minutes at 30° C. Thereafter, the reaction is extracted with 200 μl of ethyl acetate. Undissolved components are sedimented, phase separation is brought about by brief centrifugation (5 minutes at 16 100 g) and the ethyl acetate phase is analyzed by means of LC-ESI-MS. The products are identified by analyzing the relevant mass trajectories and the $MS^2$ spectra.

The activity of an enzyme $E_2$ can be determined by disrupting, in a manner known to the skilled worker, cells which comprise this activity, for example with the aid of a ball mill, a French press or an ultrasonic disintegrator, and intact cells, cell debris and disruption aids such as, for example, glass beads can subsequently be removed by centrifugation for 10 minutes at 13 000 rpm and 4° C. Then, enzyme assays followed by LC-ESI-MS detection of the products can be carried out with the resulting cell-free crude extract. As an alternative, the enzyme can be concentrated or else purified until homogeneous in a manner known to a person skilled in the art by chromatographic methods (such as nickel/nitrilotriacetic acid affinity chromatography, streptavidin affinity chromatography, gel filtration chromatography or ion-exchange chromatography). A standard assay can consist of 185 μl of 10 mM Tris-HCl (pH 7.5), 10 μl of 125 mM UDP-glucose and 50 μl of crude protein extract (approx. 1 mg of total protein) or purified protein in solution (10 μg of purified protein). The reaction is started by the addition of a) 5 μl of a 10 mM solution of the substrate (such as, for example, 18-hydroxy-Z-9-octadecenoic acid) in ethanol or of b) 5 μl of a 10 mM solution of the substrate (such as, for example, 18-hydroxy-Z-9-octadecenoic acid) in 0.1% Triton X-100 which had previously been pretreated by two sonication treatments for in each case 30 seconds and incubated for 30 minutes at 30° C. Thereafter, the reaction is extracted with 200 μl of ethyl acetate. Undissolved components are sedimented, phase separation is brought about by brief centrifugation (5 minutes at 16 100 g) and the ethyl acetate phase is analyzed by means of LC-ESI-MS. The products are identified by analyzing the relevant mass trajectories and the $MS^2$ spectra. In this assay it is preferred to employ, as the substrate, 18-hydroxy-Z-9-octadecenoic acid because it is commercially available and because it has already been demonstrated variously that the enzymes of the sophorolipid biosynthesis accept, as substrate, not only 18-hydroxy-Z-9-octadecenoic acid, 17-hydroxy-Z-9-octadecenoic acid and also hydroxy fatty acids of different chain lengths (saturated or unsaturated) and hydroxylated on the ω- or ω-1-carbon, but also the mono- and diglucosides generated therefrom during sophorolipid biosynthesis (Asmer, H.J., Lang, S., Wagner, F., Wray, V. (1988). Microbial production, structure elucidation and bioconversion of sophorose lipids. J. Am. Oil Chem. Soc. 65:1460-1466; Nunez, A., Ashby, R., Foglia, T. A. et al. (2001). Analysis and characterization of sophorolipids by liquid chromatography with atmospheric pressure chemical ionization. Chromatographia 53:673-677; Ashby, R. D., Solaiman, D. K., Foglia, T. A. (2008). Property control of sophorolipids: influence of fatty acid substrate and blending. Biotechnology Letters 30:1093-1100).

The activity of an enzyme $E_3$ can be determined by disrupting, in a manner known to the skilled worker, cells which comprise this activity, for example with the aid of a ball mill, a French press or an ultrasonic disintegrator, and intact cells, cell debris and disruption aids such as, for example, glass beads can subsequently be removed by centrifugation for 10 minutes at 13 000 rpm and 4° C. Then, enzyme assays followed by LC-ESI-MS detection of the products can be carried out with the resulting cell-free crude extract. As an alternative, the enzyme can be concentrated or else purified until homogeneous in a manner known to a person skilled in the art by chromatographic methods (such as nickel/nitrilotriacetic acid affinity chromatography, streptavidin affinity chromatography, gel filtration chromatography or ion-exchange chromatography). A standard assay can consist of 185 μl of 10 mM Tris-HCl (pH 7.5), 10 μl of 125 mM UDP-glucose and 50 μl of crude protein extract (approx. 1 mg of total protein) or purified protein in solution (10 μg of purified protein). The reaction is started by the addition of a) 5 μl of a 10 mM solution of the substrate (such as, for example, 18-(β-D-glucopyranosyloxy)-Z-9-octadecenoic acid) in ethanol or of b) 5 μl of a 10 mM solution of the substrate (18-(β-D-glucopyranosyloxy)-Z-9-octadecenoic acid) in 0.1% Triton X-100 which had previously been pretreated by two sonication treatments for in each case 30 seconds or c) by addition of the reaction mixture described for the activity determination of the enzyme $E_2$, and incubated for 30 minutes at 30° C. Thereafter, the reaction is extracted with 200 μl (substrate added, as described in a) and b)) or 400 μl (substrate added, as described in c)) of ethyl acetate. Undissolved components are sedimented, phase separation is brought about by brief centrifugation (5 minutes at 16 100 g) and the ethyl acetate phase is analyzed by means of LC-ESI-MS. The products are identified by analyzing the relevant mass trajectories and the $MS^2$ spectra. In this assay it is preferred to employ, as the substrate, because its precursor molecule 18-hydroxy-Z-9-octadecenoic acid is commercially available and because it has already been demonstrated variously that the enzymes of the sophorolipid biosynthesis accept, as substrate, not only 18-hydroxy-Z-9-octadecenoic acid, 17-hydroxy-Z-9-octadecenoic acid and also hydroxy fatty acids of different chain lengths (saturated or unsaturated) and hydroxylated on the ω- or ω-1-carbon, but also the mono- and diglucosides generated therefrom during sophorolipid biosynthesis.

The activity of an enzyme $E_4$ can be determined by disrupting, in a manner known to the skilled worker, cells which comprise this activity, for example with the aid of a ball mill, a French press or an ultrasonic disintegrator, and intact cells, cell debris and disruption aids such as, for example, glass beads can subsequently be removed by centrifugation for 10 minutes at 13 000 rpm and 4° C. Then, enzyme assays followed by LC-ESI-MS detection of the products can be carried out with the resulting cell-free crude extract. As an alternative, the enzyme can be concentrated or else purified until homogeneous in a manner known to a person skilled in the art by chromatographic methods (such as nickel/nitrilotriacetic acid affinity chromatography, streptavidin affinity chromatography, gel filtration chromatography or ion-exchange chromatography). A standard assay can consist of 185 µl of 10 mM Tris-HCl (pH 7.5), 2.5 µl of 100 mM acetyl-coenzyme A and 50 µl of crude protein extract (approx. 1 mg of total protein) or purified protein in solution (10 µg of purified protein). The reaction is started by the addition of a) 5 µl of a 10 mM solution of the substrate (chemically deacetylated sophorolipids) in ethanol or of b) 5 µl of a 10 mM solution of the substrate (chemically deacetylated sophorolipids) in 0.1% Triton X-100 which had previously been pretreated by two sonication treatments for in each case 30 seconds, or c) by addition of the reaction mixture described for the activity determination of the enzyme $E_3$ (in the manner of the substrate addition described therein under c) followed by incubation for 30 minutes at 30° C.), and incubated for 30 minutes at 30° C. Thereafter, the reaction is extracted with 200 µl (substrate added as described in a) and b)) or 600 µl (substrate added as described in c)) of ethyl acetate. Undissolved components are sedimented, phase separation is brought about by brief centrifugation (5 minutes at 16 100 g) and the ethyl acetate phase is analyzed by means of LC-ESI-MS. The products are identified by analyzing the relevant mass trajectories and the $MS^2$ spectra. It is preferred in accordance with the invention that the enzyme $E_4$ not only accepts as substrates the lactone forms of the sophorolipids as chosen here for the reference activities, but is also capable of at least monoacetylating the acid form of the sophorolipids at suitable sites, as shown in general in formula (Ia) where $R^1$ and $R^2$=H.

The modified activity of an enzyme $E_5$ in comparison with its wild type can be determined in the simplest manner indirectly via the absolute amount of enzyme $E_5$ per cell, since it can be assumed that an increased presence causes an increased activity and a reduced presence a reduced activity based on the cell and that these relationships are directly dependent on each other. The modified presence of the enzyme $E_5$ in comparison with the wild type can be determined by conventional methods. Thus, the protein concentration can be analyzed by Western Blot hybridization with an antibody which is specific for the protein to be detected (Sambrook et al., *Molecular Cloning: a laboratory manual,* 2nd Ed. Cold Spring Harbor Laboratory Press, Cold Spring Harbor, N.Y. USA, 1989), followed by visual evaluation with suitable software for the concentration determination (Lohaus and Meyer (1989) *Biospektrum,* 5: 32-39; Lottspeich (1999), *Angewandte Chemie* 111: 2630-2647).

Cells which are preferred in accordance with the invention are microorganisms, preferably bacterial cells, yeast cells or fungal cells, with Ascomycetes of the genera *Candida* and *Wickerhamiella*, in particular *Candida bombicola, Candida bogoriensis, Candida batistae, Candida apicola* and *Wickerhamiella domericqiae* being especially preferred. The strains *Candida bombicola* ATCC 22214, *Candida bogoriensis* NRRL Y-5980, *Candida batistae* CBS 8550, *Candida apicola* IMET 42747 and *Wickerhamiella domericqiae*, in particular, are especially suitable cells.

Since the sophorolipids are formed by the cell according to the invention starting from glucose and fatty acids, it is advantageous when cells according to the invention are at least partially blocked in their β-oxidation since this prevents the outflow of substrate and therefore makes possible higher product concentrations and carbon yields. *Candida* cells which are blocked in their β-oxidation are described for example in WO 03/100013, *Candida bombicola* cells which are blocked in the β-oxidation in Van Bogaert et al. FEMS Yeast Res. 2009 June; 9(4):610-7.

In cells which are preferred in accordance with the invention, the modified enzyme activity is preferably an increased enzyme activity.

In accordance with the invention, preferred cells are those which show increased activities of the following enzyme combinations:

$E_1E_2$, $E_1E_3$, $E_1E_4$, $E_1E_5$, $E_2E_3$, $E_2E_4$, $E_2E_5$, $E_3E_4$, $E_3E_5$, $E_4E_5$, $E_1E_2E_3$, $E_1E_2E_4$, $E_1E_2E_5$, $E_1E_3E_4$, $E_1E_3E_5$, $E_1E_4E_5$, $E_2E_3E_4$, $E_2E_4E_5$, $E_3E_4E_5$, $E_1E_2E_3E_4$, $E_2E_3E_4E_5$, $E_1E_3E_4E_5$, $E_1E_2E_4E_5$, $E_1E_2E_3E_5$, $E_1E_2E_3E_4$ and $E_1E_2E_3E_4E_5$, with the combinations $E_1E_2$, $E_1E_3$, $E_1E_4$, $E_1E_5$, $E_2E_3$, $E_2E_4$, $E_2E_5$, $E_3E_4$, $E_3E_5$, $E_4E_5$, $E_1E_2E_3$, $E_1E_2E_4$, $E_1E_2E_5$, $E_1E_3E_4$, $E_1E_3E_5$, $E_1E_4E_5$, $E_2E_3E_4$, $E_2E_4E_5$, $E_3E_4E_5$ and $E_1E_2E_3E_4E_5$, in particular $E_1E_2$, $E_1E_3$, $E_1E_4$, $E_1E_5$, $E_2E_3$, $E_2E_4$, $E_2E_5$, $E_3E_4$, $E_3E_5$, $E_4E_5$ and $E_1E_2E_3E_4E_5$ being preferred.

To prepare sophorolipids of the general formula (Ia) where n=0, as little as possible enzymatic activity of an enzyme $E_3$ should be present in the cell. Thus, in a specific embodiment of the cell according to the invention, the modified activity of an enzyme $E_3$ is a reduced activity.

Cells which are preferred in accordance with the invention in this context are those which show a reduced activity of an enzyme $E_3$ and optionally simultaneously an increased activity of at least one of the enzymes $E_1$, $E_2$, $E_4$ and $E_5$ and which show in particular besides the reduced activity of an enzyme $E_3$ an increased activity of the following enzyme combinations:

$E_1E_2$, $E_1E_4$, $E_1E_5$, $E_2E_4$, $E_2E_5$, $E_4E_5$, $E_1E_2E_4$, $E_1E_2E_5$, $E_1E_4E_5$ and $E_1E_2E_4E_5$, especially preferably $E_1E_2$, $E_1E_4$, $E_1E_5$, $E_2E_4$, $E_2E_5$, $E_4E_5$ and $E_1E_2E_4E_5$.

In this context, the cell according to the invention is preferably a *Candida bombicola, Candida bogoriensis, Candida batistae, Candida apicola* or *Wickerhamiella domericqiae* cell.

Furthermore preferred in this context are cells according to the invention in which the reduction of the enzymatic activity is achieved by the modification of a gene comprising a nucleic acid sequence selected from the group consisting of SEQ ID NO:6 and a sequence which is to at least 80%, especially preferably to at least 90%, more preferably to at least 95% and most preferably to at least 99% identical to the reference sequence SEQ ID NO:6, where the modification is selected from the group comprising, preferably consisting of, insertion of foreign DNA into the gene, deletion of at least portions of the gene, point mutations in the gene sequence, RNA interference (siRNA), antisense RNA or modification (insertion, deletion or point mutations) of regulatory sequences which flank the gene.

A nucleic acid which is suitable for the preparation of such cells is, for example, one with the SEQ ID NO:16, which is also subject matter of the invention.

To prepare sophorolipids of the general formula (Ia) or (Ib) where $R^1$ and $R^2$ equal H, as little as possible enzymatic activity of an enzyme $E_4$ should be present in the cell. Thus, in a specific embodiment of the cell according to the invention, the modified activity of an enzyme $E_4$ is a reduced activity.

In this context, cells which are preferred in accordance with the invention are those which show a reduced activity of at least one enzyme $E_4$ and which optionally simultaneously show an increased activity of at least one of the enzymes $E_1$, $E_2$, $E_3$ and $E_5$ and which show in particular besides the reduced activity of an enzyme $E_4$ an increased activity of the following enzyme combinations:

$E_1E_2$, $E_1E_3$, $E_1E_5$, $E_2E_3$, $E_2E_5$, $E_3E_5$, $E_1E_2E_3$, $E_1E_2E_5$, $E_1E_3E_5$ and $E_1E_2E_3E_5$, especially preferably $E_1E_2$, $E_1E_3$, $E_1E_5$, $E_2E_3$, $E_2E_5$, $E_3E_5$ and $E_1E_2E_3E_5$.

In this context, the cell according to the invention is preferably a *Candida bombicola, Candida bogoriensis, Candida batistae, Candida apicola* or *Wickerhamiella domericqiae* cell.

Furthermore preferred in this context are cells according to the invention in which the reduction of the enzymatic activity is achieved by the modification of a gene comprising a nucleic acid sequence selected from the group consisting of SEQ ID NO:4 and a sequence which is to at least 80%, especially preferably to at least 90%, more preferably to at least 95% and most preferably to at least 99% identical to SEQ ID NO:4, where the modification is selected from the group comprising, preferably consisting of, insertion of foreign DNA into the gene, deletion of at least portions of the gene, point mutations in the gene sequence, RNA interference (siRNA), antisense RNA or modification (insertion, deletion or point mutations) of regulatory sequences which flank the gene.

A nucleic acid which is suitable for the preparation of such cells is, for example, one with the SEQ ID NO:14, which is also subject matter of the invention.

To prepare sophorolipids of the general formula (Ia) where n=0 and $R^1$ equals H, as little as possible enzymatic activity of the enzymes $E_3$ and $E_4$ should be present in the cell. Thus, in a specific embodiment of the cell according to the invention, the modified activity of the enzymes $E_3$ and $E_4$ is a reduced activity.

In this context, cells which are preferred in accordance with the invention are those which show a reduced activity of in each case at least one enzyme $E_3$ and $E_4$ and which simultaneously show an increased activity of at least one of the enzymes $E_1$, $E_2$ and $E_5$ and which show in particular besides the reduced activity of the in each case at least one enzyme $E_3$ and $E_4$ an increased activity of the following enzyme combinations:

$E_1E_2$, $E_1E_5$, $E_2E_5$, $E_1E_2E_5$, especially preferably $E_1E_2$, $E_1E_5$ and $E_2E_5$.

In this context, the cell according to the invention is preferably a *Candida bombicola, Candida bogoriensis, Candida batistae, Candida apicola* or *Wickerhamiella domericqiae* cell.

Furthermore preferred in this context are cells according to the invention in which the reduction of the enzymatic activity is achieved by the modification of a gene comprising a nucleic acid sequence selected from the group consisting of SEQ ID NO:4 and a sequence which is to at least 80%, especially preferably to at least 90%, more preferably to at least 95% and most preferably to at least 99% identical to SEQ ID NO:4 and of a gene comprising a nucleic acid sequence selected from the group consisting of SEQ ID NO:6 and a sequence which is to at least 80%, especially preferably to at least 90%, more preferably to at least 95% and most preferably to at least 99% identical to the reference sequence SEQ ID NO:6, where the modification is selected from the group comprising, preferably consisting of, insertion of foreign DNA into the gene, deletion of at least portions of the gene, point mutations in the gene sequence, RNA interference (siRNA), antisense RNA or modification (insertion, deletion or point mutations) of regulatory sequences which flank the genes.

Nucleic acids which are suitable for preparing such cells are, for example, those of SEQ ID NO:14 and 16.

What will be said hereinbelow regarding the increasing of the enzyme activity in cells applies both to increasing the activity of the enzymes $E_1$ to $E_5$ and to all enzymes mentioned hereinbelow whose activity may optionally be increased.

In principle, an increase of the enzymatic activity can be achieved by increasing the copy number of the gene sequence(s) which encode(s) the enzyme, by using a strong promoter, by modifying the codon usage of the gene, by increasing in various ways the half-life of the mRNA or of the enzyme, by modifying the regulation of gene expression or by using a gene or allele which encodes a suitable enzyme with an increased activity, and optionally by combining these measures. Cells which are genetically modified in accordance with the invention are generated for example by transformation, transduction, conjugation or a combination of these methods with a vector which comprises the desired gene, an allele of this gene or parts thereof and a promoter which makes possible the expression of the gene. Heterologous expression in particular is achieved by integrating the gene or the alleles into the chromosome of the cell or into an extrachromosomally replicating vector.

An overview over the possibilities of increasing the enzyme activity in cells with reference to the enzyme isocitrate lyase can be found in EP0839211, which is herewith incorporated by reference and whose disclosure content in respect of the possibilities of increasing the enzyme activity in cells forms part of the disclosure of the present invention.

The expression of the enzymes or genes mentioned hereinabove, and the expression of all enzymes or genes mentioned hereinbelow, can be detected with the aid of 1- and 2-dimensional protein gel separation followed by visual identification of the protein concentration in the gel using suitable evaluation software. If the increase of an enzyme activity is based exclusively on an increase of the expression of the gene in question, the quantitative determination of the increase of the enzyme activity can be determined in a simple manner by comparing the 1- or 2-dimensional protein separations between the wild type and the genetically modified cell. A customary method of preparing the protein gels in coryneform bacteria and of identifying the proteins is the procedure described by Hermann et al. (Electrophoresis, 22: 1712.23 (2001)). The protein concentration can also be analyzed by Western Blot hybridization with an antibody which is specific for the protein to be detected (Sambrook et al., Molecular Cloning: a laboratory manual, 2nd ed. Cold Spring Harbor Laboratory Press, Cold Spring Harbor, N.Y. USA, 1989) followed by visual evaluation using suitable concentration determination software (Lohaus and Meyer (1989) Biospektrum, 5: 32-39; Lottspeich (1999), Angewandte Chemie 111: 2630-2647). The activity of DNA-binding proteins can be measured by means of DNA band shift assays (also referred to as gel retardation) (Wilson et al. (2001) Journal of Bacteriology, 183: 2151-2155). The effect of DNA-binding proteins on the expression of other genes can be detected by various well-described reporter gene assay methods (Sambrook et al., Molecular Cloning: a laboratory manual, 2nd ed. Cold Spring Harbor Laboratory Press, Cold Spring Harbor, N.Y. USA, 1989). The intracellular (specific) enzymatic activities can be determined by various described methods (Donahue et al. (2000) Journal of Bacteriology 182 (19): 5624-5627; Ray et al. (2000) Journal of Bacteriology 182 (8): 2277-2284; Freedberg et al. (1973) Journal of Bacteriology 115 (3): 816-823). Unless specific methods for determining the activity of a specific enzyme are stated in what follows, the increase of the enzyme activity, but also the reduction of an enzyme activity, are preferably determined by the methods described in Hermann et al., Electrophoresis, 22: 1712-23 (2001), Lohaus et al., Biospektrum 5 32-39 (1998), Lottspeich, Angewandte Chemie 111: 2630-2647 (1999) and Wilson et al., Journal of Bacteriology 183: 2151-2155 (2001).

If the enzyme activity is increased by mutating the endogenous gene, such mutations can either be generated in an undirected manner using traditional methods, such as, for example, by UV irradiation or by mutagenic chemicals, or in a specific fashion by means of recombinant methods such as deletion(s), insertion(s) and/or nucleotide substitution(s). These mutations give rise to modified cells. Especially preferred mutants of enzymes are, in particular, also those enzymes which are no longer feedback-inhibitable, or at least show a degree of reduced feedback inhibition in comparison with the wild-type enzyme.

If the enzyme activity is increased by increasing the synthesis of an enzyme, then for example the copy number of the genes in question is increased or the promoter region and the regulation region or the ribosomal binding site which is located upstream of the structural gene are mutated. Expression cassettes which are introduced upstream of the structural gene are active in the same manner. In addition, inducible promoters allow the expression to be increased at any desired point in time. Furthermore, the enzyme gene may also have assigned to it regulatory sequences also referred to as "enhancers", which likewise bring about an increased gene expression via improving the interaction between RNA polymerase and DNA. Measures for extending the life of the mRNA likewise improve expression. Furthermore, the enzyme activity will also be increased by preventing enzyme degradation. Here, the genes or gene constructs are either present in plasmids with different copy numbers or else are integrated into and amplified in the chromosome. As an alternative, overexpression of the genes in question may furthermore be achieved by modifying the media composition and the culture conditions. A person skilled in the art may find information in this context in Martin et al. (Bio/Technology 5, 137-146 (1987)), in Guerrero et al. (Gene 138, 35-41 (1994)), Tsuchiya and Morinaga (Bio/Technology 6, 428-430 (1988)), in Eikmanns et al. (Gene 102, 93-98 (1991)), in EP-A-0 472 869, in U.S. Pat. No. 4,601,893, in Schwarzer and Pahler (Bio/Technology 9, 84-87 (1991)), in Reinscheid et al. (Applied and Environmental Microbiology 60, 126-132 (1994)), in LaBarre et al. (Journal of Bacteriology 175, 1001-1007 (1993)), in WO-A-96/15246, in Malumbres et al. (Gene 134, 15-24 (1993)), in JP-A-10-229891, in Jensen and Hammer (Biotechnology and Bioengineering 58, 191-195 (1998)) and in known textbooks of genetics and molecular biology, inter alia. The above-described measures result in genetically modified cells, as do the mutations.

Expression of the genes in question is increased for example by using episomal plasmids. Suitable plasmids and vectors are, in principle, all embodiments available to a person skilled in the art for this purpose. Such plasmids and vectors may be found for example in brochures from Novagen, Promega, New England Biolabs, Clontech or Gibco BRL. Other preferred plasmids and vectors may be found in: Glover, D. M. (1985), DNA cloning: a practical approach, Vol. I-III, IRL Press Ltd., Oxford; Rodriguez, R. L. and Denhardt, D. T (ed.) (1988), Vectors: a survey of molecular cloning vectors and their uses, 179-204, Butterworth, Stoneham; Goeddel, D. V. (1990), Systems for heterologous gene expression, Methods Enzymol. 185, 3-7; Sambrook, J.; Fritsch, E. F. and Maniatis, T. (1989), Molecular cloning: a laboratory manual, 2nd ed., Cold Spring Harbor Laboratory Press, New York.

The vectors, such as expression vectors, gene deletion cassettes, gene insertion cassettes or gene overexpression cassettes, which comprise the gene to be amplified or portions of the gene to be inactivated are subsequently transferred into the desired strain by means of transformation. Transformation methods, in particular electroporation, lithium-acetate-mediated transformation, freeze-thaw transformation, are described for example in Gietz, R. D., Schiestl, R. H. (2007). Frozen competent yeast cells that can be transformed with high efficiency using the LiAc/SS carrier DNA/PEG method. Nat. Protoc. 2:1-4; Suga, M., Hatakeyama, T. (2003). High-efficiency electroporation by freezing intact yeast cells with addition of calcium. Curr Genet. 43:206-211; Hubberstey, A. V., Wildeman, A. G. (1991). Transformation of *Saccharomyces cerevisiae* by use of frozen spheroplasts. Trends Genet. 7:41; Bröker, M. (1993). Rapid transformation of cryopreserved competent *Schizosaccharomyces pombe* cells. Biotechniques. 15:598-600; Gietz, R. D., Schiestl, R. H. (1989). High efficiency transformation of intact yeast cells using single stranded nucleic acids as a carrier. Curr Genet. 16:339-346 and in "Nonconventional yeast in biotechnology" (ed. Klaus Wolf, Springer-Verlag Berlin, 1996). After the transformation, the vectors, in particular gene deletion cassettes, gene insertion cassettes or gene overexpression cassettes, integrate by means of a crossover event into the chromosome of the desired strain as a result of homologous or heterologous, preferably homologous, recombination. As an alternative, the vectors, in particular expression vectors, may also replicate episomally, in other words as an independent replication unit, in cells of the desired strain. This ensures in all cases that the vectors, such as expression vectors, gene deletion cassettes, gene insertion cassettes or gene overexpression cassettes, will also be passed on to the daughter cells upon cell division.

The wording "an activity of an enzyme $E_x$ which is increased in comparison with its wild type" used hereinabove and in what follows preferably always means an activity of the respective enzyme $E_x$ which is increased by a factor of at least 1.5, especially preferably of at least 10, more preferably of at least 100, even more preferably of at least 1000 and most preferably of at least 10 000. Furthermore, the cell according to the invention which shows "an activity of an enzyme $E_x$ which is increased in comparison with its wild type" comprises in particular also a cell whose wild type shows no, or at least no detectable, activity of this enzyme $E_x$ and which only shows a detectable activity of this enzyme $E_x$ after increasing the enzyme activity, for example by overexpression. In this context, the term "overexpression" or the wording "increase of the expression" used in what follows also comprises the case in which a starting cell, for example a wild-type cell, shows no or at least no detectable expression and a detectable synthesis of the enzyme $E_x$ is induced only by recombinant methods.

Accordingly, the wording "reduced activity of an enzyme $E_x$" used is understood as meaning an activity which is reduced preferably by a factor of at least 0.5, especially preferably of at least 0.1, more preferably of at least 0.01, even more preferably of at least 0.001 and most preferably of at least 0.0001. The wording "reduced activity" also includes no detectable activity ("zero activity"). The activity of a specific enzyme may be reduced for example by targeted mutation or by other measures of reducing the activity of a specific enzyme which are known to a person skilled in the art.

Methods of reducing enzymatic activities in microorganisms are known to a person skilled in the art.

Techniques of molecular biology, in particular, are the method of choice here. Information on modifying and reducing protein expression and the associated reduction of enzymatic activities specifically for *Candida*, in particular for disrupting specific genes, can be found by a person skilled in the art in WO91/006660 and WO03/100013. Cells which are preferred in accordance with the invention are characterized in that the reduction of the enzymatic activity is achieved by modifying a gene comprising one of the abovementioned nucleic acid sequences, with the modification being selected from the group comprising, preferably from the group consisting of, insertion of foreign DNA into the gene, deletion of at least parts of the gene, point mutations in the gene sequence, RNA interference (siRNA), antisense RNA or modification (insertion, deletion or point mutations) of regulatory sequences which flank the gene.

In this context, foreign DNA is understood as meaning any DNA sequence which is "foreign" to the gene (and not to the organism), in other words *Candida-bombicola*-endogenous DNA sequences may in this context also act as "foreign DNA". In this context, it is especially preferred for the gene to be interrupted by the insertion of a selection marker gene, the foreign DNA thus being a selection marker gene, where the insertion has preferably been performed by homologous recombination into the gene locus.

Cells which are preferred in accordance with the invention are characterized in that they have been transformed with at least one nucleic acid according to the invention described hereinbelow and/or a vector according to the invention described hereinbelow.

Cells according to the invention may be used advantageously for the production of sophorolipids.

Thus, a further object of the invention is the use of cells according to the invention for the production of compounds of the general formulae (Ia) and (Ib)

in which $R^1$=H or CO—$CH_3$, $R^2$=H or CO—$CH_3$, $R^3$=a divalent organic moiety which comprises 6 to 32, preferably 7 to 19 carbon atoms and which is unsubstituted or substituted by hydroxyl functions, is unbranched and optionally comprises one to three double or triple bonds, $R^4$=H, $CH_3$ or a monovalent organic radical which comprises 2 to 10 carbon atoms and which is unsubstituted or substituted by hydroxyl functions, which is unbranched and which optionally comprises one to three double or triple bonds, and n=0 or 1, in particular of those compounds of the general formulae (Ia) and (Ib)

in which $R^1$=H or CO—$CH_3$, $R^2$=H or CO—$CH_3$, $R^3$=a divalent organic moiety which comprises 6 to 32, preferably 7 to 19 carbon atoms and which is unsubstituted or substituted by hydroxyl functions, is unbranched and optionally comprises one to three double or triple bonds, $R^4$=H, $CH_3$ or $C_9H_{19}$, and n=0 or 1, and very especially preferably compounds of the general formulae (Ia) and (Ib)

in which $R^1$=H or CO—$CH_3$, $R^2$=H or CO—$CH_3$, $R^3$=a divalent organic moiety which comprises 6 to 32, preferably 7 to 19 carbon atoms and which is unsubstituted or substituted by hydroxyl functions, is unbranched and optionally comprises one to three double or triple bonds, in particular $C_8H_{15}$=$C_7H_{14}$, $R^4$=H, $CH_3$ or $C_9H_{19}$, in particular H or $CH_3$, and n=1.

A further subject matter of the present invention is a process for the production of sophorolipids, preferably of compounds of the general formulae (Ia) and (Ib)

in which $R^1$=H or CO—$CH_3$, $R^2$=H or CO—$CH_3$, $R^3$=a divalent organic moiety which comprises 6 to 32, preferably 7 to 19 carbon atoms and which is unsubstituted or substituted by hydroxyl functions, is unbranched and optionally comprises one to three double or triple bonds, $R^4$=H, $CH_3$ or a monovalent organic radical which comprises 2 to 10 carbon atoms and which is unsubstituted or substituted by hydroxyl functions, which is unbranched and which optionally comprises one to three double or triple bonds, and n=0 or 1, in particular of those compounds of the general formulae (Ia) and (Ib)

in which $R^1$=H or CO—$CH_3$, $R^2$=H or CO—$CH_3$, $R^3$=a divalent organic moiety which comprises 6 to 32, preferably 7 to 19 carbon atoms and which is unsubstituted or substituted by hydroxyl functions, is unbranched and optionally comprises one to three double or triple bonds, $R^4$=H, $CH_3$ or $C_9H_{19}$, and n=0 or 1, and very especially preferably of compounds of the general formulae (Ia) and (Ib)

in which $R^1$=H or CO—$CH_3$, $R^2$=H or CO—$CH_3$, $R^3$=a divalent organic moiety which comprises 6 to 32, preferably 7 to 19 carbon atoms and which is unsubstituted or substituted by hydroxyl functions, is unbranched and optionally comprises one to three double or triple bonds, in particular $C_8H_{15}$=$C_7H_{14}$, $R^4$=H, $CH_3$ or $C_9H_{19}$, in particular H or $CH_3$, and n=1 comprising the process steps:

I) bringing a cell according to the invention into contact with a medium comprising a carbon source II) culturing the cell under conditions which allow the cell to form a sophorolipid from the carbon source, and III) optionally isolating the formed sophorolipids.

The genetically modified cells according to the invention may be brought into contact with the nutrient medium continuously or batchwise by the batch method or the fed-batch method or the repeated-fed-batch method for the purposes of producing the abovementioned products and thereby cultured. Also feasible is a semicontinuous process as described in GB-A-1009370. An overview of known cultivation methods can be found in the textbook by Chmiel ("Bioprozesstechnik 1. Einführung in die Bioverfahrenstechnik" (Gustav Fischer Verlag, Stuttgart, 1991)) or in the textbook by Storhas ("Bioreaktoren and periphere Einrichtungen", Vieweg Verlag, Brunswick/Wiesbaden, 1994).

The culture medium to be used in each case must satisfy the demands of the strains in question in a suitable manner. The textbook "Nonconventional yeast in biotechnology" (ed. Klaus Wolf, Springer-Verlag Berlin, 1996) contains descriptions of culture media for various yeast strains. Carbon sources which can be employed are carbohydrates such as, for example, glucose, sucrose, arabinose, xylose, lactose, fructose, maltose, molasses, starch, cellulose and hemicelluloses, vegetable and animal oils and fats such as, for example, soya oil, safflower oil, groundnut oil, hemp oil, jatropha oil, coconut fat, pumpkinseed oil, linseed oil, corn oil, poppyseed oil, evening primrose oil, olive oil, palm kernel oil, palm oil, rapeseed oil, sesameseed oil, sunflower oil, grapeseed oil, walnut oil, wheatgerm oil and coconut fat, fatty acids such as, for example, caprylic acid, capric acid, lauric acid, myristic acid, palmitic acid, palmitolenic acid, stearic acid, arachidonic acid, behenic acid, oleic acid, linoleic acid, linolenic acid, gamma-linolenic acid and their methyl or ethyl esters, and fatty acid mixtures, mono-, di- and triglycerides with the fatty acids which have just been mentioned, alcohols such as, for example, glycerol, ethanol and methanol, hydrocarbons such as methane, carbon-containing gases and gas mixtures, such as CO, $CO_2$, synthesis gas, flue gas, amino acids such as L-glutamate or L-valine or organic acids such as, for example, acetic acid. These substances may be employed singularly or as a mixture. It is especially preferred to employ carbohydrates, in particular monosaccharides, oligosaccharides or polysaccharides, as the carbon source, as is described in U.S. Pat. Nos. 6,01,494 and 6,136,576, and hydrocarbons, in particular alkanes, alkenes and alkynes and the monocarboxylic acids derived from these and the mono-, di- and triglycerides derived from these monocarboxylic acids, and glycerol and acetate. Very especially preferred are mono-, di- and triglycerides comprising the esterification products of glycerol with caprylic acid, capric acid, lauric acid, myristic acid, palmitic acid, palmitolenic acid, stearic acid, arachidonic acid, behenic acid, oleic acid, linoleic acid, linolenic acid and/or gamma-linoleic acid.

Nitrogen sources which may be used are organic compounds comprising nitrogen, such as peptones, yeast extract, meat extract, malt extract, corn steep liquor, soybean meal and urea or inorganic compounds such as ammonium sulfate, ammonium chloride, ammonium phosphate, ammonium carbonate and ammonium nitrate, ammonia, ammonium hydroxide or ammonia water. The nitrogen sources may be employed singularly or as a mixture.

Phosphorus sources which may be used are phosphoric acid, potassium dihydrogen phosphate or dipotassium hydrogen phosphate or the corresponding sodium-containing salts. The culture medium must furthermore comprise salts of metals, such as, for example, magnesium sulfate or iron sulfate, which are required for growth. Finally, essential growth factors such as amino acids and vitamins may be employed in addition to the abovementioned substances. Furthermore, suitable precursors may be added to the culture medium. The feedstock mentioned may be added to the culture as a single batch or fed in a suitable manner during culturing.

The pH of the culture is controlled by employing basic compounds such as sodium hydroxide, potassium hydroxide, ammonia or ammonia water, or acidic compounds such as phosphoric acid and sulfuric acid. Foaming may be controlled by using antifoams such as, for example, fatty acid polyglycol esters. To maintain the stability of plasmids, suitable selective substances such as, for example, antibiotics may be added to the medium. Oxygen or oxygen-containing gas mixtures such as, for example, air are introduced into the culture in order to maintain aerobic conditions.

The temperature of the culture is normally more than 20° C., preferably more than 25° C., it may also be more than 40° C., with a culture temperature of 95° C., especially preferably 90° C. and most preferably 80° C. not being exceeded.

In step III) of the process according to the invention, the sophorolipids formed by the cells may optionally be isolated from the cells and/or the nutrient medium, where all methods of isolating low-molecular-weight substances from complex compositions which are known to a person skilled in the art may be used for the isolation, such as, for example, filtration, extraction, adsorption (chromatography) or crystallization. As a rule, work-up of the sophorolipids is performed as a function of the product form. In the case of a sophorolipid which is present in the water-insoluble lactone form, the following procedure may be the procedure of choice: the product in lactone form is removed from the aqueous phase by centrifugation.

In addition, the product phase comprises biomass residues and various contaminants such as oils, fatty acids and other nutrient media components. Oil residues can be removed for example by extraction by means of suitable solvents, advantageously by means of organic solvents. An alkane such as, for example, n-hexane, is preferred by way of solvent. The product may be removed from the aqueous phase for example by means of a suitable ester, for example by means of ethyl acetate. The abovementioned extraction steps may be carried out in any order.

Alternatively, sophorolipids may be isolated from the nutrient medium by converting the lactone form into the water-soluble open acid form. For example, the conversion into the open acid form is performed by means of hydrolysis, advantageously by alkaline hydrolysis. Thereafter, the open-chain sophorolipids are dissolved in an aqueous acid, for example aqueous sulfuric acid, in order to remove any salts which may have formed in the solution. The further purification of the product is carried out by means of extraction. Here, it is preferred to employ solvents, in particular organic solvents. n-Pentanol is preferred by way of solvent. To remove the solvent, for example a distillation is performed. Thereafter, the lyophilized product may be purified further, for example by means of chromatographic methods. Examples which may be mentioned at this point are the precipitation by means of suitable solvents, the extraction by means of suitable solvents, complexing, for example by means of cyclodextrins or cyclodextrin derivatives, crystallization, purification or isolation by means of chromatographic methods, or the conversion of the sophorolipids into derivatives which can be removed readily.

The sophorolipids produced by the process according to the invention may be employed advantageously in cleaning compositions, in cosmetic or pharmaceutical formulations and in crop protection formulations.

Thus, a further subject of the present invention is the use of the sophorolipids obtained by the process according to the invention for the preparation of cosmetic, dermatological or pharmaceutical formulations, crop protection formulations and care and cleaning compositions and surfactant concentrates.

The term "care composition" is understood here as meaning a formulation which satisfies the purpose of retaining an object in its original form, of reducing or avoiding the effects of external influences (for example time, light, temperature, pressure, soiling, chemical reaction with other reactive compounds that come into contact with the object) such as, for example, ageing, soiling, material fatigue, bleaching, or even of improving desired positive properties of the object. For the last point, mention may be made for example of improved hair shine or greater elasticity of the object under consideration.

"Crop protection formulations" are to be understood as meaning those formulations which are obviously used for the protection of plants depending on the nature of their preparation; this is the case especially if at least one compound from the classes of the herbicides, fungicides, insecticides, acaricides, nematicides, bird repellents, plant nutrients and soil conditioners is present in the formulation.

It is preferred in accordance with the invention to use sophorolipids prepared by the process according to the invention in care and cleaning compositions for domestic purposes, for industry, in particular for hard surfaces, leather or textiles.

A contribution to solve the problem is provided by an isolated DNA which is selected from among the following sequences:

A1a) a sequence according to SEQ ID NO:2, SEQ ID NO:52 or SEQ ID NO:54, in particular SEQ ID NO:2, where this sequence encodes a protein which is capable of converting Z-9-octadecenoic acid into 17-hydroxy-Z-9-octadecenoic acid, B1a) an intron-free sequence which is derived from a sequence according to A1a) and which encodes for the same protein or peptide as the sequence according to SEQ ID NO:2, SEQ ID NO:52 or SEQ ID NO:54, in particular according to SEQ ID NO:2, C1a) a sequence which encodes a protein or peptide which comprises the amino acid sequence according to SEQ ID NO:7, SEQ ID NO:53 or SEQ ID NO:55, in particular SEQ ID NO:7, and which is preferably capable of converting Z-9-octadecenoic acid into 17-hydroxy-Z-9-octadecenoic acid, D1a) a sequence which is identical to at least 80%, especially preferably to at least 90%, more preferably to at least 95% and most preferably to at least 99% to a sequence according to any of groups A1a) to C1a), especially preferably according to group A1a), where this sequence preferably encodes a protein or peptide which is capable of converting Z-9-octadecenoic acid into 17-hydroxy-Z-9-octadecenoic acid, E1a) a sequence which hybridizes, or which, taking into consideration the degeneracy of the genetic code, would hybridize with the counterstrand of a sequence according to any of groups A1a) to D1a), especially preferably according to group A1a), where this sequence preferably encodes a protein or peptide which is capable of converting Z-9-octadecenoic acid into 17-hydroxy-Z-9-octadecenoic acid, F1a) a derivative of a sequence according to any of groups A1a) to E1a), especially preferably according to group A1a), which is obtained by substitution, addition, inversion and/or deletion of at least one base, preferably of at least 2 bases, more preferably of at least 5 bases and most preferably of at least 10 bases, but preferably of no more than 100 bases, especially preferably of no more than 50 bases and most preferably of no more than 25 bases, where this derivative preferably encodes a protein or peptide which is capable of converting Z-9-octadecenoic acid into 17-hydroxy-Z-9-octadecenoic acid, and G1a) a sequence which is complementary to a sequence according to any of groups A1a) to F1a), especially preferably according to group A1a).

A further contribution to the solution of the problem is provided by an isolated DNA which is selected from among the following sequences:

A1b) a sequence according to SEQ ID NO:56, SEQ ID NO:58 or SEQ ID NO:60, where this sequence encodes a protein which is capable of converting Z-9-octadecenoic acid into 17-hydroxy-Z-9-octadecenoic acid, B1b) an intron-free sequence which is derived from a sequence according to A1b) and which encodes for the same protein or peptide as the sequence according to SEQ ID NO:56, SEQ ID NO:58 or SEQ ID NO:60, C1b) a sequence which encodes a protein or peptide which comprises the amino acid sequence according to SEQ ID NO:57, SEQ ID NO:59 or SEQ ID NO:61, and which is preferably capable of converting Z-9-octadecenoic acid into 17-hydroxy-Z-9-octadecenoic acid, D1b) a sequence which is identical to at least 80%, especially preferably to at least 86%, more preferably to at least 95% and most preferably to at least 99% to a sequence according to any of groups A1b) to C1b), especially preferably according to group A1b), where this sequence preferably encodes a protein or peptide which is capable of converting Z-9-octadecenoic acid into 17-hydroxy-Z-9-octadecenoic acid, E1b) a sequence which hybridizes, or which, taking into consideration the degeneracy of the genetic code, would hybridize with the counterstrand of a sequence according to any of groups A1b) to D1b), especially preferably according to group A1b), where this sequence preferably encodes a protein or peptide which is capable of converting Z-9-octadecenoic acid into 17-hydroxy-Z-9-octadecenoic acid, F1b) a derivative of a sequence according to any of groups A1b) to E1b), especially preferably according to group A1b), which is obtained by substitution, addition, inversion and/or deletion of at least one base, preferably of at least 2 bases, more preferably of at least 5 bases and most preferably of at least 10 bases, but preferably of no more than 100 bases, especially preferably of no more than 50 bases and most preferably of no more than 25 bases, where this derivative preferably encodes a protein or peptide which is capable of converting Z-9-octadecenoic acid into 17-hydroxy-Z-9-octadecenoic acid, and G1b) a sequence which is complementary to a sequence according to any of groups A1b) to F1b), especially preferably according to group A1b).

A further contribution to the solution of the problem is provided by an isolated DNA which is selected from among the following sequences:

A1c) a sequence according to SEQ ID NO:62, where this sequence encodes a protein which is capable of converting Z-9-octadecenoic acid into 17-hydroxy-Z-9-octadecenoic acid, B1c) an intron-free sequence which is derived from a sequence according to A1c) and which encodes for the same protein or peptide as the sequence according to SEQ ID NO:62, C1c) a sequence which encodes a protein or peptide which comprises the amino acid sequence according to SEQ ID NO:63, and which is preferably capable of converting Z-9-octadecenoic acid into 17-hydroxy-Z-9-octadecenoic acid, D1c) a sequence which is identical to at least 60%, especially preferably to at least 85%, more preferably to at least 90% and most preferably to at least 99% to a sequence according to any of groups A1c) to C1c), especially preferably according to group A1c), where this sequence preferably encodes a protein or peptide which is capable of converting Z-9-octadecenoic acid into 17-hydroxy-Z-9-octadecenoic acid, E1c) a sequence which hybridizes, or which, taking into consideration the degeneracy of the genetic code, would hybridize with the counterstrand of a sequence according to any of groups A1c) to D1c), especially preferably according to group A1c), where this sequence preferably encodes a protein or peptide which is capable of converting Z-9-octadecenoic acid into 17-hydroxy-Z-9-octadecenoic acid, F1c) a derivative of a sequence according to any of groups A1c) to E1c), especially preferably according to group A1c), which is obtained by substitution, addition, inversion and/or deletion of at least one base, preferably of at least 2 bases, more preferably of at least 5 bases and most preferably of at least 10 bases, but preferably of no more than 100 bases, especially preferably of no more than 50 bases and most preferably of no more than 25 bases, where this derivative preferably encodes a protein or peptide which is capable of converting Z-9-octadecenoic acid into 17-hydroxy-Z-9-octadecenoic acid, and G1c) a sequence which is complementary to a sequence according to any of groups A1c) to F1c), especially preferably according to group A1c).

A further subject of the invention is an isolated DNA which is selected from among the following sequences:

A2) a sequence according to SEQ ID NO:3, where this sequence encodes a protein which is capable of converting UDP-glucose and 17-hydroxy-Z-9-octadecenoic acid into 17-(β-D-glucopyranosyloxy)-Z-9-octadecenoic acid, B2) an intron-free sequence which is derived from a sequence according to A2) and which encodes for the same protein or peptide as the sequence according to SEQ ID NO:3, C2) a sequence which encodes a protein or peptide which comprises the amino acid sequence according to SEQ ID NO:8 and which is preferably capable of converting UDP-glucose and 17-hydroxy-Z-9-octadecenoic acid into 17-(β-D-glucopyranosyloxy)-Z-9-octadecenoic acid, D2) a sequence which is to at least 80%, especially preferably to at least 90%, more preferably to at least 95% and most preferably to at least 99% identical to a sequence according to any of groups A2) to C2), especially preferably according to group A2), where this sequence preferably encodes a protein or peptide which is capable of converting UDP-glucose and 17-hydroxy-Z-9-octadecenoic acid into 17-(β-D-glucopyranosyloxy)-Z-9-octadecenoic acid, E2) a sequence which hybridizes or which, taking into consideration the degeneracy of the genetic code, would hybridize to the counterstrand of a sequence according to any of groups A2) to D2), especially preferably according to group A2), where this sequence preferably encodes a protein or peptide which is capable of converting UDP-glucose and 17-hydroxy-Z-9-octadecenoic acid into 17-(β-D-glucopyranosyloxy)-Z-9-octadecenoic acid, F2) a derivative of a sequence according to any of groups A2) to E2), especially preferably according to group A2), which is obtainable by substitution, addition, inversion and/or deletion of at least one base, preferably of at least 2 bases, more preferably of at least 5 bases and most preferably of at least 10 bases, but preferably of no more than 100 bases, especially preferably of no more than 50 bases and most preferably of no more than 25 bases, where this derivative preferably encodes a protein or peptide which is capable of converting UDP-glucose and 17-hydroxy-Z-9-octadecenoic acid into 17-(β-D-glucopyranosyloxy)-Z-9-octadecenoic acid, and G2) a sequence which is complementary to a sequence according to any of groups A2) to F2), especially preferably according to group A2).

A further subject matter of the invention is an isolated DNA which is selected from among the following sequences:

A3) a sequence according to SEQ ID NO:4, where this sequence encodes a protein which is capable of converting 17-L-[(2'-O-β-D-glucopyranosyl-β-D-glucopyranosyl)oxy]-Z-9-octadecenoic acid 1',4"-lactone and acetyl-coenzyme A into 17-L-[(2'-O-β-D-glucopyranosyl-β-D-glucopyranosyl)oxy]-Z-9-octadecenoic acid 1',4"-lactone monoacetate or 17-L-[(2'-O-β-D-glucopyranosyl-β-D-glucopyranosyl)oxy]-Z-9-octadecenoic acid 1',4"-lactone monoacetate and acetyl-coenzyme A into 17-L-[(2'-O-β-D-glucopyranosyl-β-D-glucopyranosyl)oxy]-Z-9-octadecenoic acid 1',4"-lactone diacetate or 17-L-[(2'-O-β-D-glucopyranosyl-β-D-glucopyranosyl)oxy]-Z-9-octadecenoic acid 1',4"-lactone and acetyl-coenzyme A into 17-L-[(2'-O-β-D-glucopyranosyl-β-D-glucopyranosyl)oxy]-Z-9-octadecenoic acid 1',4"-lactone diacetate, with the first option being preferred, B3) an intron-free sequence which is derived from a sequence according to A3) and which encodes for the same protein or peptide as the sequence according to SEQ ID NO:4, C3) a sequence which encodes a protein or peptide which comprises the amino acid sequence according to SEQ ID NO:9 and which is preferably capable of converting 17-L-[(2'-O-β-D-glucopyranosyl-β-D-glucopyranosyl)oxy]-Z-9-octadecenoic acid 1',4"-lactone and acetyl-coenzyme A into 17-L-[(2'-O-β-D-glucopyranosyl-β-D-glucopyranosyl)oxy]-Z-9-octadecenoic acid 1',4"-lactone monoacetate or 17-L-[(2'-O-β-D-glucopyranosyl-β-D-glucopyranosyl)oxy]-Z-9-octadecenoic acid 1',4"-lactone monoacetate and acetyl-coenzyme A into 17-L-[(2'-O-β-D-glucopyranosyl-β-D-glucopyranosyl)oxy]-Z-9-octadecenoic acid 1',4"-lactone diacetate or 17-L-[(2'-O-β-D-glucopyranosyl-β-D-glucopyranosyl)oxy]-Z-9-octadecenoic acid 1',4"-lactone and acetyl-coenzyme A into 17-L-[(2'-O-β-D-glucopyranosyl-β-D-glucopyranosyl)oxy]-Z-9-octadecenoic acid 1',4"-lactone diacetate, with the first option being preferred, D3) a sequence which is identical to at least 80%, especially preferably to at least 90%, more preferably to at least 95% and most preferably to at least 99% to a sequence according to any of groups A3) to C3), especially preferably according to group A3), where this sequence preferably encodes a protein or peptide which is capable of converting 17-L-[(2'-O-β-D-glucopyranosyl-β-D-glucopyranosyl)oxy]-Z-9-octadecenoic acid 1',4"-lactone and acetyl-coenzyme A into 17-L-[(2'-O-β-D-glucopyranosyl-β-D-glucopyranosyl)oxy]-Z-9-octadecenoic acid 1',4"-lactone monoacetate or 17-L-[(2'-O-β-D-glucopyranosyl-β-D-glucopyranosyl)oxy]-Z-9-octadecenoic acid 1',4"-lactone monoacetate and acetyl-coenzyme A into 17-L-[(2'-O-β-D-glucopyranosyl-β-D-glucopyranosyl)oxy]-Z-9-octadecenoic acid 1',4"-lactone diacetate or 17-L-[(2'-O-β-D-glucopyranosyl-β-D-glucopyranosyl)oxy]-Z-9-octadecenoic acid 1',4"-lactone and acetyl-coenzyme A into 17-L-[(2'-O-β-D-glucopyranosyl-β-D-glucopyranosyl)oxy]-Z-9-octadecenoic acid 1',4"-lactone diacetate, with the first option being preferred, E3) a sequence which hybridizes or, taking into consideration the degeneracy of the genetic code, would hybridize with the counterstrand of a sequence according to any of groups A3) to D3), especially preferably according to group A3), where this sequence preferably encodes a protein or peptide which is capable of converting 17-L-[(2'-O-β-D-glucopyranosyl-β-D-glucopyranosyl)oxy]-Z-9-octadecenoic acid 1',4"-lactone and acetyl-coenzyme A into 17-L-[(2'-O-β-D-glucopyranosyl-β-D-glucopyranosyl)oxy]-Z-9-octadecenoic acid 1',4"-lactone monoacetate or 17-L-[(2'-O-β-D-glucopyranosyl-β-D-glucopyranosyl)oxy]-Z-9-octadecenoic acid 1',4"-lactone monoacetate and acetyl-coenzyme A into 17-L-[(2'-O-β-D-glucopyranosyl-β-D-glucopyranosyl)oxy]-Z-9-octadecenoic acid 1',4"-lactone diacetate or 17-L-[(2'-O-β-D-glucopyranosyl-β-D-glucopyranosyl)oxy]-Z-9-octadecenoic acid 1',4"-lactone and acetyl-coenzyme A into 17-L-[(2'-O-β-D-glucopyranosyl-β-D-glucopyranosyl)oxy]-Z-9-octadecenoic acid 1',4"-lactone diacetate, with the first option being preferred, F3) a derivative of a sequence according to any of groups A3) to E3), especially preferably according to group A3), which has been obtained by substitution, addition, inversion and/or deletion of at least one base, preferably of at least 2 bases, more preferably of at least 5 bases and most preferably of at least 10 bases, but preferably of no more than 100 bases, especially preferably of no more than 50 bases and most preferably of no more than 25 bases, where this derivative preferably encodes a protein or peptide which is capable of converting 17-L-[(2'-O-β-D-glucopyranosyl-β-D-glucopyranosyl)oxy]-Z-9-octadecenoic acid 1',4"-lactone and acetyl-coenzyme A into 17-L-[(2'-O-β-D-glucopyranosyl-β-D-glucopyranosyl)oxy]-Z-9-octadecenoic acid 1',4"-lactone monoacetate or 17-L-[(2'-O-β-D-glucopyranosyl-β-D-glucopyranosyl)oxy]-Z-9-octadecenoic acid 1',4"-lactone monoacetate and acetyl-coenzyme A into 17-L-[(2'-O-β-D-glucopyranosyl-β-D-glucopyranosyl)oxy]-Z-9-octadecenoic acid 1',4"-lactone diacetate or 17-L-[(2'-O-β-D-glucopyranosyl-β-D-glucopyranosyl)oxy]-Z-9-octadecenoic acid 1',4"-lactone and acetyl-coenzyme A into 17-L-[(2'-O-β-D-glucopyranosyl-β-D-glucopyranosyl)oxy]-Z-9-octadecenoic acid 1',4"-lactone diacetate, with the first option being preferred, and G3) a sequence which is complementary to a sequence according to any of groups A3) to F3), especially preferably according to group A3).

A further subject matter of the invention is an isolated DNA which is selected from among the following sequences:

A4) a sequence according to SEQ ID NO:5, where this sequence encodes a protein which is capable of transferring a sophorolipid out of a cell into the surrounding medium, B4) an intron-free sequence which is derived from a sequence according to A4) and which encodes for the same protein or peptide as the sequence according to SEQ ID NO:5, C4) a sequence which encodes a protein or peptide which comprises the amino acid sequence according to SEQ ID NO:10 and which is preferably capable of transferring a sophorolipid out of a cell into the surrounding medium, D4) a sequence which is to at least 80%, especially preferably to at least 90%, more preferably to at least 95% and most preferably to at least 99% identical to a sequence according to any of groups A4) to C4), especially preferably according to group A4), where this sequence preferably encodes a protein or peptide which is capable of transferring a sophorolipid out of a cell into the surrounding medium, E4) a sequence which hybridizes, or which, taking into consideration the degeneracy of the genetic code, would hybridize with the counterstrand of a sequence according to any of groups A4) to D4), especially preferably according to group A4), where the sequence preferably encodes a protein or peptide which is capable of transferring a sophorolipid out of a cell into the surrounding medium, F4) a derivative of a sequence according to any of groups A4) to E4), especially preferably according to group A4), which has been obtained by substitution, addition, inversion and/or deletion of at least one base, preferably of at least 2 bases, more preferably of at least 5 bases and most preferably of at least 10 bases, but preferably of no more than 100 bases, especially preferably of no more than 50 bases and most preferably of no more than 25 bases, where this derivative preferably encodes a protein or peptide which is capable of transferring a sophorolipid out of a cell into the surrounding medium, and G4) a sequence which is complementary to a sequence according to any of groups A4) to F4), especially preferably according to group A4).

A further subject matter of the invention is an isolated DNA which is selected from among the following sequences:

A5) a sequence according to SEQ ID NO:6, where this sequence encodes a protein which is capable of converting UDP-glucose and 17-hydroxy-Z-9-octadecenoic acid into 17-(β-D-glucopyranosyloxy)-Z-9-octadecenoic acid or 17-(β-D-glucopyranosyloxy)-Z-9-octadecenoic acid and UDP-glucose into 17-L-[(2'-O-β-D-glucopyranosyl-β-D-glucopyranosyl)oxy]-Z-9-octadecenoic acid, with the latter option being preferred, B5) an intron-free sequence which is derived from a sequence according to A5) and which encodes for the same protein or peptide as the sequence according to SEQ ID NO:6, C5) a sequence which encodes a protein or peptide which comprises the amino acid sequence according to SEQ ID NO:11 and which is preferably capable of converting UDP-glucose and 17-hydroxy-Z-9-octadecenoic acid into 17-(β-D-glucopyranosyloxy)-Z-9-octadecenoic acid or 17-(β-D-glucopyranosyloxy)-Z-9-octadecenoic acid and UDP-glucose into 17-L-[(2'-O-β-D-glucopyranosyl-β-D-glucopyranosyl)oxy]-Z-9-octadecenoic acid, with the latter option being preferred, D5) a sequence which is to at least 80%, especially preferably to at least 90%, more preferably to at least 95% and most preferably to at least 99% identical to a sequence according to any of groups A5) to C5), especially preferably according to group A5), where this sequence preferably encodes a protein or peptide which is capable of converting UDP-glucose and 17-hydroxy-Z-9-octadecenoic acid into 17-(β-D-glucopyranosyloxy)-Z-9-octadecenoic acid or 17-(β-D-glucopyranosyloxy)-Z-9-octadecenoic acid and UDP-glucose into 17-L-[(2'-O-β-D-glucopyranosyl-β-D-glucopyranosyl)oxy]-Z-9-octadecenoic acid, with the latter option being preferred, E5) a sequence which hybridizes or which, taking into consideration the degeneracy of the genetic code, would hybridize to the counterstrand of a sequence according to any of groups A5) to D5), especially preferably according to group A5), where this sequence preferably encodes a protein or peptide which is capable of converting UDP-glucose and 17-hydroxy-Z-9-octadecenoic acid into 17-(β-D-glucopyranosyloxy)-Z-9-octadecenoic acid or 17-(β-D-glucopyranosyloxy)-Z-9-octadecenoic acid and UDP-glucose into 17-L-[(2'-O-β-D-glucopyranosyl-β-D-glucopyranosyl)oxy]-Z-9-octadecenoic acid, with the latter option being preferred, F5) a derivative of a sequence according to any of groups A5) to E5), especially preferably according to group A5), which has been obtained by substitution, addition, inversion and/or deletion of at least one base, preferably of at least 2 bases, more preferably of at least 5 bases and most preferably of at least 10 bases, but preferably of no more than 100 bases, especially preferably of no more than 50 bases and most preferably of no more than 25 bases, where this derivative preferably encodes a protein or peptide which is capable of converting UDP-glucose and 17-hydroxy-Z-9-octadecenoic acid into 17-(β-D-glucopyranosyloxy)-Z-9-octadecenoic acid or 17-(β-D-glucopyranosyloxy)-Z-9-octadecenoic acid and UDP-glucose into 17-L-[(2'-O-β-D-glucopyranosyl-β-D-glucopyranosyl) oxy]-Z-9-octadecenoic acid, with the latter option being preferred, and G5) a sequence which is complementary to a sequence according to any of groups A5) to F5), especially preferably according to group A5).

The "nucleotide identity" or "amino acid identity" here is determined with the aid of known methods. In general, one uses special computer programs with algorithms, taking into consideration specific requirements.

Preferred methods of determining the identity first generate the largest match between the sequences to be compared. Computer programs for determining the identity comprise, but are not limited to, the GCG software package, including GAP (Deveroy, J. et al., Nucleic Acid Research 12 (1984), page 387, Genetics Computer Group University of Wisconsin, Medicine (Wi), and BLASTP, BLASTN and FASTA (Altschul, S. et al., Journal of Molecular Biology 215 (1990), pages 403-410. The BLAST program can be obtained from the National Center For Biotechnology Information (NCBI) and from other sources (BLAST Handbuch, Altschul S. et al., NCBI NLM NIH Bethesda N. Dak. 22894; Altschul S. et al., hereinabove).

Likewise, the known Smith-Waterman algorithm may be used for determining the nucleotide identity.

Preferred parameters for determining the "nucleotide identity" when using the BLASTN program (Altschul, S. et al., Journal of Molecular Biology 215 (1990), pages 403-410) are:

Expect Threshold: 10
Word size: 28
Match Score: 1
Mismatch Score: −2
Gap costs: Linear The above parameters are the default parameters for comparing nucleotide sequences.

The GAP program is likewise suitable for use with the above parameters.

Preferred parameters for determining the "amino acid identity" when using the BLASTP program (Altschul, S. et al., Journal of Molecular Biology 215 (1990), pages 403-410) are:

Expect Threshold: 10
Word size: 3
Matrix: BLOSUM62
Gap costs: Existence: 11; Extension: 1
Compositional adjustments: Conditional compositional score matrix adjustment The above parameters are the default parameters when comparing amino acid sequences.

The GAP program is likewise suitable for use with the above parameters.

An identity of 80% according to the above algorithm means 80% identity in connection with the present invention. The same applies to higher identities.

The feature "sequence which hybridizes or which, taking into consideration the degeneracy of the genetic code, would hybridize to the counterstrand of a sequence" indicates a sequence which hybridizes or which, taking into consideration the degeneracy of the genetic code, would hybridize with the counterstrand of a reference sequence under preferably stringent conditions. For example, the hybridizations may be carried out at 68° C. in 2×SSC or according to the protocol of the digoxigenin labeling kit from Boehringer (Mannheim). Preferred hybridization conditions are, for example, incubation at 65° C. overnight in 76 SDS, 1% BSA, 1 mM EDTA, 250 mM sodium phosphate buffer (pH 7.2), followed by washing at 65° C. with 2×SSC; 0.1% SDS.

The derivatives of the isolated DNA according to the invention which, according to alternative F1a), F1b), F1b), F1c), F2), F3), F4) or F5), can be obtained by substitution, addition, inversion and/or deletion of one or more bases of a sequence according to any of groups A1a) to E1a), A1b) to E1b), A1c) to E1c), A2) to E2), A3) to E3), A4) to E4) and A5) to E5), include in particular the sequences which, in the protein which they encode, result in conservative amino acid substitutions such as, for example, the substitution of glycine for alanine or of aspartic acid for glutamic acid. Such function-neutral mutations are referred to as sense mutations and do not lead to any major modification of the activity of the polypeptide. Furthermore, it is known that modifications of the N- and/or C-terminal end of a polypeptide do not have a profound adverse effect on its function and indeed are even capable of stabilizing it, so that, accordingly, DNA sequences in which bases are added at the 3'-end or at the 5'-end of the sequence with the nucleic acids according to the invention are comprised by the present invention, too. Information in this context can be found by a person skilled in the art in, inter alia, Ben-Bassat et al. (Journal of Bacteriology 169:751-757 (1987)), in O'Regan et al. (Gene 77:237-251 (1989)), in Sahin-Toth et al. (Protein Sciences 3:240-247 (1994)), in Hochuli et al. (Bio/Technology 6:1321-1325 (1988)) and in known textbooks of genetics and molecular biology.

A contribution to solving the problems specified at the outset is furthermore provided by a vector, preferably an expression vector, a gene deletion cassette, gene insertion cassette or gene overexpression cassette, comprising a DNA with a sequence according to any of groups A1a) to G1a), A1b) to G1b), A1c) to G1c), A2) to G2), A3) to G3), A4) to G4) and A5) to G5), as defined hereinabove. Suitable vectors are all the vectors which are known to a person skilled in the art and which are conventionally employed for introducing DNA into a host cell. These vectors are not only capable of autonomous replication since they have origins of replication such as for example those of the 2μ plasmid or of the ARS (autonomously replicating sequences) but are also capable of integration into the chromosomes (nonreplicating plasmids). Vectors are also understood as meaning linear DNA fragments which have no origins of replication whatsoever, such as, for example, gene deletion cassettes, gene insertion cassettes or gene overexpression cassettes. Gene deletion cassettes are usually composed of a selection marker and DNA fragments which flank the region to be deleted. Gene insertion cassettes are usually composed of a marker and fragments of the gene to be inactivated. Gene overexpression cassettes are usually composed of a marker, the gene to be overexpressed and regulatory regions which are relevant for the expression of the gene, such as, for example, promoter and terminator. Preferred vectors are selected from the group comprising plasmids and cassettes, such as, for example *E. coli* yeast shuttle plasmids; especially preferred are expression vectors, gene deletion cassettes, gene insertion cassettes or gene overexpression cassettes, in particular the gene deletion cassettes described hereinbelow with SEQ ID NO:12, SEQ ID NO:13, SEQ ID NO:14, SEQ ID NO:15 and SEQ ID NO:16 and the expression cassettes with SEQ ID NO:70, SEQ ID NO:71, SEQ ID NO:72, SEQ ID NO:73 and SEQ ID NO:74. According to a preferred embodiment of the vector according to the invention, the DNA with a sequence according to any of groups A1) to F5) is under the control of a constitutive promoter or a promoter capable of being regulated, which promoter is suitable for expressing the polypeptide encoded by these DNA sequences in the cell of a microorganism, preferably a bacterial cell, a yeast cell or a fungal cell, especially preferably a yeast cell, most preferably a *Candida bombicola, Candida bogoriensis, Candida batistae, Candida apicola* or *Wickerhamiella domericqiae* cell. Examples of such constitutive promoters are for example the TSC3 promoter, the ENO1 promoter, the FBA1 promoter, the GPD promoter, the GPM promoter, the FBA1 promoter, the ICL1 promoter or the ACT1 promoter. Examples of such promoters which are capable of being regulated are for example the GAL1 promoter, the GAL2 promoter, the GAL7 promoter, the MEL1 promoter, the GAL10 promoter, the SBG1 promoter, the SBG2 promoter, the SBG3 promoter, the SBG4 promoter, the SBG5 promoter or the MAL2 promoter.

Besides a promoter, the vector according to the invention should preferably comprise a ribosome binding site and a terminator. In this context, it is especially preferred that the DNA according to the invention is incorporated into an expression cassette of the vector comprising the promoter, the ribosome binding site and the terminator. Besides the above-mentioned structural elements, the vector may furthermore comprise selection marker genes which are known to a person skilled in the art.

The nucleic acids SEQ ID NO:12, SEQ ID NO:13, SEQ ID NO:14, SEQ ID NO:15, SEQ ID NO:16, IntEx-CbSBG1 (SEQ ID NO:70), IntEx-CbSBG2 (SEQ ID NO:71), IntEx-CbSBG3 (SEQ ID NO:72), IntEx-CbSBG4 (SEQ ID NO:73) and IntEx-CbSBG5 (SEQ ID NO:74) described in the examples are vectors which are preferred in accordance with the invention.

A further contribution to the solution of the problem is provided by the novel enzymes $E_1$ to $E_5$.

Thus, a further subject matter of the invention is an isolated polypeptide selected from the group consisting of an enzyme $E_1$ with the polypeptide sequence SEQ ID NO:7, SEQ ID NO:53, SEQ ID NO:55, SEQ ID NO:57, SEQ ID NO:59, SEQ ID NO:61 or SEQ ID NO:63, especially SEQ ID NO:7, or with a polypeptide sequence where up to 25%, preferably up to 20%, especially preferably up to 15%, in particular up to 10, 9, 8, 7, 6, 5, 4, 3, 2, 1% of the amino acid residues are modified over the respective reference sequence SEQ ID NO:7, SEQ ID NO:53, SEQ ID NO:55, SEQ ID NO:57, SEQ ID NO:59, SEQ ID NO:61 or SEQ ID NO:63, especially SEQ ID NO:7, by deletion, insertion, substitution or a combination of these and which retains at least 50%, preferably 65%, especially preferably 80%, in particular more than 90% of the enzymatic activity of the enzyme with the respective reference sequence, where enzymatic activity for an enzyme $E_1$ is understood as meaning the ability to convert Z-9-octadecenoic acid into 17-hydroxy-Z-9-octadecenoic acid, an enzyme $E_2$ with the polypeptide sequence SEQ ID NO:8 or SEQ ID NO:11 or with a polypeptide sequence where up to 60%, preferably up to 25%, especially preferably up to 15%, in particular up to 10, 9, 8, 7, 6, 5, 4, 3, 2, 1% of the amino acid residues are modified over SEQ ID NO:8 or SEQ ID NO:11 by deletion, insertion, substitution or a combination of these and which retains at least 50%, preferably 65%, especially preferably 80%, in particular more than 90% of the enzymatic activity of the enzyme with the respective reference sequence No. 8 or 11, where enzymatic activity for an enzyme $E_2$ is understood as meaning the ability to convert UDP-glucose and 17-hydroxy-Z-9-octadecenoic acid into 17-(β-D-glucopyranosyloxy)-Z-9-octadecenoic acid, an enzyme $E_3$ with the polypeptide sequence SEQ ID NO:11 or with a polypeptide sequence where up to 60%, preferably up to 25%, especially preferably up to 15%, in particular up to 10, 9, 8, 7, 6, 5, 4, 3, 2, 1% of the amino acid residues are modified over SEQ ID NO:11 by deletion, insertion, substitution or a combination of these and which retains at least 50%, preferably 65%, especially preferably 80%, in particular more than 90% of the enzymatic activity of the enzyme with the respective reference sequence No. 11, where enzymatic activity for an enzyme $E_3$ is understood as meaning the ability to convert 17-(β-D-glucopyranosyloxy)-Z-9-octadecenoic acid and UDP-glucose into 17-L-[(2'-O-β-D-glucopyranosyl-β-D-glucopyranosyl)oxy]-Z-9-octadecenoic acid, an enzyme $E_4$ with the polypeptide sequence SEQ ID NO:9 or with a polypeptide sequence where up to 50%, preferably up to 25%, especially preferably up to 15%, in particular up to 10, 9, 8, 7, 6, 5, 4, 3, 2, 1% of the amino acid residues are modified over SEQ ID NO:9 by deletion, insertion, substitution or a combination of these and which retains at least 50%, preferably 65%, especially preferably 80%, in particular more than 90% of the enzymatic activity of the enzyme with SEQ ID NO:9, where enzymatic activity for an enzyme $E_4$ is understood as meaning the ability to convert 17-L-[(2'-O-β-D-glucopyranosyl-β-D-glucopyranosyl)oxy]-Z-9-octadecenoic acid 1',4"-lactone and acetyl-coenzyme A into 17-L-[(2'-O-β-D-glucopyranosyl-β-D-glucopyranosyl)oxy]-Z-9-octadecenoic acid 1',4"-lactone monoacetate or 17-L-[(2'-O-β-D-glucopyranosyl-β-D-glucopyranosyl)oxy]-Z-9-octadecenoic acid 1',4"-lactone monoacetate and acetyl-coenzyme A into 17-L-[(2'-O-β-D-glucopyranosyl-β-D-glucopyranosyl)oxy]-Z-9-octadecenoic acid 1',4"-lactone diacetate or 17-L-[(2'-O-β-D-glucopyranosyl-β-D-glucopyranosyl)oxy]-Z-9-octadecenoic acid 1',4"-lactone and acetyl-coenzyme A into 17-L-[(2'-O-β-D-glucopyranosyl-β-D-glucopyranosyl)oxy]-Z-9-octadecenoic acid 1',4"-lactone diacetate, with the first option being preferred, and an enzyme $E_5$ with the polypeptide sequence SEQ ID NO:10 or with a polypeptide sequence where up to 45%, preferably up to 25%, especially preferably up to 15% and in particular up to 10, 9, 8, 7, 6, 5, 4, 3, 2, 1% of the amino acid residues are modified over SEQ ID NO:10 by deletion, insertion, substitution or a combination of these and which retains at least 50%, preferably 65%, especially preferably 80%, in particular more than 90% of the enzymatic activity of the enzyme with SEQ ID NO:10, where enzymatic activity for an enzyme $E_5$ is understood as meaning the ability to transfer a sophorolipid out of a cell into the surrounding medium.

In the examples given hereinbelow, the present invention is described by way of example without it being intended to limit the invention, whose scope is clear from all of the description and the claims, to the embodiments mentioned in the examples.

Figure 2:
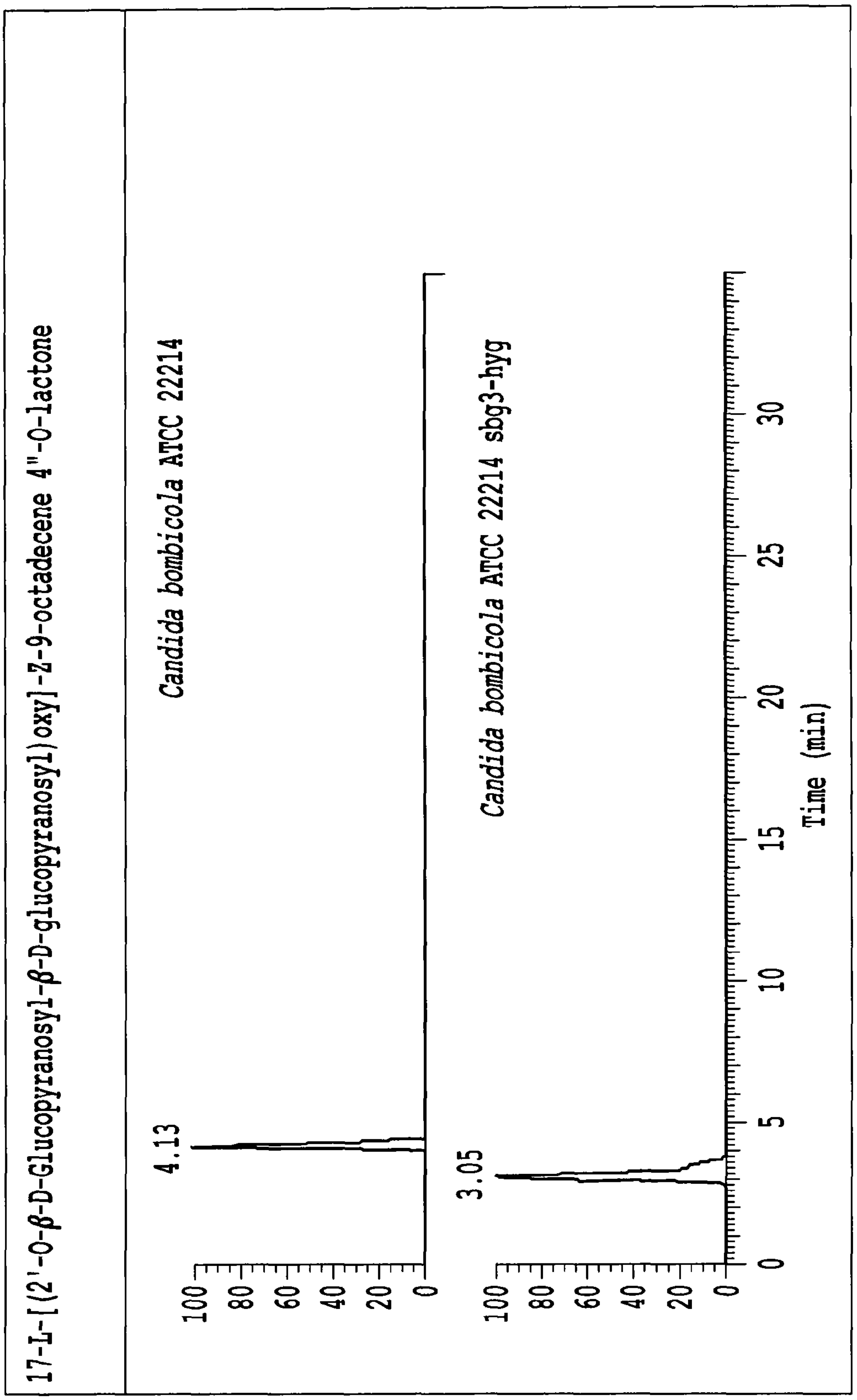

The following figures are part of the examples:

FIG. 1: Accurate mass trajectory for 17-L-[(6'-O-acetyl-2'-O-β-D-glucopyranosyl-6"-O-acetyl-β-D-glucopyranosyl)oxy]-Z-9-octadecene 4"-O-lactone FIG. 2: Accurate mass trajectory for 17-L-[(2'-O-β-D-glucopyranosyl-β-D-glucopyranosyl)oxy]-Z-9-octadecene 4"-O-lactone

EXAMPLES

Example 1

Generation of Uracil-Auxotrophic Mutants of *Candida bombicola* ATCC 22214

A uracil-auxotrophic mutant of *Candida bombicola* ATCC 22214 was generated as described hereinabove (van Bogaert et al. Yeast. 2007. 24(3):201-8). This strain was named *C. bombicola* ATCC 22214 ura⁻.

Example 2

Inactivation of the Structural Genes of the Enzymes Involved in Sophorolipid Biosynthesis in *Candida bombicola* ATCC 22214

In order to be able to identify enzymes involved in sophorolipid biosynthesis, the genome of *Candida bombicola* ATCC 22214 was first sequenced by means of GLS Flex Titanium technology. Upon inspection of the genetic information of *Candida bombicola* ATCC 22214, a cluster of five genes (SEQ ID NO:01) was identified whose coding regions (SEQ ID NO:02, SEQ ID NO:03, SEQ ID NO:04, SEQ ID NO:05, SEQ ID NO:06) encode gene products (SEQ ID NO:07, SEQ ID NO:08, SEQ ID NO:09, SEQ ID NO:10, SEQ ID NO:11).

The five genes were named SBG1 (SEQ ID NO:02), SBG2 SEQ ID NO:03), SBG3 (SEQ ID NO:04), SBG4 (SEQ ID NO:05) and SBG5 (SEQ ID NO:06) (SBG stands for Sophorolipid Biosynthesis Gene).

They encode the following proteins: Sbg1p (SEQ ID NO:07), Sbg2p (SEQ ID NO:08), Sbg3p (SEQ ID NO:09), Sbg4p SEQ ID NO:10) and Sbg1p (SEQ ID NO:11).

TABLE 1

Sbg1p, Sbg2p, Sbg3p, Sbg4p and Sbg5p and their functions in the biosynthesis and the export of sophorolipids.

| SEQ ID NO:. | Protein | PFAM domain | NCBI conserved domain | Function |
|---|---|---|---|---|
| 07 | Sbg1p | P450 (PFAM PF00067) | cytochrome P450 | monooxygenase which hydroxylates fatty acids [ω, ω-1, ω-2, ω-3] |
| 08 | Sbg2p | UDP glycosyltransferase (PFAM PF00201) | glycosyltransferase | UDP-glucose: [ω, ω-1, ω-2, ω-3]-hydroxy fatty acid glucosyltransferase |
| 09 | Sbg3p | none | Maltose O-acetyltransferase (PRK10092) | acetyl-CoA: sophorolipid acetyltransferase |
| 10 | Sbg4p | ABC transporter (PFAM 00667) | ABC transporter | Sophorolipid export protein |
| 11 | Sbg5p | UDP glycosyltransferase (PFAM PF00201) | glycosyltransferase | UDP-glucose: [ω, ω-1, ω-2, ω-3]-hydroxy fatty acid glucosyltransferase; UDP-glucose: [ω, ω-1, ω-2, ω-3]-(β-D-glucopyranosyl)oxy fatty acid glucosyltransferase |

The genes SBG1, SBG2, SBG3, SBG4 and SBG5 are inactivated individually, and the phenotype of the corresponding mutants is characterized in respect of the sophorolipid biosynthesis. To construct the corresponding mutants in *C. bombicola* ATCC 22214, deletion cassettes are first synthesized by GeneArt AG (Regensburg). These deletion cassettes (SEQ ID NO:12, SEQ ID NO:13, SEQ ID NO:14, SEQ ID NO:15, SEQ ID NO:16) are composed of the above-described gene CbURA3 (van Bogaert et al. Yeast. 2007. 24(3):201-8) which encodes the *C. bombicola* ATCC 22214 orotidin-5-phosphate decarboxylase and which is flanked upstream and downstream by in each case approximately 1000 bp of the regions flanking the genes to be inactivated. loxP-loci, which optionally permit the deletion of the CbURA3 gene by temporarily introducing the Cre-recombinase-coding gene and permit its functional expression, are inserted in each case between the flanking regions and the CbURA3 gene (for an overview see Kühn & Torres. Methods Mol Biol. 2002. 180:175-204). In this context, the individual deletion cassettes are constructed as shown in Table 2:

TABLE 2

Structure of the deletion cassettes for the Sbg1p, Sbg2p, Sbg3p, Sbg4p and Sbg5p encoding structural genes of *C. bombicola* ATCC 22214.

| SEQ ID NO: | Gene | 5'-flanking region | loxP-locus 1 | CbURA3 | loxP-locus 2 | 3'-flanking region |
|---|---|---|---|---|---|---|
| 12 | SBG1 | 1-1003 | 1004-1037 | 1038-3106 | 3107-3140 | 3141-4143 |
| 13 | SBG2 | 1-0999 | 1000-1033 | 1034-3102 | 3103-3136 | 3137-4143 |
| 14 | SBG3 | 1-1002 | 1003-1036 | 1037-3105 | 3106-3139 | 3140-4140 |
| 15 | SBG4 | 1-0997 | 0998-1031 | 1032-3100 | 3101-3134 | 3135-4130 |
| 16 | SBG5 | 1-1002 | 1003-1036 | 1037-3105 | 3106-3139 | 3140-4141 |

To provide the deletion cassettes for the subsequent transformation of *C. bombicola* ATCC 22214 ura⁻ in a sufficient amount, the former are amplified by PCR. The following oligonucleotides are used:

Amplification of the deletion cassettes for the inactivation of CbSBG1:

```
SBG1-fw:
                                              (SEQ ID NO: 17)
5'-AAT TGT TCG ATG GAT AGC TTT GGA GTC -3'

SBG1-rv:
                                              (SEQ ID NO: 18)
5'-TTC GGG GCT CCT GTC GTT GTC -3'
```

Amplification of the deletion cassettes for the inactivation of CbSBG2:

```
SBG2-fw:
                                              (SEQ ID NO: 19)
5'- GAA ATC TGA TCA ATT CTG CAA ACC TG -3'

SBG2-rv:
                                              (SEQ ID NO: 20)
5'- ATG ACT CCT AGA AAA GAA ATT GAC CAG -3'
```

Amplification of the deletion cassettes for the inactivation of CbSBG3:

```
SBG3-fw:
                                              (SEQ ID NO: 21)
5'- TGC AGA CAA GTT CCT GCA GCT G -3'

SBG3-rv:
                                              (SEQ ID NO: 22)
5'- ATG CTT TAT TCA GGC ACG CTA CG -3'
```

Amplification of the deletion cassettes for the inactivation of CbSBG4:

```
SBG4-fw:
                                              (SEQ ID NO: 23)
5'- GGA TGA GTC GCA GTC ACG AAC -3'

SBG4-rv:
                                              (SEQ ID NO: 24)
5'- TCA ATC ATT GGC TCA AGA CTA GGA AC -3'
```

Amplification of the deletion cassettes for the inactivation of CbSBG5:

```
SBG5-fw:
                                              (SEQ ID NO: 25)
5'- ATT CTG GTG CTG ACC TCG CCA C -3'

SBG5-rv:
                                              (SEQ ID NO: 26)
5'- ACT CAT GTC GTA CTT GCA AGA ACT G -3'
```

The following parameters are employed for the PCR: 1×: initial denaturation, 98° C., 3 min; 25×: denaturation, 98° C., 0:10 min, annealing, 60° C., 0:30 min; elongation, 72° C., 2:00 min; 1×: terminal elongation, 72° C., 10 min. The Phusion™ High-Fidelity Master Mix from New England Biolabs (Frankfurt) is employed for the amplification, following the manufacturer's recommendations. The PCR products are purified using the QIAquick PCR purification kit (Qiagen, Hilden) following the manufacturer's instructions. The procedure of the PCR, the verifying of the successful amplification of the PCR by means of agarose gel electrophoresis, staining the DNA with ethidium bromide, determining the PCR fragment sizes, purification of the PCR products and determining the DNA concentration are all performed in a manner with which the skilled worker is familiar.

The transformation of *C. bombicola* ATCC 22214 ura⁻ is performed as previously described (van Bogaert et al. Yeast. 2008. 25:273-278); van Bogaert et al. FEMS Yeast Res. 2009. 9:610-617).

To verify the deletion of the genes SBG1, SBG2, SBG3, SBG4 and SBG5 in *C. bombicola* ATCC 22214 ura⁻ transformants following the transformation with the deletion cassettes for CbSBG1 (SEQ ID NO:12), CbSBG2 (SEQ ID NO:13), CbSBG3 (SEQ ID NO:14), CbSBG4 (SEQ ID NO:15) and CbSBG5 (SEQ ID NO:16), the respective loci of in each case 5 transformants and *C. bombicola* ATCC 22214 ura⁻ are amplified by means of colony PCR. The following oligonucleotides are employed for this:

Verification of the genomic deletion of CbSBG1:

```
SBG1-KO-fw:
                                              (SEQ ID NO: 27)
5'- GTG TCG ACT CGC CAA ATT CCA TCG GAG -3'

SEG1-KO-rv:
                                              (SEQ ID NO: 28)
5'- GGT TCA TAG CGA GTT TCT TTG CAT GTG

C -3'
```

Verification of the genomic deletion of CbSBG2:

```
SBG2-KO-fw:
                                              (SEQ ID NO: 29)
5'- CTC CTT TAT TAA CTC CGC AGC ATG ACT

G -3'

SBG2-KO-rv:
                                              (SEQ ID NO: 30)
5'- CTC CTC GAA GGA CCC TCA AAA CAA

AGG -3'
```

Verification of the genomic deletion of CbSBG3:

```
SBG3-KO-fw:
                                              (SEQ ID NO: 31)
5'- CAA ATT TAT CTG GGA GCA CAG TTA CAT

TGC -3'

SBG3-KO-rv:
                                              (SEQ ID NO: 32)
5'- CAC ACA TTG CTT TAG TCC AGC AAG AAC

C -3'
```

Verification of the genomic deletion of CbSBG4:

```
SBG4-KO-fw:
                                              (SEQ ID NO: 33)
5'- ATT CTC CTC GCA CGT TTC TCG GGG C -3'

SBG4-KO-rv:
                                              (SEQ ID NO: 34)
5'- GGT TGA AAT ACT TGT TGC CGC ACT AAA

G -3'
```

Verification of the genomic deletion of CbSBG5:

```
SBG5-KO-fw:
                                   (SEQ ID NO: 35)
5'- CGC TTC CTG AAT TGA GTT GGT ATC GTT AAT

G -3'

SBG5-KO-rv:
                                   (SEQ ID NO: 36)
5'- GAC ATT GTT GGA ATT GGC TGC TTA GTG

G -3'
```

The following parameters are employed in the PCR: 1×: initial denaturation, 94° C., 3 min; 25×: denaturation, 94° C., 1:00 min, annealing, 60° C., 1:00 min; elongation, 72° C., 5:00 min; 1×: terminal elongation, 72° C., 10 min. The Taq PCR Master Mix Kit from Qiagen (Hilden) is employed for the amplification following the manufacturer's recommendations. In each case 10 μl of the PCR reactions are subsequently separated on a 0.8% agarose gel. The procedure of the PCR, of the agarose gel electrophoresis, staining the DNA with ethidium bromide and determining the PCR fragment sizes are all performed in a manner with which the skilled worker is familiar.

The amplification of the corresponding loci should give rise to the PCR fragment sizes specified in Table 3:

TABLE 3

Expected PCR fragment sizes for the amplification of the chromosomal SBG1, SBG2, SBG3, SBG4 and SBG5 loci upon successful deletion and in the wild-type situation.

| Gene | Size of the PCR product upon chromosomal deletion | Size of the PCR product in the wild-type situation |
|---|---|---|
| SBG1 | 4201 bp | 3678 bp |
| SBG2 | 4199 bp | 3451 bp |
| SBG3 | 4199 bp | 2839 bp |
| SBG4 | 4190 bp | 5950 bp |
| SBG5 | 4201 bp | 3360 bp |

Upon amplification of the CbSBG1, CbSBG2, CbSBG3, CbSBG4 and CbSBG5 loci from *C. bombicola* ATCC 22214 ura$^-$, only the fragment sizes expected when a wild-type situation is present, i.e. 3.7 kbp, 3.5 kbp, 2.8 kbp, 5.9 kbp and 3.4 kbp, respectively, are obtained.

Upon amplification of the SBG1 locus from transformants following transformation of the deletion cassettes for CbSBG1, only the fragment size to be expected after successful chromosomal deletion of CbSBG1, i.e. approximately 4.2 kbp, is obtained.

Upon amplification of the SBG2 locus from transformants following transformation of the deletion cassettes for CbSBG2, only the fragment size to be expected after successful chromosomal deletion of CbSBG2, i.e. approximately 4.2 kbp, is obtained.

Upon amplification of the SBG3 locus from transformants following transformation of the deletion cassettes for CbSBG3, only the fragment size to be expected after successful chromosomal deletion of CbSBG3, i.e. approximately 4.2 kbp, is obtained.

Upon amplification of the SBG4 locus from transformants following transformation of the deletion cassettes for CbSBG4, only the fragment size to be expected after successful chromosomal deletion of CbSBG4, i.e. approximately 4.2 kbp, is obtained.

Upon amplification of the SBG5 locus from transformants following transformation of the deletion cassettes for CbSBG5, only the fragment size to be expected after successful chromosomal deletion of CbSBG5, i.e. approximately 4.2 kbp, is obtained.

Thus, it is possible to identify in all five cases clones in which the genes CbSBG1, CbSBG2, CbSBG3, CbSBG4 or CbSBG5 have undergone chromosomal deletion. The corresponding strains are hereinbelow referred to as *C. bombicola* ATCC 22214 sbg1, *C. bombicola* ATCC 22214 sbg2, *C. bombicola* ATCC 22214 sbg3, *C. bombicola* ATCC 22214 sbg4 and *C. bombicola* ATCC 22214 sbg5, respectively.

Example 3

Characterization of the sophorolipid formation by *C. bombicola* ATCC 22214, *C. bombicola* ATCC 22214 sbg1, *C. bombicola* ATCC 22214 sbg2, *C. bombicola* ATCC 22214 sbg3, *C. bombicola* ATCC 22214 sbg4 and *C. bombicola* ATCC 22214 sbg5.

The propagation of strains *C. bombicola* ATCC 22214, *C. bombicola* ATCC 22214 sbg1, *C. bombicola* ATCC 22214 sbg2, *C. bombicola* ATCC 22214 sbg3, *C. bombicola* ATCC 22214 sbg4 and *C. bombicola* ATCC 22214 sbg5 is done on YPD agar plates.

The medium referred to hereinbelow as SL production medium is used for the production of the sophorolipids. It is composed of 0.1% $KH_2PO_4$, 0.5% $MgSO_4 \times 7\ H_2O$, 0.01% $FeCl_3$, 0.01% NaCl, 0.01% uracil, 0.4% yeast extract, 0.1% urea, 10.5% rapeseed oil and 10% glucose. The pH is brought to 4.5 and the medium is then sterilized in an autoclave (121° C., 20 min). It is not necessary to adjust the pH during the cultivation.

To study the sophorolipid production in the shake flask, a preculture is first established. To this end, 10 ml of YPD medium in a 100 ml Erlenmeyer flask are inoculated with one loop of a strain freshly plated onto a YPD agar plate. Cultivation was done overnight at 30° C. and 200 rpm. This preculture is used hereinbelow for inoculating 100 ml of SL medium in a 1000 ml Erlenmeyer flask (starting $OD_{600}$ 0.2). The cultures are grown for 7 days at 200 rpm and 30° C., and a sample of 2 ml of broth is taken every day, good care being taken that the culture medium was mixed thoroughly before sampling.

The samples are prepared for the subsequent chromatographic analyses as follows: using a positive-displacement pipette (Combitip), 800 μl of acetone are placed into a 2-ml reaction vessel and the reaction vessel is sealed immediately to minimize evaporation. 200 μl of broth are added. After vortexing the broth/acetone mixture, the latter is centrifuged for 1 min at 13 000 rpm, and 800 μl of the supernatant are transferred into an HPLC vessel. An evaporative light scattering detector (ELSD) is used for the detection and quantitative determination of sophorolipids and/or oleic acid. The actual measurement is performed by means of the Agilent Technologies 1200 series (Santa Clara, Calif.) and the Zorbax SB-C8 Rapid Resolution column (4.6×150 mm, 3.5 μm, Agilent). The injection volume is 5 μl, and the running time of the method is 20 min. The mobile phase used is $H_2O$ and 0.1% of TFA (trifluoroacetic acid, solution A) and methanol (solution B). The column temperature is 40° C. The detectors used were the ELSD (detector temperature 60° C.) and the DAD (diode array, 210 nm). The gradient used in the method is shown in Table 4.

TABLE 4

| Description of the gradient profile of the mobile phase to be used for the HPLC-based quantitative determination of sophorolipids. | | |
|---|---|---|
| t [min] | Solution B % | Flow rate [ml/min] |
| 0.00 | 70% | 1.00 |
| 15.00 | 100% | 1.00 |
| 15.01 | 70% | 1.00 |
| 20.00 | 70% | 1.00 |

While *C. bombicola* ATCC 22214 produced sophorolipids, no sophorolipid formation can be detected in the strains *C. bombicola* ATCC 22214 sbg1, *C. bombicola* ATCC 22214 sbg2 and *C. bombicola* ATCC 22214 sbg4. This demonstrates clearly that these genes are involved in sophorolipid formation, where they exert the functions specified above. While strains *C. bombicola* ATCC 22214 sbg3 and *C. bombicola* ATCC 22214 sbg5 are capable of forming sophorolipids, they have a modified retention time in the HPLC analysis.

It can be demonstrated by LC-$MS^2$ that, in contrast to the sophorolipids formed by *C. bombicola* ATCC 22214, the sophorolipids formed by *C. bombicola* ATCC 22214 sbg3 correspond exclusively to compounds of the general formulae (Ia) and (Ib) in which $R^1$=H and $R^2$=H.

This proves the function of Sbg3p as acetyltransferase ($E_4$) in sophorolipid biosynthesis.

Likewise, it can be demonstrated by LC-MS that, in contrast to the sophorolipids formed by *C. bombicola* ATCC 22214, the sophorolipids formed by *C. bombicola* ATCC 22214 sbg5 exclusively correspond to compounds of the general formula (Ia) in which n=0.

This demonstrates the function of Sbg5p as glycosyltransferase II ($E_3$) in sophorolipid biosynthesis.

Example 4

Construction of *Candida bombicola* ATCC 22214 Strains which Overproduce Enzymes Involved in Sophorolipid Biosynthesis To make possible the construction of *Candida bombicola* ATCC 22214 strains which overproduce the enzymes involved in sophorolipid biosynthesis, an integration/overexpression cassette is first synthesized by GeneArt AG (SEQ ID NO:75).

This integration/overexpression cassette comprises the components specified in Table 5:

TABLE 5

| Overview over the modules present in the integration/overexpression cassette to be developed for *Candida bombicola* ATCC 22214, and important restriction cleavage sites. | |
|---|---|
| Position (bp) | Component |
| 1-8 | NotI recognition site |
| 9-507 | DNA segment upstream of the *C. bombicola* ATCC 22214 LEU2 gene |
| 508-513 | PciI recognition site |
| 514-1217 | Promoter region of the *C. bombicola* ATCC 22214 URA3 gene |
| 1217-2005 | Coding region of the *C. bombicola* ATCC 22214 URA3 gene |
| 2006-2586 | Terminator region of the *C. bombicola* ATCC 22214 URA3 gene |
| 2587-2592 | PciI recognition site |
| 2593-2600 | AsiSI recognition site |
| 2601-3012 | Promoter region of the *C. bombicola* ATCC 22214 TSC3 gene |
| 3011-3016 | NdeI recognition site |
| 3025-3032 | FseI recognition site |
| 3033-3210 | Terminator region of the *C. bombicola* ATCC 22214 TSC3 gene |
| 3211-3218 | AsiSI recognition site |
| 3219-3224 | MluI recognition site |
| 3225-3724 | DNA segment downstream of the *C. bombicola* ATCC 22214 LEU2 gene |
| 3725-3732 | SbfI recognition site |

This integration/overexpression cassette makes possible the insertion of any desired structural genes from the start codon to the stop codon via NdeI and FseI between the promoter and the terminator region of the *C. bombicola* ATCC 22214 TSC3 gene, which encodes glyceraldehyde-3-phosphate dehydrogenase (van Bogaert et al.; 2008). Glyceraldehyde-3-phosphate dehydrogenase is a protein which is highly abundant in many yeasts, so that it can be assumed that a strong expression of the inserted gene can be achieved in this manner. The *C. bombicola* ATCC 22214 URA3 gene is selected as a selection marker so that this integration/overexpression cassette may only be used for the transformation of uracil-auxotrophic strains of *C. bombicola* ATCC 22214. Its generation, and the C. bombicola ATCC 22214 URA3 gene, have already been described (van Bogaert et al., 2007; van Bogaert et al., 2008). The 5'- and 3'-terminal DNA segments permit the cassette to be inserted at the *C. bombicola* ATCC 22214 LEU2 locus (SEQ ID NO:37), which inactivates the LEU2 gene. LEU2 encodes the only isopropylmalate dehydrogenase in *C. bombicola* ATCC 22214. Since isopropylmalate dehydrogenase is an essential component of leucine biosynthesis, transformants with a correct integration of the integration/overexpression cassette can be identified via their leucine auxotrophism. Various unique and redundant recognition sequences (NotI, PciI, AseSI, MluI, SbfI) permit the substitution of individual modules of the integration/overexpression cassette. The cassette is cloned by GeneArt AG into the proprietary vector pMA which comprises none of the above-described cleavage sites so that these cleavage sites may be used to their full extent.

To insert the genes CbSBG1, CbSBG3 and CbSBG5 into the integration/overexpression cassettes described, the genes are amplified by PCR from chromosomal DNA of *C. bombicola* ATCC 22214 and at the same time an NdeI cleavage site is introduced upstream of the start codon and an FseI cleavage site downstream of the stop codon via the oligonucleotides used. To insert the genes CbSBG2 and CbSBG4 into the integration/overexpression cassette described, the former are first synthesized de novo by GeneArt AG (Regensburg) in order to modify their sequence such that the internal FseI and NotI cleavage sites (CbSBG2) and NdeI cleavage sites (CbSBG4), respectively, are removed without modifying the amino acid sequence of the encoded protein. Thereafter, the modified genes CbSBG2mod and CbSBG4mod provided by GeneArt AG (Regensburg) are amplified by PCR, and an NdeI cleavage site upstream of the start codon and an FseI cleavage site downstream of the stop codon are introduced simultaneously via the oligonucleotides used. The following oligonucleotides are used:

```
CbSBG1:
SBG1-OE-fw:
                                        (SEQ ID NO: 38)
5'- ATA TAT ATA CAT ATG TTA ATC AAA GAC ATT

ATT CTA ACT CCA ATG-3'

SBG1-OE-rv:
                                        (SEQ ID NO: 39)
5'- ATA TAT GGC CGG CCA ACT TAA GAA AAC CGC

ACA ACC ACA CCG-3'

CbSBG2mod:
SBG2-OE-fw:
                                        (SEQ ID NO: 40)
5'- ATA TAT ATA CAT ATG AGC CCT TCA TCA CAC

AAA CCC CTG -3'

SBG2-OE-rv:
                                        (SEQ ID NO: 41)
5'- ATA TAT GGC CGG CCA TTC TAA GAA CTC ACC

GCT AAG GCC -3'

CbSBG3:
SBG3-OE-fw:
                                        (SEQ ID NO: 42)
5'- ATA TAT ATA CAT ATG GTT GTA AAC TCC TCG

AAG GAC CC-3'

SBG3-OE-rv:
                                        (SEQ ID NO: 43)
5'- ATA TAT GGC CGG CCT ACC TAG ACC TTC TGG

TTA GCG GTA TTG -3'

CbSBG4mod:
SBG4-OE-fw:
                                        (SEQ ID NO: 44)
5'- ATA TAT ATA CAT ATG GTG GAT GAT ATA CAG

GTA GAG AAG C-3'

SBG4-OE-rv:
                                        (SEQ ID NO: 45)
5'- ATA TAT GGC CGG CCA CGT CAA ATC TCT CCG

AGA CCT TGC AAG -3'

CbSBG5:
SBG5-OE-fw:
                                        (SEQ ID NO: 46)
5'- ATA TAT ATA CAT ATG GCC ATC GAG AAA CCA

GTG ATA GTT G -3'

SBG5-OE-rv:
                                        (SEQ ID NO: 47)
5'- ATA TAT GGC CGG CCA GGT TAA GAA GCT AAT

TCA CTA ATT GCC GAC -3'
```

The following parameters are employed for the PCR: 1×: initial denaturation, 98° C., 3 min; 25×: denaturation, 98° C., 0:10 min, annealing, 60° C., 0:30 min; elongation, 72° C., 2:00 min; 1×: terminal elongation, 72° C., 10 min. The Phusion™ High-Fidelity Master Mix by New England Biolabs (Frankfurt) is employed for the amplification, following the manufacturer's recommendations. In each case 10 μl of the PCR reactions are subsequently separated on a 0.8% agarose gel. The procedure of the PCR, of the agarose gel electrophoresis, staining the DNA with ethidium bromide and determining the PCR fragment sizes are performed in a manner known to a person skilled in the art.

In all cases it is possible to amplify PCR fragments of the expected size. These sizes are: for CbSBG1 1646 bp; for CbSBG2 1421 bp; for CbSBG3 809 bp; for CbSBG4 3929 bp and for CbSBG5 1328 bp. The PCR products are digested with NdeI and FseI following the recommendations of the manufacturer of the restriction endonucleases (New England Biolabs; Frankfurt/Main) and ligated into the NdeI- and FseI-cut vector pMA-ExCat (SEQ ID NO:64). Ligation and the transformation of chemically competent *E. coli* DH5α cells (New England Biolabs; Frankfurt/Main) are performed in a manner known to the skilled worker. The correct insertion of the CbSBG1, CbSBG2, CbSBG3, CbSBG4 and CbSBG5 fragments into pMA-ExCat is verified and confirmed by a restriction with NdeI and FseI. The resulting vectors are named pMA_ExCat-CbSBG1 (SEQ ID NO:65), pMA_ExCat-CbSBG2 (SEQ ID NO:66), pMA_ExCat-CbSBG3 (SEQ ID NO:67), pMA_ExCat-CbSBG4 (SEQ ID NO:68) and pMA_ExCat-CbSBG5 (SEQ ID NO:69).

To provide the individual integration/overexpression cassettes and the control cassette ExCat for the subsequent transformation of *C. bombicola* ATCC 22214 $ura^-$ in a sufficient amount, the former are amplified by PCR. The following oligonucleotides are applied:

```
OEx-LEU2-fw:
                                        (SEQ ID NO: 48)
5'- GGA CCT GCG CCC TAA AAT GGG AC -3'

OEx-LEU2-rv:
                                        (SEQ ID NO: 49)
5'- ATC CTA GAA AAC AGC TGG ATA TGG ATA

AAC -3'
```

The PCR products are purified by means of the QIAquick PCR Purification Kit (Qiagen, Hilden) following the manufacturer's information. In the procedure of the PCR, the verification of the successful amplification of the PCR by means of agarose gel electrophoresis, staining the DNA with ethidium bromide, determining the PCR fragment sizes, purification of the PCR products and determination of the DNA concentration are performed in a manner known to the skilled worker.

The resulting integration/overexpression cassettes are given the names IntEx-CbSBG1 (SEQ ID NO:70), IntEx-CbSBG2 (SEQ ID NO:71), IntEx-CbSBG3 (SEQ ID NO:72), IntEx-CbSBG4 (SEQ ID NO:73) and IntEx-CbSBG5 (SEQ ID NO:74).

The control cassette ExCat (SEQ ID NO:75) is also obtained.

*C. bombicola* ATCC 22214 $ura^-$ is transformed as previously described (van Bogaert et al. Yeast. 2008. 25:273-278); van Bogaert et al. FEMS Yeast Res. 2009. 9:610-617).

To verify the insertion of the integration/overexpression cassettes for the overexpression CbSBG1, CbSBG2, CbSBG3, CbSBG4 and CbSBG5 and of the control cassette ExCat into the LEU2 locus of *C. bombicola* ATCC 22214 $ura^-$, the LEU2 locus of in each case 5 transformants (after transformation of the integration/overexpression cassettes for CbSBG1, CbSBG2, CbSBG3, CbSBG4 and CbSBG5 and of the control cassette ExCat) and of *C. bombicola* ATCC 22214 $ura^-$ is amplified by colony PCR. The following oligonucleotides are employed:

```
LEU2-KI-fw:
                                        (SEQ ID NO: 50)
5'- GTG CCC GAC CAC CAT GAG CTG TC -3'

LEU2-KI-rv:
                                        (SEQ ID NO: 51)
5'- CCC AAG CAT GAG GGT CGT GCC GG -3'
```

The following parameters are employed in the PCR: 1×: initial denaturation, 94° C., 3 min; 25×: denaturation, 94° C., 1:00 min, annealing, 60° C., 1:00 min; elongation, 72° C., 5:00 min; 1×: terminal elongation, 72° C., 10 min. The Taq PCR Master Mix Kit from Qiagen (Hilden) is employed for the amplification following the manufacturer's recommendations. In each case 10 μl of the PCR reactions are subsequently separated on a 0.8% agarose gel. The procedure of the PCR, of the agarose gel electrophoresis, staining the DNA with ethidium bromide and determining the PCR fragment sizes are all performed in a manner with which the skilled worker is familiar.

The amplification of the corresponding loci should give rise to the PCR fragment sizes specified in Table 6:

TABLE 6

Expected PCR fragment sizes upon amplification of the chromosomal LEU2 locus following homologous recombination of the SBG1, SBG2, SBG3, SBG4 and SBG5 expression cassettes and the control cassette ExCat into the chromosomal *C. bombicola* LEU2 locus and upon nonhomologous integration.

| Gene | Size of the PCR product upon homologous integration into the CbLEU2 locus | Size of the PCR product upon nonhomologous integration at a different site of the genome |
|---|---|---|
| SBG1 | 5452 bp | 2235 bp |
| SBG2 | 5227 bp | 2235 bp |
| SBG3 | 4615 bp | 2235 bp |
| SBG4 | 7735 bp | 2235 bp |
| SBG5 | 5125 bp | 2235 bp |
| ExCat | 3844 bp | 2235 bp |

Upon amplification of the LEU2 locus from *C. bombicola* ATCC 22214 ura$^-$, only the fragment expected when the wild-type situation is present, which has a size of 2.2 kbp, is obtained.

Upon amplification of the LEU2 locus from *C. bombicola* ATCC 22214 transformants after transformation with integration/overexpression cassettes for the overexpression of CbSBG1, CbSBG2 mod, CbSBG3, CbSBG4 mod and CbSBG5, only the fragment sizes expected upon successful chromosomal integration of the integration/overexpression cassettes IntEx-CbSBG1 (SEQ ID NO:70), IntEx-CbSBG2 (SEQ ID NO:71), IntEx-CbSBG3 (SEQ ID NO:72), IntEx-CbSBG4 (SEQ ID NO:73) and IntEx-CbSBG5 (SEQ ID NO:74), which are approximately 5.5 kbp, 5.2 kbp, 4.6 kbp, 7.7 kbp and 5.1 kbp, respectively, are obtained.

Thus, it is possible to identify in all five cases clones in which it was possible to bring the genes CbSBG1, CbSBG2, CbSBG3, CbSBG4 or CbSBG5 under the control of the *C. bombicola* ATCC 22214 TSC3 promoter so that it is possible to postulate the overexpression.

The strains in question are hereinbelow referred to as *C. bombicola* ATCC 22214 $P_{TSC3}$-SBG1-$T_{TSC3}$, *C. bombicola* ATCC 22214 $P_{TSC3}$-SBG2-$T_{TSC3}$, *C. bombicola* ATCC 22214 $P_{TSC3}$-SBG3-$T_{TSC3}$, *C. bombicola ATCC* 22214 $P_{TSC3}$-SBG4-$T_{TSC3}$ and *C. bombicola* ATCC 22214 $P_{TSC3}$-SBG5-$T_{TSC3}$.

Example 5

Characterization of the Sophorolipid Formation by *C. bombicola* ATCC 22214 ExCat, *C. bombicola* ATCC 22214 $P_{TSC3}$-SBG1-$T_{TSC3}$/*C. bombicola* ATCC 22214 $P_{TSC3}$-SBG2-$T_{TSC3}$, *C. bombicola* ATCC 22214 $P_{TSC3}$-SEG3-$T_{TSC3}$, *C. bombicola* ATCC 22214 $P_{TSC3}$-SBG4-$T_{TSC3}$ and *C. bombicola* ATCC 22214 $P_{TSC3}$-SBG5-$T_{TSC3}$ The propagation of the strains *C. bombicola* ATCC 22214 ExCat, *C. bombicola* ATCC 22214 $P_{TSC3}$-SBG1-$T_{TSC3}$, *C. bombicola* ATCC22214 $P_{TSC3}$-SEG2-$T_{TSC3}$, *C. bombicola* ATCC 22214 $P_{TSC3}$-SBG3-$T_{TSC3}$, *C. bombicola* ATCC 22214 $P_{TSC3}$-SBG4-$T_{TSC3}$ and *C. bombicola* ATCC 22214 $P_{TSC3}$-SBG5-$T_{TSC3}$ is performed on YPD agar plates. The medium referred to hereinbelow as SL production medium is used for producing the sophorolipids. This medium is composed of 0.1% $KH_2PO_4$, 0.5% $MgSO_4 \times 7\ H_2O$, 0.01% $FeCl_3$, 0.01% NaCl, 0.01% uracil, 0.4% yeast extract, 0.1% urea, 10.5% rapeseed oil and 10% glucose. The pH is brought to 4.5 and the medium is then sterilized in an autoclave (121° C., 20 min). It is not necessary to adjust the pH during the cultivation.

To study the sophorolipid production in the shake flask, a preculture is first established. To this end, 10 ml of YPD medium in a 100 ml Erlenmeyer flask are inoculated with one loop of a strain freshly plated onto a YPD agar plate. Cultivation was done overnight at 30° C. and 200 rpm. This preculture is used hereinbelow for inoculating 100 ml of SL medium in a 1000 ml Erlenmeyer flask (starting $OD_{600}$ 0.2). The cultures are grown for 7 days at 200 rpm and 30° C., and a sample of 2 ml of broth is taken every day, good care being taken that the culture medium was mixed thoroughly before sampling.

The samples are prepared for the subsequent chromatographic analyses as follows: using a positive-displacement pipette (Combitip), 800 μl of acetone are placed into a 2-ml reaction vessel and the reaction vessel is sealed immediately to minimize evaporation. 200 μl of broth are added. After vortexing the broth/acetone mixture, the latter is centrifuged for 1 min at 13 000 rpm, and 800 μl of the supernatant are transferred into an HPLC vessel. An evaporative light scattering detector (ELSD) is used for the detection and quantitative determination of sophorolipids and/or oleic acid. The actual measurement is performed by means of the Agilent Technologies 1200 series (Santa Clara, Calif.) and the Zorbax SB-C8 Rapid Resolution column (4.6×150 mm, 3.5 μm, Agilent). The injection volume is 5 μl, and the running time of the method is 20 min. The mobile phase used is $H_2O$ and 0.1% of TFA (trifluoroacetic acid, solution A) and methanol (solution B). The column temperature is 40° C. The detectors used were the ELSD (detector temperature 60° C.) and the DAD (diode array, 210 nm). The gradient used in the method is shown in Table 3.

Like the control strain *C. bombicola* ATCC 22214 ExCat, all strains produce sophorolipids. However, the strains *C. bombicola* ATCC 22214 $P_{TSC3}$-SBG1-$T_{TSC3}$, *C. bombicola* ATCC 22214 $P_{TSC3}$-SBG2-$T_{TSC3}$, *C. bombicola* ATCC 22214 $P_{TSC3}$ SBG3-$T_{TsC3}$, *C. bombicola* ATCC 22214 $P_{TSC3}$-SBG4-$T_{TSC3}$ and *C. bombicola* ATCC 22214 $P_{TSC3}$-SBG5-$T_{TSC3}$ show an increased space-time yield of the sophorolipid formation in comparison with *C. bombicola* ATCC 22214 ExCat. While *C. bombicola* ATCC 22214 ExCat produces approximately 2 mg of sophorolipids per liter, hour and $OD_{600}$ under the conditions chosen, these parameters are between 2.5 mg and 6 mg for the strains *C. bombicola* ATCC 22214 $P_{TSC3}$-SBG1-$T_{TSC3}$, *C. bombicola* ATCC 22214 $P_{TSC3}$-SBG2-$T_{TSC3}$, *C. bombicola* ATCC 22214 $P_{TSC3}$-SBG3-$T_{TSC3}$, *C. bombicola* ATCC 22214 $P_{TSC3}$-SBG4-$T_{TSC3}$ and *C. bombicola* ATCC 22214 $P_{TSC3}$-SBG5-$T_{TSC3}$. Thus, it is possible to demonstrate that enhancing the enzymes CbSBG1, CbSBG2, CbSBG3, CbSBG4 and CbSBG5 in *C. bombicola* ATCC 22214 results in an increased sophorolipid formation.

Example 6

Vector pTZ_E02_His-GlcTrI for overexpressing the *Candida bombicola* gene SBG2 with N-terminal His-tag To overexpress the *Candida bombicola* ATCC22214 gene SBG2 SEQ ID NO:03) in *Escherichia coli*, the plasmid pTZ_E02_His-GlcTrI was constructed. Chromosomal DNA from *Candida bombicola* ATCC22214 was used as the template for a PCR with the "Expand™ High Fidelity" PCR kit from Roche Diagnostics (Mannheim), following the manufacturer's information. The SBG2 gene was amplified from the chromosomal DNA with the aid of oligonucleotides 1373_GlcTrI_BsmBI_His_fp (SEQ ID NO:76) and 1373_GlcTrI_AscI_rp (SEQ ID NO:77) ("PCR protocols. A guide to methods and applications", 1990, Academic Press) and in this manner provided at the 5' end with a 6-fold N-terminal histidine tag. In addition, the cleavage sites BsmBI and AscI were introduced. The following oligonucleotides were employed:

```
1373_GlcTrI_BsmBI_His_fp (SEQ ID NO: 76):
5'-AAACGTCTCAGATGCACCACCACCACCACCACATGGTTGTAAACTCC

TCG-3'

1373_GlcTrI_AscI_rp (SEQ ID NO: 77):
5'-AAAGGCGCGCCCTAGACCTTCTGGTTAGCG-3'
```

The PCR product (1435 bp) was purified by means of the QIAquick PCR purification kit (Qiagen, Hilden) following the manufacturer's instructions, cleaved with BsmBI and AscI and subsequently ligated into the expression vector pTZ_E02 (pET24d-based vector; Merck Chemicals, Darmstadt) from Trenzyme GmbH, Konstanz, which had been cleaved in the same manner. The resulting plasmid pTZ_E02_His-GlcTrI (SEQ ID NO:78) is 6700 base pairs in size. The ligation and the transformation of chemically competent *E. coli* DH5α cells (Gibco-BRL, Karlsruhe) were performed in the manner known to the skilled worker.

The authenticity of the insert was verified by a DNA sequence analysis.

The plasmid pTZ_E02_His-GlcTrI was introduced into the strains *Escherichia coli* BL21(DE3) and *Escherichia coli* Rosetta (DE3) (both from Merck Chemicals, Darmstadt) by means of transformation. The resulting strains were named *E. coli* BL21(DE3)/pTZ_E02_His-GlcTrI and *E. coli* Rosetta (DE3)/pTZ_E02_His-GlcTrI.

Example 7

Vector pTZ_E02_His-GlcTrII for overexpressing the *Candida bombicola* gene SBG5 with N-terminal His-tag To overexpress the *Candida bombicola* ATCC22214 gene SBG5 SEQ ID NO:06) in *Escherichia coli*, the plasmid pTZ_E02_His-GlcTrII was constructed. Chromosomal DNA from *Candida bombicola* ATCC22214 was used as the template for a PCR with the "Expand™ High Fidelity" PCR kit from Roche Diagnostics (Mannheim), following the manufacturer's information. The SBG5 gene was amplified from the chromosomal DNA with the aid of oligonucleotides 1373_GlcTrII_BsmBI_His_fp (SEQ ID NO:79) and 1373_GlcTrII_AscI_rp (SEQ ID NO:80) ("PCR protocols. A guide to methods and applications", 1990, Academic Press) and in this manner provided at the 5' end with a 6-fold N-terminal histidine tag. In addition, the cleavage sites BsmBI and AscI were introduced. The following oligonucleotides were employed:

```
1373_GlcTrII_BsmBI_His_fp (SEQ ID NO: 79):
5'-AAACGTCTCAGATGCACCACCACCACCACCACATGGCCATCGAGAAA

CCAG-3'

1373_GlcTrII_AscI_rp (SEQ ID NO: 80):
5'-AAAGGCGCGCCTTAAGAAGCTAATTCACTAATTGCC-3'
```

The PCR product (1342 bp) was purified by means of the QIAquick PCR purification kit (Qiagen, Hilden) following the manufacturer's instructions, cleaved with BsmBI and AscI and subsequently ligated into the expression vector pTZ_E02 (pET24d-based vector; Merck Chemicals, Darmstadt) from Trenzyme GmbH, Konstanz, which had been cleaved in the same manner. The resulting plasmid pTZ_E02_His-GlcTrII SEQ ID NO:81) is 6607 base pairs in size. The ligation and the transformation of chemically competent *E. coli* DH5α cells (Gibco-BRL, Karlsruhe) were performed in the manner known to the skilled worker.

The authenticity of the insert was verified by a DNA sequence analysis.

The plasmid pTZ_E02_His-GlcTrII was introduced into the strains *Escherichia coli* BL21(DE3) and *Escherichia coli* Rosetta (DE3) (both from Merck Chemicals, Darmstadt) by means of transformation. The resulting strains were named *E. coli* BL21(DE3)/pTZ_E02_His-GlcTrII and *E. coli* Rosetta (DE3)/pTZ_E02_His-GlcTrII.

Example 8

Vector pTZ_E02_His-AcTr for overexpressing the *Candida bombicola* gene SBG3 with N-terminal His-tag To overexpress the *Candida bombicola* ATCC22214 gene SBG3 (SEQ ID NO:04) in *Escherichia coli*, the plasmid pTZ_E02_His-AcTr was constructed. Chromosomal DNA from *Candida* bombicola ATCC22214 was used as the template for a PCR with the "Expand™ High Fidelity" PCR kit from Roche Diagnostics (Mannheim), following the manufacturer's information. The SBG3 gene was amplified from the chromosomal DNA with the aid of oligonucleotides 1373_AcTr_BsmBI_His_fp (SEQ ID NO:82) and 1373_AcTr_AscI_rp (SEQ ID NO:83) ("PCR protocols. A guide to methods and applications", 1990, Academic Press) and in this manner provided at the 5' end with a 6-fold N-terminal histidine tag. In addition, the cleavage sites BsmBI and AscI were introduced. The following oligonucleotides were employed:

```
1373_AcTr_BsmBI_His_fp (SEQ ID NO: 82):
5'-AAACGTCTCAGATGCACCACCACCACCACCACATGGTTGTAAACTCC

TCG-3'

1373_AcTr_AscI_rp (SEQ ID NO: 83):
5'-AAAGGCGCGCCCTAGACCTTCTGGTTAGCG-3'
```

The PCR product (823 bp) was purified by means of the QIAquick PCR purification kit (Qiagen, Hilden) following the manufacturer's instructions, cleaved with BsmBI and AscI and subsequently ligated into the expression vector pTZ_E02 (pET24d-based vector; Merck Chemicals, Darmstadt) from Trenzyme GmbH, Konstanz, which had been cleaved in the same manner. The resulting plasmid pTZ_E02_His-AcTr (SEQ ID NO:84) is 6088 base pairs in size. The ligation and the transformation of chemically competent *E. coli* DH5α cells (Gibco-BRL, Karlsruhe) were performed in the manner known to the skilled worker.

The authenticity of the insert was verified by a DNA sequence analysis.

The plasmid pTZ_E02_His-AcTr was introduced into the strains *Escherichia coli* BL21(DE3) and *Escherichia coli* Rosetta (DE3) (both from Merck Chemicals, Darmstadt) by means of transformation. The resulting strains were named *E. coli* BL21(DE3)/pTZ_E02_His-AcTr and *E. coli* Rosetta (DE3)/pTZ_E02_His-AcTr.

Example 9

Heterologous Expression of the Enzymes SBG2, SBG3 and SBG5 Involved in Sophorolipid Biosynthesis In each case one single colony of the *E. coli* strains constructed under item 1-3 was first grown for 8 hours in 5 ml of LB medium (10 g/l tryptone, 5 g/l yeast extract, 10 g/l NaCl) with 50 μg/ml kanamycin at 37° C. and 175 rpm. Thereafter, 100 ml of LB medium in 500 ml shake flasks were inoculated with the first preculture and grown overnight at 37° C. and 175 rpm. On the next morning, 1 l of LB medium with a starting $OD_{600}$ of 0.1 were inoculated with the second preculture (5-1 shake flask). All cultures were incubated at 37° C. and 175 rpm. The growth of the cultures was monitored with reference to the apparent optical density ($OD_{600}$). When an $OD_m$) of ~0.3 was reached, the culture temperature was reduced from 37° C. to 20° C. The expression of the target genes in question was induced at an $OD_{600}$ of 0.6 by adding 0.5 mM IPTG (final concentration). During all of the culture steps, the relevant antibiotics were added (kanamycin 50 μg/ml). Samples for analyses were taken both before the addition of IPTG and 24 h after the induction. The cells were disrupted by Bugbuster (Merck Chemicals, Darmstadt) following the manufacturer's instructions in order to separate soluble and insoluble proteins from each other. Comparable amounts of the cell extracts were separated by means of SDS-PAGE and the gels were subsequently stained with colloidal Coomassie. An overproduction in the soluble cell extract fraction was detected for all three recombinantly produced proteins Sbg2p, Sbg3p and Sbg5p with His tags.

Example 10

Purification of the Enzymes Sbg2p, Sbg3p and Sbg5p Involved in Sophorolipid Biosynthesis 24 h after induction of the gene expression the cells were harvested by centrifugation (8000 g, 20 min, 4° C.). 1 liter of culture resulted in ~5 g fresh biomass. The cell pellets were resuspended in 100 ml of buffer A (100 mM Tris, pH 7.8, 50 mM NaCl, 20 mM imidazole) which additionally comprised a protease inhibitor (Roche, Order No. 11 873 580 001). The resuspended cells were disrupted by six passages through a Microfluidizer. After a further centrifugation step (10 000 g, 20 min, 4° C.), the supernatant was filtered (pore diameter: 0.45 μm) to give the soluble protein fraction. The target proteins were purified via a his-tag affinity chromatography column (GE, HisTrap FF 1 ml columns, Order No. 17-5319-01). The flow rate was 1 ml/min. A linear elution from 0-100% with buffer B (100 mM Tris, pH 7.8, 50 mM NaCl, 500 mM imidazole) was performed. To this end, 20-fold column volume of buffer B was employed, and 2 ml fractions were collected. The eluate fractions with protein were pooled and concentrated by means of a filtration unit (Amicon Ultra-15, NMWL 10 kDa Centricons, Millipore, Order No. UFC901024). Thereafter, the respective protein fractions were subjected to a buffer exchange into the final buffer (100 mM Tris, pH 7.8, 50 mM NaCl) by gel filtration with Sephadex 25 (PD-10 columns, GE, Order No. 17-0851-01). The protein purification was verified by SDS-PAGE. 3.3 mg of Sbg2p (protein concentration 1.0 μg/μl), 7.3 mg of Sbg5p (protein concentration 2.2 μg/μl) and 6.9 mg of Sbg3p (protein concentration 2.1 μg/μl) were isolated from 1 l of culture.

Example 11

Characterization of the Enzymes Sbg2p, Sbg3p and Sbg5p Involved in Sophorolipid Biosynthesis To detect the function of the enzymes Sbg2p, Sbg3p and Sbg5p which are involved in sophorolipid biosynthesis, enzyme assays were performed with the three isolated enzymes Sbg2p, Sbg3p and Sbg5p, in each case individually and in all possible combinations. This was done in a total volume of 350 μl, following the scheme hereinbelow:

TABLE 7

| Composition of the enzyme assay mixtures in μl | | | | | | | | |
|---|---|---|---|---|---|---|---|---|
| | 1 | 2 | 3 | 4 | 5 | 6 | 7 | 8 |
| 10 mM Tris-HCl (pH 7.5) | 327.5 | 277.5 | 227.5 | 277.5 | 177.5 | 227.5 | 177.5 | 227.5 |
| 125 mM UDP-glucose | 5 | 5 | 5 | 5 | 5 | 5 | 5 | 5 |
| 100 mM Acetyl-CoA | 3.5 | 3.5 | 3.5 | 3.5 | 3.5 | 3.5 | 3.5 | 3.5 |
| Sbg3p (2.1 μg/μl) | — | 50 | — | — | 50 | 50 | — | 50 |
| Sbg2p (1 μg/μl) | — | — | 100 | — | 100 | — | 100 | 100 |
| Sbg5p (2.2 μg/μl) | — | — | — | 50 | | 50 | 50 | 50 |
| 13.4 mM 18-hydroxy-Z-9-octadecenoic acid | 14 | 14 | 14 | 14 | 14 | 14 | 14 | 14 |
| Σ | 350 | 350 | 350 | 350 | 350 | 350 | 350 | 350 |

The reaction was started by adding 14 μl of 13.4 mM solution of the substrate (18-hydroxy-Z-9-octadecenoic acid) in ethanol and incubated for 6 h at 30° C., with shaking (600 rpm). Thereafter, the reaction was stopped by adding 1.4 ml of acetone. Undissolved components were sedimented by centrifugation (16 100 g, 5 min, RT). The supernatant was subsequently transferred into a fresh container and concentrated by vacuum evaporator (25° C.) to the original reaction volume (350 μl). The samples were analyzed by LC-ESI-MS, and the products were identified by analyzing the corresponding mass trajectories and the MS spectra.

To identify the products formed, 5 μl were injected into a UPLC system Accela (Thermo Scientific, Dreieich). The substances to be studied were analyzed with a semi-UPLC column "Pursuit XRs ULTRA" (C8, 2.8 μm, 2.1×100 mm) (Varian, Darmstadt). The separation was performed within 25 min using a gradient composed of the mobile phase A1 ($H_2O$, 0.1% (v/v) TFA) and the mobile phase B1 (methanol, 0.1% (v/v) TFA) with a flow rate of 0.3 ml/min at 40° C. The course of the gradient over time is shown in Table 8.

TABLE 8

| Course of the HPLC gradient | | |
|---|---|---|
| Time [min] | Mobile phase A1 [%] | Mobile phase B1 [%] |
| 0 | 30 | 70 |
| 15 | 0 | 100 |
| 25 | 0 | 100 |
| 25.01 | 30 | 70 |
| 32 | 30 | 70 |

The detection was by DAD detector in the wavelength range of 200-600 nm and mass-selectively with a highly-resolving FT-ICR mass spectrometer LTQ-FT (Thermo Scientific, Dreieich) in the scanning range m/z 100-1000. Ionization was by ESI (electrospray ionization). The precise masses and the empirical chemical formulae were determined with the aid of the FT-ICR mass analyzer with a resolution of R=100 000 and a mass accuracy of ≤2 ppm.

The control reaction used was a mixture which only comprised the substrates UDP-glucose, acetyl-CoA and 18-hydroxy-Z-9-octadecenoic acid, but no enzymes (see Table 7). In this sample, only the substrate 18-hydroxy-Z-9-octadecenoic acid ($C_{18}H_{34}O_3$; 298.2502 g/mol) was detected by MS.

Mixture 2 (see Table 7) comprised, besides the substrates, 105 μg of Sbg3p. As in mixture 1, only 18-hydroxy-Z-9-octadecenoic acid was detected in this sample.

Mixture 3 (see Table 7) comprised, besides the substrates, 100 μg of Sbg2p. Besides the substrate 18-hydroxy-Z-9-octadecenoic acid, 18-(β-D-glucopyranosyloxy)-Z-9-octadecenoic acid (empirical formula $C_{24}H_{44}O_8$; molecular weight 460.3031 g/mol) was detected. This proves that Sbg2p is capable of converting UDP-glucose and 18-hydroxy-Z-9-octadecenoic acid into 18-(β-D-glucopyranosyloxy)-Z-9-octadecenoic acid.

Mixture 4 (see Table 7) comprised, besides the substrates, in addition 110 μg of Sbg5p. Besides the substrate 18-hydroxy-Z-9-octadecenoic acid, 18-(β-D-glucopyranosyloxy)-Z-9-octadecenoic acid and 18-L-[(2'-O-(β-D-glucopyranosyl-β-D-glucopyranosyl)oxy]-Z-9-octadecenoic acid (empirical formula $C_{30}H_{54}O_{13}$; molecular weight 622.3559 g/mol) were detected. This proves that Sbg5p is capable of converting UDP-glucose and 18-hydroxy-Z-9-octadecenoic acid into 18-(β-D-glucopyranosyloxy)-Z-9-octadecenoic acid and further into 18-L-[(2'-O-β-D-glucopyranosyl-β-D-glucopyranosyl)oxy]-Z-9-octadecenoic acid.

Mixture 5 (see Table 7) comprised, besides the substrates, additionally 100 μg of Sbg2p and 105 μg of Sbg3p. Besides the substrate 18-hydroxy-Z-9-octadecenoic acid, 18-(β-D-glucopyranosyloxy)-Z-9-octadecenoic acid and 18-(6-O-acetyl-β-D-glucopyranosyloxy)-Z-9-octadecenoic acid (empirical formula $C_{26}H_{46}O_9$; molecular weight 502.3136 g/mol) were detected. This confirms that, as has already been demonstrated for mixture 3, Sbg2p is capable of converting UDP-glucose and 18-hydroxy-Z-9-octadecenoic acid into 18-(β-D-glucopyranosyloxy)-Z-9-octadecenoic acid and it proves furthermore that Sbg3p is capable of acetylating 18-(β-D-glucopyranosyloxy)-Z-9-octadecenoic acid in the presence of acetyl-CoA to give 18-(6-O-acetyl-β-D-glucopyranosyloxy)-Z-9-octadecenoic acid.

Mixture 6 (see Table 7) comprised, besides the substrates, additionally 110 μg of Sbg5p and 105 μg of Sbg3p. Besides the substrate 18-hydroxy-Z-9-octadecenoic acid, 18-(β-D-glucopyranosyloxy)-Z-9-octadecenoic acid, 18-(6-O-acetyl-β-D-glucopyranosyloxy)-Z-9-octadecenoic acid, 18-L-[(2'-O-β-D-glucopyranosyl-3-D-glucopyranosyl)oxy]-Z-9-octadecenoic acid, 18-L-[(6'-O-acetyl-2'-O-β-D-glucopyranosyl-β-D-glucopyranosyl)oxy]-Z-9-octadecenoic acid (empirical formula $C_{32}H_{56}O_{14}$; molecular weight 664.3665 g/mol) and 18-L-[(6'-O-acetyl-2'-O-β-D-glucopyranosyl-6"-O-acetyl-β-D-glucopyranosyl)oxy]-Z-9-octadecenoic acid (empirical formula $C_{34}H_{58}O_{15}$; molecular weight 706.3770 g/mol) were detected. This confirms that, as has already been demonstrated for mixture 4, Sbg5p is capable of converting UDP-glucose and 18-hydroxy-Z-9-octadecenoic acid into 18-(β-D-glucopyranosyloxy)-Z-9-octadecenoic acid and further into 18-L-[(2'-O-β-D-glucopyranosyl-β-D-glucopyranosyl)oxy]-Z-9-octadecenoic acid and furthermore proves that the formed products can be acetylated by Sb3gp in the presence of acetyl-CoA to give 18-L-[(6'-O-acetyl-2'-O-β-D-glucopyranosyl-β-D-glucopyranosyl)oxy]-Z-9-octadecenoic acid and/or 18-L-[(2'-O-β-D-glucopyranosyl-6"-O-acetyl-β-D-glucopyranosyl)oxy]-Z-9-octadecenoic acid and also 18-L-[(6'-O-acetyl-2'-O-β-D-glucopyranosyl-6"-O-acetyl-β-D-glucopyranosyl)oxy]-Z-9-octadecenoic acid.

Mixture 7 (see Table 7) comprised, besides the substrates, additionally 100 μg of Sbg2p and 110 μg of Sbg5p. Besides the substrate 18-hydroxy-Z-9-octadecenoic acid, 18-(β-D-glucopyranosyloxy)-Z-9-octadecenoic acid and 18-L-[(2'-O-β-D-glucopyranosyl-β-D-glucopyranosyl)oxy]-Z-9-octadecenoic acid were detected. This proves that Sbg2p and Sbg5p are capable of converting, in one mixture, UDP-glucose and 18-hydroxy-Z-9-octadecenoic acid into 18-(β-D-glucopyranosyloxy)-Z-9-octadecenoic acid and further into 18-L-[(2'-O-β-D-glucopyranosyl-β-D-glucopyranosyl)oxy]-Z-9-octadecenoic acid.

Mixture 8 (see Table 7) comprised, besides the substrates, additionally 100 μg of Sbg2p, 105 μg of Sbg3p and 110 μg of Sbg5p. Besides the substrate 18-hydroxy-Z-9-octadecenoic acid, 18-(R-D-glucopyranosyloxy)-Z-9-octadecenoic acid, 18-(6-O-acetyl-β-D-glucopyranosyloxy)-Z-9-octadecenoic acid, 18-L-[(2'-O-β-D-glucopyranosyl-β-D-glucopyranosyl)oxy]-Z-9-octadecenoic acid, 18-L-[(6'-O-acetyl-2'-O-β-D-glucopyranosyl-β-D-glucopyranosyl)oxy]-Z-9-octadecenoic acid and 18-L-[(6'-O-acetyl-2'-O-β-D-glucopyranosyl-6"-O-acetyl-β-D-glucopyranosyl)oxy]-Z-9-octadecenoic acid were detected. This confirms that, as has already been mentioned for mixture 7, Sbg2p and Sbg5p together are capable of converting UDP-glucose and 18-hydroxy-Z-9-octadecenoic acid into 18-(β-D-glucopyranosyloxy)-Z-9-octadecenoic acid and further into 18-L-[(2'-O-β-D-glucopyranosyl-β-D-glucopyranosyl)oxy]-Z-9-octadecenoic acid and also proves that, as has already been demonstrated for mixtures 5 and 6, the formed products are capable of being acetylated by Sbg3p in the presence of acetyl-CoA to give 18-L-[(6'-β-acetyl-2'-O-β-D-glucopyranosyl-β-D-glucopyranosyl)oxy]-Z-9-octadecenoic acid and/or 18-L-[(2'-O-β-D-glucopyranosyl-6"-O-acetyl-β-D-glucopyranosyl)oxy]-Z-9-octadecenoic acid and also 18-L-[(6'-O-acetyl-2'-O-β-D-glucopyranosyl-6"-O-acetyl-β-D-glucopyranosyl)oxy]-Z-9-octadecenoic acid.

Example 12

Alternative Route to Inactivating Acetyltransferase (SBG3) in *Candida bombicola* ATCC 22214

In an alternative route, the gene SBG3 was inactivated individually, and the phenotype of the corresponding mutant was characterized in terms of the sophorolipid biosynthesis. To construct the corresponding mutant in *C. bombicola*

ATCC 22214, a deletion cassette for CbSBG3 was first synthesized by GeneArt AG (Regensburg) (SEQ ID NO:14; cf. Example 2). Thereafter, the gene CbURA3, from Trenzyme GmbH (Konstanz), which encodes the *C. bombicola* ATCC 22214 orotidine-5-phosphate decarboxylase (van Bogaert et al. Yeast. 2007. 24(3):201-8) was substituted by a hygromycin resistance cassette. To this end, the hygromycin cassette was amplified from the DNA of the vector p-Col-5 (SEQ ID NO:85) using the following oligonucleotides:

```
1390_hygR_fp_EcoRV:
                                    (SEQ ID NO: 86)
5'- AAA GAT ATC TCT ATG CGC ACC

CGT TCT C -3'

1390_hygR_rp_Hind/Bgl:
                                    (SEQ ID NO: 87)
5'- TTT AGA TCT AAG CTT GAG ACA

CCT CAG CAT GCA CCA TTC -3'
```

The following parameters were employed for the PCR: 1×: initial denaturation, 98° C., 3 min; 25×: denaturation, 98° C., 0:10 min, annealing, 60° C., 0:30 min; elongation, 72° C., 2:00 min; 1×: terminal elongation, 72° C., 10 min. The Phusion™ High-Fidelity Master Mix from New England Biolabs (Frankfurt) was used for the amplification following the manufacturer's recommendations. The PCR product was purified by means of the QIAquick PCR purification kit (Qiagen, Hilden) following the manufacturer's instructions. The PCR product obtained had a size of 1831 bp. The PCR procedure, the verification of the successful amplification of the PCR by means of agarose gel electrophoresis, the staining of the DNA with ethidium bromide, the determination of the PCR fragment sizes, the purification of the PCR products and the determination of the DNA concentration were carried out in a manner known to the skilled worker. The hygromycin cassette was cloned into the vector pCR4_AcTr_URA (SEQ ID NO:88) by linearizing the vector with the restriction endonucleases BglII and PmlI. The insert was prepared for the subsequent ligation using the restriction endonucleases EcoRV and BglII. The ligation and the subsequent transformation into *E. coli* DH5α cells were carried out in a manner known to the skilled worker. The authenticity of the insert was verified by DNA sequence analysis.

The plasmid generated was named pCR4_AcTr_HygR (SEQ ID NO:89) and has a size of 8578 bp.

The deletion cassette CbSbg3-hyg (SEQ ID NO:90) is composed of the *Klebsiella pneumoniae* hygromycin resistance gene (hph), which encodes the hygromycin B phosphatase (Gritz L and Davies J 1983 Plasmid-encoded hygromycin B resistance: the sequence of hygromycin B phosphotransferase gene and its expression in *Escherichia coli* and *Saccharomyces cerevisiae*. Gene 25 (2-3): 179-188). The promoter for the resistance gene is the constitutive hybrid promoter hp4d (Madzak et al. 2000, Strong hybrid promoters and integrative expression/secretion vectors for quasi-constitutive expression of heterologous proteins in the yeast *Yarrowia lipolytica*. J. Mol. Microbiol. Biotechnol. 2, 207-216). The resistance gene is flanked by the terminator of the XPR2 gene, which encodes an extracellular protease from *Y. lipolytica* (Nicaud et al. 1989a. Cloning, sequencing and amplification of the alkaline extracellular protease (XPR2) gene of the yeast *Yarrowia lipolytica*. J. Biotechnol. 12, 285-298). The resistance gene is flanked upstream and downstream by approximately 1000 bp of the adjoining region of the gene to be inactivated.

loxP-Loci which optionally permit the deletion of the hph gene by temporarily producing the Cre-recombinase-encoding gene and permit its functional expression (for an overview, see Kühn & Torres. Methods Mol. Biol. 2002. 180:175-204) were introduced in each case between the flanking regions and the hph gene. The deletion cassette is constructed following the information in Table 9 hereinbelow:

TABLE 9

Structure of the deletion cassette for the Sbg3p-encoding structural gene of *C. bombicola* ATCC 22214.

| SEQ ID NO: | Gene | 5'-flanking region | loxP locus 1 | hph | loxP locus 2 | 3'-flanking region |
|---|---|---|---|---|---|---|
| 90 | SBG3 | 1-1033 | 1034-1066 | 1067-3599 | 3600-3633 | 3634-4635 |

To provide the deletion cassette for the subsequent transformation of *C. bombicola* ATCC 22214 in a sufficient amount, it was amplified by PCR. The following oligonucleotides were used:

Amplification of the deletion cassette for the inactivation of CbSBG3:

```
SBG3-fw:
                                    (SEQ ID NO: 21)
5'- TGC AGA CAA GTT CCT GCA GCT G -3'

SBG3-rv:
                                    (SEQ ID NO: 22)
5'- ATG CTT TAT TCA GGC ACG CTA CG -3'
```

The following parameters were employed for the PCR: 1×: initial denaturation, 98° C., 3 min; 25×: denaturation, 98° C., 0:10 min, annealing, 60° C., 0:30 min; elongation, 72° C., 2:00 min; 1×: terminal elongation, 72° C., 10 min. The Phusion™ High-Fidelity Master Mix from New England Biolabs (Frankfurt) was used for the amplification following the manufacturer's recommendations. The PCR product was purified by means of the QIAquick PCR purification kit (Qiagen, Hilden) following the manufacturer's instructions. The PCR procedure, the verification of the successful amplification of the PCR by means of agarose gel electrophoresis, the staining of the DNA with ethidium bromide, the determination of the PCR fragment sizes, the purification of the PCR products and the determination of the DNA concentration were carried out in a manner known to the skilled worker.

Transformation of *C. bombicola* ATCC 22214 was as described before (van Bogaert et al. Yeast. 2008. 25:273-278); van Bogaert et al. FEMS Yeast Res. 2009. 9:610-617). To verify the deletion of the gene SBG3 in *C. bombicola* ATCC 22214 transformants following transformation with the deletion cassette for CbSBG3 (SEQ ID NO:90), the respective locus was amplified from in each case 5 transformants and *C. bombicola* ATCC 22214 by means of colony PCR. The following oligonucleotides were used:

Verification of the genomic deletion of CbSBG3:

```
SBG3-KO-fw:
                                    (SEQ ID NO: 31)
5'- CAA ATT TAT CTG GGA GCA CAG TTA CAT

TGC -3'

SBG3-KO-rv:
                                    (SEQ ID NO: 32)
5'- CAC ACA TTG CTT TAG TCC AGC AAG AAC

C -3'
```

The following parameters were employed for the PCR: 1×: initial denaturation, 94° C., 3 min; 25×: denaturation, 94° C., 1:00 min, annealing, 60° C., 1:00 min; elongation, 72° C., 5:00 min; 1×: terminal elongation, 72° C., 10 min. The Tag PCR Master Mix Kit from Qiagen (Hilden) was used for the amplification following the manufacturer's recommendations. In each case 10 μl of the PCR reactions were subsequently separated on a 0.8% agarose gel. The procedure of the PCR, of the agarose gel electrophoresis, the staining of the DNA with ethidium bromide and the determination of the PCR fragment sizes were performed in a manner known to the skilled worker.

Upon amplification of the CbSBG3 locus from *C. bombicola* ATCC 22214, only the fragment sizes to be expected when the wild-type situation is present, i.e. 2839 bp, were determined.

Upon amplification of the SBG3 locus from transformants following the transformation of the deletion cassette CbSBG3-hyg, only the fragment size to be expected after the successful deletion of CbSBG3 from the chromosome, i.e. 4693 bp, was obtained.

In this manner, it was possible to identify clones in which the gene CbSBG3 had been deleted from the chromosome. The strain in question was henceforth referred to as *C. bombicola* ATCC 22214 sbg3-hyg.

Example 13

Characterization of the Sophorolipid Formation by *C. bombicola* ATCC 22214 sbg3-hyg The strains *C. bombicola* ATCC 22214 and *C. bombicola* ATCC 22214 sbg3-hyg were propagated on YPD agar plates. The medium referred to hereinbelow as SL production medium was used for producing the sophorolipids. This medium is composed of 0.1% $KH_2PO_4$, 0.5% $MgSO_4 \times 7 H_2O$, 0.01% $FeCl_3$, 0.01% NaCl, 0.4% yeast extract, 0.1% urea, 10.5% rapeseed oil and 10% glucose. The pH is brought to 4.5 and the medium is then sterilized in an autoclave (121° C., 20 min). It is not necessary to adjust the pH during the cultivation.

To study the sophorolipid production in the shake flask, a preculture was first established. To this end, 10 ml of YPD medium in a 100 ml Erlenmeyer flask were inoculated with one loop of a strain freshly plated onto a YPD agar plate. Cultivation was done overnight at 30° C. and 200 rpm. This preculture was used hereinbelow for inoculating 100 ml of SL medium in a 1000 ml Erlenmeyer flask (starting $OD_{600}$ 0.2). The cultures were grown for 7 days at 200 rpm and 30° C., and a sample of 2 ml of broth was taken every day, good care being taken that the culture medium was mixed thoroughly before sampling.

The samples were prepared for the subsequent chromatographic analyses as follows: using a positive-displacement pipette (Combitip), 800 μl of acetone were placed into a 2-ml reaction vessel and the reaction vessel was sealed immediately to minimize evaporation. 200 μl of broth were added. After vortexing the broth/acetone mixture, the latter was centrifuged for 1 min at 13 000 rpm, and 800 μl of the supernatant were transferred into an HPLC vessel.

An evaporative light scattering detector (ELSD) was used for the detection and quantitative determination of sophorolipids and/or oleic acid. The actual measurement was performed by means of the Agilent Technologies 1200 series (Santa Clara, Calif.) and the Zorbax SB-C8 Rapid Resolution column (4.6×150 mm, 3.5 μm, Agilent). The injection volume was 5 μl, and the running time of the method was 20 min. The mobile phase used was $H_2O$ and 0.1% of TFA (trifluoroacetic acid, solution A) and methanol (solution B). The column temperature was 40° C. The detectors used were the ELSD (detector temperature 60° C.) and the DAD (diode array, 210 nm). The gradient used in the method is shown in Table 10 hereinbelow.

TABLE 10

Description of the gradient profile of the mobile phase to be used for the HPLC-based quantification of sophorolipids.

| t [min] | Solution B % | Flow rate [ml/min] |
|---|---|---|
| 0.00 | 70% | 1.00 |
| 15.00 | 100% | 1.00 |
| 15.01 | 70% | 1.00 |
| 20.00 | 70% | 1.00 |

The analysis showed that both *C. bombicola* ATCC 22214 and *C. bombicola* ATCC 22214 sbg3-hyg produce sophorolipids. It was confirmed by $LC-MS^2$ that, in contrast to the sophorolipids formed by *C. bombicola* ATCC 22214, the sophorolipids formed by *C. bombicola* ATCC 22214 sbg3-hyg exclusively correspond to compounds of the general formulae (Ia) and (Ib) in which $R^1$=H and $R^2$=H (see FIGS. 1 and 2) and that the concentration of these compounds is increased by the factor 10 in comparison with *C. bombicola* ATCC 22214. This proves the function of Sbg3p as acetyltransferase in sophorolipid biosynthesis.

Embodiments:

1. A sophorolipid-forming cell which is genetically modified in such a way that it has an activity, as specified in each case hereinbelow, of at least one of the enzymes selected from the group hereafter, which activity is modified in comparison with its wild type:
   at least one enzyme $E_1$ with the polypeptide sequence SEQ ID NO: 7, SEQ ID NO: 53, SEQ ID NO: 55, SEQ ID NO: 57, SEQ ID NO: 59, SEQ ID NO: 61 or SEQ ID NO: 63 or with a polypeptide sequence where up to 250 of the amino acid residues are modified over SEQ ID NO: 7, SEQ ID NO: 53, SEQ ID NO: 55, SEQ ID NO: 57, SEQ ID NO: 59, SEQ ID NO: 61 or SEQ ID NO: 63 by deletion, insertion, substitution or a combination of these and which retains at least 50% of the enzymatic activity of the enzyme with the respective reference sequence SEQ ID NO: 7, SEQ ID NO: 53, SEQ ID NO: 55, SEQ ID NO: 57, SEQ ID NO: 59, SEQ ID NO: 61 or SEQ ID NO: 63, where enzymatic activity for an enzyme $E_1$ is understood as meaning the ability to convert Z-9-octadecenoic acid into 17-hydroxy-Z-9-octadecenoic acid,
   at least one enzyme $E_2$ with the polypeptide sequence SEQ ID NO: 8 or SEQ ID NO: 11 or with a polypeptide sequence where up to 60% of the amino acid residues are modified over SEQ ID NO: 8 or SEQ ID NO: 11 by deletion, insertion, substitution or a combination of these and which retains at least 50% of the enzymatic activity of the enzyme with the respective reference sequence SEQ ID NO: 8 or SEQ ID NO: 11, where enzymatic activity for an enzyme $E_2$ is understood as meaning the ability to convert UDP-glucose and 17-hydroxy-Z-9-octadecenoic acid into 17-(β-D-glucopyranosyloxy)-Z-9-octadecenoic acid,
   at least one enzyme $E_3$ with the polypeptide sequence SEQ ID NO: 11 or with a polypeptide sequence where up to 600 of the amino acid residues are modified over SEQ ID NO: 11 by deletion, insertion, substitution or a combination of these and which retains at least 500 of the enzymatic activity of the enzyme with the reference sequence SEQ ID NO: 11, where enzymatic activity for an enzyme $E_3$ is understood as meaning the ability to convert 17-(β-D-glucopyranosyloxy)-Z-9-octadecenoic acid and UDP-glucose into 17-L-[(2'-O-β-D-glucopyranosyl-β-D-glucopyranosyl)oxy]-Z-9-octadecenoic acid, at least one enzyme $E_4$ with the polypeptide sequence SEQ ID NO: 9 or with a polypeptide sequence where up to 500 of the amino acid residues are modified over SEQ ID NO: 9 by deletion, insertion, substitution or a combination of these and which retains at least 500 of the enzymatic activity of the enzyme with SEQ ID NO: 9, where enzymatic activity for an enzyme $E_4$ is understood as meaning the ability to convert 17-L-[(2'-O-β-D-glucopyranosyl-β-D-glucopyranosyl)oxy]-Z-9-octadecenoic acid 1',4"-lactone and acetyl-coenzyme A into 17-L-[(2'-O-β-D-glucopyranosyl-β-D-glucopyranosyl)oxy]-Z-9-octadecenoic acid 1',4"-lactone monoacetate or 17-L-[(2'-O-β-D-glucopyranosyl-β-D-glucopyranosyl)oxy]-Z-9-octadecenoic acid 1',4"-lactone monoacetate and acetyl-coenzyme A into 17-L-[(2'-O-β-D-glucopyranosyl-β-D-glucopyranosyl)oxy]-Z-9-octadecenoic acid 1',4"-lactone diacetate or 17-L-[(2'-O-β-D-glucopyranosyl-β-D-glucopyranosyl)oxy]-Z-9-octadecenoic acid 1',4"-lactone and acetyl-coenzyme A into 17-L-[(2'-O-β-D-glucopyranosyl-β-D-glucopyranosyl)oxy]-Z-9-octadecenoic acid 1',4"-lactone diacetate, at least one enzyme $E_5$ with the polypeptide sequence SEQ ID NO: 10 or with a polypeptide sequence where up to 45% of the amino acid residues are modified over SEQ ID NO: 10 by deletion, insertion, substitution or a combination of these and which retains at least 50% of the enzymatic activity of the enzyme with SEQ ID NO: 10, where enzymatic activity for an enzyme $E_5$ is understood as meaning the ability to transfer a sophorolipid out of a cell into the surrounding medium.

2. The cell as embodied in embodiment 1, characterized in that it is at least partially blocked in its β-oxidation.

3. The cell as embodied in embodiment 1 or 2, characterized in that the modified activity is an increased activity.

4. The cell as embodied in embodiment 3, characterized in that it has increased activities of the following enzyme combinations:

$E_1E_2$, $E_1E_3$, $E_1E_4$, $E_1E_5$, $E_2E_3$, $E_2E_4$, $E_2E_5$, $E_3E_4$, $E_3E_5$, $E_4E_5$, $E_1E_2E_3$, $E_1E_2E_4$, $E_1E_2E_5$, $E_1E_3E_4$, $E_1E_3E_5$, $E_1E_4E_5$, $E_2E_3E_4$, $E_2E_4E_5$, $E_3E_4E_5$, $E_1E_2E_3E_4$, $E_2E_3E_4E_5$, $E_1E_3E_4E_5$, $E_1E_2E_4E_5$, $E_1E_2E_3E_5$, $E_1E_2E_3E_4$ and $E_1E_2E_3E_4E_5$.

5. The cell as embodied in embodiment 1 or 2, characterized in that it has a reduced activity of the enzyme $E_3$ and optionally an increased activity of the following enzyme combinations:

$E_1E_2$, $E_1E_4$, $E_1E_5$, $E_2E_4$, $E_2E_5$, $E_4E_5$, $E_1E_2E_4$, $E_1E_2E_5$, $E_1E_4E_5$ and $E_1E_2E_4E_5$.

6. The cell as embodied in embodiment 1 or 2, characterized in that it has a reduced activity of the enzyme $E_4$ and optionally an increased activity of the following enzyme combinations:

$E_1E_2$, $E_1E_3$, $E_1E_5$, $E_2E_3$, $E_2E_5$, $E_3E_5$, $E_1E_2E_3$, $E_1E_2E_5$, $E_1E_3E_5$ and $E_1E_2E_3E_5$.

7. The cell as embodied in embodiment 1 or 2, characterized in that it has a reduced activity of the enzymes $E_3$ and $E_4$ and optionally an increased activity of the following enzyme combinations:

$E_1E_2$, $E_1E_5$, $E_2E_5$, $E_1E_2E_5$.

8. The cell as embodied in at least one of embodiments 1 to 7, characterized in that it is transformed with at least one nucleic acid as embodied in embodiment 10 or 11.

9. A process for the production of sophorolipids, comprising the process steps:

I) bringing a cell as embodied in at least one of embodiments 1 to 8 into contact with a medium comprising a carbon source, II) culturing the cell under conditions which allow the cell to form a sophorolipid from the carbon source, and III) optionally isolating the formed sophorolipids.

10. The use of the sophorolipids obtained by the process as embodied in embodiment 9 for the preparation of cosmetic, dermatological or pharmaceutical formulations, crop protection formulations and care and cleaning compositions and surfactant concentrates.

11. An isolated DNA which is selected from among the following sequences:

A) a sequence according to SEQ ID NO: 2, SEQ ID NO: 3, SEQ ID NO: 4, SEQ ID NO: 5, SEQ ID NO: 6, SEQ ID NO: 52, SEQ ID NO: 54, SEQ ID NO: 56, SEQ ID NO: 58, SEQ ID NO: 60 or SEQ ID NO: 62, where the sequence according to SEQ ID NO: 2, SEQ ID NO: 52, SEQ ID NO: 54, SEQ ID NO: 56, SEQ ID NO: 58, SEQ ID NO: 60 or SEQ ID NO: 62 encodes a protein which is capable of converting Z-9-octadecenoic acid into 17-hydroxy-Z-9-octadecenoic acid, where the sequence SEQ ID NO: 3 encodes a protein which is capable of converting UDP-glucose and 17-hydroxy-Z-9-octadecenoic acid into 17-(β-D-glucopyranosyloxy)-Z-9-octadecenoic acid, where the sequence SEQ ID NO: 4 encodes a protein which is capable of converting 17-L-[(2'-O-β-D-glucopyranosyl-β-D-glucopyranosyl)oxy]-Z-9-octadecenoic acid 1',4"-lactone and acetyl-coenzyme A into 17-L-[(2'-O-β-D-glucopyranosyl-β-D-glucopyranosyl)oxy]-Z-9-octadecenoic acid 1',4"-lactone monoacetate or 17-L-[(2'-O-β-D-glucopyranosyl-β-D-glucopyranosyl)oxy]-Z-9-octadecenoic acid 1',4"-lactone monoacetate and acetyl-coenzyme A into 17-L-[(2'-O-β-D-glucopyranosyl-β-D-glucopyranosyl)oxy]-Z-9-octadecenoic acid 1',4"-lactone diacetate or 17-L-[(2'-O-β-D-glucopyranosyl-β-D-glucopyranosyl)oxy]-Z-9-octadecenoic acid 1',4"-lactone and acetyl-coenzyme A into 17-L-[(2'-O-β-D-glucopyranosyl-β-D-glucopyranosyl)oxy]-Z-9-octadecenoic acid 1',4"-lactone diacetate, where the sequence SEQ ID NO: 5 encodes a protein which is capable of transferring a sophorolipid out of a cell into the surrounding medium, where the sequence SEQ ID NO: 6 encodes a protein which is capable of converting UDP-glucose and 17-hydroxy-Z-9-octadecenoic acid into 17-(β-D-glucopyranosyloxy)-Z-9-octadecenoic acid or 17-(β-D-glucopyranosyloxy)-Z-9-octadecenoic acid and UDP-glucose into 17-L-[(2'-O-β-D-glucopyranosyl-β-D-glucopyranosyl)oxy]-Z-9-octadecenoic acid, B) an intron-free sequence which is derived from a sequence according to A) and which encodes the same protein or peptide as the sequence according to SEQ ID NO: 2, SEQ ID NO: 3, SEQ ID NO: 4, SEQ ID NO: 5, SEQ ID NO: 6, SEQ ID NO: 52, SEQ ID NO: 54, SEQ ID NO: 56, SEQ ID NO: 58, SEQ ID NO: 60 or SEQ ID NO: 62, C) a sequence which encodes a protein or peptide which comprises the amino acid sequence according to SEQ ID NO: 7, SEQ ID NO: 8, SEQ ID NO: 9, SEQ ID NO: 10, SEQ ID NO: 11, SEQ ID NO: 53, SEQ ID NO: 55, SEQ ID NO: 57, SEQ ID NO: 59, SEQ ID NO: 61 or SEQ ID NO: 63, where the protein or peptide which comprises the amino acid sequence according to SEQ ID NO: 7, SEQ ID NO: 53, SEQ ID NO: 55, SEQ ID NO: 57, SEQ ID NO: 59, SEQ ID NO: 61 or SEQ ID NO: 63 is capable of converting Z-9-octadecenoic acid into 17-hydroxy-Z-9-octadecenoic acid, D) a sequence which is to at least 80-17 identical to a sequence according to one of groups A) to C), E) a sequence which hybridizes or, taking into consideration the degeneracy of the genetic code, would hybridize to the counterstrand of a sequence according to one of groups A) to D), F) a derivative of a sequence according to one of groups A) to E) which is obtained by substitution, addition, inversion and/or deletion of one or more bases, and G) a complementary sequence to a sequence according to one of groups A) to F).

12. A vector comprising a DNA sequence according to one of groups A) to G) as defined in embodiment 11.

13. The use of the vector as embodied in embodiment 12 for transforming a cell.

14. An isolated polypeptide selected from the group consisting of an enzyme $E_1$ with the polypeptide sequence SEQ ID NO: 7, SEQ ID NO: 53, SEQ ID NO: 55, SEQ ID NO: 57, SEQ ID NO: 59, SEQ ID NO: 61 or SEQ ID NO: 63, especially SEQ ID NO: 7, or with a polypeptide sequence where up to 25% of the amino acid residues are modified over the respective reference sequence SEQ ID NO: 7, SEQ ID NO: 53, SEQ ID NO: 55, SEQ ID NO: 57, SEQ ID NO: 59, SEQ ID NO: 61 or SEQ ID NO: 63, especially SEQ ID NO: 7, by deletion, insertion, substitution or a combination of these and which retains at least 50% of the enzymatic activity of the enzyme with the respective reference sequence, where enzymatic activity for an enzyme $E_1$ is understood as meaning the ability to convert Z-9-octadecenoic acid into 17-hydroxy-Z-9-octadecenoic acid, an enzyme $E_2$ with the polypeptide sequence SEQ ID NO: 8 or SEQ ID NO: 11 or with a polypeptide sequence where up to 60% of the amino acid residues are modified over SEQ ID NO: 8 or SEQ ID NO: 11 by deletion, insertion, substitution or a combination of these and which retains at least 50% of the enzymatic activity of the enzyme with the respective reference sequence No. 8 or 11, where enzymatic activity for an enzyme $E_2$ is understood as meaning the ability to convert UDP-glucose and 17-hydroxy-Z-9-octadecenoic acid into 17-(β-D-glucopyranosyloxy)-Z-9-octadecenoic acid, an enzyme $E_3$ with the polypeptide sequence SEQ ID NO: 11 or with a polypeptide sequence where up to 60% of the amino acid residues are modified over SEQ ID NO: 11 by deletion, insertion, substitution or a combination of these and which retains at least 50% of the enzymatic activity of the enzyme with the respective reference sequence 11, where enzymatic activity for an enzyme $E_3$ is understood as meaning the ability to convert 17-(β-D-glucopyranosyloxy)-Z-9-octadecenoic acid and UDP-glucose into 17-L-[(2'-O-β-D-glucopyranosyl-β-D-glucopyranosyl)oxy]-Z-9-octadecenoic acid, an enzyme $E_4$ with the polypeptide sequence SEQ ID NO: 9 or with a polypeptide sequence where up to 50% of the amino acid residues are modified over SEQ ID NO: 9 by deletion, insertion, substitution or a combination of these and which retains at least 50% of the enzymatic activity of the enzyme with SEQ ID NO: 9, where enzymatic activity for an enzyme $E_4$ is understood as meaning the ability to convert 17-L-[(2'-O-β-D-glucopyranosyl-β-D-glucopyranosyl)oxy]-Z-9-octadecenoic acid 1',4"-lactone and acetyl-coenzyme A into 17-L-[(2'-O-1-D-glucopyranosyl-β-D-glucopyranosyl)oxy]-Z-9-octadecenoic acid 1',4"-lactone monoacetate or 17-L-[(2'-O-β-D-glucopyranosyl-β-D-glucopyranosyl)oxy]-Z-9-octadecenoic acid 1',4"-lactone monoacetate and acetyl-coenzyme A into 17-L-[(2'-O-β-D-glucopyranosyl-β-D-glucopyranosyl)oxy]-Z-9-octadecenoic acid 1',4"-lactone diacetate or 17-L-[(2'-O-β-D-glucopyranosyl-β-D-glucopyranosyl)oxy]-Z-9-octadecenoic acid 1',4"-lactone and acetyl-coenzyme A into 17-L-[(2'-O-β-D-glucopyranosyl-β-D-glucopyranosyl)oxy]-Z-9-octadecenoic acid 1',4"-lactone diacetate and an enzyme $E_5$ with the polypeptide sequence SEQ ID NO: 10 or with a polypeptide sequence where up to 45% of the amino acid residues are modified over SEQ ID NO: 10 by deletion, insertion, substitution or a combination of these and which retains at least 50% of the enzymatic activity of the enzyme with SEQ ID NO: 10, where enzymatic activity for an enzyme $E_5$ is understood as meaning the ability to transfer a sophorolipid out of a cell into the surrounding medium.

We claim:

1. An isolated or purified sophorolipid-producing cell: (A) transformed with a nucleic acid encoding an $E_4$ polypeptide; or (B) modified to disrupt at least one endogenous gene encoding an $E_4$ polypeptide;

wherein said $E_4$ comprises (a) the amino acid sequence of SEQ ID NO: 9; or (b) a variant of the amino acid sequence of SEQ ID NO: 9 which is identical to the amino acid sequence of SEQ ID NO: 9 except that at least one residue up to 5% of the amino acid residues of SEQ ID NO: 9 have been modified by deletion, substitution, and/or insertion, wherein the $E_4$ polypeptide has the ability to catalyze the conversion of:

(i) 17-L-[(2'-O-β-D-glucopyranosyl-β-D-glucopyranosyl)oxy]-Z-9-octadecenoic acid 1',4"-lactone and acetyl-coenzyme A into 17-L-[(2'-O-β-D-glucopyranosyl-β-D- glucopyranosyl)oxy]-Z-9-octadecenoic acid 1',4"-lactone monoacetate;

(ii) 17-L-[(2'-O-β-D-glucopyranosyl-β-D-glucopyranosyl)oxy]-Z-9-octadecenoic acid 1',4"-lactone monoacetate and acetyl-coenzyme A into 17-L-[(2'-O-β-D -glucopyranosyl-β-D-glucopyranosyl)oxy]-Z-9-octadecenoic acid 1',4"-lactone diacetate; or (iii) 17-L-[(2'-O-β-D-glucopyranosyl-β-D-glucopyranosyl)oxy]-Z-9-octadecenoic acid ',4"-lactone and acetyl-coenzyme A into 17-L-[(2'-O-β-D-glucopyranosyl-β-D-glucopyranosyl) oxy]-Z-9-octadecenoic acid 1',4"-lactone diacetate;

wherein said cell may optionally contain a nucleic acid encoding at least one $E_1$, $E_2$, $E_3$ or $E_5$ polypeptide or wherein said cell may optionally have a disruption in an endogenous gene encoding an $E_3$ polypeptide; wherein:

$E_1$ comprises (a) an amino acid sequence selected from the group consisting of SEQ ID NO: 7, 53, 55, 57, 59, 61 and 63; or (b) a variant of the amino acid sequence of SEQ ID NO: 7, 53, 55, 57, 59, 61 or 63 which is identical to SEQ ID NO: 7, 53, 55, 57, 59, 61 or 63 except that at least one residue up to 5% of the amino acid residues of SEQ ID NO: 7, 53, 55, 57, 59, 61 or 63 have been modified by deletion, substitution, and/or insertion; wherein the $E_1$ polypeptide catalyzes the conversion of Z-9-octadecenoic acid into 17-hydroxy-Z-9-octadecenoic acid;

$E_2$ comprises (a) an amino acid sequence selected from the group consisting of SEQ ID NO: 8 and 11; or (b) a variant of the amino acid sequence of SEQ ID NO: 8 or 11 which is identical to the amino acid sequence of SEQ ID NO: 8 or 11 except that at least one residue up to 5% of the amino acid residues of SEQ ID NO: 8 or 11 have been modified by deletion, substitution, and/or insertion, wherein the $E_2$ polypeptide catalyzes the conversion of UDP-glucose and 17-hydroxy-Z-9-octadecenoic acid into 17-(β-D-glucopyranosyloxy)-Z-9-octadecenoic acid;

$E_3$ comprises (a) the amino acid sequence of SEQ ID NO: 11; or (b) a variant of the amino acid sequence of SEQ ID NO: 11 which is identical to the amino acid sequence of SEQ ID NO: 11 except that at least one residue up to 5% of the amino acid residues of SEQ ID NO: 11 have been modified by deletion, substitution, and/or insertion, wherein the $E_3$ polypeptide has the ability to catalyze the conversion of 17-(β-D-glucopyranosyloxy)-Z-9-octadecenoic acid and UDP-glucose into 17-L-[(2'-O-β-D-glucopyranosyl-β-D-glucopyranosyl)oxy]-Z-9-octadecenoic acid; and $E_5$ comprises (a) the amino acid sequence of SEQ ID NO: 10; or (b) a variant of the amino acid sequence of SEQ ID NO: 10 which is identical to the amino acid sequence of SEQ ID NO: 10 except that at least one residue up to 5% of the amino acid residues of SEQ ID NO: 10 have been modified by deletion, substitution, and/or insertion, wherein the $E_5$ polypeptide has the ability to transfer a sophorolipid out of the sophorolipid-producing cell into the surrounding medium.

2. The isolated or purified sophorolipid-producing cell of claim 1, wherein said sophorolipid-producing cell has been transformed with at least one extrachromosomally replicating vector carrying said nucleic acid(s).

3. The isolated or purified sophorolipid-producing cell of claim 1, wherein said sophorolipid-producing cell has been transformed with a nucleic acid encoding the $E_4$ polypeptide, wherein said nucleic acid is operably linked to a promoter, a regulation region, a ribosome binding site, an expression cassette or an enhancer that increases the expression of said $E_4$ polypeptide.

4. The isolated or purified sophorolipid-producing cell of claim 1, wherein said sophorolipid-producing cell has been transformed with a nucleic acid encoding the $E_4$ polypeptide, wherein said transformed sophorolipid-producing cell expresses more of the polypeptide of SEQ ID NO: 9 than the identical non-transformed cell.

5. The isolated or purified sophorolipid-producing cell of claim 1, wherein said sophorolipid-producing cell has been transformed with a nucleic acid encoding the $E_4$ polypeptide, wherein said transformed sophorolipid-producing cell produces a greater yield of acetylated sophorolipids than the identical non-transformed cell.

6. The isolated or purified sophorolipid-producing cell of claim 1, wherein said sophorolipid-producing cell has been transformed with a nucleic acid encoding the polypeptide of SEQ ID NO: 9.

7. The isolated or purified sophorolipid-producing cell of claim 1, wherein said sophorolipid-producing cell has been transformed with a nucleic acid encoding an $E_4$ polypeptide that comprises a variant of the amino acid sequence of SEQ ID NO: 9 which is identical to the amino acid sequence of SEQ ID NO: 9 except that at least one residue up to 5% of the amino acid residues of SEQ ID NO: 9 have been modified by deletion, substitution, and/or insertion, wherein the $E_4$ polypeptide has the ability to catalyze the conversion of:

(i) 17-L-[(2'-O-β-D-glucopyranosyl-β-D-glucopyranosyl) oxy]-Z-9-octadecenoic acid 1',4"-lactone and acetyl-coenzyme A into 17-L-[(2'-O-β-D-glucopyranosyl-β--D -glucopyranosyl)oxy]-Z-9-octadecenoic acid 1',4"-lactone monoacetate;

(ii) 17-L-[(2'-O-β-D-glucopyranosyl-β-D-glucopyranosyl)oxy]-Z-9-octadecenoic acid 1',4"-lactone monoacetate and acetyl-coenzyme A into 17-L-[(2'-O-β-D- glucopyranosyl-β-D-glucopyranosyl)oxy]-Z-9-octadecenoic acid 1',4"-lactone diacetate; or (iii) 17-L-[(2'-O-β-D-glucopyranosyl-β-D-glucopyranosyl)oxy]-Z-9-octadecenoic acid 1',4"-lactone and acetyl-coenzyme A into 17-L-[(2'-O-β-D-glucopyranosyl-β-D-glucopyranosyl)oxy]-Z-9-octadecenoic acid 1',4"-lactone diacetate.

8. The isolated or purified sophorolipid-producing cell of claim 1, wherein said sophorolipid-producing cell is a yeast or fungal cell.

9. The isolated or purified sophorolipid-producing cell of claim 1, wherein said sophorolipid-producing cell is selected from the group consisting of *Candida bombicola, Candida bogoriensis, Candida batistae, Candida apicola* and *Wickerhamiella domericqiae.*

10. The isolated or purified sophorolipid-producing cell of claim 1, wherein said sophorolipid-producing cell has been further modified to block or partially block β- oxidation in said cell.

11. The isolated or purified sophorolipid-producing cell of claim 1, wherein said sophorolipid-producing cell has been further transformed with a nucleic acid encoding at least one $E_1$ polypeptide.

12. The isolated or purified sophorolipid-producing cell of claim 1, wherein said sophorolipid-producing cell has been further transformed with a nucleic acid encoding at least one $E_2$ polypeptide.

13. The isolated or purified sophorolipid-producing cell of claim 1, wherein said sophorolipid-producing cell has been further transformed with a nucleic acid encoding at least one $E_3$ polypeptide.

14. The isolated or purified sophorolipid-producing cell of claim 1, wherein said sophorolipid-producing cell has been further transformed with a nucleic acid encoding at least one $E_5$ polypeptide.

15. The isolated or purified sophorolipid-producing cell of claim 1, wherein said sophorolipid-producing cell has been transformed with nucleic acid(s) encoding a combination of polypeptides selected from the group consisting of $E_1E_2$, $E_1E_3$, $E_1E_4$, $E_1E_5$, $E_2E_3$, $E_2E_4$, $E_2E_5$, $E_3E_4$, $E_3E_5$, $E_4E_5$, $E_1E_2E_3$, $E_1E_2E_4$, $E_1E_2E_5$, $E_1E_3E_4$, $E_1E_3E_5$, $E_1E_4E_5$, $E_2E_3E_4$, $E_2E_4E_5$, $E_3E_4E_5$, $E_1E_2E_3E_4$, $E_2E_3E_4E_5$, $E_1E_3E_4E_5$, $E_1E_2E_4E_5$, $E_1E_2E_3E_5$, $E_1E_2E_3E_4$ and $E_1E_2E_3E_4E_5$ polypeptides.

16. The isolated or purified sophorolipid-producing cell of claim 1, wherein said sophorolipid-producing cell has been further modified to disrupt at least one endogenous gene encoding an $E_3$ polypeptide.

17. The isolated or purified sophorolipid-producing cell of claim 1, wherein said sophorolipid-producing cell has been modified to disrupt at least one endogenous gene encoding an $E_4$ polypeptide.

18. The isolated or purified sophorolipid-producing cell of claim 1, wherein said sophorolipid-producing cell has been modified to disrupt at least one endogenous gene encoding an $E_4$ polypeptide and further modified to disrupt at least one endogenous gene encoding an $E_3$ polypeptide.

19. A process for producing a sophorolipid comprising:

culturing the cell of claim 1 on a medium containing a carbon source under conditions suitable for producing a sophorolipid from the carbon source and, optionally, isolating or recovering the sophorolipid;

wherein said cell may optionally contain a nucleic acid encoding at least one $E_1$, $E_2$, $E_3$ or $E_5$ polypeptide or wherein said cell may optionally have a disruption in an endogenous gene encoding an $E_3$ polypeptide; wherein:

$E_1$ comprises (a) an amino acid sequence selected from the group consisting of SEQ ID NO: 7, 53, 55, 57, 59, 61 and 63; or (b) a variant of the amino acid sequence of SEQ ID NO: 7, 53, 55, 57, 59, 61 or 63 which is identical to SEQ ID NO: 7, 53, 55, 57, 59, 61 or 63 except that at least one residue up to 5% of the amino acid residues of SEQ ID NO: 7, 53, 55, 57, 59, 61 or 63 have been modified by deletion, substitution, and/or insertion; wherein the $E_1$ polypeptide catalyzes the conversion of Z-9-octadecenoic acid into 17-hydroxy-Z-9-octadecenoic acid;

$E_2$ comprises (a) an amino acid sequence selected from the group consisting of SEQ ID NO: 8 and 11; or (b) a variant of the amino acid sequence of SEQ ID NO: 8 or 11 which is identical to the amino acid sequence of SEQ ID NO: 8 or 11 except that at least one residue up to 5% of the amino acid residues of SEQ ID NO: 8 or 11 have been modified by deletion, substitution, and/or insertion, wherein the $E_2$ polypeptide catalyzes the conversion of UDP-glucose and 17-hydroxy-Z-9-octadecenoic acid into 17-(β-D-glucopyranosyloxy)-Z-9-octadecenoic acid;

$E_3$ comprises (a) the amino acid sequence of SEQ ID NO: 11; or (b) a variant of the amino acid sequence of SEQ ID NO: 11 which is identical to the amino acid sequence of SEQ ID NO: 11 except that at least one residue up to 5% of the amino acid residues of SEQ ID NO: 11 have been modified by deletion, substitution, and/or insertion, wherein the $E_3$ polypeptide has the ability to catalyze the conversion of 17-(β-D-glucopyranosyloxy)-Z-9-octadecenoic acid and UDP-glucose into 17-L-[(2'-O-β-D-glucopyranosyl-β-D-glucopyranosyl)oxy]-Z-9-octadecenoic acid; and $E_5$ comprises (a) the amino acid sequence of SEQ ID NO: 10; or (b) a variant of the amino acid sequence of SEQ ID NO: 10 which is identical to the amino acid sequence of SEQ ID NO: 10 except that at least one residue up to 5% of the amino acid residues of SEQ ID NO: 10 have been modified by deletion, substitution, and/or insertion, wherein the $E_5$ polypeptide has the ability to transfer a sophorolipid out of the sophorolipid-producing cell into the surrounding medium.

20. The process of claim 19, wherein said sophorolipid-producing cell has been transformed with a nucleic acid encoding the polypeptide of SEQ ID NO: 9.

21. The process of claim 19, wherein said sophorolipid-producing cell has been transformed with a nucleic acid encoding an $E_4$ polypeptide that comprises a variant of the amino acid sequence of SEQ ID NO: 9 which is identical to the amino acid sequence of SEQ ID NO: 9 except that at least one residue up to 5% of the amino acid residues of SEQ ID NO: 9 have been modified by deletion, substitution, and/or insertion, wherein the $E_4$ polypeptide has the ability to catalyze the conversion of:

(i) 17-L-[(2'-O-β-D-glucopyranosyl-β-D-glucopyranosyl)oxy]-Z-9-octadecenoic acid 1',4"-lactone and acetyl-coenzyme A into 17-L-[(2'-O-β-D-glucopyranosyl-β-D-glucopyranosyl)oxy]-Z-9-octadecenoic acid 1',4"-lactone monoacetate;

(ii) 17-L-[(2'-O-β-D-glucopyranosyl-β-D-glucopyranosyl)oxy]-Z-9-octadecenoic acid 1',4"-lactone monoacetate and acetyl-coenzyme A into 17-L-[(2'-O-β-D- glucopyranosyl-β-D-glucopyranosyl)oxy]-Z-9-octadecenoic acid 1',4"-lactone diacetate; or (iii) 17-L-[(2'-O-β-D-glucopyranosyl-β-D-glucopyranosyl)oxy]-Z-9-octadecenoic acid 1',4"-lactone and acetyl-coenzyme A into 17-L-[(2'-O-β-D-glucopyranosyl-β-D -glucopyranosyl)oxy]-Z-9-octadecenoic acid 1',4"-lactone diacetate.

22. The process of claim 19, wherein said sophorolipid-producing cell has been transformed with nucleic acid(s) encoding a combination of polypeptides selected from the group consisting of $E_1E_2$, $E_1E_3$, $E_1E_4$, $E_1E_5$, $E_2E_3$, $E_2E_4$, $E_2E_5$, $E_3E_4$, $E_3E_5$, $E_4E_5$, $E_1E_2E_3$, $E_1E_2E_4$, $E_1E_2E_5$, $E_1E_3E_4$, $E_1E_3E_5$, $E_1E_4E_5$, $E_2E_3E_4$, $E_2E_4E_5$, $E_3E_4E_5$, $E_1E_2E_3E_4$, $E_2E_3E_4E_5$, $E_1E_3E_4E_5$, $E_1E_2E_4E_5$, $E_1E_2E_3E_5$, $E_1E_2E_3E_4$ and $E_1E_2E_3E_4E_5$ polypeptides.

23. The process of claim 19, wherein said sophorolipid-producing cell:

(a) has been modified to disrupt endogenous gene(s) encoding $E_3$ polypeptide(s); and (b) has been further transformed with a nucleic acid(s) encoding $E_1$, $E_2$, $E_4$, and/or $E_5$ polypeptides.

24. The process of claim 19, wherein said sophorolipid-producing cell:

(a) has been modified to disrupt endogenous gene(s) encoding $E_4$ polypeptide(s); and (b) has been further transformed with a nucleic acid(s) encoding $E_1$, $E_2$, $E_3$, and/or $E_5$ polypeptides.

25. The process of claim 19, wherein said sophorolipid-producing cell:

(a) has been modified to disrupt endogenous gene(s) encoding $E_3$ and $E_4$ polypeptide(s); and (b) has been further transformed with a nucleic acid(s) encoding $E_1$, $E_2$, and/or $E_5$ polypeptides.

* * * * *